United States Patent
Huang et al.

(10) Patent No.: US 7,172,881 B2
(45) Date of Patent: Feb. 6, 2007

(54) ISOLATED NUCLEIC ACIDS ENCODING FARNESYL TRANSFERASE ALPHA

(75) Inventors: Yafan Huang, Kingston (CA); Maryse Chalifoux, Kingston (CA); Yang Wang, Kingston (CA); Monika Maria Kuzma, Glenburnie (CA); Angela Patricia Gilley, Inverary (CA)

(73) Assignee: Performance Plants, Inc., Kingston (CA)

( * ) Notice: Subject to any disclaimer, the term of this patent is extended or adjusted under 35 U.S.C. 154(b) by 399 days.

(21) Appl. No.: 10/160,764

(22) Filed: May 31, 2002

(65) Prior Publication Data

US 2003/0167535 A1    Sep. 4, 2003

Related U.S. Application Data

(60) Provisional application No. 60/294,766, filed on May 31, 2001, provisional application No. 60/348,909, filed on Oct. 22, 2001.

(51) Int. Cl.
*C12N 15/09* (2006.01)
*C12N 15/10* (2006.01)
*A01H 5/00* (2006.01)

(52) U.S. Cl. .................... 435/69.1; 536/23.6; 536/23.2; 435/320.1

(58) Field of Classification Search ................ 800/278, 800/290, 295, 298, 286; 435/320.1, 468, 435/430, 69.1; 536/23.6, 23.2
See application file for complete search history.

(56) References Cited

FOREIGN PATENT DOCUMENTS

| WO | WO 99/06580 | 2/1999 |
|---|---|---|
| WO | WO 00/14207 | 3/2000 |

OTHER PUBLICATIONS

Bird et al, Biology and Genetic Review, vol. 9, pp. 220-221 (1991).*
Sandler et al. Plant Molecular Biology, vol. 11, pp. 301-310 (1988).*
Napoli et al. The Plant Cell, vol. 2, pp. 279-289, (1990).*
Stam et al. Annals of Botany 79:3-12, 1997.*
Pei et al., Science, 282:287-90 (1998).
Partial International Search Report for PCT/IB02/03033. Mailed on Jul. 1, 2003.

* cited by examiner

*Primary Examiner*—Medina A. Ibrahim
(74) *Attorney, Agent, or Firm*—Ivor R. Elrifi; Cynthia A. Kozakiewicz; Mintz Levin

(57) ABSTRACT

The present invention provides isolated polynucleotides encoding farnesyltransferase polypeptides, vectors and transgenic host cells comprising farnesyltransferase polynucleotides.

10 Claims, 15 Drawing Sheets

NO ABA

1 μM ABA

| DNA | Brassica napus | Arabidopsis thaliana | PPI Glycine max | Zea mays | Rice | Soy 1 | Soy 2 | Triticum | Tomato | Pea |
|---|---|---|---|---|---|---|---|---|---|---|
| Brassica napus | X | | | | | | | | | |
| Arabidopsis thaliana | 89 | X | | | | | | | | |
| PPI Glycine max | 61 | 55 | X | | | | | | | |
| Zea mays | 57 | 45 | 52 | X | | | | | | |
| Rice | 55 | 46 | 54 | 63 | X | | | | | |
| Soy 1 | 61 | 50 | 98 | 43 | 47 | X | | | | |
| Soy 2 | 61 | 50 | 99 | 41 | 46 | 99 | X | | | |
| Triticum | 58 | 45 | 52 | 56 | 66 | 43 | 41 | X | | |
| Tomato | 65 | 53 | 63 | 44 | 51 | 52 | 49 | 41 | X | |
| Pea | 66 | 55 | 78 | 46 | 50 | 70 | 69 | 44 | 49 | X |

| PROTEIN | Brassica napus | Arabidopsis thaliana | PPI Glycine max | Pea | Tomato | Rice | Zea mays | Soy 1 | Soy 2 | Triticum |
|---|---|---|---|---|---|---|---|---|---|---|
| Brassica napus | X | | | | | | | | | |
| Arabidopsis thaliana | 89 | X | | | | | | | | |
| PPI Glycine max | 65 | 63 | X | | | | | | | |
| Pea | 61 | 61 | 77 | X | | | | | | |
| Tomato | 60 | 59 | 57 | 58 | X | | | | | |
| Rice | 64 | 63 | 56 | 58 | 58 | X | | | | |
| Zea mays | 61 | 56 | 58 | 57 | 56 | 75 | X | | | |
| Soy 1 | 66 | 64 | 98 | 77 | 58 | 57 | 58 | X | | |
| Soy 2 | 66 | 64 | 98 | 78 | 58 | 57 | 58 | 99 | X | |
| Triticum | 61 | 60 | 57 | 59 | 60 | 80 | 73 | 58 | 58 | X |

Fig.8

| DNA | Brassica napus | Arabidopsis thaliana | Wiggun | PPI Glycine max | Glycine max | PPI Zea maize | Zea maize | Pea | Tomato | Tobacco |
|---|---|---|---|---|---|---|---|---|---|---|
| Brassica napus | X | | | | | | | | | |
| Arabidopsis thaliana | 88 | X | | | | | | | | |
| Wiggum | 88 | 99 | X | | | | | | | |
| PPI Glycine max | 60 | 64 | 65 | X | | | | | | |
| Glycine max | 60 | 64 | 65 | 99 | X | | | | | |
| PPI Zea maize | 38 | 54 | 59 | 63 | 63 | X | | | | |
| Zea maize | 54 | 54 | 59 | 62 | 62 | 99 | X | | | |
| Pea | 65 | 57 | 45 | 78 | 77 | 56 | 56 | X | | |
| Tomato | 68 | 62 | 52 | 70 | 70 | 64 | 64 | 51 | X | |
| Tobacco | 68 | 64 | 60 | 71 | 71 | 65 | 65 | 55 | 83 | X |

| PROTEIN | Brassica napus | Arabidopsis thaliana | Wiggun | PPI Glycine max | Glycine max | PPI Zea maize | Zea maize | Pea | Tomato | Tobacco |
|---|---|---|---|---|---|---|---|---|---|---|
| Brassica napus | X | | | | | | | | | |
| Arabidopsis thaliana | 84 | X | | | | | | | | |
| Wiggun | 84 | 99 | X | | | | | | | |
| PPI Glycine max | 54 | 58 | 59 | X | | | | | | |
| Glycine max | 53 | 58 | 58 | 99 | X | | | | | |
| PPI Zea maize | 52 | 50 | 52 | 58 | 58 | X | | | | |
| Zea maize | 51 | 50 | 52 | 58 | 58 | 99 | X | | | |
| Pea | 58 | 56 | 57 | 78 | 78 | 56 | 56 | X | | |
| Tomato | 60 | 62 | 55 | 63 | 63 | 58 | 58 | 62 | X | |
| Tobacco | 62 | 63 | 59 | 64 | 63 | 58 | 58 | 64 | 83 | X |

ISOLATED NUCLEIC ACIDS ENCODING FARNESYL TRANSFERASE ALPHA

RELATED APPLICATIONS

This application claims priority to U.S. Ser. No. 60/294,766, filed May 31, 2001 and U.S. Ser. No. 60/348,909, filed Oct. 22, 2001 each of which are incorporated herein by reference in their entireties.

FIELD OF THE INVENTION

The invention relates in part to novel plant farnesyl transferase alpha and beta subunit polynucleotides and polypeptides. Also included are transgenic plants expressing the novel polynucleotides and polypeptides. The invention also includes transgenic plant cells, tissues and plants having novel phenotypes resulting from the expression of these polynucleotides in either the sense or antisense orientation.

BACKGROUND OF THE INVENTION

Most higher plants encounter at least transient decreases in relative water content at some stage of their life cycle and, as a result, have evolved a number of desiccation protection mechanisms. If however, the change in water deficit is prolonged the effects on the plants growth and development can be profound. Decreased water content due to drought, cold or salt stress can irreparably damage plant cells which in turn limits plant growth and crop productivity in agriculture.

Plants respond to adverse conditions of drought, salinity and cold with a variety of morphological and physiological changes. Although our understanding of plant tolerance mechanisms to these stresses is incomplete, the plant hormone abscisic acid (ABA) is believed to be an essential mediator between environmental stimulus and plant responses. ABA levels increase in response to water deficits and exogenously applied ABA mimics many of the responses induced by water-stress. Once ABA is synthesized it causes the closure of the leaf stomata thereby decreasing water loss through transpiration.

The identification of genes that transduce ABA into a cellular response opens the possibility of exploiting these regulators to enhance desiccation tolerance in crop species. In principle, these ABA signaling genes can be coupled with the appropriate controlling elements to allow optimal plant growth, development and productivity. Thus, not only would these genes allow the genetic tailoring of crops to withstand transitory environmental stresses, but they should also broaden the environments where traditional crops can be grown.

The recent isolation of an *Arabidopsis thaliana* mutant, era1, is hypersensitive to ABA and has been shown to also be tolerant to conditions of water deprivation. ERA1 has been identified as a β subunit of farnesyl transferase. Farnesyl transferase is a heterodimeric enzyme that provides the specific addition of a farnesyl pyrophosphate moiety onto the substrate target sequence. The target sequence is defined as a sequence of four amino acids which are present at the carboxy terminus of the protein and is referred to as a CaaX motif in which the "C" is cysteine, "a" is any aliphatic amino acid and "X" is any amino acid. The α subunit is common with a second prenylation enzyme, geranylgeranyl transferase, that has a different β subunit and adds a geranylgeranyl isoprenyl pyrophosphate moiety to the target sequence.

Prenylation is a multistep pathway which includes prenylation of the cysteine residue of the CaaX site, cleavage of the -aaX tripeptide and methylation of the prenyl-cysteine residue. Potentially, each of these steps could represent a target for genetic manipulation of the prenylation process to generate a desired phenotype such as stress tolerance.

In plants, prenylation has been linked to cell cycle control, meristem development, and phytohormone signal transduction, however, few details of the role of prenylation, the substrate proteins or the extent to which the plant system will be analogous to the mammalian and yeast systems are known. The most characterized substrates for CaaX modification are the Ras and a-factor proteins of yeast. Although there are three steps to complete protein maturation, abolition or modification of any one step does not necessarily result in cessation of target biological activities. Ras function is attenuated if the -aaX tripeptide is not cleaved but not abolished and some proteins retain the -aaX tripeptide after farnesylation. These observations may be substrate specific as, in contrast, there are examples indicating some proteins are fully functional only after being properly prenylated such as in regulating processes such as mitogen response in mammals and mating pheromone in yeast.

In *Arabidopsis thaliana,* more than 600 proteins contain a CaaX motif, suggesting a role for the post-translational modification by prenylation in numerous cellular processes. In *Arabidopsis thaliana,* it has been demonstrated that the loss-of-function of the β-subunit of farnesyl transferase will result in a ABA-hypersensitive phenotype. Although it is still not clear why plants lacking the functional β-subunit of farnesyl transferase become more sensitive to ABA, it clearly suggests that protein prenylation is involved in regulation of the homeostasis of ABA sensitivity. The balance of ABA cellular responses, whether more sensitive or less sensitive to ABA, is possibly regulated by the relative activities of prenylated proteins.

This invention is directed at the manipulation of the farnesyl transferase (FT) subunits, either α or β (FTA, FTB) to alter farnesyl transferase enzyme expression and activity. Farnesyl transferase catalyses the first step of farnesylation in which a 15-carbon farnesyl moiety is added to the cysteine residue of the target sequence CaaX. Included in this invention are vector constructs containing FTA or FTB sequences under the control of appropriate regulatory sequences to produce phenotypes such as, but not limited to, water-stress tolerance, increased biomass accumulation, increased yield or delayed senescence. Manipulation of the FTA subunit may also affect the activity of geranylgeranyl transferase and the phenoytypes associated with this manipulation are encompassed by this invention.

SUMMARY OF THE INVENTION

The present invention is based in part upon the discovery of novel farnesyl transferase nucleic acid sequences and polypeptides from *Arabidopsis thaliana, Brassica napus, Glycine max* and *Zea maize.* The nucleic acids, polynucleotides, proteins and polypeptides, or fragments thereof described herein are collectively referred to as FT nucleic acids and polypeptides.

Accordingly, in one aspect, the invention provides an isolated nucleic acid molecule that includes the sequence of SEQ ID NO:1, SEQ ID NO:6, SEQ ID NO:8, SEQ ID NO:31, SEQ ID NO:34, or SEQ ID NO:37, or a fragment, homolog, analog or derivative thereof. The nucleic acid can include, e.g., a nucleic acid sequence encoding a polypeptide at least 99% identical to a polypeptide that includes the amino acid sequences of SEQ ID NO:5, SEQ ID NO:7, or SEQ ID NO:9, SEQ ID NO:33, SEQ ID NO:36, or SEQ ID NO:37, a nucleic acid sequence encoding a polypeptide at least 85% identical to a polypeptide that includes the amino acid sequences of SEQ ID NO:5, SEQ ID NO:7, or SEQ ID NO:9 or a nucleic acid sequence encoding a polypeptide at least 99% identical to a polypeptide that includes the amino acid sequences of SEQ ID NO:33, SEQ ID NO:36, or SEQ ID NO:39 The nucleic acid can be, e.g., a genomic DNA fragment, or a cDNA molecule.

The invention also includes the nucleic acid sequences of SEQ ID NO: 2, 3, 4, 29, 30, 32, 35, 38, 40–57 or 58. Also included in the invention is a vector containing one or more of the nucleic acids described herein, and a cell containing the vectors or nucleic acids described herein. In some aspects the FT nucleic acid is operably linked to a promoter. Examples of promoter includes a constitutive promoter (e.g., 35S CaMV, MuA), an ABA inducible promoter (e.g., RD29A), tissue specific promoters (e.g., CUT1) or a guard cell-specific promoter (e.g., 35S, MuA and RD29A)

The invention is also directed to host cells transformed with a vector comprising any of the nucleic acid molecules described herein.

The invention is also directed to plants and cells transformed with a FT nucleic acid or a vector comprising a FT nucleic acid. Also included in the invention is the seed, and progeny of the transformed plants or cells.

The invention is also further directed to the use of plants and cells transformed with a FT nucleic acid or a vector comprising a FT nucleic acid in generation of mutant libraries and genetic screening protocols.

In a further aspect, the invention includes a substantially purified FT polypeptide, e.g., any of the FT polypeptides encoded by an FT nucleic acid, and fragments, homologs, analogs, and derivatives thereof.

In still a further aspect, the invention provides an antibody that binds specifically to an FT polypeptide. The antibody can be, e.g., a monoclonal or polyclonal antibody, and fragments, homologs, analogs, and derivatives thereof. The invention is also directed to isolated antibodies that bind to an epitope on a polypeptide encoded by any of the nucleic acid molecules described above.

The invention also includes a method of producing a transgenic plant which has increased stress resistance such as, but not limited to, water deficit, or increased biomass, increased yield; delayed senescence or increases ABA sensitivity by introducing into one or more cells of a plant a compound that alters FT expression or activity in the plant. In one aspect the compound is a FT nucleic acid. The nucleic acid can be for example a inhibitor or farnesylation or genanylgerylation. Alternatively, the compound is a FT double stranded RNA-inhibition hair-pin nucleic acid or FT antisense nucleic acid.

The invention further provides a method for producing a FT polypeptide by providing a cell containing an FT nucleic acid, e.g., a vector that includes a FT nucleic acid, and culturing the cell under conditions sufficient to express the FT polypeptide encoded by the nucleic acid. The expressed FT polypeptide is then recovered from the cell. Preferably, the cell produces little or no endogenous FT polypeptide. The cell can be, e.g., a prokaryotic cell or eukaryotic cell.

The invention is also directed to methods of identifying a FT polypeptide or nucleic acid in a sample by contacting the sample with a compound that specifically binds to the polypeptide or nucleic acid, and detecting complex formation, if present.

The invention further provides methods of identifying a compound that modulates the activity of a FT polypeptide by contacting a FT polypeptide with a compound and determining whether the FT polypeptide activity is modified.

The invention is also directed to compounds that modulate FT polypeptide activity identified by contacting a FT polypeptide with the compound and determining whether the compound modifies activity of the FT polypeptide, binds to the FT polypeptide, or binds to a nucleic acid molecule encoding a FT polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

Other features and advantages of the invention will be apparent from the following detailed description and claims.

BRIEF DESCRIPTION OF THE DRAWINGS

FIG. 8 is an illustration of the homology among FTA nucleic acid (A) and amino acid (B) sequences from various plant species based on ClustalW anaysis (percent identity shown).

FIG. 9 is an illustration of the homology among FTB nucleic acid and amino acid sequences from various plant species based on ClustalW anaysis (percent identity shown).

DETAILED DESCRIPTION OF INVENTION

Figure 1:
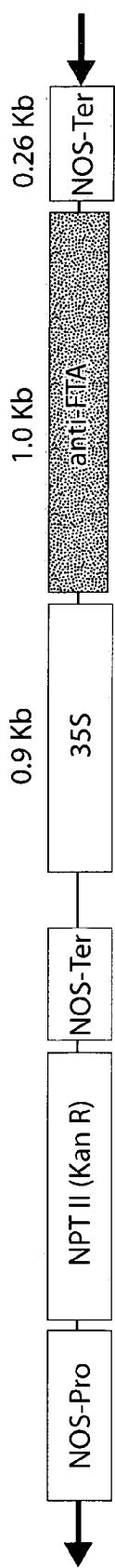
FIG. 1 is an illustration depicting the pBI121 antisense FTA vector construct.

The present invention provides a novel farnesyl transferase (FT) nucleic acid sequences (SEQ ID NO:1, SEQ ID NO:6, SEQ ID NO:8, SEQ ID NO:31, SEQ ID NO:34, or SEQ ID NO:37) and their encoded polypeptides (SEQ ID NO:5, SEQ ID NO:7, SEQ ID NO:9, SEQ ID NO:33, SEQ ID NO:36 or SEQ ID NO:39) isolated from *Brassica napus* (Bn), *Arabidopsis thaliana* (At), *Glycine max* (Gm) and *Zea maize* (Zm). The sequences are collectively referred to as "FT nucleic acids" or FT polynucleotides" and the corresponding encoded polypeptide is referred to as a "FT polypeptide" or "FT protein". Farnesyl transferase subunits, Alpha (α) and Beta (β) are referred to as FTA and FTB, respectively. *Glycine max* is also refered to as soy of soybean throughout the specification. *Zea maize* is also refered to as *Zea mays* or corn throughout the specification. These terms are interchangeable. Unless indicated otherwise, "FT" is meant to refer to any of the novel sequences disclosed herein.

Table A provides a summary of the FT nucleic acids and their encoded polypeptides.

TABLE A

Sequences and Corresponding SEQ ID Numbers

| FT Assignment | Identification | SEQ ID NO (nucleic acid) | SEQ ID NO (polypeptide) |
|---|---|---|---|
| 1 | *Arabidopsis thaliana* farnesyl transerase alpha subunit | 1 | 5 |
| 2 | *Brassica napus* farnesyl transerase alpha subunit | 6 | 7 |
| 3 | *Brassica napus* farnesyl transerase beta subunit | 8 | 9 |
| 4 | *Glycine max* alpha subunit | 31 | 33 |
| 5 | *Glycine max* beta subunit | 34 | 36 |
| 6 | *Zea maize* beta subunit | 37 | 39 |

Also included in the invention are nucleic acids that are complementary to the disclosed FT nucleic acid sequences. For example, SEQ ID NO: 2, 3, 29, 30, 32, 35 or 38. Further provide by the invention are constructs comprising FT antisense nucleic acid molecules as disclosed in for example SEQ ID NO:4, 40–58.

Based on their structural and functional relatedness to known farnesyl transferase proteins the FT proteins are novel members of the farnesyl transferase family of proteins. (See, Example 3) FT nucleic acids, and their encoded polypeptides, according to the invention are useful in a variety of applications and contexts. For example, the nucleic acids can be used produce transgenic plants that have an increase resistance to biotic and abiotic stresses, e.g., chilling stress, salt stress, heat stress, water stress, wound healing, pathogen challenge, or herbicides.

This invention includes methods to up-regulate the FT enzyme activity in transgenic plants, cells and tissue cultures by using an over-expression vector construct and methods to down-regulate the FT enzyme activity in transgenic plants, cells and tissue cultures by using a double stranded RNA-inhibition, hairpin vector construct. These methods are by way of example to produce the up-regulation or down-regulation effects and are not meant to be limiting as to the method of achieving this outcome.

Additionally, the nucleic acids and polypeptides according to the invention may be used as targets for the identification of small molecules that modulate or inhibit, FT activity. Alternatively, the FT nucleic acids and polypeptides can be used to identify proteins that are members of the farnesyl transferase family of associated proteins.

Further, the modulation or inhibition of FT activity maybe achieved by modifications to the nucleic acid sequences of FTA or FTB by the actions of chemical mutagens or irradiation. Expression of FT nucleic acids which encode enzymatically non-functional FT polypeltides can be used to evoke a dominant-negative inhibitory effect on FT activity.

Additional utilities for FT nucleic acids and polypeptides according to the invention are disclosed herein.

FT Nucleic Acids

The nucleic acids of the invention include those that encode a FT polypeptide or protein. As used herein, the terms polypeptide and protein are interchangeable.

In some embodiments, a FT nucleic acid encodes a mature FT polypeptide. As used herein, a "mature" form of a polypeptide or protein described herein relates to the product of a naturally occurring polypeptide or precursor form or proprotein. The naturally occurring polypeptide, precursor or proprotein includes, by way of nonlimiting example, the full length gene product, encoded by the corresponding gene. Alternatively, it may be defined as the polypeptide, precursor or proprotein encoded by an open reading frame described herein. The product "mature" form arises, again by way of nonlimiting example, as a result of one or more naturally occurring processing steps that may take place within the cell in which the gene product arises. Examples of such processing steps leading to a "mature" form of a polypeptide or protein include the cleavage of the N-terminal methionine residue encoded by the initiation codon of an open reading frame, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

Among the FT nucleic acids is the nucleic acid whose sequence is provided in SEQ ID NO:1, SEQ ID NO:6, SEQ ID NO:8, SEQ ID NO:31, SEQ ID NO:34, or SEQ ID NO:37 or a fragment thereof. Additionally, the invention includes mutant or variant nucleic acids of SEQ ID NO:1, SEQ ID NO:6, SEQ ID NO:8, SEQ ID NO:31, SEQ ID NO:34, or SEQ ID NO:37, or a fragment thereof, any of whose bases may be changed from the corresponding base shown in SEQ ID NO:1, SEQ ID NO:6, SEQ ID NO:8, SEQ ID NO:31, SEQ ID NO:34, or SEQ ID NO:37, while still encoding a protein that maintains at least one of its FT-like activities and physiological functions. The invention further includes the complement of the nucleic acid sequence of SEQ ID NO:1, SEQ ID NO:6, SEQ ID NO:8, SEQ ID NO:31, SEQ ID NO:34, or SEQ ID NO:37, including fragments, derivatives, analogs and homologs thereof. The invention additionally includes nucleic acids or nucleic acid fragments, or complements thereto, whose structures include chemical modifications.

One aspect of the invention pertains to isolated nucleic acid molecules that encode FT proteins or biologically active portions thereof. Also included are nucleic acid fragments sufficient for use as hybridization probes to identify FT-encoding nucleic acids (e.g., FT mRNA) and fragments for use as polymerase chain reaction (PCR) primers for the amplification or mutation of FT nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but preferably is double-stranded DNA.

"Probes" refer to nucleic acid sequences of variable length, preferably between at least about 10 nucleotides (nt), 100 nt, or as many as about, e.g., 6,000 nt, depending on use. Probes are used in the detection of identical, similar, or complementary nucleic acid sequences. Longer length probes are usually obtained from a natural or recombinant source, are highly specific and much slower to hybridize than oligomers. Probes may be single- or double-standard and designed to have specificity in PCR, membrane-based hybridization technologies, or ELISA-like technologies.

An "isolated" nucleic acid molecule is one that is separated from other nucleic acid molecules that are present in the natural source of the nucleic acid. Examples of isolated nucleic acid molecules include, but are not limited to, recombinant DNA molecules contained in a vector, recombinant DNA molecules maintained in a heterologous host cell, partially or substantially purified nucleic acid molecules, and synthetic DNA or RNA molecules. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated FT nucleic acid molecule can contain less than about 50 kb, 25 kb, 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the present invention, e.g., a nucleic acid molecule having the nucleotide sequence of SEQ ID NO:1, SEQ ID NO:6, SEQ ID NO:8, SEQ ID NO:31, SEQ ID NO:34, or SEQ ID NO:37, or a complement of any one of the nucleotide sequences, can be isolated using standard molecular biology techniques and the sequence information provided herein. Using all or a portion of the nucleic acid sequence of SEQ ID NO:1, SEQ ID NO:6, SEQ ID NO:8, SEQ ID NO:31, SEQ ID NO:34, or SEQ ID NO:37 as a hybridization probe, FT nucleic acid sequences can be isolated using standard hybridization and cloning techniques (e.g., as described in Sambrook et al., eds., MOLECULAR CLONING: A LABORATORY MANUAL $2^{nd}$ Ed., Cold Spring Harbor Laboratory Press, Cold Spring Harbor, N.Y., 1989; and Ausubel, et al., eds., CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to FT nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment, an oligonucleotide comprising a nucleic acid molecule less than 100 nt in length would further comprise at lease 6 contiguous nucleotides of SEQ ID NO:1, SEQ ID NO:6, SEQ ID NO:8, SEQ ID NO:31, SEQ ID NO:34, or SEQ ID NO:37, or a complement thereof. Oligonucleotides may be chemically synthesized and may be used as probes.

In another embodiment, an isolated nucleic acid molecule of the invention includes a nucleic acid molecule that is a complement of the nucleotide sequence shown in SEQ ID NO:1, SEQ ID NO:6, SEQ ID NO:8, SEQ ID NO:31, SEQ ID NO:34, or SEQ ID NO:37. For example, a complimentary nucleic acid sequence of SEQ ID NO:2, SEQ ID NO:3, SEQ ID NO:29, SEQ ID NO:30, SEQ ID NO:32, SEQ ID NO:35 or SEQ ID NO:38. In another embodiment, an isolated nucleic acid molecule of the invention comprises a nucleic acid molecule that is a complement of the nucleotide sequence shown in SEQ ID NO:1, SEQ ID NO:6, SEQ ID NO:8, SEQ ID NO:31, SEQ ID NO:34, or SEQ ID NO:37, or a portion of this nucleotide sequence. A nucleic acid molecule that is complementary to the nucleotide sequence shown in SEQ ID NO:1, SEQ ID NO:6, SEQ ID NO:8, SEQ ID NO:31, SEQ ID NO:34, or SEQ ID NO:37 is one that is sufficiently complementary to the nucleotide sequence shown in SEQ ID NO:1, SEQ ID NO:6, SEQ ID NO:8, SEQ ID NO:31, SEQ ID NO:34, or SEQ ID NO:37 that it can hydrogen bond with little or no mismatches to the nucleotide sequence shown in SEQ ID NO:1, SEQ ID NO:6, SEQ ID NO:8, SEQ ID NO:31, SEQ ID NO:34, or SEQ ID NO:37, thereby forming a stable duplex.

As used herein, the term "complementary" refers to Watson-Crick or Hoogsteen base pairing between nucleotide units of a nucleic acid molecule, and the term "binding" means the physical or chemical interaction between two polypeptides or compounds or associated polypeptides or compounds or combinations thereof Binding includes ionic, non-ionic, Von der Waals, hydrophobic interactions, etc. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Moreover, the nucleic acid molecule of the invention can comprise only a portion of the nucleic acid sequence of SEQ ID NO:1, SEQ ID NO:6, SEQ ID NO:8, SEQ ID NO:31, SEQ ID NO:34, or SEQ ID NO:37, e.g., a fragment that can be used as a probe or primer, or a fragment encoding a biologically active portion of FT. Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, 85%, 90%, 95%, 98%, or even 99% identity (with a preferred identity of 80–99%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below. An exemplary program is the Gap program (Wisconsin Sequence Analysis Package, Version 8 for UNIX, Genetics Computer Group, University Research Park, Madison, Wis.) using the default settings, which uses the algorithm of Smith and Waterman (Adv. Appl. Math., 1981, 2: 482–489, which is incorporated herein by reference in its entirety).

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of a FT polypeptide. Isoforms can be expressed in different tissues of the same organism as a result of, for example, alternative splicing of RNA. Alternatively, isoforms can be encoded by different genes. Homologous nucleotide sequences also include, but are not limited to, naturally occurring allelic variations and mutations of the nucleotide sequences set forth herein. Homologous nucleic acid sequences include those nucleic acid sequences that encode conservative amino acid substitutions (see below) in SEQ ID NO:5, SEQ ID NO:7, SEQ ID NO:9, SEQ ID NO:33, SEQ ID NO:36 or SEQ ID NO:39, as well as a polypeptide having FT activity, e.g. substrate binding.

The nucleotide sequence determined from the cloning of the *Arabidopsis thaliana* FT gene allows for the generation of probes and primers designed for use in identifying and/or cloning FT homologues in other cell types, e.g., from other tissues, as well as FT homologues from other plants. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 or more consecutive sense strand nucleotide sequence of SEQ ID NO:1, SEQ ID NO:6, SEQ ID NO:8, SEQ ID NO:31, SEQ ID NO:34, or SEQ ID NO:37; or an anti-sense strand nucleotide sequence of SEQ ID NO:1, SEQ ID NO:6, SEQ ID NO:8, SEQ ID NO:31, SEQ ID NO:34, or SEQ ID NO:37; or of a naturally occurring mutant of SEQ ID NO:1, SEQ ID NO:6, SEQ ID NO:8, SEQ ID NO:31, SEQ ID NO:34, or SEQ ID NO:37.

Probes based on the *Arabidopsis thaliana* FT nucleotide sequence can be used to detect transcripts or genomic sequences encoding the same or homologous proteins. In various embodiments, the probe further comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a FT protein, such as by measuring a level of a FT-encoding nucleic acid in a sample of cells from a subject e.g., detecting FT mRNA levels or determining whether a genomic FT gene has been mutated or deleted.

A "polypeptide having a biologically active portion of FT" refers to polypeptides exhibiting activity similar, but not necessarily identical to, an activity of a polypeptide of the present invention, including mature forms, as measured in a particular biological assay, with or without dose dependency. A nucleic acid fragment encoding a "biologically active portion of FT" can be prepared by isolating a portion of SEQ ID NO:1, SEQ ID NO:6, SEQ ID NO:8, SEQ ID NO:31, SEQ ID NO:34, or SEQ ID NO:37 that encodes a polypeptide having a FT biological activity (biological activities of the FT proteins are described below), expressing the encoded portion of FT protein (e.g., by recombinant expression in vitro) and assessing the activity of the encoded portion of FT. In another embodiment, a nucleic acid fragment encoding a biologically active portion of FT includes one or more regions.

FT Variants

The invention further encompasses nucleic acid molecules that differ from the nucleotide sequences shown in SEQ ID NO:1, SEQ ID NO:6, SEQ ID NO:8, SEQ ID NO:31, SEQ ID NO:34, or SEQ ID NO:37 due to the degeneracy of the genetic code. These nucleic acids thus encode the same FT protein as that encoded by the nucleotide sequence shown in SEQ ID NO:1, SEQ ID NO:6, SEQ ID NO:8, SEQ ID NO:31, SEQ ID NO:34, or SEQ ID NO:37, e.g., the polypeptide of SEQ ID NO:5, SEQ ID NO:7, SEQ ID NO:9, SEQ ID NO:33, SEQ ID NO:36 or SEQ ID NO:39. In another embodiment, an isolated nucleic acid molecule of the invention has a nucleotide sequence encoding a protein having an amino acid sequence shown in SEQ ID NO:5, SEQ ID NO:7, SEQ ID NO:9, SEQ ID NO:33, SEQ ID NO:36 or SEQ ID NO:39.

In addition to the *Arabidopsis thaliana* FT nucleotide sequence shown in SEQ ID NO:1, SEQ ID NO:6, SEQ ID NO:8, SEQ ID NO:31, SEQ ID NO:34, or SEQ ID NO:37, it will be appreciated by those skilled in the art that DNA sequence polymorphisms that lead to changes in the amino acid sequences of FT may exist within a population (e.g., the plant). Such genetic polymorphism in the FT gene may exist among individuals within a population due to natural allelic variation. As used herein, the terms "gene" and "recombinant gene" refer to nucleic acid molecules comprising an open reading frame encoding a FT protein, preferably a plant FT protein. Such natural allelic variations can typically result in 1–5% variance in the nucleotide sequence of the FT gene. Any and all such nucleotide variations and resulting amino acid polymorphisms in FT that are the result of natural allelic variation and that do not alter the functional activity of FT are intended to be within the scope of the invention.

Moreover, nucleic acid molecules encoding FT proteins from other species, and thus that have a nucleotide sequence that differs from the sequence of SEQ ID NO:1, SEQ ID NO:6, SEQ ID NO:8, SEQ ID NO:31, SEQ ID NO:34, or SEQ ID NO:37 are intended to be within the scope of the invention. Nucleic acid molecules corresponding to natural allelic variants and homologues of the FT cDNAs of the invention can be isolated based on their homology to the Arabidopsis thaliana FT nucleic acids disclosed herein using the cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37. In another embodiment, the nucleic acid is at least 10, 25, 50, 100, 250, 500 or 750 nucleotides in length. In another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs (i.e., nucleic acids encoding FT proteins derived from species other than Arabidopsis thaliana) or other related sequences (e.g., paralogs) can be obtained by low, moderate or high stringency hybridization with all or a portion of the particular sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point ($T_m$) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in CURRENT PROTOCOLS IN MOLECULAR BIOLOGY, John Wiley & Sons, N.Y. (1989), 6.3.1–6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. An isolated nucleic acid molecule of the invention that hybridizes under stringent conditions to the sequence of SEQ ID NO:1, SEQ ID NO:6, SEQ ID NO:8, SEQ ID NO:31, SEQ ID NO:34, or SEQ ID NO:37 corresponds to a naturally occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37, or fragments, analogs or derivatives thereof, under conditions of moderate stringency is provided. A non-limiting example of moderate stringency hybridization conditions are hybridization in 6×SSC, 5× Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well known in the art. See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY.

In a third embodiment, a nucleic acid that is hybridizable to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37, or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo and Weinberg, 1981, Proc Natl Acad Sci USA 78: 6789–6792.

Conservative Mutations

In addition to naturally-occurring allelic variants of the FT sequence that may exist in the population, the skilled artisan will further appreciate that changes can be introduced by mutation into the nucleotide sequence of SEQ ID NO:1, SEQ ID NO:6, SEQ ID NO:8, SEQ ID NO:31, SEQ ID NO:34, or SEQ ID NO:37, thereby leading to changes in the amino acid sequence of the encoded FT protein, without altering the functional ability of the FT protein. For example, nucleotide substitutions leading to amino acid substitutions at "non-essential" amino acid residues can be made in the sequence of SEQ ID NO:1, SEQ ID NO:6, SEQ ID NO:8, SEQ ID NO:31, SEQ ID NO:34, or SEQ ID NO:37. A "non-essential" amino acid residue is a residue that can be altered from the wild-type sequence of FT without altering the biological activity, whereas an "essential" amino acid residue is required for biological activity. For example, amino acid residues that are conserved among the FT proteins of the present invention, are predicted to be particularly unamenable to alteration.

Another aspect of the invention pertains to nucleic acid molecules encoding FT proteins that contain changes in amino acid residues that are not essential for activity. Such FT proteins differ in amino acid sequence from SEQ ID NO:5, SEQ ID NO:7, SEQ ID NO:9, SEQ ID NO:33, SEQ ID NO:36 or SEQ ID NO:39, yet retain biological activity. In one embodiment, the isolated nucleic acid molecule comprises a nucleotide sequence encoding a protein, wherein the protein comprises an amino acid sequence at least about 75% homologous to the amino acid sequence of SEQ ID NO:5, SEQ ID NO:7, SEQ ID NO:9, SEQ ID NO:33, SEQ ID NO:36 or SEQ ID NO:39. Preferably, the protein encoded by the nucleic acid is at least about 80% homologous to SEQ ID NO:5, SEQ ID NO:7, SEQ ID NO:9, SEQ ID NO:33, SEQ ID NO:36 or SEQ ID NO:39, more preferably at least about 90%, 95%, 98%, and most preferably at least about 99% homologous to SEQ ID NO:5, SEQ ID NO:7, SEQ ID NO:9, SEQ ID NO:33, SEQ ID NO:36 or SEQ ID NO:39.

An isolated nucleic acid molecule encoding a FT protein homologous to the protein of SEQ ID NO:5, SEQ ID NO:7, SEQ ID NO:9, SEQ ID NO:33, SEQ ID NO:36 or SEQ ID NO:39 can be created by introducing one or more nucleotide substitutions, additions or deletions into the nucleotide sequence of SEQ ID NO:1, SEQ ID NO:6, SEQ ID NO:8, SEQ ID NO:31, SEQ ID NO:34, or SEQ ID NO:37, such that one or more amino acid substitutions, additions or deletions are introduced into the encoded protein.

Mutations can be introduced into the nucleotide sequence of SEQ ID NO:1, SEQ ID NO:6, SEQ ID NO:8, SEQ ID NO:31, SEQ ID NO:34, or SEQ ID NO:37 by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in FT is replaced with another amino acid residue from the same side chain family. Alternatively, in another embodiment, mutations can be introduced randomly along all or part of a FT coding sequence, such as by saturation mutagenesis, and the resultant mutants can be screened for FT biological activity to identify mutants that retain activity. Following mutagenesis of SEQ ID NO:1, SEQ ID NO:6, SEQ ID NO:8, SEQ ID NO:31, SEQ ID NO:34, or SEQ ID NO:37 the encoded protein can be expressed by any recombinant technology known in the art and the activity of the protein can be determined.

In one embodiment, a mutant FT protein can be assayed for (1) the ability to form protein:protein interactions with other FT proteins, other cell-surface proteins, or biologically active portions thereof, (2) complex formation between a mutant FT protein and a FT receptor; (3) the ability of a mutant FT protein to bind to an intracellular target protein or biologically active portion thereof; (e.g., avidin proteins); (4) the ability to bind FT protein; or (5) the ability to specifically bind an anti-FT protein antibody.

Antisense FT Nucleic Acids

Another aspect of the invention pertains to isolated antisense nucleic acid molecules that are hybridizable to or complementary to the nucleic acid molecule comprising the nucleotide sequence of SEQ ID NO:1, SEQ ID NO:6, SEQ ID NO:8, SEQ ID NO:31, SEQ ID NO:34, or SEQ ID NO:37, or fragments, analogs or derivatives thereof. An “antisense” nucleic acid comprises a nucleotide sequence that is complementary to a “sense” nucleic acid encoding a protein, e.g., complementary to the coding strand of a double-stranded cDNA molecule or complementary to an mRNA sequence. In specific aspects, antisense nucleic acid molecules are provided that comprise a sequence complementary to at least about 10, 25, 50, 100, 250 or 500 nucleotides or an entire FT coding strand, or to only a portion thereof. Nucleic acid molecules encoding fragments, homologs, derivatives and analogs of a FT protein of SEQ ID NO:5, SEQ ID NO:7, SEQ ID NO:9, SEQ ID NO:33, SEQ ID NO:36 or SEQ ID NO:39, or antisense nucleic acids complementary to a FT nucleic acid sequence of SEQ ID NO:1, SEQ ID NO:6, SEQ ID NO:8, SEQ ID NO:31, SEQ ID NO:34, or SEQ ID NO:37 are additionally provided.

In one embodiment, an antisense nucleic acid molecule is antisense to a “coding region” of the coding strand of a nucleotide sequence encoding FT (e.g. SEQ ID NO:1, SEQ ID NO:6, SEQ ID NO:8, SEQ ID NO:31, SEQ ID NO:34, or SEQ ID NO:37). The term “coding region” refers to the region of the nucleotide sequence comprising codons which are translated into amino acid residues (e.g., the protein coding region of *Arabidopsis thaliana* FT corresponds to SEQ ID NO:5, SEQ ID NO:7, SEQ ID NO:9, SEQ ID NO:33, SEQ ID NO:36 or SEQ ID NO:39). In another embodiment, the antisense nucleic acid molecule is antisense to a “noncoding region” of the coding strand of a nucleotide sequence encoding FT (e.g. SEQ ID NO:1, SEQ ID NO:6, SEQ ID NO:8, SEQ ID NO:31, SEQ ID NO:34, or SEQ ID NO:37). The term “noncoding region” refers to 5' and 3' sequences which flank the coding region that are not translated into amino acids (i.e., also referred to as 5' and 3' untranslated regions).

In various embodiments the anti-sense FT nucleic acid molecule includes the sequences of SEQ ID NO: 2, 3, 29, 30, 32, 35 or 38.

Given the coding strand sequences encoding FT disclosed herein (e.g., SEQ ID NO:1, SEQ ID NO:6, SEQ ID NO:8, SEQ ID NO:31, SEQ ID NO:34, or SEQ ID NO:37), antisense nucleic acids of the invention can be designed according to the rules of Watson and Crick or Hoogsteen base pairing. The antisense nucleic acid molecule can be complementary to the entire coding region of FT mRNA, but more preferably is an oligonucleotide that is antisense to only a portion of the coding or noncoding region of FT mRNA. For example, the antisense oligonucleotide can be complementary to the region surrounding the translation start site of FT mRNA. An antisense oligonucleotide can be, for example, about 5, 10, 15, 20, 25, 30, 35, 40, 45 or 50 nucleotides in length. An antisense nucleic acid of the invention can be constructed using chemical synthesis or enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used.

Examples of modified nucleotides that can be used to generate the antisense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are generated in situ such that they hybridize with or bind to cellular mRNA and/or genomic DNA encoding a FT protein to thereby inhibit expression of the protein, e.g., by inhibiting transcription and/or translation. The hybridization can be by conventional nucleotide complementarity to form a stable duplex, or, for example, in the case of an antisense nucleic acid molecule that binds to DNA duplexes, through specific interactions in the major groove of the double helix.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids Res* 15: 6625–6641). The antisense nucleic acid molecule can also comprise a 2'-o-methylribonucleotide (Inoue et al. (1987) *Nucleic Acids Res* 15: 6131–6148) or a chimeric RNA-DNA analogue (Inoue et al. (1987) *FEBS Lett* 215: 327–330).

Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in applications.

Double Stranded RNA Inhibition (RNAi) by Hairpin Nucleic Acids

Another aspect of the invention pertains to the use of post transcriptional gene silencing (PTGS) to repress gene expression. Double stranded RNA can initiate the sequence specific repression of gene expression in plants and animals. Double stranded RNA is processed to short duplex oligomers of 21–23 nucleotides in length. These small interfering RNA's suppress the expression of endogenous and heterologous genes in a sequence specific manner (Fire et al. Nature 391:806–811, Carthew, Curr. Opin. in Cell Biol., 13:244–248, Elbashir et al., Nature 411:494–498). A RNAi suppressing construct can be designed in a number of ways, for example, transcription of a inverted repeat which can form a long hair pin molecule, inverted repeats separated by a spacer sequence that could be an unrelated sequence such as GUS or an intron sequence. Transcription of sense and antisense strands by opposing promoters or cotranscription of sense and antisense genes.

FT Ribozymes and PNA Moieties

In still another embodiment, an antisense nucleic acid of the invention is a ribozyme. Ribozymes are catalytic RNA molecules with ribonuclease activity that are capable of cleaving a single-stranded nucleic acid, such as a mRNA, to which they have a complementary region. Thus, ribozymes (e.g., hammerhead ribozymes (described in Haselhoff and Gerlach (1988) *Nature* 334:585–591)) can be used to catalytically cleave FT mRNA transcripts to thereby inhibit translation of FT mRNA. A ribozyme having specificity for a FT-encoding nucleic acid can be designed based upon the nucleotide sequence of a FT DNA disclosed herein (i.e., SEQ ID NO:1, SEQ ID NO:6, SEQ ID NO:8, SEQ ID NO:31, SEQ ID NO:34, or SEQ ID NO:37). For example, a derivative of a Tetrahymena L-19 IVS RNA can be constructed in which the nucleotide sequence of the active site is complementary to the nucleotide sequence to be cleaved in a FT-encoding mRNA. See, e.g., Cech et al. U.S. Pat. No. 4,987,071; and Cech et al. U.S. Pat. No. 5,116,742. Alternatively, FT mRNA can be used to select a catalytic RNA having a specific ribonuclease activity from a pool of RNA molecules. See, e.g., Bartel et al., (1993) *Science* 261: 1411–1418.

Alternatively, FT gene expression can be inhibited by targeting nucleotide sequences complementary to the regulatory region of the FT (e.g., the FT promoter and/or enhancers) to form triple helical structures that prevent transcription of the FT gene in target cells. See generally, Helene. (1991) *Anticancer Drug Des.* 6: 569–84; Helene. et al. (1992) *Ann. N.Y. Acad. Sci.* 660:27–36; and Maher (1992) *Bioassays* 14: 807–15.

In various embodiments, the nucleic acids of FT can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al. (1996) *Bioorg Med Chem* 4: 5–23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996) above; Perry-O'Keefe et al. (1996) *PNAS* 93: 14670–675.

PNAs of FT can be used in therapeutic and diagnostic applications. For example, PNAs can be used as antisense or antigene agents for sequence-specific modulation of gene expression by, e.g., inducing transcription or translation arrest or inhibiting replication. PNAs of FT can also be used, e.g., in the analysis of single base pair mutations in a gene by, e.g., PNA directed PCR clamping; as artificial restriction enzymes when used in combination with other enzymes, e.g., S1 nucleases (Hyrup B. (1996) above); or as probes or primers for DNA sequence and hybridization (Hyrup et al. (1996), above; Perry-O'Keefe (1996), above)

In another embodiment, PNAs of FT can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras of FT can be generated that may combine the advantageous properties of PNA and DNA. Such chimeras allow DNA recognition enzymes, e.g., RNase H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup (1996) above). The synthesis of PNA-DNA chimeras can be performed as described in Hyrup (1996) above and Finn et al. (1996) *Nucl Acids Res* 24: 3357–63. For example, a DNA chain can be synthesized on a solid support using standard phosphoramidite coupling chemistry, and modified nucleoside analogs, e.g., 5'-(4-methoxytrityl) amino-5'-deoxy-thymidine phosphoramidite, can be used between the PNA and the 5' end of DNA (Mag et al. (1989) *Nucl Acid Res* 17: 5973–88). PNA monomers are then coupled in a stepwise manner to produce a chimeric molecule with a 5' PNA segment and a 3' DNA segment (Finn et al. (1996) above). Alternatively, chimeric molecules can be synthesized with a 5' DNA segment and a 3'PNA segment. See, Petersen et al. (1975) *Bioorg Med Chem Lett* 5: 1119–11124.

FT Polypeptides

A FT polypeptide of the invention includes the protein whose sequence is provided in SEQ ID NO:5, SEQ ID NO:7, OR SEQ ID NO:9. The invention also includes a mutant or variant protein any of whose residues may be changed from the corresponding residue shown in SEQ ID NO:5, SEQ ID NO:7, SEQ ID NO:9, SEQ ID NO:33, SEQ ID NO:36 or SEQ ID NO:39 while still encoding a protein that maintains its FT-like activities and physiological functions, or a functional fragment thereof. In some embodiments, up to 20% or more of the residues may be so changed in the mutant or variant protein. In some embodiments, the FT polypeptide according to the invention is a mature polypeptide.

In general, a FT-like variant that preserves FT-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated FT proteins, and biologically active portions thereof, or derivatives, fragments, analogs or homologs thereof. Also provided are polypeptide fragments suitable for use as immunogens to raise anti-FT antibodies. In one embodiment, native FT proteins can be isolated from cells or tissue sources by an appropriate purification scheme using standard protein purification techniques. In another embodiment, FT proteins are produced by recombinant DNA techniques. Alternative to recombinant expression, a FT protein or polypeptide can be synthesized chemically using standard peptide synthesis techniques.

An "isolated" or "purified" protein or biologically active portion thereof is substantially free of cellular material or other contaminating proteins from the cell or tissue source from which the FT protein is derived, or substantially free from chemical precursors or other chemicals when chemically synthesized. The language "substantially free of cellular material" includes preparations of FT protein in which the protein is separated from cellular components of the cells from which it is isolated or recombinantly produced. In one embodiment, the language "substantially free of cellular material" includes preparations of FT protein having less than about 30% (by dry weight) of non-FT protein (also referred to herein as a "contaminating protein"), more preferably less than about 20% of non-FT protein, still more preferably less than about 10% of non-FT protein, and most preferably less than about 5% non-FT protein. When the FT protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of FT protein in which the protein is separated from chemical precursors or other chemicals that are involved in the synthesis of the protein. In one embodiment, the language "substantially free of chemical precursors or other chemicals" includes preparations of FT protein having less than about 30% (by dry weight) of chemical precursors or non-FT chemicals, more preferably less than about 20% chemical precursors or non-FT chemicals, still more preferably less than about 10% chemical precursors or non-FT chemicals, and most preferably less than about 5% chemical precursors or non-FT chemicals.

Biologically active portions of a FT protein include peptides comprising amino acid sequences sufficiently homologous to or derived from the amino acid sequence of the FT protein, e.g., the amino acid sequence shown in SEQ ID NO:5, SEQ ID NO:7, SEQ ID NO:9, SEQ ID NO:33, SEQ ID NO:36 or SEQ ID NO:39 that include fewer amino acids than the full length FT proteins, and exhibit at least one activity of a FT protein, e.g. substrate binding. Typically, biologically active portions comprise a domain or motif with at least one activity of the FT protein. A biologically active portion of a FT protein can be a polypeptide which is, for example, 10, 25, 50, 100 or more amino acids in length.

A biologically active portion of a FT protein of the present invention may contain at least one of the above-identified domains conserved between the FT proteins. Moreover, other biologically active portions, in which other regions of the protein are deleted, can be prepared by recombinant techniques and evaluated for one or more of the functional activities of a native FT protein.

A biologically active portion or a FT protein can be the N-terminal domain of the FT polypeptide. Alternatively, a biologically active portion or a FT protein can be the C-terminal domain of the FT polypeptide. Preferably, the biologically active portion comprises at least 75 amino acids of the C-terminal domain. More preferably, the biologically active portion comprises at least 25 amino acids of the C-terminal domain. Most preferably, the biologically active portion comprises at least 10 amino acids of the C-terminal.

In an embodiment, the FT protein has an amino acid sequence of SEQ ID NO:5, SEQ ID NO:7, SEQ ID NO:9, SEQ ID NO:33, SEQ ID NO:36 or SEQ ID NO:39. In other embodiments, the FT protein is substantially homologous to SEQ ID NO:5, SEQ ID NO:7, SEQ ID NO:9, SEQ ID NO:33, SEQ ID NO:36 or SEQ ID NO:39 and retains the functional activity of the protein of SEQ ID NO:5, SEQ ID NO:7, SEQ ID NO:9, SEQ ID NO:33, SEQ ID NO:36 or SEQ ID NO:39, yet differs in amino acid sequence due to natural allelic variation or mutagenesis, as described in detail below. Accordingly, in another embodiment, the FT protein is a protein that comprises an amino acid sequence at least 45% homologous to the amino acid sequence of SEQ ID NO:5, SEQ ID NO:7, SEQ ID NO:9, SEQ ID NO:33, SEQ ID NO:36 or SEQ ID NO:39 and retains the functional activity of the FT proteins of SEQ ID NO:5, SEQ ID NO:7, SEQ ID NO:9, SEQ ID NO:33, SEQ ID NO:36 or SEQ ID NO:39.

Determining Homology Between Two or More Sequence

To determine the percent homology of two amino acid sequences or of two nucleic acids, the sequences are aligned for optimal comparison purposes (e.g., gaps can be introduced in either of the sequences being compared for optimal alignment between the sequences). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP software provided in the GCG program package. See, Needleman and Wunsch 1970 *J Mol Biol* 48: 443–453. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NO:1, SEQ ID NO:6, SEQ ID NO:8, SEQ ID NO:31, SEQ ID NO:34, or SEQ ID NO:37.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (i.e., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison, region. The term "percentage of positive residues" is calculated by comparing two optimally aligned sequences over that region of comparison, determining the number of positions at which the identical and conservative amino acid substitutions, as defined above, occur in both sequences to yield the number of matched positions, dividing the number of matched positions by the total number of positions in the region of comparison (i.e., the window size), and multiplying the result by 100 to yield the percentage of positive residues.

Chimeric and Fusion Proteins

The invention also provides FT chimeric or fusion proteins. As used herein, a FT "chimeric protein" or "fusion protein" comprises a FT polypeptide operatively linked to a non-FT polypeptide. An "FT polypeptide" refers to a polypeptide having an amino acid sequence corresponding to FT, whereas a "non-FT polypeptide" refers to a polypeptide having an amino acid sequence corresponding to a protein that is not substantially homologous to the FT protein, e.g., a protein that is different from the FT protein and that is derived from the same or a different organism. Within a FT fusion protein the FT polypeptide can correspond to all or a portion of a FT protein. In one embodiment, a FT fusion protein comprises at least one biologically active portion of a FT protein. In another embodiment, a FT fusion protein comprises at least two biologically active portions of a FT protein. Within the fusion protein, the term "operatively linked" is intended to indicate that the FT polypeptide and the non-FT polypeptide are fused in-frame to each other. The non-FT polypeptide can be fused to the N-terminus or C-terminus of the FT polypeptide.

A FT chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide, a 6×His-tag). A FT-encoding nucleic acid can be cloned into such an expression vector such that the fusion moiety is linked in-frame to the FT protein.

FT Agonists and Antagonists

The present invention also pertains to variants of the FT proteins that function as either FT agonists (mimetics) or as FT antagonists. An agonist can be for example an antisense nucleic acid molecule. Variants of the FT protein can be generated by mutagenesis, e.g., discrete point mutation or truncation of the FT protein. An agonist of the FT protein can retain substantially the same, or a subset of, the biological activities of the naturally occurring form of the FT protein. An antagonist of the FT protein can inhibit one or more of the activities of the naturally occurring form of the FT protein by, for example, competitively binding to a downstream or upstream member of a cellular signaling cascade which includes the FT protein. Thus, specific biological effects can be elicited by treatment with a variant of limited function.

Variants of the FT protein that function as either FT agonists (mimetics) or as FT antagonists can be identified by screening combinatorial libraries of mutants, e.g., truncation mutants, of the FT protein for FT protein agonist or antagonist activity. In one embodiment, a variegated library of FT variants is generated by combinatorial mutagenesis at the nucleic acid level and is encoded by a variegated gene library. A variegated library of FT variants can be produced by, for example, enzymatically ligating a mixture of synthetic oligonucleotides into gene sequences such that a degenerate set of potential FT sequences is expressible as individual polypeptides, or alternatively, as a set of larger fusion proteins (e.g., for phage display) containing the set of FT sequences therein. There are a variety of methods which can be used to produce libraries of potential FT variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential FT sequences. Methods for synthesizing degenerate oligonucleotides are known in the art (see, e.g., Narang (1983) *Tetrahedron* 39:3; Itakura et al. (1984) *Annu Rev Biochem* 53:323; Itakura et al. (1984) *Science* 198:1056; Ike et al. (1983) *Nucl Acid Res* 11:477.

Polypeptide Libraries

In addition, libraries of fragments of the FT protein coding sequence can be used to generate a variegated population of FT fragments for screening and subsequent selection of variants of a FT protein. In one embodiment, a library of coding sequence fragments can be generated by treating a double stranded PCR fragment of a FT coding sequence with a nuclease under conditions wherein nicking occurs only about once per molecule, denaturing the double stranded DNA, renaturing the DNA to form double stranded DNA that can include sense/antisense pairs from different nicked products, removing single stranded portions from reformed duplexes by treatment with S1 nuclease, and ligating the resulting fragment library into an expression vector. By this method, an expression library can be derived which encodes N-terminal and internal fragments of various sizes of the FT protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of FT proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique that enhances the frequency of functional mutants in the libraries, can be used in combination with the screening assays to identify FT variants (Arkin and Yourvan (1992) PNAS 89:7811–7815; Delgrave et al. (1993) Protein Engineering 6:327–331).

FT Antibodies

FT polypeptides, including chimeric polypeptides, or derivatives, fragments, analogs or homologs thereof, may be utilized as immunogens to generate antibodies that immunospecifically-bind these peptide components. Such antibodies include, e.g., polyclonal, monoclonal, chimeric, single chain, Fab fragments and a Fab expression library. In a specific embodiment, fragments of the FT polypeptides are used as immunogens for antibody production. Various procedures known within the art may be used for the production of polyclonal or monoclonal antibodies to a FT polypeptides, or derivative, fragment, analog or homolog thereof.

For the production of polyclonal antibodies, various host animals may be immunized by injection with the native peptide, or a synthetic variant thereof, or a derivative of the foregoing. Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as *Bacille Calmette-Guerin* and *Corynebacterium parvum.*

For preparation of monoclonal antibodies directed towards a FT polypeptides, or derivatives, fragments, analogs or homologs thereof, any technique that provides for the production of antibody molecules by continuous cell line culture may be utilized. Such techniques include, but are not limited to, the hybridoma technique (see, Kohler and Milstein, 1975. *Nature* 256: 495–497); the trioma technique; the human B-cell hybridoma technique (see, Kozbor, et al., 1983. *Immunol Today* 4: 72) and the EBV hybridoma technique to produce human monoclonal antibodies (see, Cole, et al., 1985. In: *Monoclonal Antibodies and Cancer Therapy,* Alan R. Liss, Inc., pp. 77–96). Human monoclonal antibodies may be utilized in the practice of the present invention and may be produced by the use of human hybridomas (see, Cote, et al., 1983. *Proc Natl Acad Sci USA* 80:2026–2030) or by transforming human B-cells with Epstein Barr Virus in vitro (see, Cole, et al., 1985. In: *Monoclonal Antibodies and Cancer Therapy* (Alan R. Liss, Inc., pp. 77–96).

According to the invention, techniques can be adapted for the production of single-chain antibodies specific to a FT polypeptides (see, e.g., U.S. Pat. No. 4,946,778). In addition, methodologies can be adapted for the construction of Fab expression libraries (see, e.g., Huse, et al., 1989. *Science* 246: 1275–1281) to allow rapid and effective identification of monoclonal Fab fragments with the desired specificity for a FT polypeptides or derivatives, fragments, analogs or homologs thereof. Antibody fragments that contain the idiotypes to a FT polypeptides may be produced by techniques known in the art including, e.g., (i) an $F(ab')_2$ fragment produced by pepsin digestion of an antibody molecule; (ii) an Fab fragment generated by reducing the disulfide bridges of an $F(ab')_2$ fragment; (iii) an Fab fragment generated by the treatment of the antibody molecule with papain and a reducing agent and (iv) Fv fragments.

In one embodiment, methodologies for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of a FT polypeptides is facilitated by generation of hybridomas that bind to the fragment of a FT polypeptides possessing such a domain. Antibodies that are specific for a domain within a FT polypeptides, or derivative, fragments, analogs or hemologs thereof, are also provided herein. The anti-FT polypeptide antibodies may be used in methods known within the art relating to the localization and/or quantitation of a FT polypeptide(e.g., for use in measuring levels of the peptide within appropriate physiological samples, for use in diagnostic methods, for use in imaging the peptide, and the like).

FT Recombinant Expression Vectors and Host Cells

Another aspect of the invention pertains to vectors, preferably expression vectors, containing a nucleic acid encoding a FT protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication). Other vectors are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors or plant transformation vectors, binary or otherwise, which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., FT proteins, mutant forms of FT proteins, fusion proteins, etc.).

The recombinant expression vectors of the invention can be designed for expression of FT proteins in prokaryotic or eukaryotic cells. For example, FT proteins can be expressed in bacterial cells such as *Escherichia coli*, insect cells (using baculovirus expression vectors) yeast cells, plant cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein, however carboxy terminus fusions are also common. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. *Gene* 67: 31–40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) *Gene* 69:301–315) and pET 11d (Studier et al., GENE EXPRESSION TECHNOLOGY: METHODS IN ENZYMOLOGY 185, Academic Press, San Diego, Calif. (1990) 60–89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119–128. Another strategy is to alter the nucleic acid sequence of the nucleic acid to be inserted into an expression vector so that the individual codons for each amino acid are those preferentially utilized in *E. coli* (see, e.g., Wada, et al., 1992. *Nucl. Acids Res.* 20: 2111–2118). Such alteration of nucleic acid sequences of the invention can be carried out by standard DNA synthesis techniques.

In another embodiment, the FT expression vector is a yeast expression vector. Examples of vectors for expression in yeast *Saccharomyces cerivisae* include pYepSec1 (Baldari, et al., 1987. *EMBO J.* 6: 229–234), pMFa (Kurjan and Herskowitz, 1982. *Cell* 30: 933–943), pJRY88 (Schultz et al., 1987. *Gene* 54: 113–123), pYES2 (Invitrogen Corporation, San Diego, Calif.), and picZ (InVitrogen Corp, San Diego, Calif.).

Alternatively, FT can be expressed in insect cells using baculovirus expression vectors. Baculovirus vectors available for expression of proteins in cultured insect cells (e.g., SF9 cells) include the pAc series (Smith, et al., 1983. *Mol. Cell. Biol.* 3: 2156–2165) and the pVL series (Lucklow and Summers, 1989. *Virology* 170: 31–39).

In yet another embodiment, a nucleic acid of the invention is expressed in mammalian cells using a mammalian expression vector. Examples of mammalian expression vectors include pCDM8 (Seed, 1987. *Nature* 329: 840) and pMT2PC (Kaufman, et al., 1987. *EMBO J.* 6: 187–195).

When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In yet another embodiment, a nucleic acid of the invention is expressed in plants cells using a plant expression vector. Examples of plant expression vectors systems include tumor inducing (Ti) plasmid or portion thereof found in *Agrobacterium,* cauliflower mosaic virus (CAMV) DNA and vectors such as pBI121.

For expression in plants, the recombinant expression cassette will contain in addition to the FT nucleic acids, a plant promoter region, a transcription initiation site (if the coding sequence to transcribed lacks one), and a transcription termination/polyadenylation sequence. The termination/polyadenylation region may be obtained from the same gene as the promoter sequence or may be obtained from different genes. Unique restriction enzyme sites at the 5' and 3' ends of the cassette are typically included to allow for easy insertion into a pre-existing vector.

Examples of suitable promoters include promoters from plant viruses such as the 35S promoter from cauliflower mosaic virus (CaMV). Odell, et al., Nature, 313: 810–812 (1985). and promoters from genes such as rice actin (McElroy, et al., Plant Cell, 163–171 (1990)); ubiquitin (Christensen, et al., Plant Mol. Biol., 12: 619–632 (1992); and Christensen, et al., Plant Mol. Biol., 18: 675–689 (1992)); pEMU (Last, et al., Theor. Appl. Genet., 81: 581–588 (1991)); MAS (Velten, et al., EMBO J., 3: 2723–2730 (1984)); maize H3 histone (Lepetit, et al., Mol. Gen. Genet., 231: 276–285 (1992); and Atanassvoa, et al., Plant Journal, 2(3): 291–300 (1992)), the 5'- or 3'-promoter derived from T-DNA of *Agrobacterium tumefaciens*, the Smas promoter, the cinnamyl alcohol dehydrogenase promoter (U.S. Pat. No. 5,683,439), the Nos promoter, the rubisco promoter, the GRP1-8 promoter, ALS promoter, (WO 96/30530), a synthetic promoter, such as, Rsyn7, SCP and UCP promoters, ribulose-1,3-diphosphate carboxylase, fruit-specific promoters, heat shock promoters, seed-specific promoters and other transcription initiation regions from various plant genes, for example, include the various opine initiation regions, such as for example, octopine, mannopine, and nopaline.

Additional regulatory elements that may be connected to a FT encoding nucleic acid sequence for expression in plant cells include terminators, polyadenylation sequences, and nucleic acid sequences encoding signal peptides that permit localization within a plant cell or secretion of the protein from the cell. Such regulatory elements and methods for adding or exchanging these elements with the regulatory elements FT gene are known, and include, but are not limited to, 3' termination and/or polyadenylation regions such as those of the *Agrobacterium tumefaciens* nopaline synthase (nos) gene (Bevan, et al., Nucl. Acids Res., 12: 369–385 (1983)); the potato proteinase inhibitor II (PINII) gene (Keil, et al., Nucl. Acids Res., 14: 5641–5650 (1986) and hereby incorporated by reference); and An, et al., Plant Cell, 1: 115–122 (1989)); and the CaMV 19S gene (Mogen, et al., Plant Cell, 2: 1261–1272 (1990)).

Plant signal sequences, including, but not limited to, signal-peptide encoding DNA/RNA sequences which target proteins to the extracellular matrix of the plant cell (Dratewka-Kos, et al., J. Biol. Chem., 264: 4896–4900 (1989)) and the *Nicotiana plumbaginifolia* extension gene (DeLoose, et al., Gene, 99: 95–100 (1991)), or signal peptides which target proteins to the vacuole like the sweet potato sporamin gene (Matsuka, et al., Proc. Nat'l Acad. Sci. (USA), 88: 834 (1991)) and the barley lectin gene (Wilkins, et al., Plant Cell, 2: 301–313 (1990)), or signals which cause proteins to be secreted such as that of PRIb (Lind, et al., Plant Mol. Biol., 18: 47–53 (1992)), or those which target proteins to the plastids such as that of rapeseed enoyl-ACP reductase (Verwaert, et al., Plant Mol. Biol., 26: 189–202 (1994)) are useful in the invention.

In another embodiment, the recombinant expression vector is capable of directing expression of the nucleic acid preferentially in a particular cell type (e.g., tissue-specific regulatory elements are used to express the nucleic acid). Tissue-specific regulatory elements are known in the art. Especially useful in connection with the nucleic acids of the present invention are expression systems which are operable in plants. These include systems which are under control of a tissue-specific promoter, as well as those which involve promoters that are operable in all plant tissues.

Organ-specific promoters are also well known. For example, the patatin class I promoter is transcriptionally activated only in the potato tuber and can be used to target gene expression in the tuber (Bevan, M., 1986, *Nucleic Acids Research* 14:4625–4636). Another potato-specific promoter is the granule-bound starch synthase (GBSS) promoter (Visser, R. G. R, et al., 1991, *Plant Molecular Biology* 17:691–699).

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, P., 1986, *Trans. R. Soc. London* B314:343).

For in situ production of the antisense mRNA of GST, those regions of the GST gene which are transcribed into GST mRNA, including the untranslated regions thereof, are inserted into the expression vector under control of the promoter system in a reverse orientation. The resulting transcribed mRNA is then complementary to that normally produced by the plant.

The resulting expression system or cassette is ligated into or otherwise constructed to be included in a recombinant vector which is appropriate for plant transformation. The vector may also contain a selectable marker gene by which transformed plant cells can be identified in culture. Usually, the marker gene will encode antibiotic resistance. These markers include resistance to G418, hygromycin, bleomycin, kanamycin, and gentamicin. After transforming the plant cells, those cells having the vector will be identified by their ability to grow on a medium containing the particular antibiotic. Replication sequences, of bacterial or viral origin, are generally also included to allow the vector to be cloned in a bacterial or phage host, preferably a broad host range prokaryotic origin of replication is included. A selectable marker for bacteria should also be included to allow selection of bacterial cells bearing the desired construct. Suitable prokaryotic selectable markers also include resistance to antibiotics such as kanamycin or tetracycline.

Other DNA sequences encoding additional functions may also be present in the vector, as is known in the art. For instance, in the case of *Agrobacterium* transformations, T-DNA sequences will also be included for subsequent transfer to plant chromosomes.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell.

A host cell of the invention, such as a prokaryotic or eukaryotic host cell in culture, can be used to produce (i.e., express) a polypeptide of the invention encoded in a an open reading frame of a polynucleotide of the invention. Accordingly, the invention further provides methods for producing a polypeptide using the host cells of the invention. In one embodiment, the method comprises culturing the host cell of invention (into which a recombinant expression vector encoding a polypeptide of the invention has been introduced) in a suitable medium such that the polypeptide is produced. In another embodiment, the method further comprises isolating the polypeptide from the medium or the host cell.

A number of types of cells may act as suitable host cells for expression of a polypeptide encoded by an open reading frame in a polynucleotide of the invention. Plant host cells include, for example, plant cells that could function as suitable hosts for the expression of a polynucleotide of the invention include epidermal cells, mesophyll and other ground tissues, and vascular tissues in leaves, stems, floral organs, and roots from a variety of plant species, such as *Arabidopsis thaliana, Nicotiana tabacum, Brassica napus, Zea mays,* and *Glycine max.*

Alternatively, it may be possible to produce a polypeptide in lower eukaryotes such as yeast or in prokaryotes such as bacteria. Potentially suitable yeast strains include *Saccharomyces cerevisiae, Schizosaccharomyces pombe, Kluyveromyces* strains, *Candida,* or any yeast strain capable of expressing heterologous proteins. Potentially suitable bacterial strains include *Escherichia coli, Bacillus subtilis, Salmonella typhimurium,* or any bacterial strain capable of expressing heterologous polypeptides. If the polypeptide is made in yeast or bacteria, it may be necessary to modify the polypeptide produced therein, for example by phosphorylation or glycosylation of the appropriate sites, in order to obtain a functional polypeptide, if the polypeptide is of sufficient length and conformation to have activity. Such covalent attachments may be accomplished using known chemical or enzymatic methods.

A polypeptide may be prepared by culturing transformed host cells under culture conditions suitable to express the recombinant protein. The resulting expressed polypeptide or protein may then be purified from such culture (e.g., from culture medium or cell extracts) using known purification processes, such as gel filtration and ion exchange chromatography. The purification of the polypeptide or protein may also include an affinity column containing agents which will bind to the protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, a polypeptide or protein may also be expressed in a form which will facilitate purification. For example, it may be expressed as a fusion protein containing a six-residue histidine tag. The histidine-tagged protein will then bind to a Ni-affinity column. After elution of all other proteins, the histidine-tagged protein can be eluted to achieve rapid and efficient purification. One or more reverse-phase high performance liquid chromatography (RP-HPLC) steps employing hydrophobic RP-HPLC media, e.g., silica gel having pendant methyl or other aliphatic groups, can be employed to further purify a polypeptide. Some or all of the foregoing purification steps, in various combinations, can also be employed to provide a substantially homogeneous isolated recombinant polypeptide. The protein or polypeptide thus purified is substantially free of other plant proteins or polypeptides and is defined in accordance with the present invention as "isolated."

Transformed Plants Cells and Transgenic Plants

The invention includes protoplast, plants cells, plant tissue and plants (e.g., monocots and dicots transformed with a FT nucleic acid, a vector containing a FT nucleic acid or an expression vector containing a FT nucleic acid. Examples of nucleic acids suitable for transforming plant cells and plants include those nucleic acid sequences of SEQ ID NO: 4, 40–57 or 58. As used herein, "plant" is meant to include not only a whole plant but also a portion thereof (i.e., cells, and tissues, including for example, leaves, stems, shoots, roots, flowers, fruits and seeds).

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco,* and *Populus.*

In some aspects of the invention, the transformed plant is resistant to biotic and abiotic stresses, e.g., chilling stress, salt stress, heat stress, water stress, disease, grazing pests and wound healing. Additionally, the invention also includes a transgenic plant that is resistant to pathogens such as for example fungi, bacteria, nematodes, viruses and parasitic weeds. Alternatively, the transgenic plant is resistant to herbicides. By resistant is meant the plant grows under stress conditions (e.g., high salt, decreased water, low temperatures) or under conditions that normally inhibit, to some degree, the growth of an untransformed plant. Methodologies to determine plant growth or response to stress include for example, height measurements, weight measurements, leaf area, ability to flower, water use, transpiration rates and yield.

The invention also includes cells, tissues, including for example, leaves, stems, shoots, roots, flowers, fruits and seeds and the progeny derived from the transformed plant Numerous methods for introducing foreign genes into plants are known and can be used to insert a gene into a plant host, including biological and physical plant transformation protocols. See, for example, Miki et al., (1993) "Procedure for Introducing Foreign DNA into Plants", In: Methods in Plant Molecular Biology and Biotechnology, Glick and Thompson, eds., CRC Press, Inc., Boca Raton, pages 67–88 and Andrew Bent in, Clough S J and Bent A F, 1998. Floral dipping: a simplified method for *Agrobacterium*-mediated transformation of *Arabidopsis thaliana*. The methods chosen vary with the host plant, and include chemical transfection methods such as calcium phosphate, polyethylene glycol (PEG) transformation, microorganism-mediated gene transfer such as *Agrobacterium* (Horsch, et al., Science, 227: 1229–31 (1985)), electroporation, protoplast transformation, micro-injection, flower dipping and particle or non-particle biolistic bombardment.

*Agrobacterium*-mediated Transformation

The most widely utilized method for introducing an expression vector into plants is based on the natural transformation system of *Agrobacterium*. *A. tumefaciens* and *A. rhizogenes* are plant pathogenic soil bacteria which genetically transform plant cells. The Ti and Ri plasmids of *A. tumefaciens* and *A. rhizogenes*, respectfully, carry genes responsible for genetic transformation of plants. See, for example, Kado, Crit. Rev. Plant Sci., 10: 1–32 (1 991). Descriptions of the *Agrobacterium* vector systems and methods for *Agrobacterium*-mediated gene transfer are provided in Gruber et al., supra; and Moloney, et al, Plant Cell Reports, 8: 238–242 (1989).

Transgenic *Arabidopsis* plants can be produced easily by the method of dipping flowering plants into an *Agrobacterium* culture, based on the method of Andrew Bent in, Clough S J and Bent A F, 1998. Floral dipping: a simplified method for *Agrobacterium*-mediated transformation of *Arabidopsis thaliana*. Wild type plants are grown until the plant has both developing flowers and open flowers. The plant are inverted for 1 minutes into a solution of *Agrobacterium* culture carrying the appropriate gene construct. Plants are then left horizontal in a tray and kept covered for two days to maintain humidity and then righted and bagged to continue growth and seed development. Mature seed was bulk harvested.

Direct Gene Transfer

A generally applicable method of plant transformation is microprojectile-mediated transformation, where DNA is carried on the surface of microprojectiles measuring about 1 to 4 mu.m. The expression vector is introduced into plant tissues with a biolistic device that accelerates the microprojectiles to speeds of 300 to 600 m/s which is sufficient to penetrate the plant cell walls and membranes. (Sanford, et al., Part. Sci. Technol., 5: 27–37 (1987); Sanford, Trends Biotech, 6: 299–302 (1988); Sanford, Physiol. Plant, 79: 206–209 (1990); Klein, et al., Biotechnology, 10: 286–291 (1992)).

Another method for physical delivery of DNA to plants is sonication of target cells as described in Zang, et al., BioTechnology, 9: 996–996 (1991). Alternatively, liposome or spheroplast fusions have been used to introduce expression vectors into plants. See, for example, Deshayes, et al., EMBO J., 4: 2731–2737 (1985); and Christou, et al., Proc. Nat'l. Acad. Sci. (USA), 84: 3962–3966 (1987). Direct uptake of DNA into protoplasts using $CaCl_2$ precipitation, polyvinyl alcohol or poly-L-ornithine have also been reported. See, for example, Hain, et al., Mol. Gen. Genet., 199: 161 (1985); and Draper, et al., Plant Cell Physiol., 23: 451–458 (1982).

Electroporation of protoplasts and whole cells and tissues has also been described. See, for example, Donn, et al., (1990) In: Abstracts of the VIIth Int;1. Congress on Plant Cell and Tissue Culture IAPTC, A2-38, page 53; D'Halluin et al., Plant Cell, 4: 1495–1505 (1992); and Spencer et al., Plant Mol. Biol., 24: 51–61 (1994).

Plants may also be transformed using the method of Held et al. (U.S. Application 20010026941). The method utilizes an accelerated aerosol beam of dropletes which carries the desired molecules, DNA, into the target cells. The size of droplets produced by this method are reported to be sufficiently small as to transform bacterial cells of 1 to 2 microns in length.

Particle Wounding/Agrobacterium Delivery

Another useful basic transformation protocol involves a combination of wounding by particle bombardment, followed by use of *Agrobacterium* for DNA delivery, as described by Bidney, et al., Plant Mol. Biol., 18: 301–31 (1992). Useful plasmids for plant transformation include Bin 19. See Bevan, Nucleic Acids Research, 12: 8711–8721 (1984), and hereby incorporated by reference.

In general, the intact meristem transformation method involves imbibing seed for 24 hours in the dark, removing the cotyledons and root radical, followed by culturing of the meristem explants. Twenty-four hours later, the primary leaves are removed to expose the apical meristem. The explants are placed apical dome side up and bombarded, e.g., twice with particles, followed by co-cultivation with *Agrobacterium*. To start the co-cultivation for intact meristems, *Agrobacterium* is placed on the meristem. After about a 3-day co-cultivation period the meristems are transferred to culture medium with cefotaxime plus kanamycin for the NPTII selection.

The split meristem method involves imbibing seed, breaking of the cotyledons to produce a clean fracture at the plane of the embryonic axis, excising the root tip and then bisecting the explants longitudinally between the primordial leaves. The two halves are placed cut surface up on the medium then bombarded twice with particles, followed by co-cultivation with *Agrobacterium*. For split meristems, after bombardment, the meristems are placed in an *Agrobacterium* suspension for 30 minutes. They are then removed from the suspension onto solid culture medium for three day co-cultivation. After this period, the meristems are transferred to fresh medium with cefotaxime plus kanamycin for selection.

Transfer by Plant Breeding

Alternatively, once a single transformed plant has been obtained by the foregoing recombinant DNA method, conventional plant breeding methods can be used to transfer the gene and associated regulatory sequences via crossing and backcrossing. Such intermediate methods will comprise the further steps of: (1) sexually crossing the disease-resistant plant with a plant from the disease susceptible taxon; (2) recovering reproductive material from the progeny of the cross; and (3) growing disease-resistant plants from the reproductive material. Where desirable or necessary, the agronomic characteristics of the susceptible taxon can be substantially preserved by expanding this method to include the further steps of repetitively: (1) backcrossing the disease-resistant progeny with disease-susceptible plants from the susceptible taxon; and (2) selecting for expression of a hydrogen peroxide producing enzyme activity (or an associated marker gene) among the progeny of the backcross, until the desired percentage of the characteristics of the susceptible taxon are present in the progeny along with the gene or genes imparting oxalic acid degrading and/or hydrogen peroxide enzyme activity.

By the term "taxon" herein is meant a unit of botanical classification. It thus includes, genus, species, cultivars, varieties, variants and other minor taxonomic groups which lack a consistent nomenclature.

Regeneration of Transformants

The development or regeneration of plants from either single plant protoplasts or various explants is well known in the art (Weissbach and Weissbach, 1988). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil.

The development or regeneration of plants containing the foreign, exogenous gene that encodes a polypeptide of interest introduced by *Agrobacterium* from leaf explants can be achieved by methods well known in the art such as described (Horsch et al., 1985). In this procedure, transformants are cultured in the presence of a selection agent and in a medium that induces the regeneration of shoots in the plant strain being transformed as described (Fraley et al., 1983). In particular, U.S. Pat. No. 5,349,124 (specification incorporated herein by reference) details the creation of genetically transformed lettuce cells and plants resulting therefrom which express hybrid crystal proteins conferring insecticidal activity against Lepidopteran larvae to such plants.

This procedure typically produces shoots within two to four months and those shoots are then transferred to an appropriate root-inducing medium containing the selective agent and an antibiotic to prevent bacterial growth. Shoots that rooted in the presence of the selective agent to form plantlets are then transplanted to soil or other media to allow the production of roots. These procedures vary depending upon the particular plant strain employed, such variations being well known in the art.

Preferably, the regenerated plants are self-pollinated to provide homozygous transgenic plants, or pollen obtained from the regenerated plants is crossed to seed-grown plants of agronomically important, preferably inbred lines. Conversely, pollen from plants of those important lines is used to pollinate regenerated plants. A transgenic plant of the present invention containing a desired polypeptide is cultivated using methods well known to one skilled in the art.

A preferred transgenic plant is an independent segregant and can transmit the FT gene and its activity to its progeny. A more preferred transgenic plant is homozygous for the gene, and transmits that gene to all of its offspring on sexual mating. Seed from a transgenic plant may be grown in the field or greenhouse, and resulting sexually mature transgenic plants are self-pollinated to generate true breeding plants. The progeny from these plants become true breeding lines that are evaluated for increased expression of the FT transgene.

Method of Producing Tansgenic Plants

Included in the invention are methods of producing a transgenic plant that has increased stress resistance, delayed senesence or increased sensitivity to ABA. The method includes introducing into one or more plant cells a compound that alters farnesyl transferase expression (i.e. farnesyl transferase alpha or beta) or activity in the plant. The compound can be, e.g., (i) a farnesyl transferase polypeptide inhibitor; (ii) a nucleic acid encoding a farnesyl transferase polypeptide inhibitor; (iii) a nucleic acid that decreases expression of a nucleic acid that encodes a farnesyl transferase polypeptide and, derivatives, fragments, analogs and homologs thereof; (iv) an antisense farnesyl transferase nucleic acid. A nucleic acid that decreases expression of a nucleic acid that encodes a farnesyl transferase polypeptide includes, e.g., antisense nucleic acids or RNA inhibitory nucleic acids. The nucleic acid can be either endogenous or exogenous. Preferably the compound is a farnesyl transferase polypeptide or a nucleic acid encoding a farnesyl transferase polypeptide. For example the compound is the nucleic acid sequence of SEQ ID NO:1, SEQ ID NO:6, SEQ ID NO:8, SEQ ID NO:31, SEQ ID NO:34, or SEQ ID NO:37. More preferably the compound is a nucleic acid complemeatrty to a nucleic acid encoding a farnesyl transferase polypeptide. For example an anti-sense nucleic acid molecule. Exemplary compounds include SEQ ID NO: 1, 3, 4, 29, 30, 32, 35, 38, 40–57 and 58.

Also included in the invention is a plant where amutation has been introduced in the gen encoding farnesyl transferase (i.e. alpha or beta) which results in a plant that has decreased farnesyl transferase acitivity and increased tolerase to stree as compared to a wild type plant. The mutation may be introdueced by chemical or mechanical means.

Examples of stresses include, for example, chilling stress, heat stress, salt stress, water stress, nutrient limitation stress, disease, grazing pests, wound healing, pathogens such as for example fungi, bacteria, nematodes, viruses or parasitic weed and herbicides.

Increases stress resistance is meant that the trangenic plant can grows under stress conditions (e.g., high salt, decreased water, low temperatures) or under conditions that normally inhibit the growth of an untransformed plant. Methodologies to determine plant growth or response to stress include for example, height measurements, weight measurements, leaf area, ability to flower, water use, transpiration rates and yield Sensitivity to ABA can be assessed using a concentration curve of ABA and germinating seeds on plates as described in Example 11. Often germination is assessed and used to determine sensitivity. However, sensitivity can be observed at more developmental stages than simply germination. For example, increased sensitivity may be observed at the stage of cotyledon expansion, expansion of the first true leaf, or developmental arrest in the seedling stage.

The concentration of ABA at which sensitivity is observed varies in a species dependent manner. For example, transgenic *Arabidopsis thaliana* will demonstrate sensitivity at a lower concentration than observed in *Brassica* or soybean.

By increased ABA sensitivity it is meant that the trangenic plant is seen to display a phenotype at a lower concentration of ABA than that used to observe the same phenotype in a wild type plant. Methodologies to determine ABA sensitivity include for example, plant germination, growth or development.

The plant can be any plant type including, for example, species from the genera *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine,*

*Pisum, Phaseolus, Lolium, Oryza, Zea, Avena, Hordeum, Secale, Triticum, Sorghum, Picea, Caco,* and *Populus*.

Screening Methods

The isolated nucleic acid molecules of the invention (e.g., SEQ ID NO:1, SEQ ID NO:6, SEQ ID NO:8, SEQ ID NO:31, SEQ ID NO:34, or SEQ ID NO:37) can be used to express FT protein (e.g., via a recombinant expression vector in a host cell), to detect FT mRNA (e.g., in a biological sample) or a genetic lesion in a FT gene, and to modulate FT activity, as described further, below. In addition, the FT proteins can be used to screen compounds that modulate the FT protein activity or expression. In addition, the anti-FT antibodies of the invention can be used to detect and isolate FT proteins and modulate FT activity.

The invention provides a method (also referred to herein as a "screening assay") for identifying modulators, i.e., candidate or test compounds or agents (e.g., peptides, peptidomimetics, small molecules or other drugs) that bind to FT proteins or have a stimulatory or inhibitory effect on, e.g., FT protein expression or FT protein activity. The invention also includes compounds identified in the screening assays described herein. The invention also includes methods of identifying related genes using the transgenic plants of this invention in screening protocols utilizing mutagenesis, gene tagging, insertional gene tagging, activation tagging or other such methods of gene or phenotype identification.

In one embodiment, the invention provides assays for screening candidate or test compounds which bind to a FT protein or polypeptide or biologically-active portion thereof. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. *Anticancer Drug Design* 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. *Proc. Natl. Acad Sci. U.S.A.* 90: 6909; Erb, et al., 1994. *Proc. Natl. Acad. Sci. U.S.A.* 91: 11422; Zuckermann, et al., 1994. *J. Med. Chem.* 37: 2678; Cho, et al., 1993. *Science* 261: 1303; Carrell, et al., 1994. *Angew. Chem. Int. Ed. Engl.* 33: 2059; Carell, et al., 1994. *Angew. Chem. Int. Ed. Engl.* 33: 2061; and Gallop, et al., 1994. *J. Med. Chem.* 37: 1233.

Libraries of compounds may be presented in solution (e.g., Houghten, 1992. *Biotechniques* 13: 412–421), or on beads (Lam, 1991. *Nature* 354: 82–84), on chips (Fodor, 1993. *Nature* 364: 555–556), bacteria (Ladner, U.S. Pat. No. 5,223,409), spores (Ladner, U.S. Pat. No. 5,233,409), plasmids (Cull, et al., 1992. *Proc. Natl. Acad. Sci. USA* 89: 1865–1869) or on phage (Scott and Smith, 1990. *Science* 249: 386–390; Devlin, 1990. *Science* 249: 404–406; Cwirla, et al., 1990. *Proc. Natl. Acad. Sci. U.S.A.* 87: 6378–6382; Felici, 1991. *J. Mol. Biol.* 222: 301–310; Ladner, U.S. Pat. No. 5,233,409.).

In one embodiment, an assay is a cell-based assay in which a cell which expresses a FT protein, or a biologically-active portion thereof, is contacted with a test compound and the ability of the test compound to bind to a FT protein determined. The cell, for example, can be of mammalian origin, plant cell or a yeast cell. Determining the ability of the test compound to bind to the FT protein can be accomplished, for example, by coupling the test compound with a radioisotope or enzymatic label such that binding of the test compound to the FT protein or biologically-active portion thereof can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a FT protein, or a biologically-active portion thereof, with a known compound which binds FT to form an assay mixture, contacting the assay mixture with a test compound, and determining the ability of the test compound to interact with a FT protein, wherein determining the ability of the test compound to interact with a FT protein comprises determining the ability of the test compound to preferentially bind to FT protein or a biologically-active portion thereof as compared to the known compound.

In another embodiment, an assay is a cell-based assay comprising contacting a cell expressing a FT protein, or a biologically-active portion thereof, with a test compound and determining the ability of the test compound to modulate (e.g., stimulate or inhibit) the activity of the FT protein or biologically-active portion thereof. Determining the ability of the test compound to modulate the activity of FT or a biologically-active portion thereof can be accomplished, for example, by determining the ability of the FT protein to bind to or interact with a FT target molecule. As used herein, a "target molecule" is a molecule with which a FT protein binds or interacts in nature, for example, a molecule on the surface of a cell which expresses a FT interacting protein, a molecule on the surface of a second cell, a molecule in the extracellular milieu, a molecule associated with the internal surface of a cell membrane or a cytoplasmic molecule. A FT target molecule can be a non-FT molecule or a FT protein or polypeptide of the invention In one embodiment, a FT target molecule is a component of a signal transduction pathway that facilitates transduction of an extracellular signal (e.g. a signal generated by binding of a compound to a membrane-bound molecule) through the cell membrane and into the cell. The target, for example, can be a second intercellular protein that has catalytic activity or a protein that facilitates the association of downstream signaling molecules with FT.

Determining the ability of the FT protein to bind to or interact with a FT target molecule can be accomplished by one of the methods described above for determining direct binding. In one embodiment, determining the ability of the FT protein to bind to or interact with a FT target molecule can be accomplished by determining the activity of the target molecule. For example, the activity of the target molecule can be determined by detecting induction of a cellular second messenger of the target (i.e. intracellular $Ca^{2+}$, diacylglycerol, IP$_3$, etc.), detecting catalytic/enzymatic activity of the target an appropriate substrate, detecting the induction of a reporter gene (comprising a FT-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the invention is a cell-free assay comprising contacting a FT protein or biologically-active portion thereof with a test compound and determining the ability of the test compound to bind to the FT protein or biologically-active portion thereof. Binding of the test compound to the FT protein can be determined either directly or indirectly as described above. In one such embodiment, the assay comprises contacting the FT protein or biologically-active portion thereof with a known compound which binds FT to form an assay mixture, contacting the assay mixture with a test compound, and determining the ability of the test compound to interact with a FT protein, wherein determining the ability of the test compound to interact with a FT protein comprises determining the ability of the test compound to preferentially bind to FT or biologically-active portion thereof as compared to the known compound.

In still another embodiment, an assay is a cell-free assay comprising contacting FT protein or biologically-active portion thereof with a test compound and determining the ability of the test compound to modulate (e.g. stimulate or inhibit) the activity of the FT protein or biologically-active portion thereof. Determining the ability of the test compound to modulate the activity of FT can be accomplished, for example, by determining the ability of the FT protein to bind to a FT target molecule by one of the methods described above for determining direct binding. In an alternative embodiment, determining the ability of the test compound to modulate the activity of FT protein can be accomplished by determining the ability of the FT protein further modulate a FT target molecule. For example, the catalytic/enzymatic activity of the target molecule on an appropriate substrate can be determined as described above.

In yet another embodiment, the cell-free assay comprises contacting the FT protein or biologically-active portion thereof with a known compound which binds FT protein to form an assay mixture, contacting the assay mixture with a test compound, and determining the ability of the test compound to interact with a FT protein, wherein determining the ability of the test compound to interact with a FT protein comprises determining the ability of the FT protein to preferentially bind to or modulate the activity of a FT target molecule.

The cell-free assays of the invention are amenable to use of both the soluble form or the membrane-bound form of FT protein. In the case of cell-free assays comprising the membrane-bound form of FT protein, it may be desirable to utilize a solubilizing agent such that the membrane-bound form of FT protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1propane sulfonate (CHAPSO).

In more than one embodiment of the above assay methods of the invention, it may be desirable to immobilize either FT protein or its target molecule to facilitate separation of complexed from uncomplexed forms of one or both of the proteins, as well as to accommodate automation of the assay. Binding of a test compound to FT protein, or interaction of FT protein with a target molecule in the presence and absence of a candidate compound, can be accomplished in any vessel suitable for containing the reactants. Examples of such vessels include microtiter plates, test tubes, and microcentrifuge tubes. In one embodiment, a fusion protein can be provided that adds a domain that allows one or both of the proteins to be bound to a matrix. For example, GST-FT fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or FT protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of FT protein binding or activity determined using standard techniques.

Other techniques for immobilizing proteins on matrices can also be used in the screening assays of the invention. For example, either the FT protein or its target molecule can be immobilized utilizing conjugation of biotin and streptavidin. Biotinylated FT protein or target molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with FT protein or target molecules, but which do not interfere with binding of the FT protein to its target molecule, can be derivatized to the wells of the plate, and unbound target or FT protein trapped in the wells by antibody conjugation. Methods for detecting such complexes, in addition to those described above for the GST-immobilized complexes, include immunodetection of complexes using antibodies reactive with the FT protein or target molecule, as well as enzyme-linked assays that rely on detecting an enzymatic activity associated with the FT protein or target molecule.

In another embodiment, modulators of FT protein expression are identified in a method wherein a cell is contacted with a candidate compound and the expression of FT mRNA or protein in the cell is determined. The level of expression of FT mRNA or protein in the presence of the candidate compound is compared to the level of expression of FT mRNA or protein in the absence of the candidate compound. The candidate compound can then be identified as a modulator of FT mRNA or protein expression based upon this comparison. For example, when expression of FT mRNA or protein is greater (i e., statistically significantly greater) in the presence of the candidate compound than in its absence, the candidate compound is identified as a stimulator of FT mRNA or protein expression. Alternatively, when expression of FT mRNA or protein is less (statistically significantly less) in the presence of the candidate compound than in its absence, the candidate compound is identified as an inhibitor of FT mRNA or protein expression. The level of FT mRNA or protein expression in the cells can be determined by methods described herein for detecting FT mRNA or protein.

In yet another aspect of the invention, the FT proteins can be used as "bait proteins" in a two-hybrid assay or three hybrid assay (see, e.g., U.S. Pat. No. 5,283,317; Zervos, et al., 1993. *Cell* 72: 223–232; Madura, et al., 1993. *J. Biol. Chem.* 268: 12046–12054; Bartel, et al., 1993. *Biotechniques* 14: 920–924; Iwabuchi, et al., 1993. *Oncogene* 8: 1693–1696; and Brent WO 94/10300), to identify other proteins that bind to or interact with FT ("FT-binding proteins" or "FT-bp" ) and modulate FT activity. Such FT-binding proteins are also likely to be involved in the propagation of signals by the FT proteins as, for example, upstream or downstream elements of the FT pathway.

The two-hybrid system is based on the modular nature of most transcription factors, which consist of separable DNA-binding and activation domains. Briefly, the assay utilizes two different DNA constructs. In one construct, the gene that codes for FT is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a FT-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with FT.

In yet another aspect of the invention are methods which utilize the transgenic plants of the invention to identify FT-interacting components via genetic screening protocols. These componets can be for example, regulatory elements which modify FT-gene expression, interacting proteins which directly modify FT activity or interacting proteins which modify componets of the same signal transduction pathway and therby exert an effect on the expression or activity of FT. Briefly, genetic screening protocols are applied to the transgenic plants of the invention and in so doing identify related genes which are not identified using a wild type background for the screen. For example an activation tagged library (Weigel, et al., 2000. *Plant Physiol.* 122: 1003–1013), can be produced using the transgenic plants of the invention as the genetic background. Plants are then screened for altered phenotypes from that displayed by the parent plants. Alternative methods of generating libraries from the transgenic plants of the invention can be used, for example, chemical or irradiation induced mutations, insertional inactivation or activation methods.

The invention further pertains to novel agents identified by the aforementioned screening assays and uses thereof.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

The invention will be further described in the following examples, which do not limit the scope of the invention described in the claims.

EXAMPLES

Example 1

Cloning of *Arabidopsis thaliana* FTA and Construction of Transformation Vector

The *Arabidopsis thaliana* FTA sequence was obtained by RT-PCR from total RNA isolated from leaf tissue using primers corresponding to SEQ ID NO:11 and SEQ ID NO:12. The resulting fragment was digested with BamHI and SmaI and cloned into the plasmid pCR2.1 The Clonetech vector pBI121 was used as the backbone for the antisense construct. The GUS gene was removed by BamHI and Eco1CRI digestion and replaced with the FTA insert that was cut from pCR2.1-FTA using SmaI and BamHI and ligated into the vector SEQ ID NO:4.

TABLE 1

SEQ ID NO:11: 5'-AAAGGATCCTCAAATTGCTGCCACTGTAAT-3'

SEQ ID NO:12: 5'-AAACCCGGGATGAATTTCGACGAGAACGTG-3'

Example 2

Cloning of Non-full Length *Brassica napus* FTA and FTB Nucleic Acid Sequences

RNA was isolated from leaf and root tissue using the Qiagen RNeasy kit. RT-PCR was performed by known techniques using the primers shown in Table 2. The FTA sequence was obtained using the primer pair SEQ ID NO:19 and SEQ ID NO:20. The FTB sequence was obtained using the primer pair SEQ ID NO:21 and SEQ ID NO:22.

TABLE 2

SEQ ID NO:19: 5'-GGATCCATGGATTACTTCCGTGCGATTTACTTCTCC-3'

SEQ ID NO:20: 5'-AAAAAGCTTCCATGCCCAATAGTTAGCTCTTATTGGATC-3'

SEQ ID NO:21: 5'-AAAAAGCTTTGGCTTTGTTACTGGATTCTTCATTCAAT-3'

SEQ ID NO:22: 5'-AAATCTAGAAGCTTCATAATACCGATCCAAGACAATGTT-3'

PCR products were separated from the RT-PCR reaction mixture using the Qiagen PCR column spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 3

Cloning of Non-full Length FTA and FTB Nucleic Acid Sequences from *Glycine max* and *Zea maize*

RNA was isolated from leaf and root tissue using the Qiagen RNeasy kit. RT-PCR was performed by known techniques using the primers shown in Table 3. The *Glycine max* FTA sequence was obtained using the primer pair SEQ ID NO:23 and SEQ ID NO:24. The *Glycine max* FTB sequence was obtained using the primer pair SEQ ID NO:25 and SEQ ID NO:26. The *Zea maize* FTB sequence was obtained using the primer pair SEQ ID NO:27 and SEQ ID NO:28.

TABLE 3

| | |
|---|---|
| SEQ ID NO:23: | 5'-AAAGGATCCATGGAATCTGGGTCTAGCGA-3' |
| SEQ ID NO:24: | 5'-AAATCTAGAAGGAAGTCTGCTCTTGCGC-3' |
| SEQ ID NO:25: | 5'-AAATCTAGAGCCACCATTCCTCGCAACG-3' |
| SEQ ID NO:26: | 5'-AAAGAGCTCGTGGTGGAGAATCTGGGTGC-3' |
| SEQ ID NO:27: | 5'-GGCGGATCCCGACCTACCGAGG-3' |
| SEQ ID NO:28: | 5'-AAAGAGCTCGTGGATGGATTGGCTCCAGC-3' |

PCR products were separated from the RT-PCR reaction mixture using the Qiagen PCR column spin kit and ligated into the cloning vector pBluescript KS+. The vector was digested with EcoRV and treated with Taq polymerase in the presence of dTTP to produce a 3' overhang for ligation with the PCR products. The ligation products were transformed into *E. coli* DH5α cells, positive colonies were selected and the resulting inserts sequenced.

Example 4

Sequence Analysis

*Arabidopsis thaliana* FTA

A disclosed nucleic acid of 999 nucleotides (also referred to as FT1) is shown in Table 4A. The primers used in the PCR are depicted in bold.

TABLE 4A

| FT1 Nucleotide Sequence (SEQ ID NO:1). |
|---|
| aaacccgggatgaatttcgacgagaccgtgccactgagccaacgattggagtggtcagacgtggt |
| cccattgactcaggacgatggtccgaatccagtggtgccaattgcctacaaggaagagttccgcg |
| agactatggattacttccgtgcgatttacttttccgacgagcgatctcctcgcgcactacgactc |
| acggaagaaaccctcctcttaaactccggcaactacacagtgtggcatttcaggcgcctagtact |
| cgaggcccttaatcacgacttgtttgaagaactcgagttcatcgaacgcattgctgaggataact |
| ctaagaactaccaactgtggcatcatcggcgatgggttgcagagaaactgggtcctgatgttgca |
| gggagagaacttgaatttacccgtagagtactttcacttgatgccaaacattatcatgcttggtc |
| acataggcagtggacactacgggcattaggaggatgggaagatgagctcgattactgtcacgagc |
| tccttgaagctgacgtctttaacaattccgcctggaatcagaggtattatgtcatcacccaatct |
| cctttgttgggaggcctagaagccatgagagaatctgaagtaagctacacaatcaaagccatttt |
| aaccaatcctgcaaacgagagctcatggcgatacctaaaagcgctttacaaagacgacaaagaat |
| cctggattagtgatccaagtgtttcctcagtctgtttgaatgttctatcccgcacagattgcttc |
| catggattcgctctgagcacccttttggatcttctatgtgatggactgagaccaaccaacgagca |
| taaagactcagtgagagctctagctaatgaagaaccagagactaacttggccaatttggtgtgta |
| ctattcttggtcgtgtagatcctataagagctaactattgggcatggaggaagagcaagattaca |
| gtggcagcaatttgaggatccttt |

A disclosed FT1 polypeptide (SEQ ID NO:5) encoded by SEQ ID NO:1 has 326 amino acid residues and is presented in Table 4B using the one-letter amino acid code.

TABLE 4B

Encoded FT1 protein sequence (SEQ ID NO:5).

MNFDETVPLSQRLEWSDVVPLTQDDGPNPVVPIAYKEEFRETMDYFRAIYFSDERSPRALRLTE

ETLLLNSGNYTVWHFRRLVLEALNHDLFEELEFIERIAEDNSKNYQLWHHRRWVAEKLGPDVAG

RELEFTRRVLSLDAKHYHAWSHRQWTLRALGGWEDELDYCHELLEADVFNNSAWNQRYYVITQS

PLLGGLEAMRESEVSYTIKAILTNPANESSWRYLKALYKDDKESWISDPSVSSVCLNVLSRTDC

FHGFALSTLLDLLCDGLRPTNEHKDSVRALANEEPETNLANLVCTILGRVDPIRANYWAWRKSK

ITVAAI

Due to the nature of the cloning strategy the sequence presented does not contain any 5' or 3' non-translated sequence. Using the sequences disclosed herein as hybridization probes, one is able to screen and isolate full length sequences from cDNA or genomic libraries or use the rapid amplification of cDNA ends (RACE) technology or other such PCR techniques. The percent identity of the *Arabidopsis thaliana* nucleotide sequence and its encoded amino acid sequence to that of published sequences is shown in FIG. 8.

The present invention also includes a nucleic acid sequence complimentary to the *Arabidopsis thaliana* farnesyl transferase alpha subunit of SEQ ID NO:1. The disclosed complimenary sequence is shown as SEQ ID NO:2. The nucleic acid sequence of SEQ ID NO:3 shows the nucleic acid sequence of SEQ ID NO:2 that has been prepared for ligation into an expression vector.

SEQ ID NO:2 aaaggatcctcaaattgctgccactgtaatcttgctcttcctccatgcccaatagttagctcttataggatctaca cgaccaagaatagtacacaccaaattggccaagttagtctctggttcttcattagctagagctctcactgagtctt tatgctcgttggttggtctcagtccatcacatagaagatccaaaagggtgctcagagcgaatccatggaagcaatc tgtgcgggatagaacattcaaacagactgaggaaacacttggatcactaatccaggattctttgtcgtctttgtaa agcgcttttaggtatcgccatgagctctcgtttgcaggattggttaaaatggctttgattgtgtagcttacttcag attctctcatggcttctaggcctcccaacaaaggagattgggtgatgacataatacctctgattccaggcggaatt gttaaagacgtcagcttcaaggagctcgtgacagtaatcgagctcatcttcccatcctcctaatgcccgtagtgtc cactgcctatgtgaccaagcatgataatgtttggcatcaagtgaaagtactctacgggtaaattcaagttctctcc ctgcaacatcaggacccagtttctctgcaacccatcgccgatgatgccacagttggtagttcttagagttatcctc agcaatgcgttcgatgaactcgagttcttcaaacaagtcgtgattaagggcctcgagtactaggcgcctgaaatgc cacactgtgtagttgccggagtttaagaggagggtttcttccgtgagtcgtagtgcgcgaggagatcgctcgtcgg aaaagtaaatcgcacggaagtaatccatagtctcgcggaactcttccttgtaggcaattggcaccactggattcgg accatcgtcctgagtcaatgggaccacgtctgaccactccaatcgttggctcagtggcacggtctcgtcgaaattc atcccgggttt

SEQ ID NO:3

*gatcc*tcaaattgctgccactgtaatcttgctcttcctccatgcccaatagttagctcttataggatctacacgac caagaatagtacacaccaaattggccaagttagtctctggttcttcattagctagagctctcactgagtctttatg ctcgttggttggtctcagtccatcacatagaagatccaaaagggtgctcagagcgaatccatggaagcaatctgtg cgggatagaacattcaaacagactgaggaaacacttggatcactaatccaggattctttgtcgtctttgtaaagcg cttttaggtatcgccatgagctctcgtttgcaggattggttaaaatggctttgattgtgtagcttacttcagattc tctcatggcttctaggcctcccaacaaaggagattgggtgatgacataatacctctgattccaggcggaattgtta aagacgtcagcttcaaggagctcgtgacagtaatcgagctcatcttcccatcctcctaatgcccgtagtgtccact -continued

```
gcctatgtgaccaagcatgataatgtttggcatcaagtgaaagtactctacgggtaaattcaagttctctccctgc aacatcaggacccagtttctctgcaacccatcgccgatgatgccacagttggtagttcttagagttatcctcagca atgcgttcgatgaactcgagttcttcaaacaagtcgtgattaagggcctcgagtactaggcgcctgaaatgccaca ctgtgtagttgccggagtttaagaggagggtttcttccgtgagtcgtagtgcgcgaggagatcgctcgtcggaaaa gtaaatcgcacggaagtaatccatagtctcgcggaactcttccttgtaggcaattggcaccactggattcggacca tcgtcctgagtcaatgggaccacgtctgaccactccaatcgttggctcagtggcacggtctcgtcgaaattcatccc
```

*Brassica napus* FTA

A disclosed nucleic acid of 822 nucleotides (also referred to as FT2) is shown in Table 5A.

TABLE 5A

FT2 Nucleotide Sequence (SEQ ID NO:6).

ATGGATTATTCCGTGCGATTTACTTCTCCGACGAGCGTTCTGCTCGCGCGCTGCGACTCACGGA

AGAAGCTCTCCGCTTAAACTCGGGCAACTACACCGTGTGGCACTTCGGGCGCTTAGTACTCGAGG

AGCTTAATAACGACTTGTATGAAGAGCTCAAGTTCATCGAAAGCATTGCTGAGGATAACTCTAAG

AACTACCAGTTGTGGCATCATCGACGATGGGTCGCAGAGAAACTGGGTCCTGATGTTGCAGGAAA

GGAACTTGAGTTTACTCGGAGGGTACTATCACTTGATGCCAAGCATTATCATGCTTGGTCACATA

GGCAGTGGGCGCTACAAGCATTAGGAGGATGGGAAAATGAGCTTAACTACTGCCACGAGCTCCTT

GAAGCTGACGTCTTTAACAACTCTGCATGGAATCAGAGGTATTACGTTATAACTAGATCACCTTC

GTTGGGAGGCCTAGAAGCCATGAGAGAATCTGAAGTAAGCTACACAGTCAAAGCCATTTTAGCAA

ATCCCGGGAACGAGAGCTCTTGGAGGTACCTGAAAGCCCTTTACAAAGACGACACAGAGTCTTGG

ATTAGTGATCCAAGTGTTTCCTCAGTCTGTTTGAAAGTTCTCTCACGCGCGGACTGCTTCCATGG

ATTCGCTCTGAGCACCCTTTTGGATCTTCTGTGCGATGGGTTGAGACCAACCAACGAGCATAGAG

ACTCGGTGAAAGCTCTAGCTAATGAAGAACCAGAGACTAACTTGGCCAATTTGGTGTGTACCATT

CTGTGTCGTGTTGATCCAATAAGAGCTAACTATTGGGCATGG

A disclosed FT2 polypeptide (SEQ ID NO:7) encoded by SEQ ID NO:6 has 274 amino acid residues and is presented in Table 5B using the one-letter amino acid code.

TABLE 5B

Encoded FT2 protein sequence (SEQ ID NO:7).

MDYFRAIYFSDERSARALRLTEEALRLNSGNYTVWHFGRLVLEELNNDLYEELKFIESIAEDNS

KNYQLWHHRRWVAEKLGPDVAGLEKEFTRRVLSLDAKHYHAWSHRQWALQALGGWENELNYCHE

LLEADVFNNSAWNQRYYVITRSPSLGGLEAMRESEVSYTVKAILANPGNESSWRYLKALYKDDT

ESWISDPSVSSVCLKVLSRADCFHGFALSTLLDLLCDGLRPTNEHRDSVKALANEEPETNLANL

VCTILCRVDPIRANYWAWKL

Due to the nature of the cloning strategy the sequence presented is not full length. Compared to the *Arabidopsis thaliana* sequence there are 42 amino acids missing from the amino terminus and 10 amino acids from the carboxy terminus. The percent identity of the *Brassica napus* nucleotide sequence and its encoded amino acid sequence to that of published sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Brassica napsus* farnesyl transferase alpha subunit of SEQ ID NO:6. The disclosed complimenary sequence is shown as SEQ ID NO:29.

```
                                                                SEQ ID NO:29
CCATGCCCAATAGTTAGCTCTTATTGGATCAACACGACACAGAATGGTACACACCAAATTGGCCAAGTTAGTCTCT

GGTTCTTCATTAGCTAGAGCTTTCACCGAGTCTCTATGCTCGTTGGTTGGTCTCAACCCATCGCACAGAAGATCCA

AAAGGGTGCTCAGAGCGAATCCATGGAAGCAGTCCGCGCGTGAGAGAACTTTCAAACAGACTGAGGAAACACTTGG

ATCACTAATCCAAGACTCTGTGTCGTCTTTGTAAAGGGCTTTCAGGTACCTCCAAGAGCTCTCGTTCCCGGGATTT

GCTAAAATGGCTTTGACTGTGTAGCTTACTTCAGATTCTCTCATGGCTTCTAGGCCTCCCAACGAAGGTGATCTAG

TTATAACGTAATACCTCTGATTCCATGCAGAGTTGTTAAAGACGTCAGCTTCAAGGAGTCGTGGCAGTAGTTAAG

CTCATTTTCCCATCCTCCTAATGCTTGTAGCGCCCACTGCCTATGTGACCAAGCATGATAATGCTTGGCATCAAGT

GATAGTACCCTCCGAGTAAACTCAAGTTCCTTTCCTGCAACATCAGGACCCAGTTTCTCTGCGACCCATCGTCGAT

GATGCCACAACTGGTAGTTCTTAGAGTTATCCTCAGCAATGCTTTCGATGAACTTGAGCTCTTCATACAAGTCGTT

ATTAAGCTCCTCGAGTACTAAGCGCCCGAAGTGCCACACGGTGTAGTTGCCCGAGTTTAAGCGGAGAGCTTCTTCC

GTGAGTCGCAGCGCGCGAGCAGAACGCTCGTCGGAGAAGTAAATCGCACGGAAGTAATCCAT
```

*Brassica napus* FTB

A disclosed nucleic acid of 1110 nucleotides (also referred to as FT3) is shown in Table 6A.

TABLE 6A

FT3 Nucleotide Sequence (SEQ ID NO:8).

```
TGGCTTTGTTACTGGATTCTTCATTCAATTGCTTTGCTTGGGGAGTCTGTGGATGATGACTTAGA

AAACAATGCAATCGATTTTCTTGGACGTTGCCAGGGTTCTGATGGTGGATATGGTGGTGGTCCTG

GCCAACTTCCACATCTTGCAACAAGTTATGCTGCAGTGAATACACTTGTTACTTTAGGAGGTGAG

AAAGCCTTCTCTTCAATTAACAGAGAACAAATGGCTTGTTTCTTAAGACGAATGAAGGATACAAA

TGGAGGTTTCAGGATGCATAATATGGGAGAAATAGATGTGCGAGCGTGCTACACTGCGATTTTGA

TTGCAAGCATCCTGAACATTGTGGATGATGAACTCACCCGCGGCTTAGGAGATTACATTTTGAGT

TGCCAAACTTATGAAGGTGGCATTGGAGGGGAACCTGGCTCCGAAGCTCATGGTGGGTACACGTA

CTGTGGGTTGGCTACTATGATTTTAATCAATGAAGTCGACCGCTTGAATTTGGATTCGTTAATGA

ATTGGGTTGTACATCGACAAGGAGTAGAAATGGGATTCCAAGGTAGGACGAACAAATTGGTCGAC

GGTTGCTACACGTTTTGGCAGGCAGCCCCTGTGTTCTACTACAGCGATTTTTTCATCCCAGGA

TATGGCACCTCATGGATCATCATCACATATGTCACAAGGGACAGATGAAGATCACGAGGAACATG

GTCATGATGAAGATGATCCTGAAGACAGTGATGAAGATGATTCTGATGAGGATAGCGATGAAGAT

TCAGGGAATGGTCACCAAGTTCATCATACGTCTACCTACATTGACAGGAGAATTCAACCTGTTTT

TGATAGCCTCGGCTTGCAAAGATATGTGCTCTTGTGCTCTCAGGTTGCTGATGGTGGATTCAGAG

ACAAGCTGAGGAAACCCCGTGACTTCTACCACACATGTTACTGCCTAAGCGGTCTTTCCGTGGCT

CAACACGCTTGGTCAAAAGACGAGGACACTCCTCCTTTGACTCGTGACATTTTGGGTGGCTACGC

AAACCACCTTGAACCTGTTCACCTCCTCCACAACATTGTCTTGGATCGGTATTATGAAGCTTCTA

GATTT
```

A disclosed FT3 polypeptide (SEQ ID NO:9) encoded by SEQ ID NO:7 has 370 amino acid residues and is presented in Table 6B using the one-letter amino acid code.

TABLE 6B

Encoded FT3 protein sequence (SEQ ID NO:9).

WLCYWILHSIALLGESVDDDLENNAIDFLGRCQGSDGGYGGGPGQLPHLA

TSYAAVNTLVTLGGEKAFSSINREQMACFLRRMKDTNGGFRMHNMGEIDV

RACYTAILIASILNIVDDELTRGLGDYILSCQTYEGGIGGEPGSEAHGGY

TYCGLATMILINEVDRLNLDSLMNWVVHRQGVEMGFQGRTNKLVDGCYTF

WQAAPCVLLQRFFSSQDMAPHGSSSHMSQGTDEDHEEHGHDEDDPEDSDE

DDSDEDSDEDSGNGHQVHHTSTYIDRRIQPVFDSLGLQRYVLLCSQVADG

GFRDKLRKPRDFYHTCYCLSGLSVAQHAWSKDEDTPPLTRDILGGYANHL

EPVHLLHNILVDRYYEASRF

Due to the nature of the cloning strategy the sequence presented is not full length. Compared to the *Arabidopsis thaliana* sequence there are 31 amino acids missing from the amino terminus and 5 amino acids from the carboxy terminus. The percent identity of the *Brassica napus* nucleotide sequence and its encoded amino acid sequence to that of published sequences is shown in FIG. 9.

Using the sequences disclosed herein as hybridization probes, one is able to screen and isolate full length sequences from cDNA or genomic libraries or use the rapid amplification of cDNA ends (RACE) technology or other such PCR techniques. Sequence comparisons have been performed and percent identities are shown in FIG. 8 and FIG. 9.

The present invention also includes a nucleic acid sequence complimentary to the *Brassica napsus* farnesyl transferase beta subunit of SEQ ID NO:8. The disclosed complimenary sequence is shown as SEQ ID NO:30.

*Glycine max* FTA

A disclosed nucleic acid of 1041 nucleotides (also referred to as FT4) is shown in Table 7A.

TABLE 7A

FT4 Nucleotide Sequence (SEQ ID NO:31).

ATGGAATCTGGGTCTAGCGAAGGAGAAGAGGTGCAGCAACGCGTGCCGTT

GAGGGAGAGAGTGGAGTGGTCAGATGTTACTCCGGTTCCTCAAAACGACG

GCCCTAACCCTGTCGTTCCGATCCAGTACACTGAAGAGTTTTCCGAAGTT

ATGGATTACTTTCGCGCCGTTTACCTCACCGATGAACGCTCCCCTCGCGC

CCTCGCTCTCACAGCCGAAGCCGTTCAATTCAACTCCGGCAACTACACTG

TGTGGCATTTCCGACGGTTGTTACTTGAGTCGCTAAAAGTCGACTTGAAC

GATGAACTGGAGTTTGTGGAGCGTATGGCCGCTGGAAATTCTAAAAATTA

TCAGATGTGnATGTTCTGTAGGCATCCTAGACGATGGGTTGCCGAGAAGT

TAGGTCCTGAAGCTAGAAACAATGAGCTCGAGTTCACCAAAAAGATACTG

TCCGTTGATGCCAAACATTATCATGCATGGTCTCATAGACAGTGGGCTCT

TCAAACACTAGGAGGATGGGAAGATGAACTTAATTATTGCACAGAACTAC

TTAAAGAAGACATTTTTAACAATTCTGCTTGGAATCAGAGATATTTTGTC

ATAACAAGGTCTCCTTTCTTGGGGGGCCTAAAAGCTATGAGAGAGTCTGA

AGTGCTTTACACCATCGAAGCCATTATAGCCTACCCTGAAAATGAAAGCT

CGTGGAGATATCTACGAGGACTTTATAAAGGTGAAACTACTTCATGGGTA

AATGATCCTCAAGTTTCTTCAGTATGCTTAAAGATTTTGAGAACTAAGAG

CAACTACGTGTTTGCTCTTAGCACTATTTTAGATCTTATATGCTTTGGTT

ATCAACCAAATGAAGACATTAGAGATGCCATTGACGCCTTAAAGACCGCA

GATATGGATAAACAAGATTTAGATGATGATGAGAAAGGGGAACAACAAAA

SEQ ID NO:30

AAATCTAGAAGCTTCATAATACCGATCCAAGACAATGTTGTGGAGGAGGTGAACAGGTTCAAGGTGGTTTGCGTAG

CCACCCAAAATGTCACGAGTCAAAGGAGGAGTGTCCTCGTCTTTTGACCAAGCGTGTTGAGCCACGGAAAGACCGC

TTAGGCAGTAACATGTGTGGTAGAAGTCACGGGGTTTCCTCAGCTTGTCTCTGAATCCACCATCAGCAACCTGAGA

GCACAAGAGCACATATCTTTGCAAGCCGAGGCTATCAAAAACAGGTTGAATTCTCCTGTCAATGTAGGTAGACGTA

TGATGAACTTGGTGACCATTCCCTGAATCTTCATCGCTATCCTCATCAGAATCATCTTCATCACTGTCTTCAGGAT

CATCTTCATCATGACCATGTTCCTCGTGATCTTCATCTGTCCCTTGTGACATATGTGATGATGATCCATGAGGTGC

CATATCCTGGGATGAAAAAAATCGCTGTAGTAGAACACAGGGGGCTGCCTGCCAAAACGTGTAGCAACCGTCGACC

AATTTGTTCGTCCTACCTTGGAATCCCATTTCTACTCCTTGTCGATGTACAACCCAATTCATTAACGAATCCAAAT

TCAAGCGGTCGACTTCATTGATTAAAATCATAGTAGCCAACCCACAGTACGTGTACCCACCATGAGCTTCGGAGCC

AGGTTCCCCTCCAATGCCACCTTCATAAGTTTGGCAACTCAAAATGTAATCTCCTAAGCCGCGGGTGAGTTCATCA

TCCACAATGTTCAGGATGCTTGCAATCAAAATCGCAGTGTAGCACGCTCGCACATCTATTTCTCCCATATTATGCA

TCCTGAAACCTCCATTTGTATCCTTCATTCGTCTTAAGAAACAAGCCATTTGTTCTCTGTTAATTGAAGAGAAGGC

TTTCTCACCTCCTAAAGTAACAAGTGTATTCACTGCAGCATAACTTGTTGCAAGATGTGGAAGTTGGCCAGGACCA

CCACCATATCCACCATCAGAACCCTGGCAACGTCCAAGAAAATCGATTGCATTGTTTTCTAAGTCATCATCCACAG

ACTCCCCAAGCAAAGCAATTGAATGAAGAATCCAGTAACAAAGCCA

TABLE 7A-continued

FT4 Nucleotide Sequence (SEQ ID NO:31).

TTTAAATATAGCACGAAATATTTGTTCTATCCTAAAACAAGTTGATCCAA

TTAGAACCAACTATTGGATTTGGCGCAAGAGCAGACTTCCT

A disclosed FT4 polypeptide (SEQ ID NO:33) encoded by SEQ ID NO:31 has 347 amino acid residues and is presented in Table 7B using the one-letter amino acid code.

TABLE 7B

Encoded FT4 protein sequence (SEQ ID NO:33).

MESGSSEGEEVQQRVPLRERVEWSDVTPVPQNDGPNPVVPIQYTEEFSEV

MDYFRAVYLTDERSPRALALTAEAVQFNSGNYTVWHFRRLLLESLKVDLN

DELEFVERMAAGNSKNYQMXMFCRHPRRWVAEKLGPEARNNELEFTKKIL

SVDAKHYHAWSHRQWALQTLGGWEDELNYCTELLKEDIFNNSAWNQRYFV

ITRSPFLGGLKAMRESEVLYTIEAIIAYPENESSWRYLRGLYKGETTSWV

NDPQVSSVCLKILRTKSNYVFALSTILDLICFGYQPNEDIRDAIDALKTA

DMDKQDLDDDEKGEQQNLNIARNICSILKQVDPIRTNYWIWRKSRLP

Due to the nature of the cloning strategy the sequence presented is not full length. The percent identity of the *Glycine max* nucleotide sequence and its encoded amino acid sequence to that of other sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Glycine max* alpha subunit of SEQ ID NO:31. The disclosed complimenary sequence is shown as SEQ ID NO:32.

*Glycine max* FTB

A disclosed nucleic acid of 1035 nucleotides (also referred to as FT5) is shown in Table 8A.

TABLE 8A

FT5 Nucleotide Sequence (SEQ ID NO:34).

GCCACCATTCCTCGCAACGCCCAAACCCTCATGTTGGAGCTTCAACGCGA

TAATCACATGCAGTATGTCTCCAAAGGCCTTCGCCATCTCAGTTCCGCAT

TTTCCGTTTTGGACGCTAATCGACCCTGGCTCTGCTACTGGATCTTCCAC

TCCATTGCTTTGTTGGGAGAATCCGTCGATGATGAACTCGAAGATAACGC

TATCGATTTTCTTAACCGTTGCCAGGATCCGAATGGTGGATATGCCGGGG

GACCAGGCCAGATGCCTCATATTGCCACAACTTATGCTGCTGTTAATTCA

CTTATTACTTTGGGTGGTGAGAAATCCCTGGCATCAATTAATAGAGATAA

ACTGTATGGGTTTCTGCGGCGGATGAAGCAACCAAATGGTGGATTCAGGA

TGCATGATGAAGGTGAAATTGATGTTCGAGCTTGCTACACTGCCATTTCT

GTTGCAAGTGTTTTGAACATTTTGGATGATGAGCTGATCCAGAATGTTGG

AGACTACATTATAAGCTGTCAAACATATGAGGGTGGCATTGCTGGTGAGC

CTGGTTCTGAGGCTCATGGTGGGTACACCTTTTGTGGATTAGCTACAATG

ATTCTGATTGGTGAGGTTAATCACTTGGATCTGCCTCGATTAGTTGACTG

GGTGGTATTCCGACAAGGTAAGGAATGTGGATTCCAGGGGAGAACAAATA

AACTGGTGGATGGATGCTATTCCTTTTGGCAGGGAGGTGCTGTTGCTCTA

TTGCAAAGATTATCTTCTATTATCAACAAACAGATGGAAGAGACATCACA

GATTTTTGCGGTATCTTATGTATCTGAAGCAAAAGAAAGTTTGGATGGAA

CCTCTAGTCATGCAACATGCCGTGGTGAGCATGAAGGCACCAGTGAATCC

AGTTCATCTGATTTTAAAAATATTGCCTATAAATTTATTAATGAGTGGAG

AGCACAAGAACCACTTTTTCACAGTATTGCTTTACAGCAATATATTCTCT

SEQ ID NO:32

AGGAAGTCTGCTCTTGCGCCAAATCCAATAGTTGGTTCTAATTGGATCAACTTGTTTTAGGATAGAACAAATATTT

CGTGCTATATTTAAATTTTGTTGTTCCCCTTTCTCATCATCATCTAAATCTTGTTTATCCATATCTGCGGTCTTTA

AGGCGTCAATGGCATCTCTAATGTCTTCATTTGGTTGATAACCAAAGCATATAAGATCTAAAATAGTGCTAAGAGC

AAACACGTAGTTGCTCTTAGTTCTCAAAATCTTTAAGCATACTGAAGAAACTTGAGGATCATTTACCCATGAAGTA

GTTTCACCTTTATAAAGTCCTCGTAGATATCTCCACGAGCTTTCATTTTCAGGGTAGGCTATAATGGCTTCGATGG

TGTAAAGCACTTCAGACTCTCTCATAGCTTTTAGGCCCCCCAAGAAAGGAGACCTTGTTATGACAAAATATCTCTG

ATTCCAAGCAGAATTGTTAAAAATGTCTTCTTTAAGTAGTTCTGTGCAATAATTAAGTTCATCTTCCCATCCTCCT

AGTGTTTGAAGAGCCCACTGTCTATGAGACCATGCATGATAATGTTTGGCATCAACGGACAGTATCTTTTTGGTGA

ACTCGAGCTCATTGTTTCTAGCTTCAGGACCTAACTTCTCGGCAACCCATCGTCTAGGATGCCTACAGAACATNCA

CATCTGATAATTTTTAGAATTTCCAGCGGCCATACGCTCCACAAACTCCAGTTCATCGTTCAAGTCGACTTTTAGC

GACTCAAGTAACAACCGTCGGAAATGCCACACAGTGTAGTTGCCGGAGTTGAATTGAACGGCTTCGGCTGTGAGAG

CGAGGGCGCGAGGGGAGCGTTCATCGGTGAGGTAAACGGCGCGAAAGTAATCCATAACTTCGGAAAACTCTTCAGT

GTACTGGATCGGAACGACAGGGTTAGGGCCGTCGTTTTGAGGAACCGGAGTAACATCTGACCACTCCACTCTCTCC

CTCAACGGCACGCGTTGCTGCACCTCTTCTCCTTCGCTAGACCCAGATTCCAT

TABLE 8A-continued

FT5 Nucleotide Sequence (SEQ ID NO:34).

TATGTGCACAGGAGCAAGAGGGTGGACTGAGAGACAAACCGGGTAAACGT

AGAGATCATTATCACACATGTTACTGTTTAAGTGGACTCTCATTGTGCCA

GTATAGTTGGTCAAAGCACCCAGATTCTCCACCAC

A disclosed FT5 polypeptide (SEQ ID NO:36) encoded by SEQ ID NO:34 has 378 amino acid residues and is presented in Table 8B using the one-letter amino acid code.

TABLE 8B

Encoded FT5 protein sequence (SEQ ID NO:36).

ATIPRNAQTLMLELQRDNHMQYVSKGLRHLSSAFSVLDANRPWLCYWIFH

SIALLGESVDDELEDNAIDFLNRCQDPNGGYAGGPGQMPHIATTYAAVNS

LITLGGEKSLASINRDKLYGFLRRMKQPNGGFRMHDEGEIDVRACYTAIS

VASVLNILDDELIQNVGDYIISCQTYEGGIAGEPGSEAHGGYTFCGLATM

ILIGEVNHLDLPRLVDWVVFRQGKECGFQGRTNKLVDGCYSFWQGGAVAL

LQRLSSIINKQMEETSQIFAVSYVSEAKESLDGTSSHATCRGEHEGTSES

SSSDFKNIAYKFINEWRAQEPLFHSIALQQYILLCAQEQEGGLRDKPGKR

RDHYHTCYCLSGLSLCQYSWSKHPDSPP

Due to the nature of the cloning strategy the sequence presented is not full length. The percent identity of the *Glycine max* nucleotide sequence and its encoded amino acid sequence to that of other sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Glycine* max beta subunit of SEQ ID NO:34. The disclosed complimenary sequence is shown as SEQ ID NO:35.

SEQ ID NO:35

GTGGTGGAGAATCTGGGTGCTTTGACCAACTATACTGGCACAATGAGAGTCCACTTAAACAGTAACATGTGTGATA

ATGATCTCTACGTTTACCCGGTTTGTCTCTCAGTCCACCCTCTTGCTCCTGTGCACATAAGAGAATATATTGCTGT

AAAGCAATACTGTGAAAAAGTGGTTCTTGTGCTCTCCACTCATTAATAAATTTATAGGCAATATTTTTAAAATCAG

ATGAACTGGATTCACTGGTGCCTTCATGCTCACCACGGCATGTTGCATGACTAGAGGTTCCATCCAAACTTTCTTT

TGCTTCAGATACATAAGATACCGCAAAAATCTGTGATGTCTCTTCCATCTGTTTGTTGATAATAGAAGATAATCTT

TGCAATAGAGCAACAGCACCTCCCTGCCAAAAGGAATAGCATCCATCCACCAGTTTATTTGTTCTCCCCTGGAATC

CACATTCCTTACCTTGTCGGAATACCACCCAGTCAACTAATCGAGGCAGATCCAAGTGATTAACCTCACCAATCAG

AATCATTGTAGCTAATCCACAAAAGGTGTACCCACCATGAGCCTCAGAACCAGGCTCACCAGCAATGCCACCCTCA

TATGTTTGACAGCTTATAATGTAGTCTCCAACATTCTGGATCAGCTCATCATCCAAAATGTTCAAAACACTTGCAA

CAGAAATGGCAGTGTAGCAAGCTCGAACATCAATTTCACCTTCATCATGCATCCTGAATCCACCATTTGGTTGCTT

CATCCGCCGCAGAAACCCATACAGTTTATCTCTATTAATTGATGCCAGGGATTTCTCACCACCCAAAGTAATAAGT

GAATTAACAGCAGCATAAGTTGTGGCAATATGAGGCATCTGGCCTGGTCCCCGGCATATCCACCATTCGGATCCT

GGCAACGGTTAAGAAAATCGATAGCGTTATCTTCGAGTTCATCATCGACGGATTCTCCCAACAAAGCAATGGAGTG

GAAGATCCAGTAGCAGAGCCAGGGTCGATTAGCGTCCAAAACGGAAAATGCGGAACTGAGATGGCGAAGGCCTTTG

GAGACATACTGCATGTGATTATCGCGTTGAAGCTCCAACATGAGGGTTTGGGCGTTGCGAGGAATGGTGGC

*Zea maize* FTB

A disclosed nucleic acid of 1235 nucleotides (also referred to as FT6) is shown in Table 9A.

TABLE 9A

FT6 Nucleotide Sequence (SEQ ID NO:37).

GGCGGATCCCGACCTACCGAGGCTCACGGTGACGCAGGTGGAGCAGATGA

AGGTGGAGGCCAGGGTTGGCGACATCTACCGCTCCCTCTTCGGGGCCGCG

CCCAACACGAAATCCATCATGCTAGAGCTGTGGCGTGATCAGCATATCGA

GTATCTGACGCCTGGGCTGAGGCATATGGGACCAGCCTTTCATGTTCTAG

ATGCCAATCGCCCTTGGCTATGCTACTGGATGGTTCATCCACTTGCTTTG

CTGGATGAAGCACTTGATGATGATCTTGAGAATGATATCATAGACTTCTT

AGCTCGATGTCAGGATAAAGATGGTGGATATAGTGGTGGACCTGGACAGT

TGCCTCACCTAGCTACGACTTATGCTGCTGTAAATACACTTGTGACAATA

GGGAGCGAAAGAGCATTGTCATCAATCAATAGGGGCAACCTGTACAATTT

TATGCTGCAGATGAAAGATGTATCAGGTGCTTTCAGAATGCATGATGGTG

GCGAAATTGATGTCCGTGCTTCCTACACCGCTATATCGGTTGCCAGCCTT

GTGAATATTCTTGATTTTAAACTGGCAAAAGGTGTAGGCGACTACATAGC

TABLE 9A-continued

FT6 Nucleotide Sequence (SEQ ID NO:37).

AAGATGTCAAACTTATGAAGGTGGTATTGCTGGGGAGCCTTATGCTGAAG

CACATGGTGGGTATACATTCTGTGGATTGGCTGCTTTGATCCTGCTTAAT

GAGGCAGAGAAAGTTGACTTGCCTAGTTTGATTGGCTGGGTGGCTTTTCG

TCAAGGAGTGGAATGCGGATTTCAAGGACGAACTAATAAATTGGTTGATG

GTTGCTACTCCTTTTGGCAGGGAGCTGCCATTGCTTTCACACAAAAGTTA

ATTACGATTGTTGATAAGCAATTGAGGTCCTCGTATTCCTGCAAAAGGCC

ATCAGGAGAGGATGCCTGCAGCACCAGTTCATATGGGTGCACCGCAATA

AGTCTTCCTCTGCTGTGGACTATGCGAAGTTTGGATTTGATTTTATACAA

CAGAGCAACCAAATTGGCCCACTCTTCCATAACATTGCCCTGCAACAATA

CATCCTACTTTGTTCTCAGGTACTAGAGGGAGGCTTGAGGGATAAGCCTG

GAAAGAACAGAGATCACTATCATTCATGCTACTGCCTCAGTGGCCTCGCA

GTTAGCCAGTACAGTGCCATGACTGATACTGGTTCGTGCCCATTACCTCA

GCATGTGCTTGGACCGTACTCTAATTTGCTGGAGCCAATCCATCC

A disclosed FT6 polypeptide (SEQ ID NO:39) encoded by SEQ ID NO:37 has 414 amino acid residues and is presented in Table 9B using the one-letter amino acid code.

TABLE 9B

Encoded FT6 protein sequence (SEQ ID NO:39).

ADPDLPRLTVTQVEQMKVEARVGDIYRSLFGAAPNTKSIMLELWRDQHIE

YLTPGLRHMGPAFHVLDANRPWLCYWMVHPLALLDEALDDDLENDIIDFL

ARCQDKDGGYSGGPGQLPHLATTYAAVNTLVTIGSERALSSINRGNLYNF

MLQMKDVSGAFRMHDGGEIDVRASYTAISVASLVNILDFKLAKGVGDYIA

RCQTYEGGIAGEPYAEAHGGYTFCGLAALILLNEAEKVDLPSLIGWVAFR

QGVECGFQGRTNKLVDGCYSFWQGAAIAFTQKLITIVDKQLRSSYSCKRP

SGEDACSTSSYGCTANKSSSAVDYAKFGFDFIQQSNQIGPLFHNIALQQY

ILLCSQVLEGGLRDKPGKNRDHYHSCYCLSGLAVSQYSAMTDTGSCPLPQ

HVLGPYSNLLEPIH

Due to the nature of the cloning strategy the sequence presented is not full length. The percent identity of the *Glycine max* nucleotide sequence and its encoded amino acid sequence to that of other sequences is shown in FIG. 8.

Using the sequences disclosed herein as hybridization probes, one is able to screen and isolate full length sequences from cDNA or genomic libraries or use the rapid amplification of cDNA ends (RACE) technology or other such PCR techniques.

The present invention also includes a nucleic acid sequence complimentary to the *Zea maize* beta subunit of SEQ ID NO:37. The disclosed complimenary sequence is shown as SEQ ID NO:38.

SEQ ID NO:38

GGATGGATTGGCTCCAGCAAATTAGAGTACGGTCCAAGCACATGCTGAGGTAATGGGCACGAACCAGTATCAGTCA

TGGCACTGTACTGGCTAACTGCGAGGCCACTGAGGCAGTAGCATGAATGATAGTGATCTCTGTTCTTTCCAGGCTT

ATCCCTCAAGCCTCCCTCTAGTACCTGAGAACAAAGTAGGATGTATTGTTGCAGGGCAATGTTATGGAAGAGTGGG

CCAATTTGGTTGCTCTGTTGTATAAAATCAAATCCAAACTTCGCATAGTCCACAGCAGAGGAAGACTTATTCGCGG

TGCACCCATATGAACTGGTGCTGCAGGCATCCTCTCCTGATGGCCTTTTGCAGGAATACGAGGACCTCAATTGCTT

ATCAACAATCGTAATTAACTTTTGTGTGAAAGCAATGGCAGCTCCCTGCCAAAAGGAGTAGCAACCATCAACCAAT

TTATTAGTTCGTCCTTGAAATCCGCATTCCACTCCTTGACGAAAAGCCACCCAGCCAATCAAACTAGGCAAGTCAA

CTTTCTCTGCCTCATTAAGCAGGATCAAAGCAGCCAATCCACAGAATGTATACCCACCATGTGCTTCAGCATAAGG

CTCCCCAGCAATACCACCTTCATAAGTTTGACATCTTGCTATGTAGTCGCCTACACCTTTTGCCAGTTTAAAATCA

AGAATATTCACAAGGCTGGCAACCGATATAGCGGTGTAGGAAGCACGGACATCAATTTCGCCACCATCATGCATTC

TGAAAGCACCTGATACATCTTTCATCTGCAGCATAAAATTGTACAGGTTGCCCCTATTGATTGATGACAATGCTCT

TTCGCTCCCTATTGTCACAAGTGTATTTACAGCAGCATAAGTCGTAGCTAGGTGAGGCAACTGTCCAGGTCCACCA

CTATATCCACCATCTTTATCCTGACATCGAGCTAAGAAGTCTATGATATCATTCTCAAGATCATCATCAAGTGCTT

CATCCAGCAAAGCAAGTGGATGAACCATCCAGTAGCATAGCCAAGGGCGATTGGCATCTAGAACATGAAAGGCTGG

TCCCATATGCCTCAGCCCAGGCGTCAGATACTCGATATGCTGATCACGCCACAGCTCTAGCATGATGGATTTCGTG

TTGGGCGCGGCCCCGAAGAGGGAGCGGTAGATGTCGCCAACCCTGGCCTCCACCTTCATCTGCTCCACCTGCGTCA

CCGTGAGCCTCGGTAGGTCGGGATCCGCC

The FTA and FTB nucleic acids and amino acids disclosed above have homology to other members of the FT protein family (GenBank ID NOs: U63298, U83707, and U73203; WO 00/14207; Cutler et al., Science 273(5279): 1239–41, 1996; Ziegelhoffer et al., Proc Natl Acad Sci USA. 97(13):7633–8, 2000). The homology between these and other sequences is shown graphically in the ClustalW analysis shown in Tables 10A–10D. In the ClustalW alignment, the black outlined amino acid residues indicate regions of conserved sequence (i.e., regions that may be required to preserve structural or functional properties), whereas non-highlighted amino acid residues are less conserved and can potentially be altered to a much broader extent without altering protein structure or function.

Table 10A. ClustalW Nucleic Acid Analysis of FT Alpha Subunits

1) BNA-12; FT2 (SEQ ID NO:6)
2) At-FT-A; FT1 (SEQ ID NO:1)
3) PPI-Soy-FTA; FT4 (SEQ ID NO:31)
4) Pea-FT-A (SEQ ID NO:59)
5) Tomato-FTA (SEQ ID NO:60)
6) Rice-FT-A (SEQ ID NO:61)
7) Zea mays-FT-A (SEQ ID NO:62)
8) Soy1-FT-A (SEQ ID NO:63)
9) Soy2-FT-A (SEQ ID NO:64)
10) Triticum-FT-A (SEQ ID NO:65)

```
                        10        20        30        40        50        60        70
                ....|....|....|....|....|....|....|....|....|....|....|....|....|....|
BnA-12          ----------------------------------------------------------------------
At-FT-A         ----------------------------------------------------------------------
PPI-Soy-FTA     ----------------------------------------------------------AT--GCA
Pea-FT-A        CAACACCTACCTAGTGCTTCTAGTTCTGGTTCTAGGACTGAGAGTAAACAGAAGTGAAGAAGAATCCACA
Tomato-FTA      ---TACCCCGAAGGCAATTCCAGTATTGAACTACCGCCGGCAGTTTTCCGATCGGATCCCGGAGCCGACT
Rice-FT-A       -----------GCACGAGGTTCTAACGCCGCCGCCGCCGCCGTCTCCGCA-GAATCTGATCGATGCC
Zea mays-FT-A   -----------------GCACGAGACAGCGCAATTACTTAAGCTATTTGTATTCGGATCTGATCCAACCC
Soy1-FT-A       ---------------------------------------GCACGAGGATTAACGAAGGAT--GCA
Soy2-FT-A       -----------------------GCACGAGCTTGCGTGTGGAGTGAAGAAGATTAACGAAGGAT--GCA
Triticum-FT-A   ----------------------------------------------------------------------

80        90       100       110       120       130       140
                ....|....|....|....|....|....|....|....|....|....|....|....|....|....|
BnA-12          ----------------------------------------------------------------------
At-FT-A         ---GAGTCGGGAACATGAATTTCGACGAG---A-CCGTG----CCACTGAGCCAACCATTGGAGTGGTC
PPI-Soy-FTA     AT----CTGGGTCTAGCGAAGGAGAAGAGGTGCAGCAACGCGTGCCGTTGAGGGAGACAGTGGAGTGGTC
Pea-FT-A        ACATGGCCGGGAATATCGAAGTTGAAGAAG---ACGATCGTGTGCCGCTAAGATTACGACCTGAGTGGTC
Tomato-FTA      ATCAAATGCACAGTTGTGAGGT--GACGAA---A-ACGCGAATTCCTTTCAAGGAAAGCCCGACTGGGC
Rice-FT-A       GCCGTCGTCGACGTCGTCGGAGGGTGCCTC-CGACGAGTGGTTGCCACCCAGCCGGCGGCCGGAGCTGGC
Zea mays-FT-A   TGGTGGTCAGCTGGACTCATCGCCCATGGA-GCACACTAAGTCAGGCCCCAGCAGTTGGCCAGAACTGGC
Soy1-FT-A       AT----CTGGGTCTAGCGAAGGAGAAGAGGTGCAGCAACGCGTGCCGTTGAGGGAGACAGTGGAGTGGTC
Soy2-FT-A       AT----CTGGGTCTAGCGAAGGAGAAGAGGTGCAGCAACGCGTGCCGTTGAGGGAGACAGTGGAGTGGTC
Triticum-FT-A   ------------------------------------------------------------------C 150       160       170       180       190       200       210
                ....|....|....|....|....|....|....|....|....|....|....|....|....|....|
BnA-12          ----------------------------------------------------------------------
At-FT-A         AGACGTGGTCCCATTGACTCAGGACGATGGTCCGAATCCAGTGGTGCCAATTGCCTACAAGGAAGAGTTC
PPI-Soy-FTA     AGATGTTACTCCCGGTTCCTCAAAACGACGGCCCTAACCCTGTCGTTCCGATCCAGTACACTGAAGAGTTT
Pea-FT-A        AGATGTTACTCCGGGTTCCCCACAAGACGATGGCCCCTAGTCCTCGTGCCGATCAACTAGTCCGAAGAGTTT
Tomato-FTA      CGATGTGAAGCCCGTTCCGCAAGACGACGGGCCCTGCCCGGTTGTTCCATAGCCTACACAGAAGACTTC
Rice-FT-A       GGACGTGGTCCCCGTGACGCAGGACGACGGGCCCCACCCCGTGGTGGCCATCGCCTACCGGGACGAGTTC
Zea mays-FT-A   CGACGTGGTGCCCGTGCCGCAGGACGATGGGCCTACCCTGTCGGTGTCCATCGCCTATCGAGATGACTTT
Soy1-FT-A       AGATGTTACTCCGGGTTCCTCAAAACGACGGCCCTAAACCCTGTCGTTCCGATCCAGTACACTGAAGAGTTT
Soy2-FT-A       AGATGTTACTCCGGTTCCTCAAAACGACGGCCCTAAACCCTGTCGTTCCGATCCAGTACACTGAAGAGTTT
Triticum-FT-A   GGACGTGGCGCCCGCTGCGCAGGCCGACGGGCCCTGCCCCGTCGTCTCCATCGCTTACGCGGCGACTTC 220       230       240       250       260       270       280
                ....|....|....|....|....|....|....|....|....|....|....|....|....|....|
BnA-12          --------ATGGATTACTTCCGTGCGATTTACTTGTCCGACGAGCCTTCTGCTCGCGCGCTGCGACTCA
At-FT-A         CGCGAGACTATGGATTACTTCCGTGCGATTTACTTTCCGACGAGCCATCTCCTCGCGCACTACGACTCA
PPI-Soy-FTA     TCCGAAGTTATGGATTACTTTCGCGCCGTTTACCTCACCGATCGAACGCTCCCCTCGCGCCCTCGCTCTCA
Pea-FT-A        TCAGAAGTTATGGATTACTTCGTGCTGTTTACTTCGCCAAAGAACTTCCTCTCGCGCTCTTGCTCTCA
Tomato-FTA      TCTGAAACCATGGACTACTTCCGGGCAATTTACGTAGCCGATGAGCCATCTACACGCGCCCTCCAGCTTA
```

```
                    290       300       310       320       330       340       350
                ....|....|....|....|....|....|....|....|....|....|....|....|....|
Rice-FT-A       CGCGAGGTCATGGACTACTTCCGCGCCCTCTACTTCGCCGGCGAGCGCAGCGTCCGCGCCCTCCACCTCA
Zea mays-FT-A   CGTGAGGTCATGGATTACTTCCGCGCCCTCTACCTCACCGGTGAGCGAAGCCCTCGCGCTCTCCGCCTCA
Soy1-FT-A       TCCGAAGTTATGGATTACTTTCGCGCCGTTTACCTCACCGATGAACGCTCCCCTCGCGCCCTCGCTCTCA
Soy2-FT-A       TCCGAAGTTATGGATTACTTTCGCGCCGTTTACCTCACCGATGAACGCTCCCCTCGCGCCCTCGCTCTCA
Triticum-FT-A   CGCGAGGTCATGGACTACTTCCGCGCCCTCTACGCCGCCGGCGAGCGCAGCCCCCGCGCCCTCCGCCTCA
```

```
                    290       300       310       320       330       340       350
                ....|....|....|....|....|....|....|....|....|....|....|....|....|
BnA-12          CGGAAGAAGCTCTCCGCTTAAACTCGGCAACTACACCGTGTGGCACTTCGGGCGCTTAGTACTCGAGGA
At-FT-A         CGGAAGAAACCCTCCTCTTAAACTCCGGCAACTACACAGTGTGGCATTTCAGGCGCCTAGTACTCGAGGC
PPI-Soy-FTA     CAGCCGAAGCCGTTCAATTCAACTCCGGCAACTACACTGTGTGGCATTTCCGACGGTTGTTACTTGAGTC
Pea-FT-A        CCGCCGAAGCTATGGTTTAAACGCCGGAAACTACACTGTGTGGCATTTCCGGCCGGTTATTACTTGAGTC
Tomato-FTA      CTGGTGAAGCTATCAGCTAAACCCTGGAAATTACACTGTATGGCAATTTAGGCGCTGTTGTGCTGGAGGC
Rice-FT-A       CCGCCGAGGTCATCGAGCTCAACCCCCGGCAACTACACACGTGTGGCATTTTAGGCGTCTTGTTCTAGAGC
Zea mays-FT-A   CCGCCGAGGCCATCGAGCTCAACCCCGGCAACTACACTGTCTGGCATTTCCGGCGCCTTATTCTGAGTC
Soy1-FT-A       CAGCCGAAGCCGTTCAATTCAACTCCGGCAACTACACTGTGTGGCATTTCCGACGGTTGTTACTTGAGTC
Soy2-FT-A       CAGCCGAAGCCGTTCAATTCAACTCCGGCAACTACACTGTGTGGCATTTCCGACGGTTGTTACTTGAGTC
Triticum-FT-A   CCGCCGACGCCATCCACCCTCAACCCCGGCAACTACACTGTATGGCATTTCAGGCGCGTTGTTCTAGAGGC
```

```
                    360       370       380       390       400       410       420
                ....|....|....|....|....|....|....|....|....|....|....|....|....|
BnA-12          GCTTAATAACGACTTGTATGAAGAGCTCAAGTTCATCGAAAGCATTGCTGAGGATAACTCTAAGAACTAC
At-FT-A         CCTTAATCACGACTTGTTTGAAGAACTCGAGTTCATCGAACGCATTGCTGAGGATAACTCTAAGAACTAC
PPI-Soy-FTA     GCTAAAAGTCGACTTGAACGATGAACTGGAGTTTGTGGAGCGTATGGCCGCTGAAATTCTAAAAATTAT
Pea-FT-A        ACTGAAAGTTGACCTACATGTTGAACGGGAATTCGTGGACGCTGTTGCCAGTGGCAATTCAAAAAATTAT
Tomato-FTA      ATTGGGTGTTGATTTACGTGAAGAATTCAAGTTTGTTGATCGCATTGCTGGGGAGAATACCAAAAATTAT
Rice-FT-A       ACTGGATGCTGATCTGCGTGAGGAAATGGATTTTGTGGACCGAATTGTCGAATGTAACCCAAAAAATTAT
Zea mays-FT-A   ACTAGATTTTGATTTACTAGAGGAGATGAAATTTGTCGAAAAAATTGCTGAATGCAATCCAAAAAATTAC
Soy1-FT-A       GCTAAAAGTCGACTTGAACGATGAACTGGATTTTGTGGAGCGTATGGCCGCTGAAATTCTAAAAATTAT
Soy2-FT-A       GCTAAAAGTCGACTTGAACGATGAACTGGAGTTTGTGGAGCGTATGGCCGCTGGAAATTCTAAAAATTAT
Triticum-FT-A   ACTGGATGCTGATTTATTGCTAGAAATGCATTTTGTGGACCAAATTGCTGAATCTAATCCAAAAAATTAC
```

```
                    430       440       450       460       470       480       490
                ....|....|....|....|....|....|....|....|....|....|....|....|....|
BnA-12          CAGTTGTGG--------------------------------CATCATCGACGATGGGTCGCAGAGA
At-FT-A         CAACTGTGG--------------------------------CATCATCGGCGATGGGTTGCAGAGA
PPI-Soy-FTA     CAGATGTGN----ATGTTCTG----------TAG---------GCATCCTAGACGATGGGTTGCCGAGA
Pea-FT-A        CAGATTTGG--------------------------------CATCATAGACGATGGGTTGCTGAGA
Tomato-FTA      CAAATATGG--------------------------------CATCATAGACGGTGGCTTGCTGAGA
Rice-FT-A       CAAATCTGG--------------------------------CATCACAAGAGATGGCTTGCGGAGA
Zea mays-FT-A   CAATTCTGG--------------------------------CACCATAAGAGATGGCTTGCTGAGA
Soy1-FT-A       CAGATGTGG--------------------------------CATCATAGACGATGGGTTGCCGAGA
Soy2-FT-A       CAGATGTGGTGTGATGCTCTGCTCTGCTCTTTCTTCCATACTTTGCATCATAGACGATGGGTTGCCGAGA
Triticum-FT-A   CAAGTCTGG--------------------------------CATCACAAGAGATGGCTTGCTGAGA
```

```
                    500       510       520       530       540       550       560
                ....|....|....|....|....|....|....|....|....|....|....|....|....|
BnA-12          AACTGGGTCCTGATGTTGCAGGAAAGGAACTTGAGTTTACTCGGAGGGTACTATCACTTGATGCCAAGCA
At-FT-A         AACTGGGTCCTGATGTTGCAGGGAGAGAACTTGAATTTACCCGTAGAGTACTTTCACTTGATGCCAAACA
PPI-Soy-FTA     AGTTAGGTCCTGAAGCTAGAAACAATGAGCTCGAGTTCACCAAAAAGATACTGTCCGTTGATGCCAAACA
Pea-FT-A        AATTAGGACCTGAAGCTAGAAACAGTGAACTTGAGTTCACCAAGAAAATATTTCTCAGGATGCAAAAAA
Tomato-FTA      AGCTGGAGACCAGATATTGCAAATAAAGAGCTACGAATTTACAAGGAAGATACTTTCTATGGATGCTAAAA
Rice-FT-A       AATTAGGACCAGATATTGCAAATAAAGAGCACGAATTTACAAGGAAGATACTTTCTATGGATGCTAAAA
Zea mays-FT-A   AATTAGGACCTGGTATTGCAAACAAAGAGCATGAATTCACAATGAAGATACTTGCTATTGATGCAAAAA
Soy1-FT-A       AGTTAGGTCCTGAAGCTAGAAACAATGAGCTCGAGTTCACCAAAAAGATACTGTCCGTTGATGCCAAACA
Soy2-FT-A       AGTTAGGTCCTGAAGCTAGAAACAATGAGCTCGAGTTCACCAAAAAGATACTGTCCGTTGATGCCAAACA
Triticum-FT-A   AAATAGGACCAGATGCTGCAAATAGTGAACATGACTTCACAAGGAAGATACTTGCTATGGATGCTAAAA
```

```
                    570       580       590       600       610       620       630
                ....|....|....|....|....|....|....|....|....|....|....|....|....|
BnA-12          TTATCATGCTTGGTCACATAGGCAGTGGGCGCTACAAGCATTAGGAGGATGGGAAAATGAGCTTAACTAC
At-FT-A         TTATCATGCTTGGTCACATAGGCAGTGGACACTACGGGCATTAGGAGGATGGGAAGATGAGCTCGATTAC
PPI-Soy-FTA     TTATCATGCATGGTCTCATAGACAGTGGGCTCTTCAAACACTAGGAGGATGGGAAGATGAACTTAATTAT
Pea-FT-A        CTATCATGCATGGTCTCATAGGCAGTGGGTTCTTCAAAATCTAGGAGGATGGGAAGATGAACTCAGTTAT
Tomato-FTA      TTATCATGCTTGGTCCCATCGGCAGTGGGTCCTTCAAGCACTTGGAGGATGGGAAGATGAGCTTGCTTAT
Rice-FT-A       TTACCATGCTTGGTCTCATAGGCAGTGGGTTCTTCAAGCACTTGGTGGATGGGAGACTGAACTACAGTAT
Zea mays-FT-A   TTATCATGCTTGGTCTCATAGGCAGTGGGTTCTTCAAGCGTTGGCGGGATGGGAGACTGAATTAGAATAC
Soy1-FT-A       TTATCATGCATGGTCTCATAGACAGTGGGCTCTTCAAACACTAGGAGGATGGGAAGATGAACTTAATTAT
Soy2-FT-A       TTATCATGCATGGTCTCATAGACAGTGGGCTCTTCAAACACTAGGAGGATGGGAAGATGAACTTAATTAT
Triticum-FT-A   CTACCATGCTTGGTCCCATAGGCAGTGGGTTCTTCAAGCATTGGGTGGATGGGAGAGTGAACTGCAGTAC
```

```
                640       650       660       670       680       690       700
                ....|....|....|....|....|....|....|....|....|....|....|....|....|
BnA-12          TGCCACGAGCTCCTTGAAGCTGACGTCTTTAACAACTCTGCATGGAATCAGAGGTATTACGTTATAACTA
At-FT-A         TGTCACGAGCTCCTTGAAGCTGACGTCTTTAACAATTCCGCCTGGAATCAGAGGTATTATGTCATCACCC
PPI-Soy-FTA     TGCACAGAACTACTTAAAGAAGACATTTTTAACAATTCTGCTTGGAATCAGAGATATTTTGTCATAACAA
Pea-FT-A        TGTAGTGAACTGCTTGCAGAAGACATATTTAACAATTCTGCTTGGAATCAGAGATACTTCGTCATAACAA
Tomato-FTA      TGTCAACAACTCCTTGAAGATGATATTCTGCTTGGAATCAGATACTTTGTCGTAACAC
Rice-FT-A       TGCAACCAGCTGCTTGACGACGTCTTCAATAATTCACGCTTGGAATCAGAGATACCTTGTAATAACAA
Zea mays-FT-A   TGTCACCACTTACTTAAGGAAGACGTCTTCAATAATTCAGCTTGGAATCAGAGATACTTTGTTATAACAA
Soy1-FT-A       TGCACAGAACTACTTAAAGAAGACATTTTTAACAATTCTGCTTGGAATCAGAGATATTTTGTCATAACAA
Soy2-FT-A       TGCACAGAACTACTTAAAGAAGACATTTTTAACAATTCTGCTTGGAATCAGAGATATTTTGTCATAACAA
Triticum-FT-A   TGCAACCAGCTTCTTGAGGAAGATGTCTTCAATAACTCAGCTTGGAATCAGAGATACCTTGTGGTAACAC 710       720       730       740       750       760       770
                ....|....|....|....|....|....|....|....|....|....|....|....|....|
BnA-12          GATCACCTTCGTTGGGAGGCCTAGAAGCCATGAGAGAATCTGAAGTAAGCTACACAGTCAAAGCCATTTT
At-FT-A         AATCTCCTTTGTTGGGAGGCCTAGAAGCCATGAGAGAATCTGAAGTAAGCTACACAATCAAAGCCATTTT
PPI-Soy-FTA     GGTCTCCTTTCTTGGGGGGCCTAAAAAGCTATGAGAGAGTCTGAAGTGCTTTACACCATCGAAGCCATTAT
Pea-FT-A        GGTCTCCGTCTTGGGAGGGCTAAAAAGCCATGAGAGAGTCTGAAGTGCTTTTCACCGTTGAAGCCATTAT
Tomato-FTA      GATCACCTCTACTAGGGGCCTAGTGGCAATGAGGGAATTGAAGTGAATTACACAGTTCAAGCCATCAG
Rice-FT-A       GTTCACCACTTCTTGGAGGCCTTGCAGCAATGCGTGACTCGGAAGTGGATTACACAGTTGGGGCTATTCT
Zea mays-FT-A   GATCACCATTTCTTGCTGGCCTTGCGGCGAATGCGTGATTCAGAAGTAGACTACACAATTGAAGCCATTAT
Soy1-FT-A       GGTCTCCTTTCTTGGGCGGCCTAAAAAGCTATGAGAGAGTCTGAAGTGCTTTACACCATTGAAGCCATTAT
Soy2-FT-A       GGTCTCCTTTCTTGGGGGGCCTAAAAAGCTATGAGAGAGTCTGAAGTGCTTTACACCATTGAAGCCATTAT
Triticum-FT-A   GATCACCAATTCTTGGGGGCCTTGCGGCAATCGCGACTCAGAAGTAGATTACACAGTTGAGGCCATTAT 780       790       800       810       820       830       840
                ....|....|....|....|....|....|....|....|....|....|....|....|....|
BnA-12          AGCAAATCCGGGAACGAGAGCTCTTGGAGGCTACCTGAAAGCCCTTTACAAAGACGACACAGAGTCTTGG
At-FT-A         AACCAATCCTGCAAACGAGAGCTCATGGCGATACCTAAAACGCTTTACAAAGACGACAAAGAATCCTGG
PPI-Soy-FTA     AGCCTACCCTGAAAATGAAAGCTCGTGGAGATATCTACGAGGACTTTATAAAGGTGAAACTACTTCATGG
Pea-FT-A        TTCTTACCCAGAAAATGAAAGCTCATGGAGATATCTTCGAGGACTTTTCAAAGATGAATCCACGTTATAT
Tomato-FTA      AGCTAGTCCAGAGAATGAAAGTCCTTGGAGGTATCTTCGTGGTCTTTACAAGAATGATACACAATCTCTA
Rice-FT-A       GGCTAACCCTCAGAATGAAAGCCCCTGGAGATACCTCAAAGCCTGTACAAGGTGAAAATAACTTGCTG
Zea mays-FT-A   AGCAAAACGCTCAGAAAATGAAAGCCCCTGGAGGTACCTCAAGGCTCTATACAAGGGTGAGAATAACCTGCTA
Soy1-FT-A       AGCCTACCCTGAAAATGAAAGCTCGTGGAGATATCTACGAGGACTTTATAAAGGTGAAACTACTTCATGG
Soy2-FT-A       AGCCTACCCTGAAAATGAAAGCTCGTGGAGATATCTACGAGGACTTTATAAAGGTGAAACTACTTCATGG
Triticum-FT-A   GGTGAACCCTCAGAATGAAAGCCCCTGGAGATACCTCAGAGGTTTATATAAGGATGATAACAATTTGCTG 850       860       870       880       890       900       910
                ....|....|....|....|....|....|....|....|....|....|....|....|....|
BnA-12          ATTAGTGATCCAAGTGTTTGCTCAGTCTGTTTGAAAGTTCTCTCACGCGCGGACTGCTTCCATGGATTCG
At-FT-A         ATTAGTGATCCAAGTGTTTGCCTCAGTCTGTTTGAATGTTCTATCCCGCACAGATTGCTTCCATGGATTCG
PPI-Soy-FTA     GTAAATGATCCTCAAGTTTCTTCAGTATGCCTAAAAGATTTTGAGAACTAAGAGCAAC---TACGTGTTTG
Pea-FT-A        GTAAATGATCGCCAAGTATCTTCATTATGTTTAAAGATTTTCAAAACTAAGAGCAAC---TATTTGTTTG
Tomato-FTA      GTTCAGGATTGTCAAGTAGCATCAGTACTTTGGGACGTCTTAACCTCCCAAAATAGT---CATGTGCACG
Rice-FT-A       ATGGCTGATGAGCGCATCTCTGATGTTTGTCTCAAGGTCCTGAAACATGATTCGACC---TGCGTATTTG
Zea mays-FT-A   GTAGAGGACGAGCGCATCTCTGCTGTTTGTTTCAAGGTCCTGAAGAATGATTGGACT---TGTGTATTTG
Soy1-FT-A       GTAAATGATCCTCAAGTTTCTTCAGTATGCCTAAAAGATTTTGAGAACTAAGAGCAAC---TACGTGTTTG
Soy2-FT-A       GTAAATGATCCTCAAGTTTCTTCAGTATGCCTAAAAGATTTTGAGAACTAAGAGCAAC---TACGTGTTTG
Triticum-FT-A   GTGGCTGATAATCGCATTTCTGATGCTTGCCTCAAGGTCCTGAATAAGGATTGGACA---TGCGTATTTG 920       930       940       950       960       970       980
                ....|....|....|....|....|....|....|....|....|....|....|....|....|
BnA-12          CTCTGAGCACCCTTTTGGATCTTCTGTGCGATGGGT-TGAGACCAACCAACCAGCATAGAAGACTCGGTGA
At-FT-A         CTCTGAGCACGCTTTTGGATCTTCTGTGTGATGGAC-TGAGACCAACCAGCAGCATAGAAGACTCAGTGA
PPI-Soy-FTA     CTCTTAGCACTATTTTAGATCTTATATGCTTGGTTAT-CAACCAAATGAAGACATTAGAGATGCCATTG
Pea-FT-A        CTCTAAGCTAGTCTGCTGGATCT-ATCTGCCTCGGTTATTCAACCAAATGAAGATTTCAGAGATGCCATTG
Tomato-FTA      CTCTGAGGTTCTTGTTGGATCTTCTTTGTCATGATT-TGGAACCGAGCCAAGAATTGAAAAGTGCTGTA
Rice-FT-A       CTTTGAGCTTGCTGCTCGATCTTCTTCAAATTGGTT-TACAACCTTCAGATGAACTCAAAGGAACTATCG
Zea mays-FT-A   CTTTGAGTTTGCTGCTCGATCTTCTCTGCACTGGTT-TGCACCCTTCAGATGAACTTAGGTCCACTCTTG
Soy1-FT-A       CTCTTAGCACTATTTTAGATCTTATATGCTTTGGTTAT-CAACCAAATGAAGACATTAGAGATGCCATTG
Soy2-FT-A       CTCTTAGCACTATTTTAGATCTTATATGCTTTGGTTAT-CAACCAAATGAAGACATTAGAGATGCCATTG
Triticum-FT-A   CTTTGAGCTTCCTGCTGATCTTCTTCGCATGGGTT-TGCAGCCTTCGAATGAACTAAAGGAACCATCG 990       1000      1010      1020      1030      1040      1050
                ....|....|....|....|....|....|....|....|....|....|....|....|....|
BnA-12          AAGCTCTAG----CT------AATGAAGA---------------------------A-CCAGAGAC
At-FT-A         GAGCTCTAG----CT------AATGAAGA---------------------------A-CCAGAGAC
PPI-Soy-FTA     ACGCCTTAAAGACCGCAGATATGGATAAACAAGATTTAGATGATGAGAAAGGGAACAACAAAATTT
Pea-FT-A        AGGCTTTAA-GACTTCAGATTTTGATAAA---------------------------A-CAAGATTC
```

```
                  1060       1070       1080       1090       1100       1110       1120
                 ....|....|....|....|....|....|....|....|....|....|....|....|....|....|
Tomato-FTA       ATGTTCTTA---CTCCC--CAGTCATGCTC--------------------------------A-CCAGATTT
Rice-FT-A        AAGCAATAAAGAACTCTGATCCTGAAGCAGATGA------------------AG---CA-GTAGATGC
Zea mays-FT-A    AAACAATAAGGAGCTCCATCCTGAAACCGC-------------------------------GGATGA
Soy1-FT-A        ACGCCTTAAAGACCGCAGATATGGATAAACAAGATTTAGATGATGATGAGAAAGGGGAACAACAAATTT
Soy2-FT-A        ACGCCTTAAAGACCGCAGATATGGATAAACAAGATTTAGATGATGATGAGAAAGGGGAACAACAAATTT
Triticum-FT-A    AAGCAATGGAGAACTCTGATCCTGAAACGGG------------------------------ACATGC 1060       1070       1080       1090       1100       1110       1120
                 ....|....|....|....|....|....|....|....|....|....|....|....|....|....|
BnA-12           TAACTTGGCCAATTTGGTGTGTACCATTCTGTGTCGTGTTGATCCAATAAGAGCTAACTATTGGGCATGG
At-FT-A          TAACTTGGCCAATTTGGTGTGTACTATTCTTGGTCGTGTAGATCCTATAAGAGCTAACTATTGGGCATGG
PPI-Soy-FTA      AAATATAGCACGAAATATTTGTTCTATCCTAAAACAAGTTGATCCAATTAGAACCAACTATTGGATTTGG
Pea-FT-A         AGATATAGCAATAACTATTTGTTCTATTTTAGAACAAGTTGATCCAATTAGAGTCAACTATTGGGTCTGG
Tomato-FTA       AGCACTGACAAAGAAATTTGTTCCATTGGAACATGCTGATCCAATGAGAGTAAAATATTGGAATTGG
Rice-FT-A        TGATCTTGCGACTGCAATCTGCTCAATATTGCAGAGATGTGATCCCCTGCGGATAAATTACTGTCCTGG
Zea mays-FT-A    TGATCCTGCAGCCGCTGTTTGCTGTATCCTGCAGAAATGTGATCCCCTGCGGGTAAATTATTGGTCTTGG
Soy1-FT-A        AAATATAGCACGAAATATTTGTTCTATCCTAAAACAAGTTGATCCAATTAGAACCAACTATTGGATTTGG
Soy2-FT-A        AAATATAGCACGAAATATTTGTTCTATCCTAAAACAAGTTGATCCAATTAGAACCAACTATTGGATTTGG
Triticum-FT-A    TGATATTGCAGTAGCTGTCTGCTCAATCCTGCAGAAATGTGATCCCCTGCGGATAAACTACTGGTCATGG 1130       1140       1150       1160       1170       1180       1190
                 ....|....|....|....|....|....|....|....|....|....|....|....|....|....|
BnA-12           -------------------------------------------------------------------
At-FT-A          AGGAAGAGCAAGATTACA----GTGGC-AGCAATTTGAATATGTGACGCCCCAAAATCACACTTGAAAAA
PPI-Soy-FTA      CGCAAGAGCAGACTTC-------CT------------------------------------------
Pea-FT-A         CGGAAGAGTAGACTTC-------CTCA-GGCAGCGTAAAGGACAAACTTATGTCATATGTGTAATTTTA
Tomato-FTA       CGCAAGAGCATGGTTCGG----GTTCA-ATTACTTCAGAGTCAGAATGCAGAGAGGTTG-GCTAATTTGA
Rice-FT-A        TACAGGACCACTATTTCT----TCTCA-AAC--CTGAAG----CATGCAGTGGCCTCCATGA------GG
Zea mays-FT-A    TTCAAGGACACTCTTTCTCAGATCCATGACTTCACATGGGTTCACCCCTTGTCCGCGCTGGTCCGGGCC
Soy1-FT-A        CGCAAGAGCAGACTTC-------CTCT-ATCAGCTTAGTAACCAAAGTAATTAAA---GGGCAACTCTGT
Soy2-FT-A        CGCAAGAGCAGACTTC-------CTCT-ATCAGCTTAGTAACCAAAGTAATTAAA---GGGCAACTCTGT
Triticum-FT-A    TACCAGACCACTCTTTCT----TCTTA-GACATCTGAAAA-TTCAGCTGAAGACAGTTTTAG------CA 1200       1210       1220       1230       1240       1250       1260
                 ....|....|....|....|....|....|....|....|....|....|....|....|....|....|
BnA-12           -------------------------------------------------------------------
At-FT-A          GACTTGATTAT--TAGT-TTTAACGT----------AATTAACTGCTTATTTATGAATCACATG-TTCAT
PPI-Soy-FTA      -------------------------------------------------------------------
Pea-FT-A         GTCTATTGGAATTTGACGTCATGGAT----------AACAGGGTGGTTGTATTTTGTTATGATAT-GTTT
Tomato-FTA       GTGTTCAAGAA--TGAC-TTGTGAGA----------ATATTGTACTGTGATTACGAAATACATA-CTTGC
Rice-FT-A        TCATAATGGAGATATCTTCTAT-----------------CTTCGTGTGA---------TTCTG
Zea mays-FT-A    CTGTGAGATAGACATGTTTTTAGATAGTTTCATTGGACACCCAAACAGAGCGGACAGAGTGTATGGCTGCT
Soy1-FT-A        GTTATGTGTAACCTAGT-TTATTGA----------AACTGGATTTTTATT--ATTATTATTT-TTTAT
Soy2-FT-A        GTTATGTGTAACCTAGT-TTATTGA----------AACTGGATTTTTATT--ATTATTATTT-TTTAT
Triticum-FT-A    GCATGATGTAAACTCAATCGAAGGGGTT--------------GACGCAGTGTATGAAAAACCT--TTCCT 1270       1280       1290       1300       1310       1320       1330
                 ....|....|....|....|....|....|....|....|....|....|....|....|....|....|
BnA-12           -------------------------------------------------------------------
At-FT-A          GT-TAACATGTATCAAAACAATCTTGATTTCTCAAAAAAAAAAAAAAAAAAAAAAAAAAAA-------
PPI-Soy-FTA      -------------------------------------------------------------------
Pea-FT-A         CC-AGATGTATTTCTATATTTAACAGCAAAGTTGATTTAACATTGGTGTTAACAAACCAATGATCTCCAA
Tomato-FTA       ATCTAAGGTGATCCTTCGGGCACATGTGCTGGGAAGTGACTGAATATCACGAAGAACTAAAAAAACTGTG
Rice-FT-A        GGCGTTGAGGTGCCT---AGCTACATTTGTTATGAACTTTCCTTGGGCATAACTGATCACTGATATTAC-
Zea mays-FT-A    ACCTTCTCCGTGACTGAAAGCAGTGCTTGTAACGA--TTTTGTTTAGTAAAATTTGTGAGTGTTACTGCT
Soy1-FT-A        GT-TGTCATGTATCTGTTTGT----GCAAATTT------ATCTTTTTGTCATGCCATTACTGGCATTTGA
Soy2-FT-A        GT-TGTCATGTATCTGTTTGT----GCAAATTT------ATCTTTTTGTCATGCCATTACTGGCATTTGA
Triticum-FT-A    GTGATCTTGGTGCGG---AGCAA--TTTGTACTGA--TTTTACTGGGAAAATCAATCAATGACAGCATG 1340       1350       1360       1370       1380       1390       1400
                 ....|....|....|....|....|....|....|....|....|....|....|....|....|....|
BnA-12           -------------------------------------------------------------------
At-FT-A          -------------------------------------------------------------------
PPI-Soy-FTA      -------------------------------------------------------------------
Pea-FT-A         AAAATCAATGTTTTATTTCTCTTCATTTGTCTGATTTTGTGGCATAACATTCTTGATGAT-TTTGTGGTA
Tomato-FTA       ATTGGCAACATTGTACTACTCCAAATAGGTCACTTTCGATGACTTTTTGTACTGCCTTGA-GTTTTGGCT
Rice-FT-A        TCCAATATTGTGTTCTAAA-----------------------------------------------
Zea mays-FT-A    CCAAACAACACCTTATGCAACCATATTTGAATAT----TTCACATGTAAGCT---TGA--------A-TC
Soy1-FT-A        GTG--TAAGGATTGAAAGCCATGCA-------GAATAAGAAATTTAAGTTTTTT-------TTTCCGTTG
Soy2-FT-A        GTG--TAAGGATTGAAAGCCATGCA-------GAATAAGAAATTTAAGTTTTTT-------TTTCCGTTG
Triticum-FT-A    CCCAACAATGTCTTGTGTGAATATGTTACTGCCTGATATTCACATGTTAGCAGAATGAGAATAACCAATC
```

```
                       1410      1420      1430      1440      1450      1460      1470
                  ....|....|....|....|....|....|....|....|....|....|....|....|....|....|
BnA-12            ----------------------------------------------------------------------
At-FT-A           ----------------------------------------------------------------------
PPI-Soy-FTA       ----------------------------------------------------------------------
Pea-FT-A          AAAAAAAAAAAAAAAAAAAAA-------------------------------------------------
Tomato-FTA        CTGCTATGTTTTGTAAGTTTTGGATATGGATGCATAGCTTATTGATACTTTTGGTGACTTAAAATACTCT
Rice-FT-A         ----------------------------------------------------------------------
Zea mays-FT-A     CAGGTGTGTTTGTTAATGTATTACACTT--G-CCATGGGAGCCTAAATGAGACCCATAATCACTTCCACT
Soy1-FT-A         AAAA------------------------------------------------------------------
Soy2-FT-A         AAAAAAAAAAAAAAAAAAAAA-------------------------------------------------
Triticum-FT-A     AAACTCCAACGAGCAGATTGTTACAGTAACGGCCACTGGTGGTGTGAAAATCCTGAAATCTGCTTCAGTC 1480      1490      1500      1510      1520      1530      1540
                  ....|....|....|....|....|....|....|....|....|....|....|....|....|....|
BnA-12            ----------------------------------------------------------------------
At-FT-A           ----------------------------------------------------------------------
PPI-Soy-FTA       ----------------------------------------------------------------------
Pea-FT-A          ----------------------------------------------------------------------
Tomato-FTA        GGAAGGCAGGTAGCATGTGTATAATTCACTGTTACTTCCCATGTCGAGTTAGATGCTTGAAAATTTTAGT
Rice-FT-A         ----------------------------------------------------------------------
Zea mays-FT-A     AGAGTCGGAAGACCGT-GTCGAGCAGTTCACTCATATGGTCACTTAAAGCAAAAAAAAAAAAAAAAAAA-
Soy1-FT-A         ----------------------------------------------------------------------
Soy2-FT-A         ----------------------------------------------------------------------
Triticum-FT-A     ACTTTGCCTTGTTTACAGTTGAGTCTGTTGTTGTGATCTGTACCTAATGCATGTACACAATCATCAAATT 1550      1560      1570      1580      1590      1600      1610
                  ....|....|....|....|....|....|....|....|....|....|....|....|....|....|
BnA-12            ----------------------------------------------------------------------
At-FT-A           ----------------------------------------------------------------------
PPI-Soy-FTA       ----------------------------------------------------------------------
Pea-FT-A          ----------------------------------------------------------------------
Tomato-FTA        AGGTGTTCTTTTATGAAGCACACATTAATGTGGAAAAAAAAAAAAAAAAAAAAAAAAAAAAAAAAAAAAA
Rice-FT-A         ----------------------------------------------------------------------
Zea mays-FT-A     ----------------------------------------------------------------------
Soy1-FT-A         ----------------------------------------------------------------------
Soy2-FT-A         ----------------------------------------------------------------------
Triticum-FT-A     ATTAGTTTTTGTACCAATGAGTATTCGATGAAAAAAAAAAAAAAAA------------------------

BnA-12            -
At-FT-A           -
PPI-Soy-FTA       -
Pea-FT-A          -
Tomato-FTA        A
Rice-FT-A         -
Zea mays-FT-A     -
Soy1-FT-A         -
Soy2-FT-A         -
Triticum-FT-A     -
```

Table 10B. ClustalW Amino Acid Analysis of FT Alpha Subunits

1) BNA-12; FT2 (SEQ ID NO:7)
2) At-FT-A; FT1 (SEQ ID NO:5)
3) PPI-Soy-FTA; FT4 (SEQ ID NO:33)
4) Pea-FT-A (SEQ ID NO:66)
5) Tomato-FTA (SEQ ID NO:67)
6) Rice-FT-A (SEQ ID NO:68)
7) Zea mays-FT-A (SEQ ID NO:69)
8) Soy1-FT-A (SEQ ID NO:70)
9) Soy2-FT-A (SEQ ID NO:71)

10) Triticum-FT-A (SEQ ID NO:72)

```
                        10        20        30        40        50        60        70
                ....|....|....|....|....|....|....|....|....|....|....|....|....|....|
BnA-12          ------------------------------------------------MDYFRAIYFSDERSARALR
At-FT-A         ---------MNFDETNPLSQRLEWDVVPLTQDGPNPVVPIAYKEEPRETMDYFRAIYFSDERSPRALR
PPI-Soy-FTA     -MESGSSEGEEVQQRVPLRERVEWSDVTPVPQNDGPNPVVPIQYTEEFSEVMDYFRAVYLIDERSPRALA
Pea-FT-A        --MAGNIEVEE-DDRVPLRLRPEWSDVTPIPQDDGPSPVVPINYSEEFSEVMDYFRAVYFAKELSSRALA
Tomato-FT-A     -----MDSCEVTKTRIPFKERPSWDVKPVPQDDGPCPVVPIAYTECFSETMDYFRAIYVADERSTRALQ
RiceFT-A        MAPSSTSSEGASDEWLPPSRRPELDVVPVTQDDGHPVVAIAYRDEFREVMDYFRALYFAGERSVRALH
Zea mays-FT-A   ---------MEHTLSGPSSWPELADVVPVPQDDGPSPVVSIAYRDEFRGVMDYFRALYLIGERSPRALR
Soy1-FT-A       -MESGSSEGEEVQQRVPLRERVEWSDVTPVPQNDGPNPVVPIQYTEEFSEVMDYFRAVYLIDERSPRALA
Soy2-FT-A       -MESGSSEGEEVQQRVPLRERVEWSDVTPVPQNDGPNPVVPIQYTEEFSEVMDYFRAVYLIDERSPRALA
Triticum-FT-A   ---------------------DVAPIPQADGPCPVVSIAYRGEFREVMDYFRALYAAGERSPRALR 80        90       100       110       120       130       140
                ....|....|....|....|....|....|....|....|....|....|....|....|....|....|
BnA-12          LTEEALRLNSGNYTVWHFGRLIVLEEINNDIYBELKPIESIAEDNSKNYOW-----------HHRRWVA
At-FT-A         LTEETLLLNSGNYTVWHFRRLIVLEALNHDLFSELKFERIAEDNSKNYQLW-----------HHRRWVA
PPI-Soy-FTA     LTAEAVQFNSGNYTVWHFRRLILESLKVDLNDELFVERMAAGNSKNYQWX--------MFCRHPRRWVA
Pea-FT-A        LTAEAIGLNAGNYTVWHFRRLILESLKVDLHVERDFVERMASGNSKNYQW-----------HHRRWVA
Tomato-FT-A     LTGEAINPGNYTVWQFRRLILEALGVDLRELKFVDRIAGENTKNYQIW-----------HHRRWIA
RiceFT-A        LTAEVIDLNPGNYTVWHFRRLVLEALDADLRBEMDFVRIVECNPKNYQIW-----------HHKRWIA
Zea mays-FT-A   LTAEAIELNPGNYTVWHFRRLISEDFDLLEMKFVELIAECNPKNYQIW-----------HHLRWIA
Soy1-FT-A       LTAEAVQFNSGNYTVWHFRRLLLESLKVDLNDELFVERMAAGNSKNYQIW-----------HHRRWVA
Soy2-FT-A       LTAEAVQFNSGNYTVWHFRRLLLESLKVDLNDELFVERMAAGNSKNYQVWCDALLCSFFHTLHHRRWVA
Triticum-FT-A   LTADAIHLNPGNYTVWHFRRVVLGALDADLLLEIHFVDCIAESNPLNYQW-----------HHKRWIA 150       160       170       180       190       200       210
                ....|....|....|....|....|....|....|....|....|....|....|....|....|....|
BnA-12          EKLGPDVAGLEKEFTRRVLSIDAKHYHAWSHRQWALQALGGWENELNYCHELLEADVFNNSAWNQRYVI
At-FT-A         EKLGPDVAGRELEFTRRVLSIDAKHYHAWSHRQWTLRALGGWEDELYCHELLEADVFNNSAWNQRYMVI
PPI-Soy-FTA     EKLGPEARNNELEFTKILSVDAKHYHAWSHRQWALQTLGGWEDELNYGTELLKEDIFNNSAWNQRYFVI
Pea-FT-A        EKLGPEARNSELEFTKILSVDAKHYHAWSHRQWVLQNLGGWEDELSYGSELLAEDLFNNSAWNQRYFVI
Tomato-FT-A     EKLGADAVTNELEFTKKIFSQDAKNYHAWSHRQWVLQALGGWEDELAYCQLLEEDIYNNSAWNQRYFVI
RiceFT-A        EKLGPDIANKEHEFTRKILSMDAKYHAWSHRQWALQALGGWETELNYCNLLEEDVFNNSAWNQRYLVI
Zea mays-FT-A   EKLGPGIANKEHEFTMKILAIDDALNYHAWSHRQWALQTLGGWETELEYGDHLLKEDIFNNSAWNQRYFVI
Soy1-FT-A       EKLGPEARNNELEFTKKILSVDAKHYHAWSHRQWALQTLGGWEDELNYCTELLKEDIFNNSAWNQRYFVI
Soy2-FT-A       EKLGPEARNNELEFTKILSVDAKHYHAWSHRQWALQTLGGWEDELNYCTELLKEDIFNNSAWNQRYFVI
Triticum-FT-A   EKLGPDAANSEHDFTRKILAMDAKNYHAWSHRQWVLQALGGWESELQYCNLLEEDVFNNSAWNQRYLMV 220       230       240       250       260       270       280
                ....|....|....|....|....|....|....|....|....|....|....|....|....|....|
BnA-12          TRSESLGGLEAMRESEVSYTVKAIANPGNESSWRYLKALYKDDTESWISDPSVSSVCLKVLSRADCFHG
At-FT-A         TQSPLLGGLEAMRESEVSYTIKAILNPANESSWRYLKALYKDKESWISDPSVSSVCLNVLSPTDCFHG
PPI-Soy-FTA     TRSPFLGGLKAMRESEVLYTIEAILAYPENESSWRYLRGLYKGETTSAVNDPCVSSVCLKILRTKSNYV
Pea-FT-A        TRSPVLGGLKAMRESEVFTVEAILSYPDNESSWRYLRGLIKDESTLIVNDACVSSICLKILKTKSNYL
Tomato-FT-A     TRSPLLGGLVAMRELEVNYTVQAIRASPENESPWRYLRGLYKNDTQSLVQDSCVASVLWDVLTSQNSHV
RiceFT-A        TSSPLLGGLAAMRDSEVDYTVGAILANPQNESPWRYLKGLYKGENNLLMADERISDVCLKVLKHDSTCV
Zea mays-FT-A   TRSPFLGGLAAMRESCVDYTIEAILANACNGSPWRYLKGLYKGENNLLVEDGPISAVCFKVLKNDWTCV
Soy1-FT-A       TRSPFLGGLKAMRESEVLYTIEAILAYPENESSWRYLRGLYKGETTSAVNDPCVSSVCLKILRTKSNYV
Soy2-FT-A       TRSPFLGGLKAMRESEVLYTIEAILAYPENESSWRYLRGLYKGETTSAVNDPCVSSVCLKILRTKSNYV
Triticum-FT-A   TRSPILGGLAAMRDSEVDYTEAIVNPNESPWRYLRGLYKDDNNLLMADNRISDACLKVLNKDWTCV 290       300       310       320       330       340       350
                ....|....|....|....|....|....|....|....|....|....|....|....|....|....|
BnA-12          FALSTLLDLLCDGLRPNEHRDSVKALANEERP---ETN--------------LANLVCTILCRVDPIRAN
At-FT-A         FALSTLLDLLCDGLRPNEHKDSVRALANEERP---ETN--------------LANLVCTILCRVDPIRAN
PPI-Soy-FTA     FALSTILDLICFGYQPNEDIRDAIDALRLQIL---IKQ--DSD---------IAITICSILKCVDPIRVN
Pea-FT-A        FALSTILDLISASVIQPNEDIRDAIDALRLQIL---IKQ--DSD---------LAITICSILECVDPIRVN
Tomato-FT-A     HALRFLLDLLCHDLEPSQELKSAVDVLTPQSC---SPD-------------LALTKKICSILCHADPMRVK
RiceFT-A        FALSLLLDLLQIGLQPSDELKGTIEALKNSDPEADBAVDA--D---------LATAICSILQRCDPLRIN
Zea mays-FT-A   FALSLLLDLLCTGLQPSDGLRSTLGTIRSSHP---ETADD--D---------PAAAVCCILQKCDPLAVN
Soy1-FT-A       FALSTILDLICFGYQPNEDIRDAIDALKTADM---DKQDLDDDEKGEQQNLNIARNICSILKCVDPIRTN
Soy2-FT-A       FALSTILDLICFGYQPNEDIRDAIDALKTADM---DKQDLDDDEKGEQQNLNIARNICSILKCVDPIRTN
Triticum-FT-A   FALSFLLDLLRMGLQPSNELKGTIEAMENSDP---ETGHA--D---------TAVAVCSILQKCDPLRIN 360       370
                ....|....|....|....|....
BnA-12          YWAWKL--------------------
```

```
At-FT-A         YWAWRKSK TVAAI---------------
PPI-Soy-FTA     YWIWRKSR P-------------------
Pea-FT-A        YWVWRKSR PQAA----------------
Tomato-FT-A     YWNWRKSM RVQLLQSQNAERLANLSVQE
RiceFT-A        YWSWYR T SSQT----------------
Zea mays-FT-A   YWSWFKDT SQIS----------------
Soy1-FT-A       YWIWRKSR PLSA----------------
Soy2-FT-A       YWIWRKSR PLSA----------------
Triticum-FT-A   YWSWYQ T SS------------------
```

Table 10C. ClustalW Nucleic Acid Analysis of FT Beta Subunits

1) PPI-BnFTb; FT3 (SEQ ID NO:8)
2) era1 (SEQ ID NO:73)
3) Wiggum (SEQ ID NO:74)
4) PPI-Soy-FTB; FT5 (SEQ ID NO:34)
5) DuP-Soy-FTB (SEQ ID NO:75)
6) PPI-Corn-FTB; FT6 (SEQ ID NO:37)
7) DuP-Corn-FTB (SEQ ID NO:76)
8) Pea-FT-B (SEQ ID NO:77)
9) Tomato (SEQ ID NO:78)
10) Tobacco (SEQ ID NO:79)

```
                 10        20        30        40        50        60        70
             ....|....|....|....|....|....|....|....|....|....|....|....|....|....|
PPI-BnFTb    ----------------------------------------------------------------------
era1         ----------------------------------------------------------------------
Wiggum       ATGCCAGTAGTAACCCGCTTGATTCGTTTGAAGTGTGTAGGGCTCAGACTTGACCGGAGTGGACTCAATC
PPI-Soy-FTB  ----------------------------------------------------------------------
DuP-Soy-FTB  ----------------------------------------------------------------------
PPI-Corn-FTB ----------------------------------------------------------------------
DuP-Corn-FTB ----------------------------------------------------------------------
Pea FT-B     ----------------------------------------------------------------------
Tomato       -------------------------------------------------GTAAACGAGCGTTGATTT
Tobacco      ----------------------------------------------------------------------

80        90       100       110       120       130       140
             ....|....|....|....|....|....|....|....|....|....|....|....|....|....|
PPI-BnFTb    ----------------------------------------------------------------------
era1         ----------------------------------------------------------------------
Wiggum       GGCGAATCTGTCACGGAGGACACGGGGAATCAACGCGGCGGAGAGTGATGGAAGAGCTTTCAAGCCTA C
PPI-Soy-FTB  ----------------------------------------------------------------------
DuP-Soy-FTB  ----------------------------------------------------------------------
PPI-Corn-FTB ------------------------------------GGCGGATCCCGACCTACCGAGGCTC C
DuP-Corn-FTB ------------------------------------GGCGGATCCCGACCTACCGAGGCTC C
Pea FT-B     ---------------------------------------CGGACCCCCCCGTCCACAATCGTG T
Tomato       GTCGCTGACGAAATTTACAGTCAAGAGTAGTAACCGGTTGTAGTGAAAAAATGGAGTCGAGGAAAGTG C
Tobacco      ----------------------------------------------GGCACGAGCGGC- C 150       160       170       180       190       200       210
             ....|....|....|....|....|....|....|....|....|....|....|....|....|....|
PPI-BnFTb    ----------------------------------------------------------------------
era1         ----------------------------------------------------------------------
Wiggum       CGTGA GTCAGCGCGAGCAATTTCTGGTGGAGAACGATGTGTTCGGGATCT TAATTACT CGACGCCAGC
PPI-Soy-FTB  ------------------------------------------------------------GCCACCATTC
DuP-Soy-FTB  ------------------------------------------------------------GCCACCATTC
PPI-Corn-FTB GGTGA CGCAGGTGGAGCAGATGAAGGTGGAGGCCAGGGTTGGCGACATCT CCGCTCCC CTTCGGGGCC
DuP-Corn-FTB GGTGA CGCAGGTGGAGCAGATGAAGGTGGAGGCCAGGGTTGGCGACATCT CCGCTCCC CTTCGGGGCC
Pea FT-B     GATGA CGTCTCCGCGAGCATTTCAACAACCAGTTACTCAAACCACCGCGG GTAACACA GGAAGCTTCA
Tomato       GAAGA CGCTGGAAGATCAATGGGTGGTGGAGCGTCGAGTCCGAGAGATAT CGATTATT CTACAGCATT
Tobacco      GAGGA CACTGGAAGATCAATGGATGGTGGAGCGTCAAGTTCGGGAGATAT CAATTTTT CTACAGCATT 220       230       240       250       260       270       280
             ....|....|....|....|....|....|....|....|....|....|....|....|....|....|
```

```
DuP-Corn-FTB  CCTGTACAATTTTATGCTGCAGATGAAAGATGTATCAGGTGCTTTCAGAATGCATGATCGTGGCGAAATT
Pea FT-B      GTTGTACGGTTTATGCGGCGGATGAAACAGCCAAACGCGGATTCAGGATGCATGACGAGGGAGAAATT
Tomato        GTTGTACACATTTTGCTGCGAATGAAAGACGCAAGTGGTGGATTCAGGATGCACGATGCTGGAGAAGTA
Tobacco       ATTGTATACATTTTGGCTGCAAATGAAAGACACAAGTGGTGGCTTCAGGATGCATGATCGTGGAGAAGTA
```

```
                   640       650       660       670       680       690       700
              ....|....|....|....|....|....|....|....|....|....|....|....|....|....|
PPI-BnFTb     GATGTGCGAGCGTGCTACACTGCGGATTTTGATTGCAAGCATCCTGAACATTGTGGATGATGAACTCACCC
eral          GATGTTCGTGCATGCTACACTGCAATTTCGGTTGCAAGCATCCTAAATATTATGGATGATGAACTCACCC
Wiggum        GATGTTCGTGCATGCTACACTGCAATTTCGGTTGCAAGCATCCTAAATATTATGGATGATGAACTCACCC
PPI-Soy-FTB   GATGTTCGAGCTTGCTACACTGCACATTTCTGTTGCAAGCTGTTTTGAACATTTTGGATGATGAGCTGATCC
DuP-Soy-FTB   GATGTTCGAGCTTGCTACACTGCACATTTCTGTTGCAAGTGTTTTGAACATTTTGGATGATGAGCTGATCC
PPI-Corn-FTB  GATGTCCGTGCTTCCTACACCGGTATATCGGTTGCCAGCCTTGTGAATATTCTTGATTTTAAACTGGCAA
DuP-Corn-FTB  GATGTCCGTGCTTCCTACACCGGTATATCGGTTGCCAGCCTTGTGAATATTCTTGATTTTAAACTGGCAA
Pea FT-B      GACGTTCGAGCTTGCTACACTGCCATCTCTGTGGCAAGTGTTCTGAACATTTTGGATGATGAGCTGATCA
Tomato        GATGTTCGTGCCTGTTATACTGCCATTTCTGTTCAAATATATTAAACATTGTGGATGACGAGCTGATTC
Tobacco       GATGTTCGTGCCTGTTATACTGCCATTTCTGTTCAAGTATATTGCAAATTGTGGATGATGAACTGATTA
```

```
                   710       720       730       740       750       760       770
              ....|....|....|....|....|....|....|....|....|....|....|....|....|....|
PPI-BnFTb     GCGGCTTAGGAGATTACATTTTGAGTTGCCAAACTTATGAAGGTGGCATTGGAGGGGAACCTGGCTCCGA
eral          AGCGCCTAGGAGATTACATCTTGACTTGCCCAAACTTATGAAGGTGGCATTGAGCGGAACCTCCTCCGA
Wiggum        AGGGCCTAGGAGATTACATCTTGAGTTGCCAAACTTATGAAGGTGGCATTGGAGGGGAACCTGGCTCCGA
PPI-Soy-FTB   AGAATGTTGGAGACTACATTATAAAGCTGTCAAACATATGAGGGTGGCATTGCTGGTGAGCCTGGTTCTGA
DuP-Soy-FTB   AGAATGTTGGAGACTACATTATAAAGCTGTCAAACATATGAGGGTGGCATTGCTGGTGAGCCTGGTTCTGA
PPI-Corn-FTB  AAGGTGTAGGCGACTACATAGCAAGATGTCAAACTTATGAAGGTGGCTATTGCTGGGGAGCCTTATGCTGA
DuP-Corn-FTB  AAGGTGTAGGCGACTACATAGCAAGATGTCAAACTTATGAAGGTGGCTATTGCTGGGGAGCCTTATGCTGA
Pea FT-B      AGAATGTTGGAGACTTCATTTTAAGCTGTCAAACATATGAGGGAGGCTTGCTGGTGAGCCTGGGTCTGA
Tomato        ATGGTGTTGGAAATTACATCCTAAGTTGTCAGACTTATGAAGGTGGAATTGCTGGCAACCAGGTTCTGA
Tobacco       ATGATGTTGGGAATTACATCCTAAGTTGTCAGACTTATGAAGGTGGAATTGCTGGCGAACCAGGTTCTGA
```

```
                   780       790       800       810       820       830       840
              ....|....|....|....|....|....|....|....|....|....|....|....|....|....|
PPI-BnFTb     AGCTCATGGTGGGTACACGTACTGTGGGTTGGCTACTATGATTTTAATCAATGAAGTCGACCGCTTGAAT
eral          AGCTCACGGTGGGTATACCTACTGTGGTTTGGCTGCTATGATTTAATCAATGAGGTCGACCGTTTGAAT
Wiggum        AGCTCACGGTGGGTATACCTACTGTGGTTTGGCTGCTATGATTTAATCAATGAGGTCGACCGTTTGAAT
PPI-Soy-FTB   GGCTCATGGTGGGTACACCTTTTGTGGATTAGCTACAATGATTCTGATTGGTGAGGTTAATCACTTGGAT
DuP-Soy-FTB   GGCTCATGGTGGGTACACCTTTTGTGGATTAGCTACAATGATTCTGATTGGTGAGGTTAATCACTTGGAT
PPI-Corn-FTB  AGCACATGGTGGGTATACAATTCTGTGGATTGGCTGCTTTGATCCTGCTTAATGAGGCAGAGAAAGTTGAC
DuP-Corn-FTB  AGCACATGGTGGGTATACAATTCTGTGGATTGGCTGCTTTGATCCTGCTTAATGAGGCAGAGAAAGTTGAC
Pea FT-B      GGCTCATGGCGGGTATACCTTTTGTGGGTTAGCTGCAATGATTCTGATTGGTGAGGTTAATCGCTTGGAT
Tomato        AGCTCATGGTGGGTATACTTTCTGTGGGTTGGCTGCAATGATTCTGATCAACGAAGTAGATCGATTGGAC
Tobacco       AGCTCATGGTGGGTATACCTTCTGTGGGTTGGCTGCAATGATTCTGATTAACGAAGCGAATCGATTGGAC
```

```
                   850       860       870       880       890       900       910
              ....|....|....|....|....|....|....|....|....|....|....|....|....|....|
PPI-BnFTb     TTGGATTCGTTAATGAATTGGGTTGTACATCGACAAGGAGTAGAAATGCGGATTCCAAGGTAGGACGAACA
eral          TTGGATTCATTAATGAATTGGGCTGTACATCGACAAGGAGTAGAAATGGGATTTCAAGGTAGGACGAACA
Wiggum        TTGGATTCATTAATGAATTGGGCTGTACATCGACAAGGAGTAGAAATGGGATTTCAAGGTAGGACGAACA
PPI-Soy-FTB   CTGCCTCGATTAGTTGACTGGGTGGTATTCCGACAAGGTAAGAATGTGGATTCCAGGGGAGAACAAATA
DuP-Soy-FTB   CTGCCTCGATTAGTTGACTGGGTGGTATTCCGACAAGGTAAGAATGTGGATTCCAGGGGAGAACAAATA
PPI-Corn-FTB  TTGCCTAGTTTGATTGGCTGGGTGGCTTTTCGTCAAGGAGTGGAATGCGGATTTCAAGGACGAACTAATA
DuP-Corn-FTB  TTGCCTAGTTTGATTGGCTGGGTGGCTTTTCGTCAAGGAGTGGAATGCGGATTTCAAGGACGAACTAATA
Pea FT-B      CTGCCTCGTTTACTTGATTGGGTTGTGTTTCGGCAAGGTAAGAGTGTGGATTTCAGGGGAGAACGAATA
Tomato        TTGCCAGGTTTAATTGATTGGGTGGTATTTAGACAAGGGTCGAAGGTGGATTTCAAGCAGGACAAATA
Tobacco       TTGCCAAGATTAATTGATTGGGTGGTATTTAGACAAGGAGTCGAAGGTGGATTTCAAGCCAGGACAAATA
```

```
                   920       930       940       950       960       970       980
              ....|....|....|....|....|....|....|....|....|....|....|....|....|....|
PPI-BnFTb     AATTGGTCGACGGTTGCTACACGTTTTGGCAGGCAGCCCCTGTGTTCTACTACAGCGATTTTTTCATC
eral          AATTGGTCGATGGTTGCTACACATTTTGGCAGGCAGCCCTTGTGTTCTACTACAAAGATTATATTCAAC
Wiggum        AATTGGTCGATGGTTGCTACACATTTTGGCAGGCAGCCCTTGTGTTCTACTACAAAGATTATATTCAAC
PPI-Soy-FTB   AACTGGTGGATGGATGCTATTCCTTTTGGCAGGGAGGTGCTGTTCTCTATTGCAAAGATTATCTTCTAT
DuP-Soy-FTB   AACTGGTGGATGGATGCTATTCCTTTTGGCAGGGAGGTGCTGTTCTCTATTGCAAAGATTATCTTCTAT
PPI-Corn-FTB  AATTGGTTGATGGTTGCTACTCCTTTTGGCAGGGAGCTGCCATTGCCTTCACACAAAGTTAATTACGAT
DuP-Corn-FTB  AATTGGTTGATGGTTGCTACTCCTTTTGGCAGGGAGCTGCCATTGCCTTCACACAAAGTTAATTACGAT
Pea FT-B      AATTGGTAGATGGATGCTACTCGTTTTGGCAGGGAGGTGCTGTTCCCTATTGCAAAGATTACATTCTAT
Tomato        AATTAGTCGATGGCTGCTATTCCTTTTGGCAGGGCGCGGTAGTGTTTCTTATACAAAGACTAAATTTGAT
Tobacco       AATTAGTCGATGGCTGCTATTCCTTTTGGCAGGCCGCGGTAGCTTTTCTTATACAAAGATTAAAATGAC
```

```
                   990       1000      1010      1020      1030      1040      1050
```

```
                75                                       76
           ....|....|....|....|....|....|....|....|....|....|....|....|....|....|....|....|
PPI-BnFTb  CCAGGAT-ATGGCACC------TCATGGATCATCATCA-----------CATATGTCACAAGGGACAGAT
era1       CAATGATCATGACGT-------TCATGGATCATCA-------------CATATATCAGAAGGGACAAAT
Wiggum     CAATGATCATGACGT-------TCATGGATCATCA-------------CATATATCAGAAGGGACAAAT
PPI-Soy-FTB TATCAACAAACAGATG------GAAGAGA-CATCA-------------CAGATTTTTGCGGTATCTTAT
DuP-Soy-FTB TATCAACAAACAGATG------GAAGAGA-CATCA-------------CAGATTTTTGCGGTATCTTAT
PPI-Corn-FTB TGTTGATAAGCAATTGAGGTCCTCGTA-----T--------------------TCCTGCAAAA----GG
DuP-Corn-FTB TGTTGATAAGCAATTGAAGTCCTCGTA-----T--------------------TCCTGCAAAA----GG
Pea FT-B   TATCGACGAACAAATG------GCAGAGG-CATCA-------------CAGTTTGTTACAGTATCTGAT
Tomato     AGTCCATGAACAACTAGGGCTGTCAAATGACCTCAGTACAGAAAGTGCTGATGATTCTTCAGAGTCAGAG
Tobacco    AGTCCATGAACAACTAGGGCTGTCAAATGAACTCAGTACAGAAAGTGCTGATGATTCTTCGGAGTCAGAG 1060      1070      1080      1090      1100      1110      1120
           ....|....|....|....|....|....|....|....|....|....|....|....|....|....|
PPI-BnFTb  GAAGATCACGAGGA-ACATGGTCATGATGAAGATGATCTGAAGACAGTGATGATGATGA---TTCTGAT
era1       GAAGAACAT-------CATGCTCATGATGAAGATGACCTTGAAGACAGTGATGATGATGATGATTCTGAT
Wiggum     GAAGAACAT-------CATGCTCATGATGAAGATGACCTTGAAGACAGTGATGATGATGATGATTCTGAT
PPI-Soy-FTB GTATCTGAAG------CAAAAGAAAGTTTGGATGGAAGCTCTAGTCA-TGCAACATGCCGTGGTGAGCAT
DuP-Soy-FTB GTATCTGAAG------CAAAAGAAAGTTTGGATGGAAGCTCTAGTCA-TGCAACATGCCGTGGTGAGCAT
PPI-Corn-FTB CCATCAGGACAG----GATGCCTGCAG----CACCAGTTCATAT----GGCTGCACC--------G-CGA
DuP-Corn-FTB CCATCAGGACAG----GATGCCTGCAG----CACCAGTTCATAT----GGCTGCACC--------G-CGA
Pea FT-B   GCACCTGAAG------AAAAGGAATGTTTGGACGGAACCTCAAGTCA-TGCAACTTCCCATATTAGGCAT
Tomato     TTATCTGATGAAGAAGAGCATTTGGAAGGGATATCCTCTCATGTTCA-GGATACTTTCCCTCTTGGACAA
Tobacco    TTATCTGATGAA---GAGCATTTGCAAGGGACATCATCTCATGTTCA-GAAGACTTGCCCTCTTGGACAA 1130      1140      1150      1160      1170      1180      1190
           ....|....|....|....|....|....|....|....|....|....|....|....|....|....|
PPI-BnFTb  GAGGAT---------AGCGATGAA---GATTCAGGGAATGGTCACCAAGTTCATCATACGTCTAC-CTAC
era1       GAGGAC---------AACGATGAA---GATTCAGTGAATGGTCACAGAATCCATCATACATCCAC-CTAC
Wiggum     GAGGAC---------AACGATGAA---GATTCAGTGAATGGTCACAGAATCCATCATACATCCAC-CTAC
PPI-Soy-FTB GAAGGC---------ACCAGTGAATGCAGTTCATCTGATTTTAAAAATATTGCCTATAAAATTTAT-TAAT
DuP-Soy-FTB GAAGGC---------ACCAGTGAATGCAGTTCATCTGATTTTAAAAATATTGCCTATAAAATTTAT-TAAT
PPI-Corn-FTB ATAAGT----------------CTTCCTCTGCTGTGGACTATGCGAAGTTTGGATTTGATTTTATACAAC
DuP-Corn-FTB AAAAGT----------------CTTCCTCTGCTGTGGACTATGCGAAGTTTGGATTTGATTTTATACAAC
Pea FT-B   GAAGGC---------ATGAATGAATCCTGCTCATCTGACGTTAAAAATATTGGTTATAACTTAT-TAGT
Tomato     GCAGGTGCTTGTCAAGAAAATGCTTCTCATAGCCCAAAATAGCAGATACTGGATATGAGTTTAT-CAAC
Tobacco    GAAGGA------CAGGAAAATGCTTCAGATCCCACAAAGATAGCAGATACTGGTTATGATTTTGT-CAAT 1200      1210      1220      1230      1240      1250      1260
           ....|....|....|....|....|....|....|....|....|....|....|....|....|....|
PPI-BnFTb  ATTGACAGGAGAATTCAACCTGTTTTTGATAGCCTCGGCTTGCAAAGATATGTGCTCTTGTGCCTCTCAGG
era1       ATTAACAGGAGAATGCAACTGGTTTTTGATAGCCTCGGCTTGCAGAGATATGTACTCTTGTGCCTCTAAGA
Wiggum     ATTAACAGGAGAATGCAACTGGTTTTTGATAGCCTCGGCTTGCAGAGATATGTACTCTTGTGCCTCTAAGA
PPI-Soy-FTB GAGTGGAGAGCACAAGAACCACTTTTTCACAGTATTGCTTTACAGCAATATATTCTCTTATGTGCACAGG
DuP-Soy-FTB GAGTGGAGAGCACAAGAACCACTTTTTCACAGTATTGCTTTACAGCAATATATTCTCTTATGTGCACAGG
PPI-Corn-FTB AGAGCAACCAA-ATTGGCCCACTCTTCCATAACATTGCCTGCAACAATACATCCTACTTTGTTCTCAGG
DuP-Corn-FTB AGAGCAACCAA-ATTGGCCCACTCTTCCATAACATTGCCTGCAACAATACATCCTACTTTGTTCTCAGG
Pea FT-B   GAGTGGAGACAAGTGAACACTTTTTCACAGCATTGCCTTACAGCAATATATTCTTTTATGTTCACAGG
Tomato     CGACCCATAGCTATGAGGCCTCTCTTTGACAGCATGTATCTGCAGCAATATGTTCTTCTTTGCTCTCAGA
Tobacco    CGNACGATAGCTATGCGACCTGTGTTTGACAGCTTTTATCTGCAGCAATACGTTCTTCTCTGCTGCCAGA 1270      1280      1290      1300      1310      1320      1330
           ....|....|....|....|....|....|....|....|....|....|....|....|....|....|
PPI-BnFTb  TTGCTGATGGTGGATTCAGAGACAAGCTGAGGAAACCCCGTGACTTCTACCACACATGTTACTGCCTGAG
era1       TCCCTGACGGTGGTGATTCAGAGACAAGCCGAGGAAACCCCGTGACTTCTACCACACATGTTACTGCCTGAG
Wiggum     TCCCTGACGGTGGTGATTCAGAGACAAGCCGAGGAAACCCCGTGACTTCTACCACACATGTTACTGCCTGAG
PPI-Soy-FTB AGCAAGAGGGTGGACTGAGAGACAAACCGGGTAAACGTAGAGATCATTATCACACATGTTACTGTTAAG
DuP-Soy-FTB AGCAAGAGGGTGGACTGAGAGACAAACCGGGTAAACGTAGAGATCATTATCACACATGTTACTGTTAAG
PPI-Corn-FTB TACTAGAGGGAGCCTTGAGGGATAAGCCTGGAAAAGAACAGAGATCACTATCATTCATGCTACTGCCTCAG
DuP-Corn-FTB TACTAGAGGGAGCCTTGAGGGATAAGCCTGGAAAAGAACAGAGATCACTACCATTCATGCTACTGCCTCAG
Pea FT-B   AGCAAGATGGTGGCTCAGGGACAAACCGGGTAAACGCACGGATCATTATCATTCATGTTACTGTTTAAG
Tomato     TTGAAGTTGGTGGTTTCAGAGACAAACCTGGGAAGGGTAGAGACTACTACCATACTTGTTACTGTTTAAG
Tobacco    T---AGATGGAGGTTTCAGAGACAAACCTGGGAAGGGTAGAGACCACTACCATACTTGCTACTGTTTAAG 1340      1350      1360      1370      1380      1390      1400
           ....|....|....|....|....|....|....|....|....|....|....|....|....|....|
PPI-BnFTb  CGGTCTTTCCGTGCTCAACACGCTTGGTCAAAAGACGAGGACACTCCTCCTTTGACTCGTGACATTTG
era1       CGGCTTGTCTGTGGCTCAGCACGCTTGGTTAAAAGACGAGGACACTCCTCCTTTGACTCGCGACATTATG
Wiggum     CGGCTTGTCTGTGGCTCAGCACGCTTGGTTAAAAGACGAGGACACTCCTCCTTTGACTCGCGACATTATG
PPI-Soy-FTB TGGACTCTCATTGTGCAGTATAGTTGGTCAAAGCACCAGATTCTCCACCAC-------------
DuP-Soy-FTB TGGACTCTCATTGTGCAGTATAGTTGGTCAAAGCACCAGATTCTCCACCAC-------------
```

```
PPI-Corn-FTB    TGGCCTCGCAGTTAGCCAGTACAGTGCCATGACTGATACTGGTTCGTGCCCATTACCTCAGCATGTGCTT
DuP-Corn-FTB    TGGCCTCGCAGTTAGCCAGTACAGTGCCATGACTGATACTGGTTCGTGCCCATTACCTCAGCATGTGCTT
Pea FT-B        TGGGTTGTCACTGTGCCAGTATAGTTGGTCGAAGCGCCAGATTCTCCACCGCTGCCTAAGGTAGTAATG
Tomato          TGGTCTTTCAATTGCTCAGTATAGCTGGACCGACGAAGCTGATTCTACACCATTACCCAGGGATGTATTT
Tobacco         TGGTCTTTCAATTGCTCAATATAGCTGGACCAACGAAGCTGATGCGCCACCATTACCCAGGGATGTATTT 1410      1420      1430      1440      1450      1460      1470
                  ....|....|....|....|....|....|....|....|....|....|....|....|....|....|
PPI-BnFTb       GGTGGCTACGCA-AA--CCACCTTGAACCTGTTCACCGTCCTCCACAACATTGTCTTGGATGGGTATTATG
eral            GGTGGCTACTCG-AA--TCTCCTTGAACCTGTTCAACTTCTTCACAACATTGTCATGGATCAGTATAATG
Wiggum          GGTGGCTACTCG-AA--TCTCCTTGAACCTGTTCAACTTCTTCACAACATTGTCATGGATCAGTATAATG
PPI-Soy-FTB     ----------------------------------------------------------------------
DuP-Soy-FTB     ----------------------------------------------------------------------
PPI-Corn-FTB    GGACCGTACTCT-AA--TTTGCTGGAGCCAATCCATCC--------------------------------
DuP-Corn-FTB    GGACCGTACTCT-AA--TTTGCTGGAGCCAATCCATCC--------------------------------
Pea FT-B        GGCCCATACTCC-AA--TCTCTTAGAACCCATCCATCCTCTCTTTAATGTTGTTTTGGATCGATATCGTG
Tomato          GGTCCTTATTCCAAAATGTCTGTTGGAACAGGTTCACCCACTCTTCAACGTAGTGTTGGATCGGTATTATG
Tobacco         GGTCCTTATTCTCAAAATCTTTTGGAACAGATTCACCCACTTTACAACGTAGTGTTGGATCGGTATTATG 1480      1490      1500      1510      1520      1530      1540
                  ....|....|....|....|....|....|....|....|....|....|....|....|....|....|
PPI-BnFTb       AAGCTTCTAGATTT--------------------------------------------------------
eral            AAGCTATCGAGTTCTTCTTTAAAGCAGCATGACCCGTTGTTGCTAATGTATGGGAAACCCCAAACATAAG
Wiggum          AAGCTATCGAGTTCTTCTTTAAAGCAGCATGACCCGTTGTTGCTAATGTATGGGAAACTCCAAACATAAG
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        AAGCTCATGAATTCTTTTCTCAGTTGTGACGGATGACAAGGTTTTAGCTACCAATAGCTC-GATCATTAG
Tomato          AAGCTCGCGAATACT-CTCAGGCTTGTGAGACTGTTTCAC-CACTTTCATTAGCACCAAC--TTTTTCAG
Tobacco         AAGCTCGTAGCTTCTTCTCATGCTTGTGATAATATTTTACGCGATAGCTGTAGCTGGAAT--GTTACC--

1550      1560      1570      1580      1590      1600      1610
                  ....|....|....|....|....|....|....|....|....|....|....|....|....|....|
PPI-BnFTb       ----------------------------------------------------------------------
eral            AGTTTCCGTAGTGTTGTAACTTGTAAGATTTCAAAAG---------------------------------
Wiggum          AGTTTTCGTAGTGTTGTAACTTGTAAGATTTCAAAAGAAGTTTCACTAATTTAACCTTAAAACCTGTTAC
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        AATGTAAAATGTAAACTAAAATATGAAATATGAAATACCAAAAAGATATTATTGGATGAAATTCACGTGG
Tomato          AAACTTAGTTGCAATCCAGAAGTTAAAAGTGTCATTGGGTTCAAAAGAGTTGTGATCGTTTATGTACATA
Tobacco         ---TCTAGTTG---TTCAGAATCAGAGACTAATCTATTATTTTGAGGGATTGGATTCAAAAAAAAAAAAA 1620      1630      1640      1650      1660      1670      1680
                  ....|....|....|....|....|....|....|....|....|....|....|....|....|....|
PPI-BnFTb       ----------------------------------------------------------------------
eral            ----------------------------------------------------------------------
Wiggum          TTTTTTATTACGTATATACCATTTATCATATCTTTGGTTTACGACTTAAAGAATTTGATGATTGTTGAAA
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        ATCTAATACAACTGCGTGGTTTTCATTCCTGATTTGATTTTGATTTACATGAGTTAAAACGTTAAACCCT
Tomato          TCCTTGCATTTGTATACGTGATACAAGTTGAGAGAATAACGGGTACTTTCTGAACTTGCTGAACTAGCAC
Tobacco         AAAAAAA---------------------------------------------------------------

1690      1700      1710      1720      1730      1740      1750
                  ....|....|....|....|....|....|....|....|....|....|....|....|....|....|
PPI-BnFTb       ----------------------------------------------------------------------
eral            ----------------------------------------------------------------------
Wiggum          ----------------------------------------------------------------------
PPI-Soy-FTB     ----------------------------------------------------------------------
DuP-Soy-FTB     ----------------------------------------------------------------------
PPI-Corn-FTB    ----------------------------------------------------------------------
DuP-Corn-FTB    ----------------------------------------------------------------------
Pea FT-B        TCTTATTCATACATTTGTTAAGAGCTTAAGGCTTAATGGTTAAGCCAATGATATAAATATTTATGCAGAA
Tomato          GTAAATTCGTCTCTGGTTTAGTGAGGTCTGTAAACATCAATGTGAAATTGCGAGATATGCATGTAATAGT
Tobacco         ----------------------------------------------------------------------
```

```
                    1760      1770      1780      1790      1800      1810      1820
                ....|....|....|....|....|....|....|....|....|....|....|....|....|....|
PPI-BnFTb       --------------------------------------------------------------------
era1            --------------------------------------------------------------------
Wiggum          --------------------------------------------------------------------
PPI-Soy-FTB     --------------------------------------------------------------------
DuP-Soy-FTB     --------------------------------------------------------------------
PPI-Corn-FTB    --------------------------------------------------------------------
DuP-Corn-FTB    --------------------------------------------------------------------
Pea FT-B        AGCTGTTGCTTATCACCAACGGTAATATTAATAAGCAAACAAGTATTCTGTGAT----------------
Tomato          GGCTAAGATTTACAAATCTGGATACCGGTTATTAGTGATCAGAAATTTCATTCAATTTCCCAAACGGTCA
Tobacco         --------------------------------------------------------------------

1830      1840      1850      1860      1870      1880      1890
                ....|....|....|....|....|....|....|....|....|....|....|....|....|....|
PPI-BnFTb       --------------------------------------------------------------------
era1            --------------------------------------------------------------------
Wiggum          --------------------------------------------------------------------
PPI-Soy-FTB     --------------------------------------------------------------------
DuP-Soy-FTB     --------------------------------------------------------------------
PPI-Corn-FTB    --------------------------------------------------------------------
DuP-Corn-FTB    --------------------------------------------------------------------
Pea FT-B        --------------------------------------------------------------------
Tomato          CCTAAGTTTAGGATATTGCTTTAAAATATTATTTATTTTTCATTTAAGAATCAAAAAAAAAAAAAAAAAA
Tobacco         --------------------------------------------------------------------

....|....
PPI-BnFTb       ---------
era1            ---------
Wiggum          ---------
PPI-Soy-FTB     ---------
DuP-Soy-FTB     ---------
PPI-Corn-FTB    ---------
DuP-Corn-FTB    ---------
Pea FT-B        ---------
Tomato          AAAAAAAAA
Tobacco         ---------
```

Table 10D. ClustalW Amino Acid Analysis of FT Beta Subunits

1) PPI-BnFTB; FT3 (SEQ ID NO:9)
2) era1 (SEQ ID NO:80)
3) Wiggum (SEQ ID NO:81)
4) PPI-Soy-FTB; FT5 (SEQ ID NO:36)
5) DuP-Soy-FTB (SEQ ID NO:82)
6) PPI-Corn-FTB; FT6 (SEQ ID NO:39)
7) DuP-Corn-FTB (SEQ ID NO:83)
8) Pea-FT-B (SEQ ID NO:84)
9) Tomato (SEQ ID NO:85)
10) Tobacco (SEQ ID NO:86)

```
                         10        20        30        40        50        60        70
                ....|....|....|....|....|....|....|....|....|....|....|....|....|....|
PPI-BnFTB       ----------------------------------------------------------------------
era1            ----------------------------------------------------------------------
Wiggum          MPVVTRLIRLKCVGLRLDRSGLNRRICHGGHGESTRRRVMEELSSLTVSQREQFLVENDVFGIYNYFDAS
PPI-Soy-FTB     -------------------------------------------------------------------ATI
DuP-Soy-FTB     -------------------------------------------------------------------ATI
PPI-Corn-FTB    ---------------------------------ADPDLPRLTVTQVEQMKVEARVGDIYRSLFGA
DuP-Corn-FTB    ---------------------------------ADPDLPRLTVTQVEQMKVEARVGDIYRSLFGA
Pea FT-B        ------------------------------------------------------------------MEA
Tomato          ---------------------------------------------MESRKVTKTLEDQWVVERRVREIYDYFYSI
Tobacco         -----------------------------------------------GTSGTRTLEDQWMVERQVREIYNFFYSI
```

```
                    80         90        100        110        120        130        140
                   ....|....|....|....|....|....|....|....|....|....|....|....|....|
PPI-BnFTB      ------------------------------------------------WLCYWI HSIALLGES DD LENNAI
era1           --------METQRDKQLDYLMYGLRQLGPQFSSLDAN-----RPWLCYWI HSIALLGET DD LE NAI
Wiggum         DVSTQKVMMETQRDKQLDYLMYGLRQLGPQFSSLDAN-----RPWLCYWI HSIALLGET DD LE NAI
PPI-Soy-FTB    PRNAQTLMLELQRDNHMQYVSKGLRHLSSAFSVLDAN-----RPWLCYWIFHSIALSGES DD LE NAI
DuP-Soy-FTB    PRNAQTLMLELQRDNHMQYVSKGLRHLSSAFSVLDAN-----RPWLCYWI HSIALSGES DD LE NAI
PPI-Corn-FTB   APNTKSIMLELWRDQHIEYLIPGLRHMGPAFHVLDAN-----RPWLCYWMVHP ALLDEA DD LEND II
DuP-Corn-FTB   APNTKSIMLELWRDQHIEYLIPGLRHMGPAFHVLDAN-----RPWLCYWMVHP ALLDEA DD LEND II
Pea FT-B       STAAETPTPTVSQRDQWIVESQ-VFHIYQLFANIPPNAQSIIRPWLCYWI HSIALLGES DD LE NTV
Tomato         SPNSPSDLIELERDKHFGYLSQGLRKLGPSFSVLDAS-----RPWLCYW  HSIALLGES GG LENDAI
Tobacco        PPNS---HLETSTENHFDYL RGLRKLGP FSVLDAN-----RPWLCYWI HSIALLGES DA LENDAI 150        160        170        180        190        200        210
                   ....|....|....|....|....|....|....|....|....|....|....|....|....|
PPI-BnFTB      DFLGRCQGSPGGYGGGPGQIPHLATSYAAVN LVTLGGEKAFSSINREQMACFLRRMKDTNGGFRMHNMG
era1           DFLGRCQGSEGGYGGGPGQ PHLATTYAAVNALVTLGG KALSSINREKMSCFLRRMKDTSGGFRMHDMG
Wiggum         DFLGRCQGSEGGYGGGPGQ PHLATTYAAVNALVTLGG KALSSINREKMSCFLRRMKDTSGGFRMHDMG
PPI-Soy-FTB    DFLNRCQDPNGGYAGGPGQ PHLATTYAAVNSLITLGG KSL SINRDKLYGFLRRMKQPNGGFRMHDEG
DuP-Soy-FTB    DFLNRCQDPNGGYAGGPGQ PHLATTYAAVNSLITLGG KSL SINRDKLYGFLRRMKQPNGGFRMHDEG
PPI-Corn-FTB   DFLARCQDKIGGYSGGPGQ PHLATTYAAVNLVTIGSEPALSSINRGNLYNP LCMKDVSGAFRMHDGG
DuP-Corn-FTB   DFLARCQDKDGGYSGGPGQ PHLATTYAAVNLVTIGSQRALSSINRGNLYNR LCMKDVSGAFRMHDGG
Pea FT-B       DFLNRCQDPNGGYAGGPGQ PHLATTYAAVN LITLGG KSL SINRNKLYGF RRMKQPNGGFRMHDEG
Tomato         DFLTRCQDKCGGYGGGPGQ PHLATTYAAVNSLITLGKPEALSSINREKLYTFLRMKDASGGFRMHDGG
Tobacco        DFLSRCQDELGGYGGGPGQ PHLATTYAAVNSLITLGSPKALSSINREKLYT WLCMKDTSGGFRMHDGG 220        230        240        250        260        270        280
                   ....|....|....|....|....|....|....|....|....|....|....|....|....|
PPI-BnFTB      EIDVRACYTAILIASILNIVDDELTRGLGDYILSCQTYEGGICGEPGSEAHGGYT CGLAIMILINEVDR
era1           EIDVRACYTAISVASILNIMDDELTQGLGDYILSCQTYEGGIGGEPGSEAHGGYT CGLAAMILINEVDR
Wiggum         EMDVRACYTAISVASILNIMDDELTQGLGDYILSCQTYEGGIGGEPGSEAHGGYT CGLAAMILINEVDR
PPI-Soy-FTB    EIDVRACYTAISVASVLNILDDELIQNVGDYI SCQTYEGGIAGEPGSEAHGGYTFCGLATMILIGEVNH
DuP-Soy-FTB    EIDVRACYTAISVASVLNILDDELIQNVGDYI SCQTYEGGIAGEPGSEAHGGYTFCGLATMILIGEVNH
PPI-Corn-FTB   EIDVRASYTAISVASLVNIDFKLAKGVGDYIARCQTYEGGIAGEPYAEAHGGYTFCGLAA ILINEAEK
DuP-Corn-FTB   EIDVRASYTAISVASLVNIDFKLAKGVGDYIARCQTYEGGIAGEPYAEAHGGYTFCGLAA ILINEAEK
Pea FT-B       EIDVRACYTAISVASLLNIDDDELIKNVGD ILSCQTYEGG AGEPGSEAHGGYTFCGLAAMILIGEVNR
Tomato         EVDVRACYTAISVANILNIVDDELIHGVG YILSCQTYEGGIAGEPGSEAHGGYTFCGLAAMILINEVDR
Tobacco        EVDVRACYTAISVASILQIVDDELINDVG YILSCQTYEGGIAGEPGSEAHGGYTFCGLAAMILINEANR 290        300        310        320        330        340        350
                   ....|....|....|....|....|....|....|....|....|....|....|....|....|
PPI-BnFTB      LNLDSLVMNVVHRQGVEMGFQGRTNKLVDGCYIFWQAAPCVLLQRFFSSQDMAPHGSSSHMSQGTDEDHE
era1           LNLDSLVMNWAVHRQGVEMGFQGRTNKLVDGCYIFWQAAPCVLLQRLYSTNDHDVHG-SSHISEGTNEEH-
Wiggum         LNLDSLVMNWAVHRQGVEMGFQGRTNKLVDGCYIFWQAAPCVLLQRLYSTNDHDVHG-SSHISEGTNEEH-
PPI-Soy-FTB    LDLPREVDWVVFRQGKECGFQGRTNKLVDGCYSFWQGGAVALLQRLSSIINKQMEETSQIFAVSYVSEA-
DuP-Soy-FTB    LDLPREVDWVVFRQGKECGFQGRTNKLVDGCYSFWQGGAVALLQRLSSIINKQMEETSQIFAVSYVSEA-
PPI-Corn-FTB   VDLPSLIGWVAFRQGVECGFQGRTNKLVDGCYSFWQGAAIAFTQKLITIVDKQLRSSYSCKRPSGEDACS
DuP-Corn-FTB   VDLPSLIGWVAFRQGVECGFQGRTNKLVDGCYSFWQGAAIAFTQKLITIVDKQLKSSYSCKRPSGEDACS
Pea FT-B       LDLPRLIDWVVFRQGKECGFQGRTNKLVDGCYSFWQGGAVALLQRLHSIIDEQMAEASQFVIVSDAPEE-
Tomato         LDLPGLIDWVVFRQGVEGGFQGRTNKLVDGCYSFWQGAVYFLIQRLNLIVHEQIGLSNDLSIESADDSSE
Tobacco        LDLPRLIDWVVFRQGVEGGFQGRTNKLVDGCYSFWQAAVAFLQRLKSTVHQLGLSNELSIESADDSSE 360        370        380        390        400        410        420
                   ....|....|....|....|....|....|....|....|....|....|....|....|....|
PPI-BnFTB      EHGHDED-DPT--DSDEDD-S--DEDS--DEDSGNGHQVHHT-STVIDR--RTGPVFDSLGLQRYVLLCS
era1           -HAHDED-DLE--DSDDDDDS--DEDN--DEDSVNGHRIHHT-STYINR--RMQLVFDSLGLQRYVLLCS
Wiggum         -HAHDED-DLE--DSDDDDDS--DEDN--DEDSVNGHRIHHT-STYINR--RMQLVFDSLGLQRYVLLCS
PPI-Soy-FTB    -----KE-SLDGTSSHATCRG--EHEG---TSESSSDFKNIAVKFINEWRAQEPLFHSLALQQYVLLCS
DuP-Soy-FTB    -----KE-SLDGTSSHATCRG--EHEG---TSESSSDFKNIAVKFINEWRAQEPLFHSLALQQYVLLCA
PPI-Corn-FTB   -----------TSSYGCTAN---------KSSSAVDYAKFGEDFIQQSNQIGPLFHNIALQQYVLLCS
DuP-Corn-FTB   -----------TSSYGCTAK---------KSSSAVDYAKFGDFIQQSNQIGPLFHNIALQQYVLLCS
Pea FT-B       -----KE-CLDGTSSHATSHI--RHEG---MNESCSSDVKNIGYNFISEWRQSEPLFHSIALQQYVLLCS
Tomato         SELSDREEHLEGISSVQDTFPLGQAGACQENASHSPKIADTGIEFINRPIAMRPLFDSMYLQQYVLLCS
Tobacco        SELSDEE-HLQGTSSHVQKTCPLGQEG--QENASDPTKIADTGYDVNRTIAMRPVFDSFYLQQYVLLCS 430        440        450        460        470        480        490
                   ....|....|....|....|....|....|....|....|....|....|....|....|....|
PPI-BnFTB      QVADGGFRDKLRKPRDFYHTCYCLSGLSVAQHAWSKDEDIPPLTRDILGGYAN-HLEPVHLLHNILVDRY
era1           KLPDGGFRDKPRKPRDFYHTCYCLSGLSVAQHAWLKDEDIPPLTRDIMGGYSN-LLEPVQLLHNIVMDQY
Wiggum         KLPDGGFRDKPRKPRDFYHTCYCLSGLSVAQHAWLKDEDIPPLTRDIMGGYSN-LLEPVQLLHNIVMDQY
```

```
PPI-Soy-FTB    QEQ GGLRDKPGKRRDHYHTCYCLSGLS CQYSWSKHPDSPP-------------------------
DuP-Soy-FTB    QEQ GGLRDKPGKRRDHYHTCYCLSGLS CQYSWSKHPDSPP-------------------------
PPI-Corn-FTB   QVLEGGLRDKPGKNRDHYHSCYCLSGLAVSQYSAMTDTGSCPLPQHVLGPYSN-LLEPIH---------
DuP-Corn-FTB   QVLEGGLRDKPGKNRDHYHSCYCLSGLAVSQYSAMTDTGSCPLPQHVLGPYSN-LLEPIH---------
Pea FT-B       QEQ GGLRDKPGKRRDHYHSCYCLSGLS CQYSWSKRPDSPPLPKVMGPYSSNLLEPIHPLFNVVLDRY
Tomato         QIEVGGFRDKPGKGRD YHTCYCLSGLSTAQYSWIDEADSTPLPRDVFGPYSKCLLEQVHPLFNVVLDRY
Tobacco        QID-GGFRDKPGKGRDHYHTCYCLSGLSLAQYSWINEADAPPLPRDVFGPYSQNLLEQLHPLYNVVLDRY
```

```
                       500        510
               ....|....|....|....|....|
PPI-BnFTB      Y EASR -------------------
era1           N AIE FFKAA---------------
Wiggum         N AIE FFKAA---------------
PPI-Soy-FTB    -------------------------
DuP-Soy-FTB    -------------------------
PPI-Corn-FTB   -------------------------
DuP-Corn-FTB   -------------------------
Pea FT-B       R AHE FSQL---------------
Tomato         Y ARE SQACETVSPLSLAPTFSET
Tobacco        Y ARS FSCL---------------
```

Also included in the invention is the farnesyl transferase alpha consensus sequence of SEQ ID NO:87 and the farnesyl transferase beta consensus sequence of SEQ ID NO:88 To generate the consensus sequence, the farnesyl transferase alpha and farnesyl transferase beta sequences of the invention were aligned using the program BioEdit. The homology between the farnesyl transferase alpha (FTA) polypeptide sequences of the invention is shown graphically in the ClustalW analysis shown in Table 10E. The homology between the farnesyl transferase beta (FTB) polypeptide sequences of the invention is shown graphically in the ClustalW analysis shown in Table 10F.

Table 10E ClustalW Amino Acid Analysis of FT Alpha

```
                    10        20        30        40        50        60        70
             ....|....|....|....|....|....|....|....|....|....|....|....|....|....|
BnA-12       --------------------------------------------------MDYFRAIYFSDERSARALRL
At-FT-A      --------MNFDETVPLSCRLEWSDVVPLTQDDGPNPVVPIAYKEEFRETMDYFRAIYFSDERSPRALRL
PPI-Soy-FTA  MESGSSEGEEVQQRVPLRERVEWSDVTPVPQNDGPNPVVPIQYTEEFSEVMDYFRAVYLSDERSPRALAL
Consensus    --------      VPL R EWSDV P  Q DGPNPVVPI Y EEF E MDYFRAIYFSDERSPRALRL 80        90       100       110       120       130       140
             ....|....|....|....|....|....|....|....|....|....|....|....|....|....|
BnA-12       TEEALRLNSGNYTVWHFGRLVLEELNSDLREELKFIESIAEDNSKNYQL----WHHRRWVAEKLGPDVAG
At-FT-A      TEETLLLNSGNYTVWHFRRLVLEALNSDLREELEFIERIAEDNSKNYQL----WHHRRWVAEKLGPDVAG
PPI-Soy-FTA  TAEAYGBNSGNYTVWHFRRLELESLKVDLNDELEFVERMAAGNSKNYQXXMFCRHPRRWVAEKLGPEARN
Consensus    TEEAL LNSGNYTVWHFRRLVLE LN DL EELEFIERIAEDNSKNYQL----WHHRRWVAEKLGPDVAG 150       160       170       180       190       200       210
             ....|....|....|....|....|....|....|....|....|....|....|....|....|....|
BnA-12       LEKEFTRRVLSLDAKHYHAWSHRQWALQALGGWENELNYCHELLEADVFNNSAWNQRYYVITRSPSLGGL
At-FT-A      RELEFTRRVLSLDAKHYHAWSHRQWTLRALGGWEDELDYCHELLEADVFNNSAWNQRYYVITGSPLLGGL
PPI-Soy-FTA  NELEFTKKILSVDAKHYHAWSHRQWALQTLGGWEDELNYCTELLKEDIFNNSAWNQRYEVITRSPFLGGL
Consensus    ELEFTRRVLSLDAKHYHAWSHRQWALQALGGWEDELNYCHELLEADVFNNSAWNQRYYVITRSP LGGL 220       230       240       250       260       270       280
             ....|....|....|....|....|....|....|....|....|....|....|....|....|....|
BnA-12       EAMRESEVSYTVKAILANPGNESSWRYLKALYKDDTESWISDPSVSSVCLKVLSRADCFHGFALSTLLDL
At-FT-A      EAMRESEVSYTIKAILTNPANESSWRYLKALYKDDKESWISDPSVSSVCLNVLSRTDCFHGFALSTLLDL
PPI-Soy-FTA  KAMRESEVLYTIBAIQAYPENESSWRYLSGLYKGTTSWNDPQVSSVCLKIL-RTKSNYVFALSTILDL
Consensus    EAMRESEVSYTIKAILANP NESSWRYLKALYKDDTESWISDPSVSSVCLKVLSRTDCFHGFALSTLLDL
```

```
                            290       300       310       320       330       340       350
                       ....|....|....|....|....|....|....|....|....|....|....|....|....|
         BnA-12        LCDGLRPTNEHRDSV ALAN--------------EEPETNLANLVCTIL RVDPIRANYWAW L------
         At-FT-A       LCDGLRPTNEH DSVR ALAN--------------EEPETNLANLVCTIL GRVDPIRANYWAWRKS TTVA
         PPI-Soy-FTA    CFGY PNE  IRDA DA KTADMDKQDLDDDEKG  QNL  ARN  S ILK VDPIR  NYW WRKS  P--
         Consensus     LCDGLRPTNEHRDSV  ALAN--------------EEPETNLANLVCTIL  RVDPIRANYWAWRKS    --
```

| | |
|---|---|
| BnA-12 | -- (SEQ ID NO:7) |
| At-FT-A | AI (SEQ ID NO:2) |
| PPI-Soy-FTA | -- (SEQ ID NO:33) |
| Consensus | -- (SEQ ID NO:87) |

Table 10F ClustalW Amino Acid Analysis of FT Beta

```
                            10        20        30        40        50        60        70
                       ....|....|....|....|....|....|....|....|....|....|....|....|....|
         PPI-BnFTB     ----------------------------------------------------------------------
         PPI-Soy-FTB   -------A  PR----------------------NAQT MLEL QRDNH MC YVSK GLRH  SSAF SVLDANR
         PPI-Corn-FTB  ADPDLPRL  T QVEQMKVEARVGDIYRSLFGAAPN TKS MLEL WRDQH  EY  PGLRHMGPAFH VLDANR
         Consensus     -------  T -----------------------N    MLEL  RD H  Y     GLRH    AF  VLDANR 80        90        100       110       120       130       140
                       ....|....|....|....|....|....|....|....|....|....|....|....|....|
         PPI-BnFTB     -WLCYWI HSIALLGESVDDDLENNAIDFL GRCQGSDGGY GGGPGQLPHLAT SYAAVNTLVTLGGEKA S
         PPI-Soy-FTB   PWLCYW  HSIALLGESVDD  LE NAIDFL NRCQDP NGGY GGPGQ PH ATTYAAVNS   TLGGEK L
         PPI-Corn-FTB  PWLCYW  HP  ALLDE  DDDLEND I IDFIARCQDKDGGY GGPGQLPHLATTYAAVNTLVT G S ALS
         Consensus     PWLCYWI  HSIALLGESVDDDLENNAIDFL  RCQD  DGGY GGPGQLPHLATTYAAVNTLVTLGGEKALS 150       160       170       180       190       200       210
                       ....|....|....|....|....|....|....|....|....|....|....|....|....|
         PPI-BnFTB     SINR  MAC FLRRMKD TNGGFRMHN MGEIDVRACYTAIL  AS  LNI  DDDELT G GDYI  SCQTYEGGIG
         PPI-Soy-FTB   SINR  LY GFLRRMKQPNGGFRMHDEGEIDVRACYTAISVAS LNILDDELI Q NVGDYI  SCQTYEGGIA
         PPI-Corn-FTB  SINRGNLYN   L MKD V GAFRMHDGGEIDVRA S YTAISVAS   NILDF  LA KGVGDYIARCQTYEGGIA
         Consensus     SINR   LY  FLRRMKD NGGFRMHD GEIDVRACYTAISVAS  LNILDDEL  GVGDYI  SCQTYEGGIA 220       230       240       250       260       270       280
                       ....|....|....|....|....|....|....|....|....|....|....|....|....|
         PPI-BnFTB     GEPGSEAHGGYT CGLATMILINEV RL NLDSL MNWVVHRQGVE MGFQGRTNKLVDGCY  FWQ A APCVLL
         PPI-Soy-FTB   GEPGSEAHGGYTFCGLATMILI GEVN HLDLPRL VDWVVFRQGK ECGFQGRTNKLVDGCYSFWQGGA ALL
         PPI-Corn-FTB  GEPY  EAHGGYTFCGLA A  IL NEA K VDLPSL  GWVA FRQGVECGFQGRTNKLVDGCYSFWQGAA  AFT
         Consensus     GEPGSEAHGGYTFCGLATMILINEV  LDLPSL  WVVFRQGVECGFQGRTNKLVDGCYSFWQGAA  ALL 290       300       310       320       330       340       350
                       ....|....|....|....|....|....|....|....|....|....|....|....|....|
         PPI-BnFTB     QRFF SS QDMAPHG SS--H MSQGT DEDH  EH G HDEDDPED SDEDDS D DS DE DSG NGHQVH  TSTYIDR R
         PPI-Soy-FTB   QRLSS I NKQ EE  SQIFA V SYVSEAKE SLD GTSS  ATCRG  HEG  SESSSSD KN ---L A KF  N WR A
         PPI-Corn-FTB  QKL I I  DKQ RS S -----Y SCKRPSG  DACS TSSS G-CTANKS----SS  VDYAK---FG FDF QQSNQ
         Consensus     QRLI  SI  DKQ   SS  -- S     E  GTSS  C    ESS    D  N---    FI     R 360       370       380       390       400       410       420
                       ....|....|....|....|....|....|....|....|....|....|....|....|....|
         PPI-BnFTB     I QPVFDS  GL QRY V LLCSQVA DGGFRDKLRK PRDE YHTCYCLSGLSVA QHAWSKDED  PPL TRD  LGG A
         PPI-Soy-FTB   Q EPLFHSIALQQYILLC  Q EQEGGLRDKPGKRRDHYHTCYCLSGLS L CQYSWSKHPDSPP----------
         PPI-Corn-FTB  IGPLFH   IALQQYILLCSQV  EGGLRDKPGKN RDHYH  CYCLSGL  V SQYSAMT DTGS CP  P QHV LGPY S
         Consensus     I  PLFHSIALQQYILLCSQV  EGGLRDKPGK  RDHYHTCYCLSGLSV  QYSWSKD  DSPPI          LG Y 430       440
                       ....|....|....|....|...
         PPI-BnFTB     NHLEP  H LLHNILVDRYYEASRF  (SEQ ID NO:9)
         PPI-Soy-FTB   -----------------------  (SEQ ID NO:36)
         PPI-Corn-FTB  N  LLEP H----------------  (SEQ ID NO:39)
         Consensus     N  LEP  H----------------  (SEQ ID NO:88)
```

Also included in the invention is the farnesyl transferase alpha consensus sequence of SEQ ID NO:89 and the farnesyl transferase beta consensus sequence of SEQ ID NO:90. To generate the consensus sequence, the farnesyl transferase alpha and farnesyl transerase beta sequences of the invention were aligned using the program BioEdit. The homology between the farnesyl transferase alpha (FTA) nucleic acid sequences of the invention is shown graphically in the ClustalW analysis shown in Table 10G. The homology between the farnesyl transferase beta (FTB) nucleic acid sequences of the invention is shown graphically in the ClustalW analysis shown in Table 10H.

Table 10G ClustalW Nucleic Acid Analysis of FT Alpha

```
                      10        20        30        40        50        60
              ....|....|....|....|....|....|....|....|....|....|....|....|
BnA-12        ------------------------------------------------------------   1
At-FT-A       -------------GAGTCGGGGAACATGAATTTCGACGAGACCGTGCCACTGAGCCAACG  47
PPI-Soy-FTA   ATGGAATCTGGGTCTAGCGAAGGAGAAGAGGTGCAGCAACGC-GTGCCGTTGAGGGAGAG  59
Consensus     -------------    CG  G AA GA  T C  CA  C-GTGCC  TGAG  A  G    23

70        80        90       100       110       120
              ....|....|....|....|....|....|....|....|....|....|....|....|
BnA-12        ------------------------------------------------------------   1
At-FT-A       ATTGGAGTGGTCAGACGTGGTCCCATTGACTCAGGACGATGGTCCGAATCCAGTGGTGCC  107
PPI-Soy-FTA   AGTGGAGTGGTCAGATGTTACTCCGGTTCCTCAAAACGACGGCCCTAACCCTGTCGTTCC  119
Consensus     A TGGAGTGGTCAGA GT   CC T  CTCA  ACGA GG CC AA CC GT GT CC     64

130       140       150       160       170       180
              ....|....|....|....|....|....|....|....|....|....|....|....|
BnA-12        ------------------------------ATGGATTACTTCCGTGCGATTTACTTCTC   29
At-FT-A       AATTGCCTACAAGGAAGAGTTCCGCGAGACTATGGATTACTTCCGTGCGATTTACTTTTC  167
PPI-Soy-FTA   GATCCAGTACACTGAAGAGTTTTCCGAAGTTATGGATTACTTTCGCGCCGTTTACCTCAC  179
Consensus        AT  TACA GAAGAGTT  CGA   TATGGATTACTTCCGTGCGATTTACTTCTC  111

190       200       210       220       230       240
              ....|....|....|....|....|....|....|....|....|....|....|....|
BnA-12        CGACGAGCGTTCTGCTCGCGCGCTGCGACTCACGGAAGAAGCTCTCCGCTTAAACTCGGG   89
At-FT-A       CGACGAGCGATCTCCTCGCGCACTACGACTCACGGAAGAAACCCTCCTCTTAAACTCCGG  227
PPI-Soy-FTA   CGATGAACGCTCCCCTCGCGCCCTCGCTCTCACAGCCGAAGCCGTTCAATTCAACTCCGG  239
Consensus     CGACGAGCG  TC CTCGCGC CT CGACTCACGGAAGAAGCCCTCC CTTAAACTCCGG  167

250       260       270       280       290       300
              ....|....|....|....|....|....|....|....|....|....|....|....|
BnA-12        CAACTACACCGTGTGGCACTTCGGGCGCTTAGTACTCGAGGAGCTTAATAACGACTTGTA  149
At-FT-A       CAACTACACAGTGTGGCATTTCAGGCGCCTAGTACTCGAGGCCCTTAATCACGACTTGTT  287
PPI-Soy-FTA   CAACTACACTGTGTGGCATTTCCGACGGTTGTTACTTGAGTCGCTAAAAGTCGACTTGAA  299
Consensus     CAACTACAC GTGTGGCATTTC GGCGCTTAGTACTCGAGGCGCTTAAT ACGACTTGTA  224

310       320       330       340       350       360
              ....|....|....|....|....|....|....|....|....|....|....|....|
BnA-12        TGAAGAGCTCAAGTTCATCGAAAGCATTGCTGAGGATAACTCTAAGAACTACCAGTTGTG  209
At-FT-A       TGAAGAACTCGAGTTCATCGAACGCATTGCTGAGGATAACTCTAAGAACTACCAACTGTG  347
PPI-Soy-FTA   CGATGAACTGGAGTTTGTGGACCGTATGGCCGCTGGAAATTCTAAAAATTATCAGATGTC  359
Consensus     TGAAGAACTCGAGTTCATCGAACGCATTGCTGAGGATAACTCTAAGAACTACCAG TGTG  283

370       380       390       400       410       420
              ....|....|....|....|....|....|....|....|....|....|....|....|
BnA-12        G-------------CATCATCGACGATGGGTCGCAGAGAAACTGGGTCCTGATGTTGCAGG  257
At-FT-A       G-------------CATCATCGGCGATGGGTTGCAGAGAAACTGGGTCCTGATGTTGCAGG  395
PPI-Soy-FTA   NATGTTCTGTAGGCATCCTAGACGATGGGTTGCCGAGAAGTTAGGTCCTGAAGCTAGAAA  419
Consensus     G-------------CATCATCGACGATGGGTTGCAGAGAAACTGGGTCCTGATGTTGCAGG  331

430       440       450       460       470       480
              ....|....|....|....|....|....|....|....|....|....|....|....|
BnA-12        AAAGGAACTTGAGTTTACTCGGAGGGTACTATCACTTGATGCCAAGCATTATCATGCTTG  317
At-FT-A       GAGAGAACTTGAATTTACCCGTAGAGTACTTTCACTTGATGCCAAACATTATCATGCTTG  455
PPI-Soy-FTA   CAATGAGCTCGAGTTCACCAAAAAGATACTGTCCGTTGATGCCAAACATTATCATGCATG  479
Consensus       A GAACTTGAGTTTACCCG AGGGTACT  TCACTTGATGCCAAACATTATCATGCTTG  387
```

```
                        490        500        510        520        530        540
                   ....|....|....|....|....|....|....|....|....|....|....|....|
BnA-12         GTCACATAGGCAGTGGGCGCTACAAGCATTAGGAGGATGGGAAAATGAGCTTAACTACTG 377
At-FT-A        GTCACATAGGCAGTGGACACTACGGGCATTAGGAGGATGGGAAGATGAGCTCGATTACTG 515
PPI-Soy-FTA    GTCTCATAGACAGTGGGCTCTTCAAACACTAGGAGGATGGGAAGATGAACTTAATTATTG 539
Consensus      GTCACATAGGCAGTGGGC CTACAAGCATTAGGAGGATGGGAAGATGAGCTTAATTACTG 446

550        560        570        580        590        600
                   ....|....|....|....|....|....|....|....|....|....|....|....|
BnA-12         CCACGAGCTCCTTGAAGCTGACGTCTTTAACAACTCTGCATGGAATCAGAGGTATTACGT 437
At-FT-A        TCACGAGCTCCTTGAAGCTGACGTCTTTAACAATTCCGCCTGGAATCAGAGGTATTATGT 575
PPI-Soy-FTA    CACAGAACTACTTAAAGAAGACATTTTTAACAATTCTGCTTGGAATCAGAGATATTTTGT 599
Consensus      CCACGAGCTCCTTGAAGCTGACGTCTTTAACAATTCTGC TGGAATCAGAGGTATTATGT 505

610        620        630        640        650        660
                   ....|....|....|....|....|....|....|....|....|....|....|....|
BnA-12         TATAACTAGATCACCTTCGTTGGGAGGCCTAGAAGCCATGAGAGAATCTGAAGTAAGCTA 497
At-FT-A        CATCAGCCAATCTCCTTTGTTGGGAGGCCTAGAAGCCATGAGAGAATCTGAAGTAAGCTA 635
PPI-Soy-FTA    CATAACAAGGTCTCCTTTCTTGGGGGCCTAAAAGCTATGAGAGAGTCTGAAGTGCTTTTA 659
Consensus      CATAAC AGATCTCCTTTGTTGGGAGGCCTAGAAGCCATGAGAGAATCTGAAGTAAGCTA 564

670        680        690        700        710        720
                   ....|....|....|....|....|....|....|....|....|....|....|....|
BnA-12         CACAGTCAAAGCCATTTTAGCAAATCCCGGGAACGAGAGCTCTTGGACGTACCTGAAAGC 557
At-FT-A        CACAATCAAAGCCATTTTAACCAATCCTGCAAACGAGAGCTCATGGCCGATACCTAAAAGC 695
PPI-Soy-FTA    CACCATCGAAGCCATTATAGCCTACCCTGAAAATGAAAGCTCGTGGAGATATCTACGAGG 719
Consensus      CACAATCAAAGCCATTTTAGCCAATCCTG AAACGAGAGCTC TGGAGATACCTAAAAGC 622

730        740        750        760        770        780
                   ....|....|....|....|....|....|....|....|....|....|....|....|
BnA-12         CTTTACAAAGACGACACAGAGTCTTGGATTAGTGATCCAAGTGTTTCCTCAGTCTGTTT 617
At-FT-A        GCTTTACAAAGACGACAAAGAATCCTGGATTAGTGATCCAAGTGTTTCCTCAGTCTGTTT 755
PPI-Soy-FTA   ACTTTATAAAGCGTGAAAACTACTTCATGGCTAAATGATCCTCAAGTTTCTTCAGTATGCTT 779
Consensus      CTTTACAAAGACGACACAGA TC TGGATTAGTGATCCAAGTGTTTCCTCAGTCTGTTT 679

790        800        810        820        830        840
                   ....|....|....|....|....|....|....|....|....|....|....|....|
BnA-12         GAAGTTCTCTCACGCGCGGACTGCTTCCATGGATTCGCTCTGAGCACCCTTTTGGATCT 677
At-FT-A        GAATGTTCTATGCCGCACAGATTGCTTCCATGGATTCGCTCTGAGCACCCTTTTGGATCT 815
PPI-Soy-FTA    AAAGATTTTGA---GAACTAAGAGCAACTACGTGTTTGCTCTTAGCACTATTTTAGATCT 836
Consensus      GAA GTTCT TC CGCAC GA TGCTTCCATGGATTCGCTCTGAGCACCCTTTTGGATCT 734

850        860        870        880        890        900
                   ....|....|....|....|....|....|....|....|....|....|....|....|
BnA-12         TCTGTGCGATGGGTTGAGACCAACCAACGAGCATAGAGACTCGGTGAAAGCTCTAGCTAA 737
At-FT-A        TCTATGTGATGGACTGAGACCAACCAACGAGCATAAAGACTCAGTGAGAGCTCTAGCTAA 875
PPI-Soy-FTA    TATATGCTTTGGTTATCAACCAAATGAAGACATTAGATGCCATTGACGCTTAAAGAC 896
Consensus      TCTATGCGATGG TTGAGACCAACCAACGAGCATAGAGACTC GTGAAAGCTCTAGCTAA 792

910        920        930        940        950        960
                   ....|....|....|....|....|....|....|....|....|....|....|....|
BnA-12         TGAAGAACCAGAGACTAACTTGGCCAATTTGGTGTGTACCATTCTGTGTCGTGTTGATCC 797
At-FT-A        TGAAGAACCAGAGACTAACTTGGCCAATTTGGTGTGTACTATTCTTGGTCGTGTAGATCC 935
PPI-Soy-FTA    CGCAGA--TATGGATAAACAAGATTTAGATGATGATGAGAAAGGGGAACAACAAAATTTA 954
Consensus      TGAAGAACCAGAGACTAACTTGGCCAATTTGGTGTGTAC ATTCTG GTCGTGTAGATCC 850

970        980        990        1000       1010       1020
                   ....|....|....|....|....|....|....|....|....|....|....|....|
BnA-12         AATA-AGAGCTAACTATTGGGC--ATGG-------------------------------- 822
At-FT-A        TATA-AGAGCTAACTATTGGGC--ATGGAGGAAGAGCAAGATTACAGTGCCAGCAATTTG 992
PPI-Soy-FTA    AATATAGCACGAAATATTTGTTCTATCCTAAAACAAGTTGATCCAATTAGAACCAACTAT 1014
Consensus      AATA-AGAGCTAACTATTGGGC--ATGG  AA  GAT  A T G A  CAA T 889

1030       1040       1050       1060       1070       1080
                   ....|....|....|....|....|....|....|....|....|....|....|....|
BnA-12         ------------------------------------------------------------ 822
At-FT-A        AATATGTGACGGCCCAAAATCACACTTGAAAAAGACTTGATTATTAGTTTTTACGTAATT 1052
PPI-Soy-FTA    TGGATTTGGCGCAAGAGCAGACTTCCT--------------------------------- 1041
Consensus         AT TG CGC  AA A   CT T  ------------------------------- 900
```

```
                     1090      1100      1110      1120      1130      1140
                ....|....|....|....|....|....|....|....|....|....|....|....|
BnA-12          ------------------------------------------------------------ 822
At-FT-A         AACTGCTTATTTATGAATCACATGTTCATGTTAACATGTATCAAAACAATCTTGATTTCT 1112
PPI-Soy-FTA     ------------------------------------------------------------ 1041
Consensus       ------------------------------------------------------------ 900

1150      1160      1170
                ....|....|....|....|....|....|.
BnA-12          ------------------------------- 822  (SEQ ID NO:6)
At-FT-A         CAAAAAAAAAAAAAAAAAAAAAAAAAAAAAA 1143 (SEQ ID NO:1)
PPI-Soy-FTA     ------------------------------- 1041 (SEQ ID NO:31)
Consensus       ------------------------------- 900  (SEQ ID NO:89)
```

Table 10H ClustalW Nucleic Acid Analysis of FT Beta

```
                     10        20        30        40        50        60
                ....|....|....|....|....|....|....|....|....|....|....|....|
PPI-BnFTb       ------------------------------------------------------------ 1
eral            ------------------------------------------------------------ 1
PPI-Soy-FTB     ------------------------------------------------------------ 1
PPI-Corn-FTB    GGCGGATCCCGACCTACCGAGGCTCACGGTGACGCAGGTGGAGCAGATGAAGGTGGAGGC 60
Consensus       ------------------------------------------------------------ 1

70        80        90        100       110       120
                ....|....|....|....|....|....|....|....|....|....|....|....|
PPI-BnFTb       ------------------------------------------------------------ 1
eral            ------------------------------------------------------------ 1
PPI-Soy-FTB     --------------------------------GCCACCATTCCTCGCAACGCCCAAACCCTCAT 32
PPI-Corn-FTB    CAGGGTTGGCGACATCTACCGCTCCCTCTTCGGGGCCGCGCCCAACACGAAATCCATCAT 120
Consensus       ---------------------------                                  1

130       140       150       160       170       180
                ....|....|....|....|....|....|....|....|....|....|....|....|
PPI-BnFTb       ------------------------------------------------------------ 1
eral            -ATGGAGATTCAGCGAGATAAGCAATTGGATTATCTGATGAAAGGCTTAAGGCAGCTTGG 59
PPI-Soy-FTB     GTTGGAGCTTCAACGCGATAATCACATGCAGTATGTCTCCAAAGGCCTTCGCCATCTCAG 92
PPI-Corn-FTB    GCTAGAGCTGTGGCGTGATCAGCATATCGAGTATCTGACGCCTGGGCTGACGCATATGGG 180
Consensus        T GAC T     CG GAT A CA T   A TAT T        GG T GCA T  G  27

190       200       210       220       230       240
                ....|....|....|....|....|....|....|....|....|....|....|....|
PPI-BnFTb       -----------------------------------TGGCTTTGTTACTGGATTCTTCATTC 26
eral            TCCGCAGTTTTCTTCCTTAGATGCTAATCGACCTGGCTTTGTTACTGGATTCTTCATTC 119
PPI-Soy-FTB     TTCCGCATTTTCCGTTTTGGACGCTAATCGACCCTGGCTCTGCTACTGGATCTTCCACTC 152
PPI-Corn-FTB    ACCAGCCTTTCATGTTCTAGATGCCAATCGCCCTTGGCTATGCTACTGGATGGTTCATCC 240
Consensus        C   TTT     T GA GC AATCG CC TGGCT TG TACTGGAT   TTCATTC  65

250       260       270       280       290       300
                ....|....|....|....|....|....|....|....|....|....|....|....|
PPI-BnFTb       AATTGCTTTGCTTGGGGAGTCTGTGGATGATGACTTAGAAAACAATGCAATCGATTTTCT 86
eral            AATAGCTTTGCTTGGGGAGACTGTGGATGATGAATTAGAAAGCAATGCCATTGACTTCCT 179
PPI-Soy-FTB     CATTGCTTTGTTGGGAGAATCCGTCGATGATGAACTCGAAGATAACGCTATCGATTTTCT 212
PPI-Corn-FTB    ACTTGCTTTGCTGGATGAAGCACTTGATGATGATCTTGAGAATGATATCATAGACTTCTT 300
Consensus       AATTGCTTTGCT GG GA  C GT GATGATGA T GAAAA AATGC AT GA TT CT 111

310       320       330       340       350       360
                ....|....|....|....|....|....|....|....|....|....|....|....|
PPI-BnFTb       TGGACGTTGCCAGGGTTCTGATGGTGGATATGGTGGTGGTCCTGGCCAACTTCCACATCT 146
eral            TGGACGCTGCCAGGGCTCTGAAGGTGGATACGGTGGTGGTCCTGGCCAACTTCCACATCT 239
PPI-Soy-FTB     TAACCGTTGCCAGGATCCGAATGGTGGATATGCCGGGGGACCAGGCCAGATGCCTCATAT 272
PPI-Corn-FTB    AGCTCGATGTCAGGATAAAGATGGTGGATATAGTGGTGGACCTGGACAGTTGCCTCACCT 360
Consensus       TG  CG TGCCAGG T C  GATGGTGGATATGGTGGTGG CCTGGCCA T CC CATCT 160

370       380       390       400       410       420
                ....|....|....|....|....|....|....|....|....|....|....|....|
PPI-BnFTb       TGCAACAAGTTATGCTGCAGTGAATACACTTGTTACTTTAGGAGGTGAGAAAGCCTTCTC 206
eral            TGCAACTACTTATGCTGCAGTGAATGCACTTGTTACTTTAGGAGGTGACAAAGCCCTTTC 299
PPI-Soy-FTB     TGCCACAACTTATGCTGCTGTTAATTCACTTATTACTTTGGGTGGTGAGAAATCCCTGGC 332
PPI-Corn-FTB    AGCTACGACTTATGCTGCTGTAAATACACTTGTGACAATAGGGAGCGAAAGAGCATTGTC 420
Consensus       TGC AC ACTTATGCTGC GT AAT CACTTGTTACTTTAGG GGTGA AAAGCC T TC 211
```

```
                    430        440        450        460        470        480
                ....|....|....|....|....|....|....|....|....|....|....|....|
PPI-BnFTb       TTCAATTAACAGAGAACAAATGGCTTGTTTCTTAAGACGAATGAAGGATACAAATGGAGG 266
eral            TTCAATTAATAGAGAAAAAATGTCTTGTTTTTTAAGACGGATGAAGGATACAAGTGGAGG 359
PPI-Soy-FTB     ATCAATTAATAGAGATAAACTGTATGGGTTCTGCGGCGGATGAAGCAACCAAATGGTGG  392
PPI-Corn-FTB    ATCAATCAATAGGGGCAACCTGTACAATTTTATGCTGCAGATGAAAGATGTATCAGGTGC 480
Consensus       TCAATTAATAGAGA AAA TGT T GTTTT T  G CGGATGAAGGAT CAA TGG GG   259

490        500        510        520        530        540
                ....|....|....|....|....|....|....|....|....|....|....|....|
PPI-BnFTb       TTTCAGGATGCATAATATGGGAGAAATAGATGTGCGAGCGTGCTACACTGCGATTTTGAT 326
eral            TTTCAGGATGCATGATATGGGAGAAATTGATGTTCGTGCATGCTACACTGCAATTTCGGT 419
PPI-Soy-FTB     ATTCAGGATGCATGATGAAGGTGAAATTGATGTTCGAGCTTGCTACACTGCCATTTCTGT 452
PPI-Corn-FTB    TTTCAGAATGCATGATGGTGGCGAAATTGATGTCCGTGCTTCCTACACCGCTATATCGGT 540
Consensus       TTTCAGGATGCATGAT  GG GAAATTGATGT CG GC TGCTACACTGC ATTTCGGT   311

550        560        570        580        590        600
                ....|....|....|....|....|....|....|....|....|....|....|....|
PPI-BnFTb       TGCAAGCATCCTGAACATTGTGGATGATGAACTCACCCGCGGCTTAGGAGATTACATTTT 386
eral            TGCAAGCATCCTAAATATTATGGATGATGAACTCACCCAGGGCCTAGGAGATTACATCTT 479
PPI-Soy-FTB     TGCAAGTGTTTTGAACATTTTGGATGATGAGCTGATCCAGAATGTTGGAGACTACATTAT 512
PPI-Corn-FTB    TGCCAGCCTTGTGAATATTCTTGATTTTAAACTGGCAAAAGCTGTAGGCGACTACATAGC 600
Consensus       TGCAAGC T  TGAA ATT TGGATGATGAACT ACCCA GG  TAGGAGA TACAT T   359

610        620        630        640        650        660
                ....|....|....|....|....|....|....|....|....|....|....|....|
PPI-BnFTb       GAGTTGCCAAACTTATGAAGGTGGCATTGGAGGGGAACCTGGCTCCGAAGCTCATGGTGG 446
eral            GAGTTGCCAAACTTATGAAGGTGGCATTGGAGGGGAACCTGGCTCCGAAGCTCACGGTGG 539
PPI-Soy-FTB     AAGCTGTCAAACATATGAGGGTGGCATTGCTGGTGAGCCTGGTTCGAGGCTCATGGTGG  572
PPI-Corn-FTB    AAGATGTCAAACTTATGAAGGTGGTATTGCTGGGGAGCCTTATGCTGAAGCACATGGTGG 660
Consensus       AG TG CAAACTTATGAAGGTGGCATTG  GGGGA CCTGG TC GAAGCTCATGGTGG   411

670        680        690        700        710        720
                ....|....|....|....|....|....|....|....|....|....|....|....|
PPI-BnFTb       GTACAGGTACTGTGGGTTGGCTACTATGATTTTAATCAATGAAGTCGACCGCTTGAATTT 506
eral            GTATACCTACTGTGGGTTTGGCTGCTATGATTTTAATCAATGAGGTCGACCGTTTGAATTT 599
PPI-Soy-FTB     GTACACCTTTTGTGGATTAGCTACAATGATTCTGATTGGTGAGGTTAATCACTTGGATCT 632
PPI-Corn-FTB    GTATACATTCTGTGGATTGGCTGCTTTGATCCTGCTTAATGAGCAGAGAAAGTTGACTT  720
Consensus       GTA AC T CTGTGG TTGGCT CTATGATT T AT AATGAGGT GA C TTG ATTT   458

730        740        750        760        770        780
                ....|....|....|....|....|....|....|....|....|....|....|....|
PPI-BnFTb       GGATTCGTTAATGAATTGGGTTGTACATCGACAAGGAGTAGAAATGGGATTCCAAGGCTAG 566
eral            GGATTCATTAATGAATTGGGCTGTACATCGACAAGGAGTAGAAATGGGATTTCAAGGTAG 659
PPI-Soy-FTB     GCCTCGATTAGTTGACTGGGTGGTATTCCGACAAGGTAAGGAATGTGGATTCCAGGGGAG 692
PPI-Corn-FTB    GCCTAGTTTCATTGGCTGGGTGGCTTTTCGTCAAGGAGTGGAATGCGGATTTCAAGGACG 780
Consensus       G  T   TTAAT A TGGGT GTA TCGACAAGGAGT GAA  GGATT CAAGG AG     501

790        800        810        820        830        840
                ....|....|....|....|....|....|....|....|....|....|....|....|
PPI-BnFTb       GACGAACAAATTGGTCGACGGTTGCTACACGTTTTGGCAGGCAGCCCCCTGTGTTCTACT 626
eral            GACGAACAAATTGGTCGATGGTTGCTACACATTTTGGCAGGCAGCCCCTTGTGTTCTACT 719
PPI-Soy-FTB     AACAAATAAACTGGTGGATGGATGCTATTCCTTTTGGCAGGGAGGTGCTGTTGCTCTATT 752
PPI-Corn-FTB    AACTAATAAATTGGTTGATGGTTGCTACTCCTTTTGGCAGGGAGCTGCCATTGCTTTCAC 840
Consensus       AC AA  AAATTGGT GATGGTTGCTAC C TTTTGGCAGG AGC C   TG TCTA T    547

850        860        870        880        890        900
                ....|....|....|....|....|....|....|....|....|....|....|....|
PPI-BnFTb       ACAGCGATTTTTTTCATCCCAGGGAT-ATGGCACCTCATGGATCATCATCACATATGTCAC 685
eral            ACAAAGATTATATTCAACCAATGATCATCACGT-TCATTGGATCATCA---CATATATCAG 775
PPI-Soy-FTB     GCAAAGATTATCTTCTATTATCAAC-AAACAGATGGAAGAGACATCA-C-----AGATTT 805
PPI-Corn-FTB    ACAAAGTTAATTACGATTGTTGAT-AAGCAA---------------------------- 871
Consensus       ACAAAGATTAT  TTC A     GAT A G       A G      CATCA- -        574

910        920        930        940        950        960
                ....|....|....|....|....|....|....|....|....|....|....|....|
PPI-BnFTb       AAGGCACAGATGAAGATCACGAGGAACATGGTCATGATGAAGATGATCCTGAAGACAGTG 745
eral            AAGGCACAAATGAAGAACAT------CATGCTCATGATGAAGATGACCTTCAAGACAGTG 829
PPI-Soy-FTB     TTGCGGTATCTTATGTATCTGAAGCAAAAGAAAGTTTGGATGGAACCTCTAGTCATGCAA 865
PPI-Corn-FTB    TTGACGT-CCTCGTATTGCTG---CAAAAGCGCATCAGGAGAGGATGCCTG--CA-GCAC 924
```

```
Consensus         G G  A   T G  C TG    A A G  CAT A GA C      CCTG  A        598
                      970       980       990      1000      1010      1020
                  ....|....|....|....|....|....|....|....|....|....|....|....|
PPI-BnFTb         ATGAAGATGAT---TCTGATGAGGATAGCGATGAAGATTCAGGGAATGGTCACCAAGTTC  802
eral              ATCATCATGATGATTCTGATGAGGACAACGATGAAGATTCACTGAATGGTCACAGAATCC  889
PPI-Soy-FTB       CATGCCGTGGTGAGCATGAAGGCACCAGTGAATCCAGTTCATCTGATTTTAAAAATATTG  925
PPI-Corn-FTB      CAGTTCATA-TGGGTGCACCGCGAATAAGTCTTCCTCTGCTGTGGACTATGCGAAGTTTG  983
Consensus            G   ATG TG  T TGA G G A  GAT    TTCAG G AT  T  AA  TT     629

1030      1040      1050      1060      1070      1080
                  ....|....|....|....|....|....|....|....|....|....|....|....|
PPI-BnFTb         ATCATACGTCTACCTACATTGACAGGAGAATTCAACCTGTTTTTGATAGCCTCGGCTTGC  862
eral              ATCATACATCCACCTACATTAACAGGAGAATGCATGGTTTTTGATAGCCTCGGCTTGC   949
PPI-Soy-FTB       CCTATAAATTTATTAATGAGTGGAGAGCACAAGAACCACTTTTTCACAGTATTGCTTTAC  985
PPI-Corn-FTB      GATTTGATTTTATACAACAGAGCAACCAAATTGGCCCACTCTTCCATAACATTGCCCTGC  1043
Consensus            ATA   T TA  A      CAG   AAT  AACC  TTTTT ATAGC T G  CTTGC  663

1090      1100      1110      1120      1130      1140
                  ....|....|....|....|....|....|....|....|....|....|....|....|
PPI-BnFTb         AAAGATATGTGCTCTTGTGCTCTCAGGTTGCTGATGGTGGATTCAGAGACAAGCTGAGGA  922
eral              AGAGATATGTACTCTTGTGCTCTAAGATCCCTGACGGTGGATTCAGAGACAAGCCGAGGA  1009
PPI-Soy-FTB       AGCAATATATTCTCTTATGTGCACAGGAGCAAGAGGGTGGACTGAGAGACAAACCGGGTA  1045
PPI-Corn-FTB      AACAATACATCCTACTTTGTTCTCAGGTACTAGAGGGAGCCTTGAGGGCATAAGCCTGAA  1103
Consensus         A  ATAT T CTCTT TG TCTCAGGT C GA GGTGGATT AGAGACAAGCCG G A    709

1150      1160      1170      1180      1190      1200
                  ....|....|....|....|....|....|....|....|....|....|....|....|
PPI-BnFTb         AACCCCGTGACTTCTACCACACATGTTACTGCCTAAGCGGTCTTTCCGTGGCTCAACACG  982
eral              AACCCCGTGACTTCTACCACACATGTTACTGCCTGAGCGGCTTGTCTGTGGCTCAGCACG  1069
PPI-Soy-FTB       AACGTAGAGATCATTATCACACATGTTACTGTTTAAGTGGACTCTCATTGTGCCAGTATA  1105
PPI-Corn-FTB      AGAACAGAGATCACTATCATTCATGCTACTGCCTCAGTGGCCTCGCAGTTAGCCAGTACA  1163
Consensus         AAC C G GA   CTA CACACATGTTACTGCCT AG GG CT TC GTG   CAG AC    752

1210      1220      1230      1240      1250      1260
                  ....|....|....|....|....|....|....|....|....|....|....|....|
PPI-BnFTb         CTTGGTCAAAGACGAGGACACTCCTCCTTTGACTCGTGACATTTGCGTGGCTACGCAA   1042
eral              CTTGGTTAAAAGACGAGGACACTCCTCCTTTGACTCGCGACATTATGGGTGGCTACTCGA  1129
PPI-Soy-FTB       GTTGGTCAAAGCACCCAGATTCTCCACCGAC-----------------------------  1135
PPI-Corn-FTB      GTGCCATGACTGATACTGGTTCGTGCCCATTACCTCAGCATGTGCTTGGACCGTACTCTA  1223
Consensus          TTGGT AAA GAC GA  CTCC CC T  CTC   A  T  GG     TAC C A     786

1270      1280      1290      1300      1310      1320
                  ....|....|....|....|....|....|....|....|....|....|....|....|
PPI-BnFTb         ACCACCTTGAACCTGTTCACCTCCTCCACAACATTGTCTTGGATCGGTATTATGAAGCTT  1102
eral              ATCTCCTTGAACCTGTTCAACTTCTTCACAACATTGTCATGGATCAGTATAATGAAGCTA  1189
PPI-Soy-FTB       ------------------------------------------------------------  1135
PPI-Corn-FTB      ATTTGCTGGAGCCAATCCATCC--------------------------------------  1245
Consensus         A  CT GA CC T CA C                                            797

1330      1340      1350      1360      1370      1380
                  ....|....|....|....|....|....|....|....|....|....|....|....|
PPI-BnFTb         CTAGATTT----------------------------------------------------  1110
eral              TCGAGTTCTTCTTTAAAGCAGCATGACCCGTTGTTGCTAATGTATGGGAAACCCCAAACA  1249
PPI-Soy-FTB       ------------------------------------------------------------  1135
PPI-Corn-FTB      ------------------------------------------------------------  1245
Consensus         ------------------------------------------------------------  797

1390      1400      1410      1420
                  ....|....|....|....|....|....|....|.
PPI-BnFTb         ------------------------------------ 1110 (SEQ ID NO:8)
eral              TAAGAGTTTCCGTAGTGTTGTAACTTGTAAGATTTCAAAAG 1290 (SEQ ID NO:73)
PPI-Soy-FTB       ------------------------------------ 1135 (SEQ ID NO:34)
PPI-Corn-FTB      ------------------------------------ 1245 (SEQ ID NO:37)
Consensus         ------------------------------------  797 (SEQ ID NO:90)
```

Example 5

Vector Constructs for Transformation

The FTA or FTB sequences have be used to produce constructs suitable for transformation into plants and under the control of appropriate regulatory sequences. The gene sequences were in either the sense orientation for overexpression or the antisense orientation for down-regulation. Portions of these sequences have been used to construct a double-stranded-RNA-inhibition (dsRNAi) construct. A sequence of preferably not less than 21 nt was cloned as an inverse repeat separated by a linker that when expressed results in down-regulation of the target gene. Double antisense (DA) vectors have been created in which a direct repeat of an antisense sequence is separated by a spacer sequence such as GUS. Promoters have been used for constitutive expression such as the 35S CaMV promoter, the MuA *Zea maize* promoter or inducible by specific environmental or cellular cues such as the ABA levels or drought conditions which induce expression of the RD29A promoter. Alternatively, tissue or organelle specific promoters such as the HIC or CUT1 promoter can be used. Such constructs have been transformed into *Arabidopsis thaliana, Brassica, Zea maize, Glycine max*. Other species can be transformed as desired. Each species to be transformed may make use of specific regulatory sequences as appropriate for those particular species. Transformed plants have be selected and their phenotypic properties analyzed. The transgenic plants were assessed for characteristics such as increased tolerance to drought, altered biomass accumulation, yield, nutritional requirements such as minerals or micro-nutrients, biotic stress such as fungal, bacterial, or other such pathogen infection or attack or any other such physical or biochemical characteristic.

Example 6

Plant Transformation

*Arabidopsis thaliana* transgenic plants were made by flower dipping method into an *Agrobacterium* culture. Wild type plants were grown under standard conditions until they began flowering. The plant was inverted for 2 min into a solution of *Agrobacterium* culture. Plants were then bagged for two days to maintain humidity and then uncovered to continue growth and seed development. Mature seed was bulk harvested.

Transformed T1 plants were selected by germination and growth on MS plates containing 50 µg/ml kanamycin. Green, kanamycin resistant seedlings were identified after 2 weeks growth and transplanted to soil. Plants were bagged to ensure self fertilization and the T2 seed of each plant harvested separately. During growth of T1 plants leaf samples were harvested, DNA extracted and Southern analysis performed.

T2 seeds were analyzed for $Kan^R$ segregation. From those lines that showed a 3:1 resistant phenotype surviving T2 plants were grown, bagged during seed set, and T3 seed harvested from each line. T3 seed was again used for $Kan^R$ segregation analysis and those lines showing 100% $Kan^R$ phenotype were selected as homozygous lines. Further analysis was done using T3 seed.

Transgenic *Brassica napus* plants were produced using *Agrobacterium* mediated transformation of cotyledon petiole tissue. Seeds were sterilized as follows. Seeds were wetted with 95% ethanol for a short period of time such as 15 seconds. Approximately 30 ml of sterilizing solution I was added (70% Javex, 100 µl Tween20) and left for approximately 15 minutes. Solution I was removed and replaced with 30 ml of solution II (0.25% mecuric chloride, 100 µl Tween20) and incubated for about 10 minutes. Seeds were rinsed with at least 500 ml double distilled sterile water and stored in a sterile dish. Seeds were germinated on plates of ½ MS medium, pH 5.8, supplemented with 1% sucrose and 0.7% agar. Fully expanded cotyledons were harvested and placed on Medium I (Murashige minimal organics (MMO), 3% sucrose, 4.5 mg/L benzyl adenine (BA), 0.7% phytoagar, pH5.8). An *Agrobacterium* culture containing the nucleic acid construct of interest was grown for 2 days in AB Minimal media. The cotyledon explants were dipped such that only the cut portion of the petiole is contacted by the *Agrobacterium* solution. The explants were then embedded in Medium I and maintained for 5 days at 24° C., with 16.8 hr light dark cycles. Explants were transferred to Medium II (Medium I, 300 mg/L timentin,) for a further 7 days and then to Medium III (Medium II, 20 mg/L kanamycin). Any root or shoot tissue which had developed at this time was dissected away. Transfer explants to fresh plates of Medium III after 14 –21 days. When regenerated shoot tissue developed the regenerated tissue was transferred to Medium IV (MMO, 3% sucrose, 1.0% phytoagar, 300 mg/L timentin, 20 mg/L 20 mg/L kanamycin). Once healthy shoot tissue developed shoot tissue dissected from any callus tissue was dipped in 10×IBA and transferred to Medium V (Murashige and Skooge (MS), 3% sucrose, 0.2 mg/L indole butyric acid (IBA), 0.7% agar, 300 mg/L timentin, 20 mg/L 20 mg/L kanamycin) for rooting. Healthy plantlets were transferred to soil.

Transgenic *Glycine max, Zea maize* and cotton can be produced using *Agrobacterium*-based methods which are known to one of skill in the art. Alternatively one can use a particle or non-particle biolistic bombardment transformation method. An example of non-particle biolistic transformation is given in U.S. Patent Application 20010026941. Viable plants are propogated and homozygous lines are generated. Plants are tested for the presence of drought tolerance, physiological and biochemical phenotypes as described elsewhere.

The following table indentifies the constructs and the species which they have been transformed.

TABLE 11

| SEQ ID NO: | SEQ | Species Transformed | | |
|---|---|---|---|---|
| SEQ ID NO:4 | pBI121-35S-anti-AtFTA | *Arabidopsis thaliana* | | |
| SEQ ID NO:40 | pBI121-35S-AtFTA | *Arabidopsis thaliana* | *Brassica napus* | |
| SEQ ID NO:41 | pBI121-rd29A-anti-AtFTA | *Arabidopsis thaliana* | *Brassica napus* | |
| SEQ ID NO:42 | pBI121-35S-DA-AtFTA | *Arabidopsis thaliana* | *Brassica napus* | |
| SEQ ID NO:43 | pBI121-RD29A-DA-AtFTA | *Arabidopsis thaliana* | *Brassica napus* | |
| SEQ ID NO:44 | MuA-anti-GmFTA | | | *Glycine max* |

TABLE 11-continued

| SEQ ID NO: | SEQ | | Species Transformed | |
|---|---|---|---|---|
| SEQ ID NO:45 | RD29A-anti-GmFTA | | | Glycine max |
| SEQ ID NO:46 | MuA-HP-GmFTA-Nos-Term | | | Glycine max |
| SEQ ID NO:47 | RD29AP-HP-GmFTA-Nos-Term | | | Glycine max |
| SEQ ID NO:48 | pBI121-35S-Anti-AtFTB | Arabidopsis thaliana | Brassica napus | |
| SEQ ID NO:49 | pBI121-RD29AP-Anti-AtFTB | Arabidopsis thaliana | Brassica napus | |
| SEQ ID NO:50 | pBI121-35S-HP-AtFTB | Arabidopsis thaliana | Brassica napus | |
| SEQ ID NO:51 | pBI121-RD29AP-HP-AtFTB | Arabidopsis thaliana | Brassica napus | |
| SEQ ID NO:52 | pBI121-35S-AtFTB | Arabidopsis thaliana | | |
| SEQ ID NO:53 | MuA-anti-GmFTB-Nos-Term | | | Glycine max |
| SEQ ID NO:54 | RD29AP-anti-GmFTB-Nos-Term | | | Glycine max |
| SEQ ID NO:55 | MuA-HP-GmFTB-Nos-Term | | | Glycine max |
| SEQ ID NO:56 | RD29AP-HP-GmFTB-Nos-Term | | | Glycine max |
| SEQ ID NO:57 | MuA-anti-Zea maizeFTB-Nos-Term | | Zea maize | |
| SEQ ID NO:58 | MuA-HP-Zea maizeFTB-Nos-Term | | Zea maize | |

Non-limiting examples of vector constructs suitable for plant transformation are given in SEQ ID NO: 4, 40–58.

SEQ ID NO:4 gtttacccgccaatatatcctgtcaaacactgatagtttaaactgaaggcgggaaacgacaatctgatcatgagcg gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag gatctcctgtcatctcaccttgctcctgccgagaaagtatccatcatggctgatgcaatgcggcggctgcatacgc ttgatccggctacctgcccattcgaccaccaagcgaaacatcgcatcgagcgagcacgtactcggatggaagccgg tcttgtcgatcaggatgatctggacgaagagcatcaggggctcgcgccagccgaactgttcgccaggctcaaggcg cgcatgcccgacggcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgg gacgccggctggatgatcctccagcgcggggatctcatgctggagttcttcgcccacgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg cgttcggatattttcgtggagttcccgccacagacccggatgatcccgatcgttcaaacatttggcaataaagtt tcttaagattgaatcctgttgccggtcttgcgatgattatcatataatttctgttgaattacgttaagcatgtaat aattaacatgtaatgcatgacgttatttatgagatgggtttttatgattagagtcccgcaattatacatttaatac gcgatagaaaacaaaatatagcgcgcaaactaggataaattatcgcgcgcggtgtcatctatgttactagatcggg cctcctgtcaatgctggcggcggctctggtggtggttctggtggcggctctgagggtggtggctctgagggtggcg gttctgagggtggcggctctgagggaggcggttccggtggtggctctggttccggtgattttgattatgaaagat ggcaaacgctaataaggggctatgaccgaaaatgccgatgaaaacgcgctacagtctgacgctaaaggcaaactt -continued gattctgtcgctactgattacggtgctgctatcgatggtttcattggtgacgtttccggccttgctaatggtaatg gtgctactggtgattttgctggctctaattcccaaatggctcaagtcggtgacggtgataattcacctttaatgaa taatttccgtcaatatttaccttccctccctcaatcggttgaatgtcgccttttgtctttggcccaatacgcaaa ccgcctctccccgcgcgttggccgattcattaatgcagctggcacgacaggtttcccgactggaaagcgggcagtg agcgcaacgcaattaatgtgagttagctcactcattaggcaccccaggctttacactttatgcttccggctcgtat gttgtgtggaattgtgagcggataacaatttcacacaggaaacagctatgaccatgattacgccaagcttgcatgc ctgcag<u>cccacagatggttagagaggcttacgcagcaggtctcatcaagacgatctacccgagcaataatctccag</u>

<u>gaaatcaaatacctccccaagaaggttaaagatgcagtcaaaagattcaggactaactgcatcaagaacacagaga</u>

<u>aagatatatttctcaagatcagaagtactattccagtatggacgattcaaggcttgcttcacaaaccaaggcaagt</u>

<u>aatagagattggagtctctaaaaaggtagttcccactgaatcaaaggccatggagtcaaagattcaaatagaggac</u>

<u>ctaacagaactcgccgtaaagactggcgaacagttcatacagagtctcttacgactcaatgacaagaagaaaatct</u>

<u>tcgtcaacatggtggagcacgacacacttgtctactccaaaaatatcaaagatacagtctcagaagaccaaagggc</u>

<u>aattgagacttttcaacaagggtaatatccggaaacctcctcggattccattgcccagctatctgtcactttatt</u>

<u>gtgaagatagtggaaaaggaaggtggctcctacaaatgccatcattgcgataaaggaaaggccatcgttgaagatg</u>

<u>cctctgccgacagtggtcccaaagatggaccccacccacgaggagcatcgtggaaaagaagacgttccaaccac</u>

<u>gtcttcaaagcaagtggattgatgtgatatctccactgacgtaagggatgacgcacaatcccactatccttcgcaa</u>

<u>gacccttcctctatataaggaagttcatttcatttggagagaacacgggggactctagaggatcc</u>tcaaattgctg ccactgtaatcttgctcttcctccatgcccaatagttagctcttataggatctacacgaccaagaatagtacacac caaattggccaagttagtctctggttcttcattagctagagctctcactgagtctttatgctcgttggttggtctc agtccatcacatagaagatccaaaagggtgctcagagcgaatccatggaagcaatctgtgcgggatagaacattca aacagactgaggaaacacttggatcactaatccaggattctttgtcgtctttgtaaagcgcttttaggtatcgcca tgagctctcgtttgcaggattggttaaaatggctttgattgtgtagcttacttcagattctctcatggcttctagg cctcccaacaaaggagattgggtgatgacataatacctctgattccaggcggaattgttaaagacgtcagcttcaa ggagctcgtgacagtaatcgagctcatcttcccatcctcctaatgcccgtagtgtccactgcctatgtgaccaagc atgataatgtttggcatcaagtgaaagtactctacgggtaaattcaagttctctccctgcaacatcaggacccagt ttctctgcaacccatcgccgatgatgccacagttggtagttcttagagttatcctcagcaatgcgttcgatgaact cgagttcttcaaacaagtcgtgattaagggcctcgagtactaggcgcctgaaatgccacactgtgtagttgccgga gtttaagaggagggtttcttccgtgagtcgtagtgcgcgaggagatcgctcgtcggaaaagtaaatcgcacggaag taatccatagtctcgcggaactcttccttgtaggcaattggcaccactggattcggaccatcgtcctgagtcaatg ggaccacgtctgaccactccaatcgttggctcagtggcacggtctcgtcgaaattcatccc<b>ctcgaatttcccga</b>

<b>tcgttcaaacatttggcaataaagtttcttaagattgaatcctgttgccggtcttgcgatgattatcatataattt</b>

<b>ctgttgaattacgttaagcatgtaataattaacatgtaatgcatgacgttatttatgagatgggtttttatgatta</b>

<b>gagtcccgcaattatacatttaatacgcgatagaaaacaaaatatagcgcgcaaactaggataaattatcgcgcgc</b>

<b>ggtgtcatctatgttactagatcgggaattcactggccgtcgttttacaacgtcgtgactgggaaaaccctggcgt</b>

<b>tacccaacttaatcgccttgcagcacatccccctttcgccagctggcgtaatagcgaagaggcccgcaccgatcgc</b>

<b>ccttcccaacagttgcgcagcctgaatggcgcccgctcctttcgctttcttcccttcctttctcgccacgttcgcc</b>

<b>ggctttccccgtcaagctctaaatcggggctccctttagggttccgatttagtgctttacggcacctcgaccccca</b>

<b>aaaaacttgatttgggtgatggttcacgtagtgggccatcgccctgatagacggtttttcgccctttgacgttgga</b>

<b>gtccacgttctttaatagtggactcttgttccaaactggaacaacactcaacccatctcgggctattcttttgat</b>

<b>ttataagggattttgccgatttcggaaccaccatcaaacaggattttcgcctgctggggcaaaccagcgtggaccg</b>

-continued cttgctgcaactctctcagggccaggcggtgaagggcaatcagctgttgcccgtctcactggtgaaaagaaaaacc acccccagtacattaaaaacgtccgcaatgtgttattaagttgtctaagcgtcaatttgtttacaccacaatatatc ctgcca SEQ ID NO:4 is the nucleic acid sequence of pBI121-antisense-FTA vector construct used to transform *Arabidopsis* plants. Italicized sequences are the right and left border repeats (1–24, 5226–5230). Underlined sequence is the 35S promoter (2515–3318). Bold sequence is the anti-sense Farnesyl transferase alpha sequence (3334–4317).

SEQ ID NO:40 gtttacccgccaatatatcctgtcaaacactgatagtttaaactgaaggcgggaaacgacaatctgatcatgagcg gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag gatctcctgtcatctcaccttgctcctgccgagaaagtatccatcatggctgatgcaatgcggcggctgcatacgc ttgatccggctacctgcccattcgaccaccaagcgaaacatcgcatcgagcgagcacgtactcggatggaagccgg tcttgtcgatcaggatgatctggacgaagagcatcaggggctcgcgccagccgaactgttcgccaggctcaaggcg cgcatgcccgacggcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgg gacgccggctggatgatcctccagcgcggggatctcatgctggagttcttcgcccacgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg cgttcggatattttcgtggagttcccgccacagacccggatgatccccgatcgttcaaacatttggcaataaagtt tcttaagattgaatcctgttgccggtcttgcgatgattatcatataatttctgttgaattacgttaagcatgtaat aattaacatgtaatgcatgacgttatttatgagatgggtttttatgattagagtcccgcaattatacatttaatac gcgatagaaaacaaaatatagcgcgcaaactaggataaattatcgcgcgcggtgtcatctatgttactagatcggg cctcctgtcaatgctggcggcggctctggtggtggttctggtggcggctctgagggtggtggctctgagggtggcg gttctgagggtggcggctctgagggaggcggttccggtggtggctctggttccggtgattttgattatgaaaagat ggcaaacgctaataaggggctatgaccgaaaatgccgatgaaaacgcgctacagtctgacgctaaaggcaaactt gattctgtcgctactgattacggtgctgctatcgatggtttcattggtgacgtttccggccttgctaatggtaatg gtgctactggtgattttgctggctctaattcccaaatggctcaagtcggtgacggtgataattcacctttaatgaa taatttccgtcaatatttaccttccctccctcaatcggttgaatgtcgcccttttgtctttggcccaatacgcaaa ccgcctctccccgcgcgttggccgattcattaatgcagctggcacgacaggtttcccgactggaaagcgggcagtg agcgcaacgcaattaatgtgagttagctcactcattaggcaccccaggctttacactttatgcttccggctcgtat -continued gttgtgtggaattgtgagcggataacaatttcacacaggaaacagctatgaccatgattacgccaagcttgcatgc ctgcag<u>cccacagatggttagagaggcttacgcagcaggtctcatcaagacgatctacccgagcaataatctccag</u>

<u>gaaatcaaataccttcccaagaaggttaaagatgcagtcaaaagattcaggactaactgcatcaagaacacagaga</u>

<u>aagatatatttctcaagatcagaagtactattccagtatggacgattcaaggcttgcttcacaaaccaaggcaagt</u>

<u>aatagagattggagtctctaaaaaggtagttcccactgaatcaaaggccatggagtcaaagattcaaatagaggac</u>

<u>ctaacagaactcgccgtaaagactggcgaacagttcatacagagtctcttacgactcaatgacaagaagaaaatct</u>

<u>tcgtcaacatggtggagcacgacacacttgtctactccaaaaatatcaaagatacagtctcagaagaccaaagggc</u>

<u>aattgagacttttcaacaaaggtaatatccggaaacctcctcggattccattgcccagctatctgtcactttatt</u>

<u>gtgaagatagtggaaaaggaaggtggctcctacaaatgccatcattgcgataaaggaaaggccatcgttgaagatg</u>

<u>cctctgccgacagtggtcccaaagatggaccccccacccacgaggagcatcgtggaaaaagaagacgttccaaccac</u>

<u>gtcttcaaagcaagtggattgatgtgatatctccactgacgtaagggatgacgcacaatcccactatccttcgcaa</u>

<u>gacccttcctctatataaggaagttcatttcatttggagagaacacgggg</u>gactctagaggatcctgaatttcga cgagaccgtgccactgagccaacgattggagtggtcagacgtggtcccattgactcaggacgatggtccgaatcca gtggtgccaattgcctacaaggaagagttccgcgagactatggattacttccgtgcgatttacttttccgacgacc gatctcctcgcgcactacgactcacggaagaaaccctcctcttaaactccggcaactacacagtgtggcatttcag gcgcctagtactcgaggcccttaatcacgacttgtttgaagaactcgagttcatcgaacgcattgctgaggataac tctaagaactaccaactgtggcatcatcggcgatgggttgcagagaaactgggtcctgatgttgcagggagagaac ttgaatttacccgtagagtactttcacttgatgccaaacattatcatgcttggtcacataggcagtggacactacg ggcattaggaggatgggaagatgagctcgattactgtcacgagctccttgaagctgacgtctttaacaattccgcc tggaatcagaggtattatgtcatcacccaatctcctttgttgggaggcctagaagccatgagagaatctgaagtaa gctacacaatcaaagccatttttaaccaatcctgcaaacgagagctcatggcgatacctaaaagctctttacaaaga cgacaaagaatcctggattagtgatccaagtgtttcctcagtctgtttgaatgttctatcccgcacagattgcttc catggattcgctctgagcacccttttggatcttctatgtgatggactgagaccaaccaacgagcataaagactcag tgagagctctagctaatgaagaaccagagactaacttggccaatttggtgtgtactattcttggtcgtgtagatcc tgtaagagctaactattgggcatggaggaagagcaagattacagtggcagcaatttgactcgaatttccccgatcg ttcaaacatttggcaataaagtttcttaagattgaatcctgttgccggtcttgcgatgattatcatataatttctg ttgaattacgttaagcatgtaataattaacatgtaatgcatgacgttatttatgagatgggttttttatgattagag tcccgcaattatacatttaatacgcgatagaaaacaaatatagcgcgcaaactaggataaattatcgcgcgcggt gtcatctatgttactagatcgggaattcactggccgtcgttttacaacgtcgtgactgggaaaaccctggcgttac ccaacttaatcgccttgcagcacatccccctttcgccagctggcgtaatagcgaagaggcccgcaccgatcgccct tcccaacagttgcgcagcctgaatggcgccgctcctttcgctttcttccctccttttctcgccacgttcgccggc tttccccgtcaagctctaaatcggggggctcccttagggttccgatttagtgctttacggcacctcgaccccaaaa aacttgatttgggtgatggttcacgtagtgggccatcgcccgatagacggttttttcgccctttgacgttggagtc cacgttctttaatagtggactcttgttccaaactggaacaacactcaacccatctcgggctattcttttgatttta taagggattttgccgatttcggaaccaccatcaaacaggattttcgcctgctggggcaaaccagcgtggaccgctt gctgcaactctctcagggccaggcggtgaagggcaatcagctgttgcccgtctcactggtgaaaagaaaaaccacc ccagtacattaaaaacgtccgcaatgtgttattaagttgtctaagcgtcaatt*tgtttacaccacaatatatcctg*

*cca*

(Underlined Seq: 35S promoter; Bold: AtFTA)

SEQ ID NO:41

*gtttacccgccaatatatcctgtcaaacactgatagtttaaactgaaggcgggaaacgacaatctgatcatgagcg*

-continued gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag gatctcctgtcatctcaccttgctcctgccgagaaagtatccatcatggctgatgcaatgcggcggctgcatacgc ttgatccggctacctgcccattcgaccaccaagcgaaacatcgcatcgagcgagcacgtactcggatggaagccgg tcttgtcgatcaggatgatctggacgaagagcatcaggggctcgcgccagccgaactgttcgccaggctcaaggcg cgcatgcccgacgcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctgggggttcgaaatgaccgaccaagcgac gcccaacctgccatcacgagatttcgattccaccgccgccttctatgaaaggttgggcttcggaatcgttttccgg gacgccggctggatgatcctccagcgcggggatctcatgctggagttcttcgcccacgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg cgttcggatattttcgtggagttcccgccacagacccggatgatccccgatcgttcaaacatttggcaataaagtt tcttaagattgaatcctgttgccggtcttgcgatgattatcatataatttctgttgaattacgttaagcatgtaat aattaacatgtaatgcatgacgttatttatgagatgggttttttatgattagagtcccgcaattatacatttaatac gcgatagaaaacaaaatatagcgcgcaaactaggataaattatcgcgcgcggtgtcatctatgttactagatcggg cctcctgtcaatgctggcggcggctctggtggtggttctggtggcggctctgagggtggtggctctgagggtggcg gttctgagggtggcggctctgagggaggcggttccggtggtggctctggttccggtgattttgattatgaaaagat ggcaaacgctaataagggggctatgaccgaaaatgccgatgaaaacgcgctacagtctgacgctaaaggcaaactt gattctgtcgctactgattacggtgctgctatcgatggtttcattggtgacgtttccggccttgctaatggtaatg gtgctactggtgattttgctggctctaattcccaaatggctcaagtcggtgacggtgataattcacctttaatgaa taatttccgtcaatatttaccttcccctcccaatcggttgaatgtcgcccttttgtctttggcccaatacgcaaa ccgcctctccccgcgcgttggccgattcattaatgcagctggcacgacaggtttcccgactggaaagcgggcagtg agcgcaacgcaattaatgtgagttagctcactcattaggcaccccaggctttacactttatgcttccggctcgtat gttgtgtggaattgtgagcggataacaatttcacacaggaaacagctatgaccatgattacgccaagcttgcatgc ctgcag<u>ggagccatagatgcaattcaatcaaactgaaatttctgcaagaatctcaaacacggagatctcaaagttt</u>

<u>gaaagaaaatttatttcttcgactcaaaacaaacttacgaaatttaggtagaacttatatacattatattgtaatt</u>

<u>ttttgtaacaaaatgttttttattattattatagaattttactggttaaattaaaaatgaatagaaaaggtgaatta</u>

<u>agaggagagaggaggtaaacattttcttctatttttttcatattttcaggataaattattgtaaaagtttacaagat</u>

<u>ttccatttgactagtgtaaatgaggaatattctctagtaagatcattatttcatctacttcttttatcttctacca</u>

<u>gtagaggaataaacaatatttagctcctttgtaaatacaaattaattttccttcttgacatcattcaattttaatt</u>

<u>ttacgtataaaataaagatcatacctattagaacgattaaggagaaatacaattcgaatgagaaggatgtgccgt</u>

<u>ttgttataataaacagccacacgacgtaaacgtaaaatgaccacatgatgggccaatagacatggaccgactacta</u>

-continued

<u>ataatagtaagttacattttaggatggaataaatatcataccgacatcagttttgaaaagaaaagggaaaaagaa</u>

<u>aaaataaataaaagatatactaccgacatgagttccaaaaagcaaaaaaaaagatcaagccgacacagacacgcgt</u>

<u>agagagcaaaatgactttgacgtcacaccacgaaaacagacgcttcatacgtgtccctttatctctctcagtctct</u>

<u>ctataaacttagtgagaccctcctctgttttactcacaaatatgcaaactagaaaacaatcatcaggaataaaggg</u>

<u>tttgattacttctattggaaag</u>actctagaggatcctcaaattgctgccactgtaatcttgctcttcctccatgcc caatagttagctcttataggatctacacgaccaagaatagtacacaccaaattggccaagttagtctctggttctt cattagctagagctctcactgagtctttatgctcgttggttggtctcagtccatcacatagaagatccaaagggt gctcagagcgaatccatggaagcaatctgtgcgggatagaacattcaaacagactgaggaaacacttggatcacta atccaggattctttgtcgtctttgtaaagcgcttttaggtatcgccatgagctctcgtttgcaggattggttaaaa tggctttgattgtgtagcttacttcagattctctcatggcttctaggcctcccaacaaaggagattgggtgatgac ataatacctctgattccaggcggaattgttaaagacgtcagcttcaaggagctcgtgacagtaatcgagctcatct tcccatcctcctaatgcccgtagtgtccactgcctatgtgaccaagcatgataatgtttggcatcaagtgaaagta ctctacgggtaaattcaagttctctccctgcaacatcaggacccagtttctctgcaacccatcgccgatgatgcca cagttggtagttcttagagttatcctcagcaatgcgttcgatgaactcgagttcttcaaacaagtcgtgattaagg gcctcgagtactaggcgcctgaaatgccacactgtgtagttgccggagtttaagaggagggtttcttccgtgagtc gtagtgcgcgaggagatcgctcgtcggaaaagtaaatcgacggaagtaatccatagtctcgcggaactcttcctt gtaggcaattggcaccactggattcggaccatcgtcctgagtcaatgggaccacgtctgaccactccaatcgttgg ctcagtggcacggtctcgtcgaaattcatcccctcgaatttccccgatcgttcaaacatttggcaataaagtttct taagattgaatcctgttgccggtcttgcgatgattatcatataatttctgttgaattacgttaagcatgtaataat taacatgtaatgcatgacgttatttatgagatgggttttttatgattagagtcccgcaattatacatttaatacgcg atagaaaacaaaatatagcgcgcaaactaggataaattatcgcgcgcggtgtcatctatgttactagatcgggaat tcactggccgtcgttttacaacgtcgtgactgggaaaaccctggcgttacccaacttaatcgccttgcagcacatc cccctttcgccagctggcgtaatagcgaagaggcccgcaccgatcgcccttcccaacagttgcgcagcctgaatgg cgcccgctcctttcgctttcttcccttcctttctcgccacgttcgccggctttccccgtcaagctctaaatcgggg gctcccctttaggggttccgatttagtgctttacggcacctcgaccccaaaaaacttgatttgggtgatggttcacgt agtgggccatcgccctgatagacggtttttcgccctttgacgttggagtccacgttctttaatagtggactcttgt tccaaactggaacaacactcaaccctatctcgggctattcttttgatttataagggattttgccgatttcggaacc accatcaaacaggattttcgcctgctggggcaaaccagcgtggaccgcttgctgcaactctctcagggccaggcgg tgaagggcaatcagctgttgcccgtctcactggtgaaaagaaaaaccacccccagtacattaaaaacgtccgcaatg tgttattaagttgtctaagcgtcaatttg*tttacaccacaatatatcctgcca*
(Underlined Seq: RD29A promoter; Bold: Anti-sense-AtFTA)

SEQ ID NO:42

*gtttacccgccaatatatcctgtc*aaacactgatagtttaaactgaaggcgggaaacgacaatctgatcatgagcg gagaattaagggagtcacgttatgacccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag -continued gatctcctgtcatctcaccttgctcctgccgagaaagtatccatcatggctgatgcaatgcggcggctgcatacgc ttgatccggctacctgcccattcgaccaccaagcgaaacaecgcatcgagcgagcacgtactcggatggaagccgg tcttgtcgatcaggatgatctggacgaagagcatcaggggctcgcgccagccgaactgttcgccaggctcaaggcg cgcatgcccgacgcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctggggttcgaaatgaccgaccaagcgac gcccaacctgccatcacgagatttcgattccaccgccgccttctatgaaaggtgggcttcggaatcgttttccgg gacgccggctggatgatcctccagcgcgggatctcatgctggagttcttcgcccacgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg cgttcggatattttcgtggagttcccgccacagaccggatgatcccgatcgttcaaacatttggcaataaagtt tcttaagattgaatcctgttgccggtcttgcgatgattatcatataatttctgttgaattacgttaagcatgtaat aattaacatgtaatgcatgacgttatttatgagatgggttttttatgattagagtcccgcaattatacatttaatac gcgatagaaaacaaatatagcgcgcaaactaggataaattatcgcgcgcggtgtcatctatgttactagatcggg cctcctgtcaatgctggcggcggctctggtggtggttctggtggcggctctgagggtggtggctctgagggtggcg gttctgagggtggcggctctgagggaggcggttccggtggtggctctggttccggtgattttgattatgaaaagat ggcaaacgctaataaggggctatgaccgaaaatgccgatgaaaacgcgctacagtctgacgctaaaggcaaactt gattctgtcgctactgattacggtgctgctatcgatggtttcattggtgacgtttccggccttgctaatggtaatg gtgctactggtgattttgctggctctaattcccaaatggctcaagtcggtgacggtgataattcaccttttaatgaa taatttccgtcaatatttaccttccctccctcaatcggttgaatgtcgcccttttgtctttggcccaatacgcaaa ccgcctctccccgcgcgttggccgattcattaatgcagctggcacgacaggtttcccgactggaaagcgggcagtg agcgcaacgcaattaatgtgagttagctcactcattaggcacccaggctttacactttatgcttccggctcgtat gttgtgtggaattgtgagcggataacaatttcacacaggaaacagctatgaccatgattacgccaagcttgcatgc ctgcag<u>cccacagatggttagagaggcttacgcagcaggtctcatcaagacgatctacccgagcaataatctccag</u>

<u>gaaatcaaatacctttcccaagaaggttaaagatgcagtcaaaagattcaggactaactgcatcaagaacacagaga</u>

<u>aagatatatttctcaagatcagaagtactattccagtatggacgattcaaggcttgcttcacaaaccaaggcaagt</u>

<u>aatagagattggagtctctaaaaaggtagttcccactgaatcaaaggccatggagtcaaagattcaaatagaggac</u>

<u>ctaacagaactcgccgtaaagactggcgaacagttcatacagagtctcttacgactcaatgacaagaagaaaatct</u>

<u>tcgtcaacatggtggagcacgacacacttgtctactccaaaaatatcaaagatacagtctcagaagaccaaagggc</u>

<u>aattgagacttttcaacaaagggtaatatccggaaacctcctcggattccattgcccagctatctgtcactttatt</u>

<u>gtgaagatagtggaaaggaaggtggctcctacaaatgccatcattgcgataaaggaaaggccatcgttgaagatg</u>

<u>cctctgccgacagtggtcccaaagatggacccccacccacgaggagcatcgtggaaaaagaagacgttccaaccac</u>

<u>gtcttcaaagcaagtggattgatgtgatatctccactgacgtaagggatgacgcacaatcccactatccttcgcaa</u>

<u>gacccttcctctatataaggaagttcatttcatttggagagaacacgggg</u>gactctagaggatcctcGCTCTTCCT

CCATGCCCAATAGTTAGCTCTTACAGGATCTACACGACCAAGAATAGTACACACCAAATTGGCCAAGTTAGTCTCT

GGTTCTTCATTAGCTAGAGCTCTCACTGAGTCTTTATGCTCGTTGGTTGGTCTCAGTCCATCACATAGAAGATCCA

AAAGGGTGCTCAGAGCGAATCCATGGAAGCAATCTGTGCGGGATAGAACATTCAAACAGACTGAGGAAACACTTGG

ATCACTAATCCAGGATTCTTTGTCGTCTTTGTAAAGAGCTTTTAGGTATCGCCATGAGCTCTCGTTTGCAGGATTG

GTTAAAATGGCTTTGATTGTGTAGCTTACTTCAGATTCTCTCATGGCTTCTAGGCCTCCCAACAAAGGAGATTGGG

-continued

TGATGACATAATACCTCTGATTCCAGGCGGAATTGTTAAAGACGTCAGCTTCAAGGAGCTCGTGACAGTAATCGAG

CTCATCTTCCCATCCTCCTAATGCCCGgaggatccccATCTACCCGCTTCGCGTCGGCATCCGGTCAGTGGCAGTG

AAGGGCGAACAGTTCCTGATTAACCACAAACCGTTCTACTTTACTGGCTTTGGTCGTCATGAAGATGCGGACTTGC

GTGGCAAAGGATTCGATAACGTGCTGATGGTGCACGACCACGCATTAATGGACTGGATTGGGGCCAACTCCTACCG

TACCTCGCATTACCCTTACGCTGAAGAGATGCTCGACTGGGCAGATGAACATGGCATCGTGGTGATTGATGAAACT

GCTGCTGTCGGCTTTTCGCTCTCTTTAGGCATTGGTTTCGAAGCGGGCAACAAGCCGAAAGAACTGTACAGCGAAG

AGGCAGTCAACGGGGAAACTCAGCAAGCGCACTTACAGGCGATTAAAGAGCTGATAGCGCGTGACAAAAACCACCC

AAGCGTGGTGATGTGGAGTATTGCCAACGAACCGGATACCCGTCCGCAAGGTGCACGGGAATATTTCGCGCCACTG

GCGGAAGCAACGCGTAAACTCGACCCGACGCGTCCGATCACCTGCGTCAATGTAATGTTCTGCGACGCTCACACCG

ATACCATCAGCGATCTCTTTGATGTGCTGTGCCTGAACCGTTATTACGGATGGTATGTCCAAAGCGGCGATTTGGA

AACGGCAGAGAAGGTACTGGAAAAAGAACTTCTGGCCTGGCAGGAGAAACTGTACACCGACATGTGGAGTGAAGAG

TATCAGTGTGCATGGCTGGATATGTATCACCGCGTCTTTGATCGCGTCAGCGCCGTCGTCGGTGAACAGGTATGGA

ATTTCGCCGATTTTGCGACCTCGCAAGGCATATTGCGCGTTGGCGGTAACAAGAAAGGGATCTTCACTCGCGACCG

CAAACCGAAGTCGGCGGCTTTTCTGCTGCAAAAACGCTGGACTGGCATGAACTTCGGTGAAAAACCGCAGCAGGGA

GGCAAACAATGAATCAACAACTCTCCTGGCGCACCATCGTCGGCTACAGCCTCGGGAATTGCTACCGAGCTCGCTC

TTCCTCCATGCCCAATAGTTAGCTCTTACAGGATCTACACGACCAAGAATAGTACACACCAAATTGGCCAAGTTAG

TCTCTGGTTCTTCATTAGCTAGAGCTCTCACTGAGTCTTTATGCTCGTTGGTTGGTCTCAGTCCATCACATAGAAG

ATCCAAAAGGGTGCTCAGAGCGAATCCATGGAAGCAATCTGTGCGGGATAGAACATTCAAACAGACTGAGGAAACA

CTTGGATCACTAATCCAGGATTCTTTGTCGTCTTTGTAAAGAGCTTTTAGGTATCGCCATGAGCTCTCGTTTGCAG

GATTGGTTAAAATGGCTTTGATTGTGTAGCTTACTTCAGATTCTCTCATGGCTTCTAGGCCTCCCAACAAAGGAGA

TTGGGTGATGACATAATACCTCTGATTCCAGGCGGAATTGTTAAAGACGTCAGCTTCAAGGAGCTCGTGACAGTAA

TCGAGCTCATCTTCCCATCCTCCTAATGCCCGctcgaatttccccgatcgttcaaacatttggcaataaagtttct taagattgaatcctgttgccggtcttgcgatgattatcatataatttctgttgaattacgttaagcatgtaataat taacatgtaatgcatgacgttatttatgagatgggttttatgattagagtcccgcaattatacatttaatacgcg atagaaaacaaaatatagcgcgcaaactaggataaattatcgcgcgcggtgtcatctatgttactagatcgggaat tcactggccgtcgttttacaacgtcgtgactgggaaaaccctggcgttacccaacttaatcgccttgcagcacatc cccctttcgccagctggcgtaatagcgaagaggcccgcaccgatcgcccttcccaacagttgcgcagcctgaatgg cgcccgctcctttcgctttcttcccttcctttctcgccacgttcgccggctttccccgtcaagctctaaatcgggg gctccctttagggttccgatttagtgctttacggcacctcgaccccaaaaaacttgatttgggtgatggttcacgt agtgggccatcgccctgatagacggtttttcgccctttgacgttggagtccacgttctttaatagtggactcttgt tccaaactggaacaacactcaaccctatctcgggctattcttttgatttataagggattttgccgatttcggaacc accatcaaacaggattttcgcctgctggggcaaaccagcgtggaccgcttgctgcaactctctcagggccaggcgg tgaagggcaatcagctgttgccgtctcactggtgaaaagaaaaaccacccagtacattaaaaacgtccgcaatg tgttattaagttgtctaagcgtcaatttg*tttacaccacaatatatcctgcca*

(Underlined Seq: 35S promoter; Bold: AtFTA anti-sense sequence separated by GUS Seq.)

SEQ ID NO:43

*gtttacccgccaatatatcctgtc*aaacactgatagtttaaactgaaggcgggaaacgacaatctgatcatgagcg gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt -continued

```
tcgcatgattgaacaagatggattgcacgcaggttctccggccgcttgggtggagaggctattcggctatgactgg
gcacaacagacaatcggctgctctgatgccgccgtgttccggctgtcagcgcaggggcgcccggttcttttttgtca
agaccgacctgtccggtgccctgaatgaactgcaggacgaggcagcgcggctatcgtggctggccacgacgggcgt
tccttgcgcagctgtgctcgacgttgtcactgaagcgggaagggactggctgctattgggcgaagtgccggggcag
gatctcctgtcatctcaccttgctcctgccgagaaagtatccatcatggctgatgcaatgcggcggctgcatacgc
ttgatccggctacctgcccattcgaccaccaagcgaaacatcgcatcgagcgagcacgtactcggatggaagccgg
tcttgtcgatcaggatgatctggacgaagagcatcaggggctcgcgccagccgaactgttcgccaggctcaaggcg
cgcatgcccgacggcgatgatctcgtcgtgacccatggcgatgcctgcttgccgaatatcatggtggaaaatggcc
gcttttctggattcatcgactgtggccggctgggtgtggcggaccgctatcaggacatagcgttggctacccgtga
tattgctgaagagcttggcggcgaatgggctgaccgcttcctcgtgctttacggtatcgccgctcccgattcgcag
cgcatcgccttctatcgccttcttgacgagttcttctgagcgggactctggggttcgaaatgaccgaccaagcgac
gcccaacctgccatcacgagatttcgattccaccgccgccttctatgaaaggttgggcttcggaatcgtttttccgg
gacgccggctggatgatcctccagcgcgggatctcatgctggagttcttcgcccacgggatctctgcggaacagg
cggtcgaaggtgccgatatcattacgacagcaacggccgacaagcacaacgccacgatcctgagcgacaatatgat
cgggcccggcgtccacatcaacggcgtcggcggcgactgcccaggcaagaccgagatgcaccgcgatatcttgctg
cgttcggatatttttcgtggagttcccgccacagaccggatgatcccgatcgttcaaacatttggcaataaagtt
tcttaagattgaatcctgttgccggtcttgcgatgattatcatataatttctgttgaattacgttaagcatgtaat
aattaacatgtaatgcatgacgttatttatgagatgggttttttatgattagagtcccgcaattatacatttaatac
gcgatagaaaacaaaatatagcgcgcaaactaggataaattatcgcgcgcggtgtcatctatgttactagatcggg
cctcctgtcaatgctggcggcggctctggtggtggttctggtggcggctctgagggtggtggctctgagggtggcg
gttctgagggtggcggctctgagggaggcggttccggtggtggctctggttccggtgattttgattatgaaaagat
ggcaaacgctaataaggggctatgaccgaaaatgccgatgaaaacgcgctacagtctgacgctaaaggcaaactt
gattctgtcgctactgattacggtgctgctatcgatggtttcattggtgacgtttccggccttgctaatggtaatg
gtgctactggtgattttgctggctctaattcccaaatggctcaagtcggtgacggtgataattcaccttttaatgaa
taatttccgtcaatatttaccttccctccctcaatcggttgaatgtcgcccttttgtctttggcccaatacgcaaa
ccgcctctccccgcgcgttggccgattcattaatgcagctggcacgacaggtttcccgactggaaagcgggcagtg
agcgcaacgcaattaatgtgagttagctcactcattaggcaccccaggctttacactttatgcttccggctcgtat
gttgtgtggaattgtgagcggataacaatttcacacaggaaacagctatgaccatgattacgccaagcttgcatgc
ctgcaggagccatagatgcaattcaatcaaactgaaatttctgcaagaatctcaaacacggagatctcaaagttt
gaaagaaaatttatttcttcgactcaaaacaaacttacgaaatttaggtagaacttatatacattatattgtaatt
ttttgtaacaaaatgttttattattattatagaattttactggttaaattaaaaatgaatagaaaggtgaatta
agaggagagaggaggtaaacattttcttctatttttttcatattttcaggataaattattgtaaaagtttacaagat
ttccatttgactagtgtaaatgaggaatattctcagtaagatcattatttcatctacttcttttatcttctacca
gtagaggaataaacaatatttagctcctttgtaaatacaaattaattttccttcttgacatcattcaatttaatt
ttacgtataaaataaaagatcatacctattagaacgattaaggagaaatacaattcgaatgagaaggatgtgccgt
ttgttataataaacagccacacgacgtaaacgtaaaatgaccacatgatgggccaatagacatggaccgactacta
ataatagtaagttacattttaggatggaataaaatatcataccgacatcagttttgaaaagaaaagggaaaaagaa
aaaataaataaaagatatactaccgacatgagttccaaaaagcaaaaaaaaagatcaagccgacacagacacgcgt
agagagcaaaatgactttgacgtcacaccacgaaaacagacgcttcatacgtgtcccttttatctctctcagtctct
ctataaacttagtgagaccctcctctgttttactcacaaatatgcaaactagaaaacaatcatcaggaataaaggg
```

-continued tttgattacttctattggaaaggactctagaggatccGCTCTCTTCCTCCATGCCCAATAGTTAGCTCTTACAGGA
TCTACACGACCAAGAATAGTACACACCAAATTGGCCAAGTTAGTCTCTGGTTCTTCATTAGCTAGAGCTCTCACTG
AGTCTTTATGCTCGTTGGTTGGTCTCAGTCCATCACATAGAAGATCCAAAAGGGTGCTCAGAGCGAATCCATGAA
GCAATCTGTGCGGGATAGAACATTCAAACAGACTGAGGAAACACTTGGATCACTAATCCAGGATTCTTTGTCGTCT
TTGTAAAGAGCTTTTAGGTATCGCCATGAGCTCTCGTTTGCAGGATTGGTTAAAATGGCTTTGATTGTGTAGCTTA
CTTCAGATTCTCTCATGGCTTCTAGGCCTCCCAACAAAGGAGATTGGGTGATGACATAATACCTCTGATTCCAGGC
GGAATTGTTAAAGACGTCAGCTTCAAGGAGCTCGTGACAGTAATCGAGCTCATCTTCCCATCCTCCTAATGCCCGg
aggatccccATCTACCCGCTTCGCGTCGGCATCCGGTCAGTGGCAGTGAAGGGCGAACAGTTCCTGATTAACCACA
AACCGTTCTACTTTACTGGCTTTGGTCGTCATGAAGATGCGGACTTGCGTGGCAAAGGATTCGATAACGTGCTGAT
GGTGCACGACCACGCATTAATGGACTGGATTGGGGCCAACTCCTACCGTACCTCGCATTACCCTTACGCTGAAGAG
ATGCTCGACTGGGCAGATGAACATGGCATCGTGGTGATTGATGAAACTGCTGCTGTCGGCTTTTCGCTCTCTTTAG
GCATTGGTTTCGAAGCGGGCAACAAGCCGAAAGAACTGTACAGCGAAGAGGCAGTCAACGGGAAACTCAGCAAGC
GCACTTACAGGCGATTAAAGAGCTGATAGCGCGTGACAAAAACCACCCAAGCGTGGTGATGTGGAGTATTGCCAAC
GAACCGGATACCCGTCCGCAAGGTGCACGGGAATATTTCGCGCCACTGGCGGAAGCAACGCGTAAACTCGACCCGA
CGCGTCCGATCACCTGCGTCAATGTAATGTTCTGCGACGCTCACACCGATACCATCAGCGATCTCTTTGATGTGCT
GTGCCTGAACCGTTATTACGGATGGTATGTCCAAAGCGGCGATTTGGAAACGGCAGAGAAGGTACTGGAAAAAGAA
CTTCTGGCCTGGCAGGAGAAACTGTACACCGACATGTGGAGTGAAGAGTATCAGTGTGCATGGCTGGATATGTATC
ACCGCGTCTTTGATCGCGTCAGCGCCGTCGTCGGTGAACAGGTATGGAATTTCGCCGATTTTGCGACCTCGCAAGG
CATATTGCGCGTTGGCGGTAACAAGAAAGGGATCTTCACTCGCGACCGCAAACCGAAGTCGGCGGCTTTTCTGCTG
CAAAAACGCTGGACTGGCATGAACTTCGGTGAAAAACCGCAGCAGGGAGGCAAACAATGAATCAACAACTCTCCTG
GCGCACCATCGTCGGCTACAGCCTCGGGAATTGCTACCGAGCTCGCTCTTCCTCCATGCCCAATAGTTAGCTCTTA
CAGGATCTACACGACCAAGAATAGTACACACCAAATTGGCCAAGTTAGTCTCTGGTTCTTCATTAGCTAGAGCTCT
CACTGAGTCTTTATGCTCGTTGGTTGGTCTCAGTCCATCACATAGAAGATCCAAAAGGGTGCTCAGAGCGAATCCA
TGGAAGCAATCTGTGCGGGATAGAACATTCAAACAGACTGAGGAAACACTTGGATCACTAATCCAGGATTCTTTGT
CGTCTTTGTAAAGAGCTTTTAGGTATCGCCATGAGCTCTCGTTTGCAGGATTGGTTAAAATGGCTTTGATTGTGTA
GCTTACTTCAGATTCTCTCATGGCTTCTAGGCCTCCCAACAAAGGAGATTGGGTGATGACATAATACCTCTGATTC
CAGGCGGAATTGTTAAAGACGTCAGCTTCAAGGAGCTCGTGACAGTAATCGAGCTCATCTTCCCATCCTCCTAATG
CCCGctcgaatttccccgatcgttcaaacatttggcaataaagtttcttaagattgaatcctgttgccggtcttgc
gatgattatcatataatttctgttgaattacgttaagcatgtaataattaacatgtaatgcatgacgttatttatg
agatgggttttatgattagagtcccgcaattatacatttaatacgcgatagaaaacaaaatatagcgcgcaaact
aggataaattatcgcgcggtgtcatctatgttactagatcggaattcactgccgtcgttttacaacgtcgtg
actgggaaaccctggcgttacccaacttaatcgccttgcagcacatccccctttcgccagctggcgtaatagcga
agaggcccgcaccgatcgcccttcccaacagttgcgcagcctgaatggcgcccgctcctttcgctttcttcccttc
ctttctcgccacgttcgccggctttccccgtcaagctctaaatcgggggctcccttttagggttccgatttagtgct
ttacggcacctcgaccccaaaaaacttgatttgggtgatggttcacgtagtgggccatcgccctgatagacggttt
ttcgccctttgacgttggagtccacgttctttaatagtggactcttgttccaaactggaacaacactcaaccctat
ctcgggctattcttttgatttataagggattttgccgatttcggaaccaccatcaaacaggattttcgcctgctgg
ggcaaaccagcgtggaccgcttgctgcaactctctcagggccaggcggtgaagggcaatcagctgttgcccgtctc
actggtgaaagaaaaaccacccagtacattaaaaacgtccgcaatgtgttattaagttgtctaagcgtcaattt
gtttacaccacaatatatcctgcca -continued (Underlined Seq: RD29A promoter; Bold: AtFTA anti-sense sequence, separated by GUS Seq.)

SEQ ID NO:44

GAATTC<u>AAATTTTTCGCCAGTTCTAAATATCCGGAAACCTCTTGGGATGCCATTGCCCATCTATCTGTAATTTATT</u>

<u>GACGAAATAGACGAAAAGGAAGGTGGCTCCTATAAAGCACATCATTGCGATAACAGAAAGGCCATTGTTGAAGATA</u>

<u>CCTCTGCTGACATTGGTCCCCAAGTGGAAGCACCACCCCATGAGGAGCACCGTGGAGTAAGAAGACGTTCGAGCCA</u>

<u>CGTCGAAAAAGCAAGTGTGTTGATGTAGTATCTCCATTGACGTAAGGGATGACGCACAATCCAACTATCCATCGCA</u>

<u>AGACCATTGCTCTATATAAGAAAGTTAATATCATTTCGAGTGGCCACGCTGAGCTC</u>AGGAAGTCTGCTCTTGCGCC

AAATCCAATAGTTGGTTCTAATTGGATCAACTTGTTTTAGGATAGAACAAATATTTCGTGCTATATTTAAATTTTG

TTGTTCCCCTTTCTCATCATCATCTAAATCTTGTTTATCCATATCTGCGGTCTTTAAGGCGTCAATGGCATCTCTA

ATGTCTTCATTTGGTTGATAACCAAAGCATATAAGATCTAAAATAGTGCTAAGAGCAAACACGTAGTTGCTCTTAG

TTCTCAAAATCTTTAAGCATACTGAAGAAACTTGAGGATCATTTACCCATGAAGTAGTTTCACCTTTATAAAGTCC

TCGTAGATATCTCCACGAGCTTTCATTTTCAGGGTAGGCTATAATGGCTTCGATGGTGTAAAGCACTTCAGACTCT

CTCATAGCTTTTAGGCCCCCCAAGAAAGGAGACCTTGTTATGACAAAATATCTCTGATTCCAAGCAGAATTGTTAA

AAATGTCTTCTTTAAGTAGTTCTGTGCAATAATTAAGTTCATCTTCCCATCCTCCTAGTGTTTGAAGAGCCCACTG

TCTATGAGACCATGCATGATAATGTTTGGCATCAACGGACAGTATCTTTTTGGTGAACTCGAGCTgagctcgaatt tccccgatcggtcaaacatttggcaataaagtttcttaagattgaatcctgttgccggtcttgcgatgattatcat ataatttctgttgaattacgttaagcatgtaataattaacatgtaatgcatgacgttatttatgagatgggttttt atgattagagtcccgcaattatacatttaatacgcgatagaaaacaaaatatagcgcgcaaactaggataaattat cgcgcgcggtgtcatctatgttactagatcgggaattc (Underlined MuA Promoter; Bold: *Glycine max* anti-FTA; lower case; NOS terminator Seq.)

SEQ ID NO:45

<u>GGAGCCATAGATGCAATTCAATCAAACTGAAATTTCTGCAAGAATCTCAAACACGGAGATCTCAAAGTTTGAAGA</u>

<u>AAATTTATTTCTTCGACTCAAAACAAACTTACGAAATTTAGGTAGAACTTATATACATTATATTGTAATTTTTGT</u>

<u>AACAAAATGTTTTTATTATTATTATAGAATTTTACTGGTTAAATTAAAAATGAATAGAAAAGGTGAATTAAGAGGA</u>

<u>GAGAGGAGGTAAACATTTTCTTCTATTTTTTCATATTTTCAGGATAAATTATTGTAAAAGTTTACAAGATTTCCAT</u>

<u>TTGACTAGTGTAAATGAGGAATATTCTCTAGTAAGATCATTATTTCATCTACTTCTTTTATCTTCTACCAGTAGAG</u>

<u>GAATAAACAATATTTAGCTCCTTTGTAAATACAAATTAATTTTCCTTCTTGACATCATTCAATTTTAATTTTACGT</u>

<u>ATAAAATAAAAGATCATACCTATTAGAACGATTAAGGAGAAATACAATTCGAATGAGAAGGATGTGCCGTTTGTTA</u>

<u>TAATAAACAGCCACACGACGTAAACGTAAAATGACCACATGATGGGCCAATAGACATGGACCGACTACTAATAATA</u>

<u>GTAAGTTACATTTTAGGATGGAATAAATATCATACCGACATCAGTTTTGAAAGAAAAGGGAAAAAAAGAAAAAATA</u>

<u>AATAAAAGATATACTACCGACATGAGTTCCAAAAAGCAAAAAAAAAGATCAAGCCGACACAGACACGCGTAGAGAG</u>

<u>CAAAATGACTTTGACGTCACACCACGAAAACAGACGCTTCATACGTGTCCCTTTATCTCTCAGTCTCTCTATAA</u>

<u>ACTTAGTGAGACCCTCCTCTGTTTTACTCACAAATATGCAAACTAGAAAACAATCATCAGGAATAAAGGGTTTGAT</u>

<u>TACTTCTATTGGAAAG</u>AGGAAGTCTGCTCTTGCGCCAAATCCAATAGTTGGTTCTAATTGGATCAACTTGTTTTAG

GATAGAACAAATATTTCGTGCTATATTTAAATTTTGTTGTTCCCCTTTCTCATCATCATCTAAATCTTGTTTATCC

ATATCTGCGGTCTTTAAGGCGTCAATGGCATCTCTAATGTCTTCATTTGGTTGATAACCAAAGCATATAAGATCTA

AAATAGTGCTAAGAGCAAACACGTAGTTGCTCTTAGTTCTCAAAATCTTTAAGCATACTGAAGAAACTTGAGGATC

ATTTACCCATGAAGTAGTTTCACCTTTATAAAGTCCTCGTAGATATCTCCACGAGCTTTCATTTCAGGGTAGGCT

ATAATGGCTTCGATGGTGTAAAGCACTTCAGACTCTCTCATAGCTTTTAGGCCCCCCAAGAAAGGAGACCTTGTTA

TGACAAAATATCTCTGATTCCAAGCAGAATTGTTAAAAATGTCTTCTTTAAGTAGTTCTGTGCAATAATTAAGTTC

ATCTTCCCATCCTCCTAGTGTTTGAAGAGCCCACTGTCTATGAGACCATGCATGATAATGTTTGGCATCAACGGAC

-continued

AGTATCTTTTTGGTGAACTCGAGCTgagctcgaatttccccgatcgttcaaacatttggcaataaagtttcttaag
attgaatcctgttgccggtcttgcgatgattatcatataatttctgttgaattacgttaagcatgtaataattaac
atgtaatgcatgacgttatttatgagatgggttttttatgattagagtcccgcaattatacatttaatacgcgatag
aaaacaaaatatagcgcgcaaactaggataaattatcgcgcgcggtgtcatctatgttactagatcgggaattc
(Underlined RD29A Promoter; Bold: *Glycine max* anti-*Glycine max* FTA; lower case: NOS terminator Seq.)

SEQ ID NO:46

GAATTCAAATTTTTCGCCAGTTCTAAATATCCGGAAACCTCTTGGGATGCCATTGCCCATCTATCTGTAATTTATT
GACGAAATAGACGAAAAGGAAGGTGGCTCCTATAAAGCACATCATTGCGATAACAGAAAGGCCATTGTTGAAGATA
CCTCTGCTGACATTGGTCCCCAAGTGGAAGCACCACCCCATGAGGAGCACCGTGGAGTAAGAAGACGTTCGAGCCA
CGTCGAAAAAGCAAGTGTGTTGATGTAGTATCTCCATTGACGTAAGGGATGACGCACAATCCAACTATCCATCGCA
AGACCATTGCTCTATATAAGAAAGTTAATATCATTTCGAGTGGCCACGCTGAGCTC<u>AGGAAGTCTGCTCTTGCGCC</u>
<u>AAATCCAATAGTTGGTTCTAATTGGATCAACTTGTTTTAGGATAGAACAAATATTTCGTGCTATATTTAAATTTTG</u>
<u>TTGTTCCCCTTTCTCATCATCATCTAAATCTTGTTTATCCATATCTGCGGTCTTTAAGGCGTCAATGGCATCTCTA</u>
<u>ATGTCTTCATTTGGTTGATAACCAAAGCATATAAGATCTAAAATAGTGCTAAGAGCAAACACGTAGTTGCTCTTAG</u>
<u>TTCTCAAAATCTTTAAGCATACTGAAGAAACTTGAGGATCATTTACCCATGAAGTAGTTTCACCTTTATAAAGTCC</u>
<u>TCGTAGATATCTCCACGAGCTTTCATTTTCAGGGTAGGCTATAATGGCTTCGATGGTGTAAAGCACTTCAGACTCT</u>
<u>CTCATAGCTTTTAGGCCCCCCAAGAAAGGAGACCTTGTTATGACAAAATATCTCTGATTCCAAGCAGAATTGTTAA</u>
<u>AAATGTCTTCTTTAAGTAGTTCTGTGCAATAATTAAGTTCATCTTCCCATCCTCCTAGTGTTTGAAGAGCCCACTG</u>
<u>TCTATGAGACCATGCATGATAATGTTTGGCATCAACGGACAGTATCTTTTTGGTGAACTCGAGCTT</u>*AAAGGTGAAA*
*CTACTTCATGGGTAAATGATCCTCAAGTTTCTTCAGTATGCTTAAAGATTTTGAGAACTAAGAGCAACTACGTGTT*
*TGCTCTTAGCACTATTTTAGATCTTATATGCTTTGGTTATCAACCAAATGAAGACATTAGAGATGCCATTGACGCC*
*TTAAAGACCGCAGATATGGATAAACAAGATTTAGATGATGATGAGAAAGGGGAACAACAAAATTTAAATATAGCAC*
*GAAATATTTGTTCTATCCTAAAACAAGTTGATCCAATTAGAACCAACTATTGGATTTGGCGCAAGAGCAGACTTCC*
*T*gagctcgaatttccccgatcgttcaaacatttggcaataaagtttcttaagattgaatcctgttgccggtcttgc
gatgattatcatataatttctgttgaattacgttaagcatgtaataattaacatgtaatgcatgacgttatttatg
agatgggttttttatgattagagtcccgcaattatacatttaatacgcgatagaaaacaaaatatagcgcgcaaact
aggataaattatcgcgcgcggtgtcatctatgttactagatcgggaattc
(Underlined: *Glycine max* FTA Anti-Sense section; Bold: MuA Promoter; Italics: *Glycine max* FTA Sense section; lower case: NOS terminator Seq.)

SEQ ID NO:47 ggagccatagatgcaattcaatcaaactgaaatttctgcaagaatctcaaacacggagatctcaaagtttgaaaga
aaatttatttcttcgactcaaaacaaacttacgaaatttaggtagaacttatatacattatattgtaattttttgt
aacaaaatgttttattattattatagaatttactggttaaattaaaaatgaatagaaaaggtgaattaagagga
gagaggaggtaaacatttcttctattttttcatattttcaggataaattattgtaaaagtttacaagatttccat
ttgactagtgtaaatgaggaatattctctagtaagatcattatttcatctacttcttttatcttctaccagtagag
gaataaacaatatttagctcctttgtaaatacaaattaattttccttcttgacatcattcaattttaattttacgt
ataaaataaagatcatacctattagaacgattaaggagaaatacaattcgaatgagaaggatgtgccgtttgtta
taataaacagccacacgacgtaaacgtaaaatgaccacatgatgggccaatagacatggaccgactactaataata
gtaagttacattttaggatggaataaatatcataccgacatcagttttgaaagaaaagggaaaaaagaaaaaata
aataaaagatatactaccgacatgagttccaaaaagcaaaaaaaaagatcaagccgacacagacacgcgtagagag
caaaatgactttgacgtcacaccacgaaaacagacgcttcatacgtgtcccttttatctctctcagtctctctataa
acttagtgagaccctcctctgttttactcacaaatatgcaaactagaaaacaatcatcaggaataaagggtttgat -continued tacttctattggaaagAGGAAGTCTGCTCTTGCGCCAAATCCAATAGTTGGTTCTAATTGGATCAACTTGTTTTAG
GATAGAACAAATATTTCGTGCTATATTTAAATTTTGTTGTTCCCCTTTCTCATCATCATCTAAATCTTGTTTATCC
ATATCTGCGGTCTTTAAGGCGTCAATGGCATCTCTAATGTCTTCATTTGGTTGATAACCAAAGCATATAAGATCTA
AAATAGTGCTAAGAGCAAACACGTAGTTGCTCTTAGTTCTCAAAATCTTTAAGCATACTGAAGAAACTTGAGGATC
ATTTACCCATGAAGTAGTTTCACCTTTATAAAGTCCTCGTAGATATCTCCACGAGCTTTCATTTTCAGGGTAGGCT
ATAATGGCTTCGATGGTGTAAAGCACTTCAGACTCTCTCATAGCTTTTAGGCCCCCCAAGAAAGGAGACCTTGTTA
TGACAAAATATCTCTGATTCCAAGCAGAATTGTTAAAAATGTCTTCTTTAAGTAGTTCTGTGCAATAATTAAGTTC
ATCTTCCCATCCTCCTAGTGTTTGAAGAGCCCACTGTCTATGAGACCATGCATGATAATGTTTGGCATCAACGGAC
AGTATCTTTTTGGTGAACTCGAGCTTAAAGGTGAAACTACTTCATGGGTAAATGATCCTCAAGTTTCTTCAGTATG
CTTAAAGATTTTGAGAACTAAGAGCAACTACGTGTTTGCTCTTAGCACTATTTTAGATCTTATATGCTTTGGTTAT
CAACCAAATGAAGACATTAGAGATGCCATTGACGCCTTAAAGACCGCAGATATGGATAAACAAGATTTAGATGATG
ATGAGAAGGGGAACAACAAAATTTAAATATAGCACGAAATATTTGTTCTATCCTAAAACAAGTTGATCCAATTAG
AACCAACTATTGGATTTGGCGCAAGAGCAGACTTCCTgagctcgaatttccccgatcgttcaaacatttggcaata
aagtttcttaagattgaatcctgttgccggtcttgcgatgattatcatataatttctgttgaattacgttaagcat
gtaataattaacatgtaatgcatgacgttatttatgagatgggtttttatgattagagtcccgcaattatacattt
aatacgcgatagaaaacaaatatagcgcgcaaactaggataaattatcgcgcgcggtgtcatctatgttactaga
tcgggaattc
(Bold lower case: RD29A Promoter; Underline, Upper case: Antisense GmFTA;
Upper case: Sense GmFTA; lower case: NOS terminator)

SEQ ID NO:48
*gtttacccgccaatatatcctgtc*aaacactgatagtttaaactgaaggcgggaaacgacaatctgatcatgagcg
gagaattaagggagtcacgttatgaccccgccgatgacgcgggacaagccgttttacgtttggaactgacagaac
cgcaacgttgaaggagccactcagccgcgggtttctggagtttaatgagctaagcacatacgtcagaaaccattat
tgcgcgttcaaaagtcgcctaaggtcactatcagctagcaaatatttcttgtcaaaaatgctccactgacgttcca
taaattcccctcggtatccaattagagtctcatattcactctcaatccaaataatctgcaccggatctggatcgtt
tcgcatgattgaacaagatggattgcacgcaggttctccggccgcttgggtggagaggctattcggctatgactgg
gcacaacagacaatcggctgctctgatgccgccgtgttccggctgtcagcgcaggggcgcccggttcttttttgtca
agaccgacctgtccggtgccctgaatgaactgcaggacgaggcagcgcggctatcgtggctggccacgacgggcgt
tccttgcgcagctgtgctcgacgttgtcactgaagcgggaagggactggctgctattgggcgaagtgccggggcag
gatctcctgtcatctcaccttgctcctgccgagaaagtatccatcatggctgatgcaatgcggcggctgcatacgc
ttgatccggctacctgcccattcgaccaccaagcgaaacaecgcatcgagcgagcacgtactcggatggaagccgg
tcttgtcgatcaggatgatctggacgaagagcatcaggggctcgcgccagccgaactgttcgccaggctcaaggcg
cgcatgcccgacggcgatgatctcgtcgtgacccatggcgatgcctgcttgccgaatatcatggtggaaaatggcc
gcttttctggattcatcgactgtggccggctgggtgtggcggaccgctatcaggacatagcgttggctacccgtga
tattgctgaagagcttggcggcgaatgggctgaccgcttcctcgtgctttacggtatcgccgctcccgattcgcag
cgcatcgccttctatcgccttcttgacgagttcttctgagcgggactctggggttcgaaatgaccgaccaagcgac
gcccaacctgccatcacgagatttcgattccaccgccgccttctatgaaaggttgggcttcggaatcgttttccgg
gacgccggctggatgatcctccagcgcggggatctcatgctggagttcttcgcccacgggatctctgcggaacagg
cggtcgaaggtgccgatatcattacgacagcaacggccgacaagcacaacgccacgatcctgagcgacaatatgat
x
cgggcccggcgtccacatcaacggcgtcggcggcgactgcccaggcaagaccgagatgcaccgcgatatcttgctg
cgttcggatattttcgtggagttcccgccacagacccggatgatccccgatcgttcaaacatttggcaataaagtt -continued tcttaagattgaatcctgttgccggtcttgcgatgattatcatataatttctgttgaattacgttaagcatgtaat
aattaacatgtaatgcatgacgttatttatgagatgggttttttatgattagagtcccgcaattatacatttaatac
gcgatagaaaacaaaatatagcgcgcaaactaggataaattatcgcgcgcggtgtcatctatgttactagatcggg
cctcctgtcaatgctggcggcggctctggtggtggttctggtggcggctctgagggtggtggctctgagggtggcg
gttctgagggtggcggctctgagggaggcggttccggtggtggctctggttccggtgattttgattatgaaagat
ggcaaacgctaataaggggctatgaccgaaaatgccgatgaaaacgcgctacagtctgacgctaaaggcaaactt
gattctgtcgctactgattacggtgctgctatcgatggtttcattggtgacgtttccggccttgctaatggtaatg
gtgctactggtgattttgctggctctaattcccaaatggctcaagtcggtgacggtgataattcacctttaatgaa
taatttccgtcaatatttaccttcctccctcaatcggttgaatgtcgcccttttgtctttggcccaatacgcaaa
ccgcctctcccgcgcgttggccgattcattaatgcagctggcacgacaggtttcccgactggaaagcgggcagtg
agcgcaacgcaattaatgtgagttagctcactcattaggcaccccaggctttacactttatgcttccggctcgtat
gttgtgtggaattgtgagcggataacaatttcacacaggaaacagctatgaccatgattacgccaagcttgcatgc
ctgcag<u>cccacagatggttagagaggcttacgcagcaggtctcatcaagacgatctacccgagcaataatctccag</u>
<u>gaaatcaaatacccttcccaagaaggttaaagatgcagtcaaaagattcaggactaactgcatcaagaacacagaga</u>
<u>aagatatatttctcaagatcagaagtactattccagtatggacgattcaaggcttgcttcacaaaccaaggcaagt</u>
<u>aatagagattggagtctctaaaaaggtagttcccactgaatcaaaggccatggagtcaaagattcaaatagaggac</u>
<u>ctaacagaactcgccgtaaagactggcgaacagttcatacagagtctcttacgactcaatgacaagaagaaaatct</u>
<u>tcgtcaacatggtggagcacgacacttgtctactccaaaaatatcaaagatacagtctcagaagaccaaagggc</u>
<u>aattgagacttttcaacaaagggtaatatccggaaacctcctcggattccattgcccagctatctgtcactttatt</u>
<u>gtgaagatagtggaaaggaaggtggctcctacaaatgccatcattgcgataaaggaaaggccatcgttgaagatg</u>
<u>cctctgccgacagtggtcccaaagatggacccccacccacgaggagcatcgtggaaaaagaagacgttccaaccac</u>
<u>gtcttcaaagcaagtggattgatgtgatatctccactgacgtaagggatgacgcacaatcccactatccttcgcaa</u>
<u>gacccttcctctatataaggaagttcatttcatttggagagaacacggggg</u>actctagaggatccgtccggaattc
ccgggtcgacccacgcgtccgggagattcagcgagataagcaattggattatctgatgaaaggcttaaggcagctt
ggtccgcagttttcttccttagatgctaatcgaccttggctttgttactggattcttcattcaatagctttgcttg
gggagactgtggatgatgaattagaaagcaatgccattgacttccttggacgctgccagggctctgaaggtggata
cggtggtggtcctggccaacttccacatcttgcaactacttatgctgcagtgaatgcacttgttactttaggaggt
gacaaagccctttcttcaattaatagagaaaaaatgtcttgtttttttaagacggatgaaggatacaagtggaggtt
tcaggatgcatgatatgggagaaatggatgttcgtgcatgctacactgcaatttcggttgcaagcatcctaaatat
tatggatgatgaactcacccagggcctaggagattacatcttgagttgccaaacttatgaaggtggcattggaggg
gaacctggctccgaagctcacggtgggtatacctactgtggtttggctgctatgattttaatcaatgaggtcgacc
gtttgaatttggattcattaatgaattgggctgtacatcgacaaggagtagaaatgggatttcaaggtaggacgaa
caaattggtcgatggttgctacacattttggcaggcagccccttgtgttctactacaaagattatattcaaccaat
gatcatgacgttaatggatcatcacatatatcagaagggacaaatgaagaacatcatgctcatgatgaagatgacc
ttgaagacagtgatgatgatgatgattctgatgaggacaacgatgaagattcagtgaatggtcacagaatccatca
tacatccacctacattaacaggagaatgcaactggttttttgatagcctcggcttgcagagatatgtactcttgtgc
tctaagatccctgacggtggattcagagacaagccgaggaaaccccgtgacttctaccacacatgttactgcctga
gcggcttgtctgtggctcagcacgcttggttaaaagacgaggacactcctcctttgactcgcgacattatgggtgg
ctactcgaatctccttgaacctgttcaacttcttcacaacattgtcatggatcagtataatgaagctatcgagttc
ttctttaaagcagcatgactcgaatttccccgatcgttcaaacatttggcaataaagtttcttaagattgaatcct -continued gttgccggtcttgcgatgattatcatataatttctgttgaattacgttaagcatgtaataattaacatgtaatgca
tgacgttatttatgagatgggttttatgattagagtcccgcaattatacatttaatacgcgatagaaaacaaaat
atagcgcgcaaactaggataaattatcgcgcgcggtgtcatctatgttactagatcgggaattcactggccgtcgt
tttacaacgtcgtgactgggaaaaccctggcgttacccaacttaatcgccttgcagcacatccccttcgccagc
tggcgtaatagcgaagaggcccgcaccgatcgcccttcccaacagttgcgcagcctgaatggcgcccgctcctttc
gctttcttccttcctttctcgccacgttcgccggctttccccgtcaagctctaaatcggggctcccttaggt
tccgatttagtgctttacggcacctcgaccccaaaaaacttgatttgggtgatggttcacgtagtgggccatcgcc
ctgatagacggtttttcgccctttgacgttggagtccacgttctttaatagtggactcttgttccaaactggaaca
acactcaaccctatctcgggctattcttttgatttataagggattttgccgatttcggaaccaccatcaaacagga
ttttcgcctgctggggcaaaccagcgtggaccgcttgctgcaactctctcagggccaggcggtgaagggcaatcag
ctgttgcccgtctcactggtgaaagaaaaaccaccccagtacattaaaaacgtccgcaatgtgttattaagttgt
ctaagcgtcaattt*gtttacaccacaatatatcctgcca*
(Underline: 35S promoter; Bold: anti-AtFTB)

SEQ ID NO:49

*gtttacccgccaatatatcctgt*caaacactgatagtttaaactgaaggcgggaaacgacaatctgatcatgagcg
gagaattaagggagtcacgttatgaccccgccgatgacgcgggacaagccgttttacgtttggaactgacagaac
cgcaacgttgaaggagccactcagccgcgggtttctggagtttaatgagctaagcacatacgtcagaaaccattat
tgcgcgttcaaaagtcgcctaaggtcactatcagctagcaaatatttcttgtcaaaaatgctccactgacgttcca
taaattcccctcggtatccaattagagtctcatattcactctcaatccaaataatctgcaccggatctggatcgtt
tcgcatgattgaacaagatggattgcacgcaggttctccggccgcttgggtggagaggctattcggctatgactgg
gcacaacagacaatcggctgctctgatgccgccgtgttccggctgtcagcgcaggggcgcccggttcttttttgtca
agaccgacctgtccggtgccctgaatgaactgcaggacgaggcagcgcggctatcgtggctggccacgacgggcgt
tccttgcgcagctgtgctcgacgttgtcactgaagcgggaagggactggctgctattgggcgaagtgccggggcag
gatctcctgtcatctcaccttgctcctgccgagaaagtatccatcatggctgatgcaatgcggcggctgcatacgc
ttgatccggctacctgcccattcgaccaccaagcgaaacaecgcatcgagcgagcacgtactcggatggaagccgg
tcttgtcgatcaggatgatctggacgaagagcatcaggggctcgcgccagccgaactgttcgccaggctcaaggcg
cgcatgcccgacgcgatgatctcgtcgtgacccatggcgatgcctgcttgccgaatatcatggtggaaaatggcc
gcttttctggattcatcgactgtggccggctgggtgtggcggaccgctatcaggacatagcgttggctacccgtga
tattgctgaagagcttggcggcgaatgggctgaccgcttcctcgtgctttacggtatcgccgctcccgattcgcag
cgcatcgccttctatcgccttcttgacgagttcttctgagcgggactctggggttcgaaatgaccgaccaagcgac
gcccaacctgccatcacgagatttcgattccaccgccgccttctatgaaaggttgggcttcggaatcgttttccgg
gacgccggctggatgatcctccagcgcggggatctcatgctggagttcttcgcccacgggatctctgcggaacagg
cggtcgaaggtgccgatatcattacgacagcaacggccgacaagcacaacgccacgatcctgagcgacaatatgat
cgggcccggcgtccacatcaacggcgtcggcggcgactgcccaggcaagaccgagatgcaccgcgatatcttgctg
cgttcggatattttcgtggagttcccgccacagacccggatgatccccgatcgttcaaacatttggcaataaagtt
tcttaagattgaatcctgttgccggtcttgcgatgattatcatataatttctgttgaattacgttaagcatgtaat
aattaacatgtaatgcatgacgttatttatgagatggttttatgattagagtcccgcaattatacatttaatac
gcgatagaaaacaaatatagcgcgcaaactaggataaattatcgcgcgcggtgtcatctatgttactagatcggg
cctcctgtcaatgctggcggcggctctggtggtggttctggtggcggctctgagggtggtggctctgagggtggcg
gttctgagggtggcggctctgagggaggcggttccggtggtggctctggttccggtgattttgattatgaaaagat
ggcaaacgctaataagggggctatgaccgaaaatgccgatgaaaacgcgctacagtctgacgctaaaggcaaactt -continued

```
gattctgtcgctactgattacggtgctgctatcgatggtttcattggtgacgtttccggccttgctaatggtaatg
gtgctactggtgattttgctggctctaattcccaaatggctcaagtcggtgacggtgataattcaccttaatgaa
taatttccgtcaatatttaccttccctccctcaatcggttgaatgtcgcccttttgtctttggcccaatacgcaaa
ccgcctctccccgcgcgttggccgattcattaatgcagctggcacgacaggtttcccgactggaaagcgggcagtg
agcgcaacgcaattaatgtgagttagctcactcattaggcaccccaggctttacactttatgcttccggctcgtat
gttgtgtggaattgtgagcggataacaatttcacacaggaaacagctatgaccatgattacgccaagcttgcatgc
ctgcagggagccatagatgcaattcaatcaaactgaaatttctgcaagaatctcaaacacggagatctcaaagttt
gaaagaaaatttatttcttcgactcaaaacaaacttacgaaatttaggtagaacttatatacattatattgtaatt
ttttgtaacaaaatgttttattattattatagaattttactggttaaattaaaaatgaatagaaaaggtgaatta
agaggagagaggaggtaaacattttcttctattttttcatattttcaggataaattattgtaaaagtttacaagat
ttccatttgactagtgtaaatgaggaatattctctagtaagatcattatttcatctacttcttttatcttctacca
gtagaggaataaacaatatttagctcctttgtaaatacaaattaattttccttcttgacatcattcaattttaatt
ttacgtataaaataaaagatcatacctattagaacgattaaggagaaatacaattcgaatgagaaggatgtgccgt
ttgttataataaacagccacacgacgtaaacgtaaaatgaccacatgatgggccaatagacatggaccgactacta
ataatagtaagttacattttaggatggaataaaatatcataccgacatcagttttgaaagaaaagggaaaaaagaa
aaaataaataaaagatatactaccgacatgagttccaaaaagcaaaaaaaaagatcaagccgacacagacacgcgt
agagagcaaaatgactttgacgtcacaccacgaaaacagacgcttcatacgtgtccctttatctctctcagtctct
ctataaacttagtgagaccctcctctgttttactcacaaatatgcaaactagaaaacaatcatcaggaataaaggg
tttgattacttctattggaaaggactctagaggatccgtccggaattcccgggtcgacccacgcgtccgggagatt
cagcgagataagcaattggattatctgatgaaaggcttaaggcagcttggtccgcagttttcttccttagatgcta
atcgaccttggctttgttactggattcttcattcaatagctttgcttggggagactgtggatgatgaattagaaag
caatgccattgacttccttggacgctgccagggctctgaaggtggatacggtggtggtcctggccaacttccacat
cttgcaactacttatgctgcagtgaatgcacttgttacttaggaggtgacaaagccctttcttcaattaatagag
aaaaaatgtcttgttttttaagacggatgaaggatacaagtggaggtttcaggatgcatgatatgggagaaatgga
tgttcgtgcatgctacactgcaatttcggttgcaagcatcctaaatattatggatgatgaactcacccagggccta
ggagattacatcttgagttgccaaacttatgaaggtggcattggaggggaacctggctccgaagctcacggtgggt
atacctactgtggtttggctgctatgattttaatcaatgaggtcgaccgtttgaatttggattcattaatgaattg
ggctgtacatcgacaaggagtagaaatgggatttcaaggtaggacgaacaaattggtcgatggttgctacacattt
tggcaggcagccccttgtgttctactacaaagattatattcaaccaatgatcatgacgttcatggatcatcacata
tatcagaagggacaaatgaagaacatcatgctcatgatgaagatgaccttgaagacagtgatgatgatgatgattc
tgatgaggacaacgatgaagattcagtgaatggtcacagaatccatcatacatccacctacattaacaggagaatg
caactggttttgatagcctcggcttgcagagatatgtactcttgtgctctaagatccctgacggtggattcagag
acaagccgaggaaaccccgtgacttctaccacacatgttactgcctgagcggcttgtctgtggctcagcacgcttg
gttaaaagacgaggacactcctcctttgactcgcgacattatgggtggctactcgaatctccttgaacctgttcaa
cttcttcacaacattgtcatggatcagtataatgaagctatcgagttcttctttaaagcagcatgactcgaatttc
cccgatcgttcaaacatttggcaataaagtttcttaagattgaatcctgttgccggtcttgcgatgattatcatat
aatttctgttgaattacgttaagcatgtaataattaacatgtaatgcatgacgttatttatgagatgggttttat
gattagagtcccgcaattatacatttaatacgcgatagaaaacaaatatagcgcgcaaactaggataaattatcg
cgcgcggtgtcatctatgttactagatcgggaattcactggccgtcgttttacaacgtcgtgactgggaaaaccct
ggcgttacccaacttaatcgccttgcagcacatccccctttcgccagctggcgtaatagcgaagaggcccgcaccg
```

-continued atcgcccttcccaacagttgcgcagcctgaatggcgcccgctcctttcgctttcttcccttcctttctcgccacgt tcgccggctttccccgtcaagctctaaatcggggctccctttagggttccgatttagtgctttacggcacctcga ccccaaaaaacttgatttgggtgatggttcacgtagtgggccatcgccctgatagacggtttttcgcccttgacg ttggagtccacgttctttaatagtggactcttgttccaaactggaacaacactcaaccctatctcgggctattctt ttgatttataagggattttgccgatttcggaaccaccatcaaacaggattttcgcctgctggggcaaaccagcgtg gaccgcttgctgcaactctctcagggccaggcggtgaagggcaatcagctgttgcccgtctcactggtgaaaagaa aaaccaccccagtacattaaaaacgtccgcaatgtgttattaagttgtctaagcgtcaattt*gtttacaccacaat*

*atatcctgcca*
(Underline: RD29A Promoter; Bold: anti-AtFTB)

SEQ ID NO:50

*gtttacccgccaatatatcctgt*caaacactgatagtttaaactgaaggcgggaaacgacaatctgatcatgagcg gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag gatctcctgtcatctcaccttgctcctgccgagaaagtatccatcatggctgatgcaatgcggcggctgcatacgc ttgatccggctacctgcccattcgaccaccaagcgaaacatcgcatcgagcgagcacgtactcggatggaagccgg tcttgtcgatcaggatgatctggacgaagagcatcaggggctcgcgccagccgaactgttcgccaggctcaaggcg cgcatgcccgacggcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgg gacgccggctggatgatcctccagcgcggggatctcatgctggagttcttcgcccacgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg cgttcggatattttcgtggagttcccgccacagacccggatgatccccgatcgttcaaacatttggcaataaagtt tcttaagattgaatcctgttgccggtcttgcgatgattatcatataatttctgttgaattacgttaagcatgtaat aattaacatgtaatgcatgacgttatttatgagatggttttttatgattagagtcccgcaattatacatttaatac gcgatagaaaacaaatatagcgcgcaaactaggataaattatcgcgcgcggtgtcatctatgttactagatcggg cctcctgtcaatgctggcggcggctctggtggtggttctggtggcggctctgagggtggtggctctgagggtggcg gttctgagggtggcggctctgagggaggcggttccggtggtggctctggttccggtgattttgattatgaaaagat ggcaaacgctaataagggggctatgaccgaaaatgccgatgaaaacgcgctacagtctgacgctaaaggcaaactt gattctgtcgctactgattacggtgctgctatcgatggtttcattggtgacgtttccggccttgctaatggtaatg gtgctactggtgattttgctggctctaattcccaaatggctcaagtcggtgacggtgataattcacctttaatgaa taatttccgtcaatattaccttcctccctcaatcggttgaatgtcgcccttttgtctttggcccaatacgcaaa ccgcctctccccgcgcgttggccgattcattaatgcagctggcacgacaggtttcccgactggaaagcgggcagtg -continued agcgcaacgcaattaatgtgagttagctcactcattaggcaccccaggctttacactttatgcttccggctcgtat
gttgtgtggaattgtgagcggataacaatttcacacaggaaacagctatgaccatgattacgccaagcttgcatgc
ctgcagcccacagatggttagagaggcttacgcagcaggtctcatcaagacgatctacccgagcaataatctccag
gaaatcaaataccttcccaagaaggttaaagatgcagtcaaaagattcaggactaactgcatcaagaacacagaga
aagatatatttctcaagatcagaagtactattccagtatggacgattcaaggcttgcttcacaaaccaaggcaagt
aatagagattggagtctctaaaaaggtagttcccactgaatcaaaggccatggagtcaaagattcaaatagaggac
ctaacagaactcgccgtaaagactggcgaacagttcatacagagtctcttacgactcaatgacaagaagaaaatct
tcgtcaacatggtggagcacgacacacttgtctactccaaaaatatcaaagatacagtctcagaagaccaaagggc
aattgagacttttcaacaaagggtaatatccggaaacctcctcggattccattgcccagctatctgtcactttatt
gtgaagatagtggaaaggaaggtggctcctacaaatgccatcattgcgataaaggaaaggccatcgttgaagatg
cctctgccgacagtggtcccaaagatggaccccacccacgaggagcatcgtggaaaagaagacgttccaaccac
gtcttcaaagcaagtggattgatgtgatatctccactgacgtaagggatgacgcacaatcccactatccttcgcaa
gacccttcctctatataaggaagttcatttcatttggagagaacacgggggactctagaggatcctcCTCCTAGGC
CCTGGGTGAGTTCATCATCCATAATATTTAGGATGCTTGCAACCGAAATTGCAGTGTAGCATGCACGAACATCCAT
TTCTCCCATATCATGCATCCTGAAACCTCCACTTGTATCCTTCATCCGTCTTAAAAAACAAGACATTTTTTCTCTA
TTAATTGAAGAAAGGGCTTTGTCACCTCCTAAAGTAACAAGTGCATTCACTGCAGCATAAGTAGTTGCAAGATGTG
GAAGTTGGCCAGGACCACCACCGTATCCACCTTCAGAGCCCTGGCAGCGTCCAAGGAAGTCAATGGCATTGCTTTC
TAATTCATCATCCACAGTCTCCCCAAGCAAAGCTATTGAATGAAGAATCCAGTAACAAAGCCAAGGTCGATTAGCA
TCTAAGGAAGAAAACTGCGGACCAAGCTGCCTTAAGCCTTTCATCAGATAATCCAATTGCTTATCTCGCTGAATCT
CCCGGACGCGTGGGTCGACCCGGGAATTCCGGACgaggatcccc ATCTACCCGCTTCGCGTCGGCATCCGGTCAGT
GGCAGTGAAGGGCGAACAGTTCCTGATTAACCACAAACCGTTCTACTTTACTGGCTTTGGTCGTCATGAAGATGCG
GACTTGCGTGGCAAAGGATTCGATAACGTGCTGATGGTGCACGACCACGCATTAATGGACTGGATTGGGGCAACT
CCTACCGTACCTCGCATTACCCTTACGCTGAAGAGATGCTCGACTGGGCAGATGAACATGGCATCGTGGTGATTGA
TGAAACTGCTGCTGTCGGCTTTTCGCTCTCTTTAGGCATTGGTTTCGAAGCGGGCAACAAGCCGAAAGAACTGTAC
AGCGAAGAGGCAGTCAACGGGGAAACTCAGCAAGCGCACTTACAGGCGATTAAAGAGCTGATAGCGCGTGACAAAA
ACCACCCAAGCGTGGTGATGTGGAGTATTGCCAACGAACCGGATACCCGTCCGCAAGGTGCACGGGAATATTTCGC
GCCACTGGCGGAAGCAACGCGTAAACTCGACCCGACGCGTCCGATCACCTGCGTCAATGTAATGTTCTGCGACGCT
CACACCGATACCATCAGCGATCTCTTTGATGTGCTGTGCCTGAACCGTTATTACGGATGGTATGTCCAAAGCGGCG
ATTTGGAAACGGCAGAGAAGGTACTGGAAAAAGAACTTCTGGCCTGGCAGGAGAAACTGTACACCGACATGTGGAG
TGAAGAGTATCAGTGTGCATGGCTGGATATGTATCACCGCGTCTTTGATCGCGTCAGCGCCGTCGTCGGTGAAGAG
GTATGGAATTTCGCCGATTTTGCGACCTCGCAAGGCATATTGCGCGTTGGCGGTAACAAGAAAGGGATCTTCACTC
GCGACCGCAAACCGAAGTCGGCGGCTTTTCTGCTGCAAAAACGCTGGACTGGCATGAACTTCGGTGAAAAACCGCA
GCAGGGAGGCAAACAATGAATCAACAACTCTCCTGGCGCACCATCGTCGGCTACAGCCTCGGGAATTGCTACCGAG
CTCgtccggaattcccgggtcgacccacgcgtccgggagattcagcgagataagcaattggattatctgatgaaag
gcttaaggcagcttggtccgcagttttcttccttagatgctaatcgaccttggctttgttactggattcttcattc
aatagctttgcttggggagactgtggatgatgaattagaaagcaatgccattgacttccttggacgctgccagggc
tctgaaggtggatacggtggtggtcctggccaacttccacatcttgcaactacttatgctgcagtgaatgcacttg
ttactttaggaggtgacaaagccctttcttcaattaatagagaaaaatgtcttgttttttaagacggatgaagga
tacaagtggaggtttcaggatgcatgatatgggagaaatggatgttcgtgcatgctacactgcaatttcggttgca
agcatcctaaatattatggatgatgaactcacccagggcctaggagctcgaatttccccgatcgttcaaacatttg -continued

```
gcaataaagtttcttaagattgaatcctgttgccggtcttgcgatgattatcatataatttctgttgaattacgtt aagcatgtaataattaacatgtaatgcatgacgttatttatgagatgggttttttatgattagagtcccgcaattat acatttaatacgcgatagaaaacaaaatatagcgcgcaaactaggataaattatcgcgcgcggtgtcatctatgtt actagatcgggaattcactggccgtcgttttacaacgtcgtgactgggaaaaccctggcgttacccaacttaatcg ccttgcagcacatccccctttcgccagctggcgtaatagcgaagaggcccgcaccgatcgcccttcccaacagttg cgcagcctgaatggcgcccgctcctttcgctttcttcccttcctttctcgccacgttcgccggctttccccgtcaa gctctaaatcggggctccctttagggttccgatttagtgctttacggcacctcgaccccaaaaaacttgatttgg gtgatggttcacgtagtgggccatcgcccgatagacggttttttcgccctttgacgttggagtccacgttctttaa tagtggactcttgttccaaactggaacaacactcaaccctatctcgggctattcttttgatttataagggattttg ccgatttcggaaccaccatcaaacaggattttcgcctgctggggcaaaccagcgtggaccgcttgctgcaactctc tcagggccaggcggtgaagggcaatcagctgttgcccgtctcactggtgaaagaaaaaccaccccagtacattaa aaacgtccgcaatgtgttattaagttgtctaagcgtcaattt*gtttacaccacaatatatcctgcca*
```
(Underline: 35S promoter; Bold uppercase: antisense AtFTB; Lower case Bold: sense AtFTB)

SEQ ID NO:51

```
gtttacccgccaatatatcctgtcaaacactgatagtttaaactgaaggcgggaaacgacaatctgatcatgagcg gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag gatctcctgtcatctcaccttgctcctgccgagaaagtatccatcatggctgatgcaatgcggcggctgcatacgc ttgatccggctacctgcccattcgaccaccaagcgaaacatcgcatcgagcgagcacgtactcggatggaagccgg tcttgtcgatcaggatgatctggacgaagagcatcaggggctcgcgccagccgaactgttcgccaggctcaaggcg cgcatgcccgacggcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgg gacgccggctggatgatcctccagcgcggggatctcatgctggagttcttcgcccacgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg cgttcggatattttcgtggagttcccgccacagacccggatgatccccgatcgttcaaacatttggcaataaagtt tcttaagattgaatcctgttgccggtcttgcgatgattatcatataatttctgttgaattacgttaagcatgtaat aattaacatgtaatgcatgacgttatttatgagatggttttttatgattagagtcccgcaattatacatttaatac gcgatagaaaacaaaatatagcgcgcaaactaggataaattatcgcgcgcggtgtcatctatgttactagatcggg cctcctgtcaatgctggcggcggctctggtggtggttctggtggcggctctgagggtggtggctctgagggtggcg gttctgagggtggcggctctgagggaggcggttccggtggtggctctggttccggtgattttgattatgaaaagat
```

-continued ggcaaacgctaataaggggggctatgaccgaaaatgccgatgaaaacgcgctacagtctgacgctaaaggcaaactt gattctgtcgctactgattacggtgctgctatcgatggtttcattggtgacgtttccggccttgctaatggtaatg gtgctactggtgattttgctggctctaattcccaaatggctcaagtcggtgacggtgataattcacctttaatgaa taatttccgtcaatatttaccttccctccctcaatcggttgaatgtcgccttttgtctttggcccaatacgcaaa ccgcctctccccgcgcgttggccgattcattaatgcagctggcacgacaggtttcccgactggaaagcgggcagtg agcgcaacgcaattaatgtgagttagctcactcattaggcaccccaggctttacactttatgcttccggctcgtat gttgtgtggaattgtgagcggataacaatttcacacaggaaacagctatgaccatgattacgccaagcttgcatgc ctgcagggagccatagatgcaattcaatcaaactgaaatttctgcaagaatctcaaacacggagatctcaaagttt gaaagaaaatttatttcttcgactcaaaacaaacttacgaaatttaggtagaacttatatacattatattgtaatt ttttgtaacaaaatgttttttattattattatagaattttactggttaaattaaaaatgaatagaaaaggtgaatta agaggagagaggaggtaaacattttcttctattttttcatattttcaggataaattattgtaaaagtttacaagat ttccatttgactagtgtaaatgaggaatattctctagtaagatcattatttcatctacttcttttatcttctacca gtagaggaataaacaatatttagctcctttgtaaatacaaattaattttccttcttgacatcattcaattttaatt ttacgtatataaaataaaagatcatacctattagaacgattaaggagaaatacaattcgaatgagaaggatgtgccgt ttgttataataaacagccacacgacgtaaacgtaaaatgaccacatgatgggccaatagacatggaccgactacta ataatagtaagttacattttaggatggaataaatatcataccgacatcagttttgaaagaaaagggaaaaaaagaa aaaataaataaaagatatactaccgacatgagttccaaaaagcaaaaaaaaagatcaagccgacacagacacgcgt agagagcaaaatgactttgacgtcacaccacgaaaacagacgcttcatacgtgtcccttttatctctctcagtctct ctataaacttagtgagaccctcctctgttttactcacaaatatgcaaactagaaaacaatcatcaggaataaaggg tttgattacttctattggaaaggactctagaggatcctcCTCCTAGGCCCTGGGTGAGTTCATCATCCATAATATT

TAGGATGCTTGCAACCGAAATTGCAGTGTAGCATGCACGAACATCCATTTCTCCCATATCATGCATCCTGAAACCT

CCACTTGTATCCTTCATCCGTCTTAAAAAACAAGACATTTTTTCTCTATTAATTGAAGAAAGGGCTTTGTCACCTC

CTAAAGTAACAAGTGCATTCACTGCAGCATAAGTAGTTGCAAGATGTGGAAGTTGGCCAGGACCACCACCGTATCC

ACCTTCAGAGCCCTGGCAGCGTCCAAGGAAGTCAATGGCATTGCTTTCTAATTCATCATCCACAGTCTCCCCAAGC

AAAGCTATTGAATGAAGAATCCAGTAACAAAGCCAAGGTCGATTAGCATCTAAGGAAGAAAACTGCGGACCAAGCT

GCCTTAAGCCTTTCATCAGATAATCCAATTGCTTATCTCGCTGAATCTCCCGGACGCGTGGGTCGACCCGGGAATT

CCGGACgaggatccccATCTACCCGCTTCGCGTCGGCATCCGGTCAGTGGCAGTGAAGGGCGAACAGTTCCTGATT

AACCACAAACCGTTCTACTTTACTGGCTTTGGTCGTCATGAAGATGCGGACTTGCGTGGCAAAGGATTCGATAACG

TGCTGATGGTGCACGACCACGCATTAATGGACTGGATTGGGGCCAACTCCTACCGTACCTCGCATTACCCTTACGC

TGAAGAGATGCTCGACTGGGCAGATGAACATGGCATCGTGGTGATTGATGAAACTGCTGCTGTCGGCTTTTCGCTC

TCTTTAGGCATTGGTTTCGAAGCGGGCAACAAGCCGAAAGAACTGTACAGCGAAGAGGCAGTCAACGGGAAACTC

AGCAAGCGCACTTACAGGCGATTAAAGAGCTGATAGCGCGTGACAAAAACCACCCAAGCGTGGTGATGTGGAGTAT

TGCCAACGAACCGGATACCCGTCCGCAAGGTGCACGGGAATATTTCGCGCCACTGGCGGAAGCAACGCGTAAACTC

GACCCGACGCGTCCGATCACCTGCGTCAATGTAATGTTCTGCGACGCTCACACCGATACCATCAGCGATCTCTTTG

ATGTGCTGTGCCTGAACCGTTATTACGGATGGTATGTCCAAAGCGGCGATTTGGAAACGGCAGAGAAGGTACTGGA

AAAAGAACTTCTGGCCTGGCAGGAGAAACTGTACACCGACATGTGGAGTGAAGAGTATCAGTGTGCATGGCTGGAT

ATGTATCACCGCGTCTTTGATCGCGTCAGCGCCGTCGTCGGTGAACAGGTATGGAATTTCGCCGATTTTGCGACCT

CGCAAGGCATATTGCGCGTTGGCGGTAACAAGAAAGGGATCTTCACTCGCGACCGCAAACCGAAGTCGGCGGCTTT

TCTGCTGCAAAAACGCTGGACTGGCATGAACTTCGGTGAAAAACCGCAGCAGGGAGGCAAACAATGAATCAACAAC

TCTCCTGGCGCACCATCGTCGGCTACAGCCTCGGGAATTGCTACCGAGCTCgtccggaattcccgggtcgacccac

-continued gcgtccgggagattcagcgagataagcaattggattatctgatgaaaggcttaaggcagcttggtccgcagttttc ttccttagatgctaatcgaccttggctttgttactggattcttcattcaatagctttgcttggggagactgtggat gatgaattagaaagcaatgccattgacttccttggacgctgccagggctctgaaggtggatacggtggtggtcctg gccaacttccacatcttgcaactacttatgctgcagtgaatgcacttgttactttaggaggtgacaaagcccttc ttcaattaatagagaaaaaatgtcttgttttttaagacggatgaaggatacaagtggaggtttcaggatgcatgat atgggagaaatggatgttcgtgcatgctacactgcaatttcggttgcaagcatcctaaatattatggatgatgaac tcacccagggcctaggagctcgaatttccccgatcgttcaaacatttggcaataaagtttcttaagattgaatcct gttgccggtcttgcgatgattatcatataatttctgttgaattacgttaagcatgtaataattaacatgtaatgca tgacgttatttatgagatgggtttttatgattagagtcccgcaattatacatttaatacgcgatagaaaacaaaat atagcgcgcaaactaggataaattatcgcgcgcggtgtcatctatgttactagatcgggaattcactggccgtcgt tttacaacgtcgtgactgggaaaaccctggcgttacccaacttaatcgccttgcagcacatccccctttcgccagc tggcgtaatagcgaagaggcccgcaccgatcgcccttcccaacagttgcgcagcctgaatggcgcccgctcctttc gctttcttcccttcctttctcgccacgttcgccggctttccccgtcaagctctaaatcggggggctccctttaggt tccgatttagtgctttacggcacctcgaccccaaaaaacttgatttgggtgatggttcacgtagtgggccatcgcc ctgatagacggtttttcgccctttgacgttggagtccacgttctttaatagtggactcttgttccaaactggaaca acactcaacccatctcggctattcttttgatttataagggattttgccgatttcggaaccaccatcaaacagga ttttcgcctgctggggcaaaccagcgtggaccgcttgctgcaactctctcagggccaggcggtgaagggcaatcag ctgttgcccgtctcactggtgaaaagaaaaaccaccccagtacattaaaaacgtccgcaatgtgttattaagttgt ctaagcgtcaattt*gtttacaccacaatatatcctgcca*

(Underline: RD29A promoter; Bold uppercase: antisense AtFTB; Lower case
Bold: sense AtFTB)

SEQ ID NO:52
*gtttacccgccaatatatcctgtc*aaacactgatagtttaaactgaaggcgggaaacgacaatctgatcatgagcg gagaattaagggagtcacgttatgaccccgccgatgacgcgggacaagccgttttacgtttggaactgacagaac cgcaacgttgaaggagccactcagccgcgggtttctggagtttaatgagctaagcacatacgtcagaaaccattat tgcgcgttcaaaagtcgcctaaggtcactatcagctagcaaatatttcttgtcaaaaatgctccactgacgttcca taaattcccctcggtatccaattagagtctcatattcactctcaatccaaataatctgcaccggatctggatcgtt tcgcatgattgaacaagatggattgcacgcaggttctccggccgcttgggtggagaggctattcggctatgactgg gcacaacagacaatcggctgctctgatgccgccgtgttccggctgtcagcgcaggggcgcccggttcttttttgtca agaccgacctgtccggtgccctgaatgaactgcaggacgaggcagcgcggctatcgtggctggccacgacgggcgt tccttgcgcagctgtgctcgacgttgtcactgaagcgggaagggactggctgctattgggcgaagtgccggggcag gatctcctgtcatctcaccttgctcctgccgagaaagtatccatcatggctgatgcaatgcggcggctgcatacgc ttgatccggctacctgcccattcgaccaccaagcgaaacatcgcatcgagcgagcacgtactcggatggaagccgg tcttgtcgatcaggatgatctggacgaagagcatcaggggctcgcgccagccgaactgttcgccaggctcaaggcg cgcatgcccgacggcgatgatctcgtcgtgacccatggcgatgcctgcttgccgaatatcatggtggaaaatggcc gcttttctggattcatcgactgtggccggctgggtgtggcggaccgctatcaggacatagcgttggctacccgtga tattgctgaagagcttggcggcgaatgggctgaccgcttcctcgtgctttacggtatcgccgctcccgattcgcag cgcatcgccttctatcgccttcttgacgagttcttctgagcgggactctggggttcgaaatgaccgaccaagcgac gcccaacctgccatcacgagatttcgattccaccgccgccttctatgaaaggttgggcttcggaatcgttttccgg gacgccggctggatgatcctccagcgcggggatctcatgctggagttcttcgcccaccgggatctctgcggaacagg cggtcgaaggtgccgatatcattacgacagcaacggccgacaagcacaacgccacgatcctgagcgacaatatgat cgggcccggcgtccacatcaacggcgtcggcggcgactgcccaggcaagaccgagatgcaccgcgatatcttgctg -continued

```
cgttcggatattttcgtggagttcccgccacagacccggatgatccccgatcgttcaaacatttggcaataaagtt
tcttaagattgaatcctgttgccggtcttgcgatgattatcatataatttctgttgaattacgttaagcatgtaat
aattaacatgtaatgcatgacgttatttatgagatgggttttttatgattagagtcccgcaattatacatttaatac
gcgatagaaacaaaatatagcgcgcaaactaggataaattatcgcgcgcggtgtcatctatgttactagatcggg
cctcctgtcaatgctggcggcggctctggtggtggttctggtggcggctctgagggtggtggctctgagggtggcg
gttctgagggtggcggctctgaggaggcggttccggtggtggctctggttccgtgattttgattatgaaagat
ggcaaacgctaataaggggctatgaccgaaaatgccgatgaaaacgcgctacagtctgacgctaaaggcaaactt
gattctgtcgctactgattacggtgctgctatcgatggtttcattggtgacgtttccggccttgctaatggtaatg
gtgctactggtgattttgctggctctaattcccaaatggctcaagtcggtgacggtgataattcacctttaatgaa
taatttccgtcaatatttaccttccctccctcaatcggttgaatgtcgccttttgtctttggcccaatacgcaaa
ccgcctctcccgcgcgttggccgattcattaatgcagctggcacgacaggtttcccgactggaaagcgggcagtg
agcgcaacgcaattaatgtgagttagctcactcattaggcacccaggctttacactttatgcttccggctcgtat
gttgtgtggaattgtgagcggataacaatttcacacaggaaacagctatgaccatgattacgccaagcttgcatgc
ctgcagcccacagatggttagagaggcttacgcagcaggtctcatcaagacgatctacccgagcaataatctccag
gaaatcaaataccttcccaagaaggttaaagatgcagtcaaaagattcaggactaactgcatcaagaacacagaga
aagatatatttctcaagatcagaagtactattccagtatggacgattcaaggcttgcttcacaaaccaaggcaagt
aatagagattggagtctctaaaaaggtagttcccactgaatcaaaggccatggagtcaaagattcaaatagaggac
ctaacagaactcgccgtaaagactggcgaacagttcatacagagtctcttacgactcaatgacaagaagaaaatct
tcgtcaacatggtggagcacgacacacttgtctactccaaaaatatcaaagatacagtctcagaagaccaaagggc
aattgagacttttcaacaaagggtaatatccggaaacctcctcggattccattgcccagctatctgtcactttatt
gtgaagatagtggaaaaggaaggtggctcctacaaatgccatcattgcgataaaggaaaggccatcgttgaagatg
cctctgccgacagtggtcccaaagatggaccccacccacgaggagcatcgtggaaaaagaagacgttccaaccac
gtcttcaaagcaagtggattgatgtgatatctccactgacgtaagggatgacgcacaatcccactatccttcgcaa
gacccttcctctatataaggaagttcatttcatttggagagaacacggggactctagaggatccatgccagtagt
aacccgcttgattcgtttgaagtgtgtagggctcagacttgaccggagtggactcaatcggcgaatctgtcacgga
ggacacggggaatcaacgcggcggagagtgatggaagagctttcaagcctaaccgtgagtcagcgcgagcaatttc
tggtggagaacgatgtgttcgggatctataattacttcgacgccagcgacgtttctactcaaaaatacatgatgga
gattcagcgagataagcaattggattatctgatgaaaggcttaaggcagcttggtccgcagttttcttccttagat
gctaatcgaccttggctttgttactggattcttcattcaatagctttgcttggggagactgtggatgatgaattag
aaagcaatgccattgacttccttggacgctgccagggctctgaaggtggatacggtggtggtcctggccaacttcc
acatcttgcaactacttatgctgcagtgaatgcacttgttactttaggaggtgacaaagccctttcttcaattaat
agagaaaaatgtcttgttttttaagacggatgaaggatacaagtggaggtttcaggatgcatgatatgggagaaa
tggatgttcgtgcatgctacactgcaatttcggttgcaagcatcctaaatattatggatgatgaactcacccaggg
cctaggagattacatcttgagttgccaaacttatgaaggtggcattggaggggaacctggctccgaagctcacggt
gggtatacctactgtggtttggctgctatgattttaatcaatgaggtcgaccgtttgaatttggattcattaatga
attgggctgtacatcgacaaggagtagaaatgggatttcaaggtaggacgaacaaattggtcgatggttgctacac
attttggcaggcagcccttgtgttctactacaaagattatattcaaccaatgatcatgacgttcatggatcatca
catatatcagaagggacaaatgaagaacatcatgctcatgatgaagatgaccttgaagacagtgatgatgatgatg
attctgatgaggacaacgatgaagattcagtgaatggtcacagaatccatcatacatccacctacattaacaggag
aatgcaactggtttttgatagcctcggcttgcagagatatgtactcttgtgctctaagatccctgacggtggattc
```

-continued agagacaagccgaggaaacccgtgacttctaccacacatgttactgcctgagcggcttgtctgtggctcagcacg cttggttaaaagacgaggacactcctcctttgactcgcgacattatgggtggctactcgaatctccttgaacctgt tcaacttcttcacaacattgtcatggatcagtataatgaagctatcgagttcttccttaaagcagcatgactcgaa tttccccgatcgttcaaacatttggcaataaagtttcttaagattgaatcctgttgccggtcttgcgatgattatc atataatttctgttgaattacgttaagcatgtaataattaacatgtaatgcatgacgttatttatgagatgggttt ttatgattagagtcccgcaattatacatttaatacgcgatagaaaacaaaatatagcgcgcaaactaggataaatt atcgcgcgcggtgtcatctatgttactagatcgggaattcactggccgtcgttttacaacgtcgtgactgggaaaa ccctggcgttacccaacttaatcgccttgcagcacatcccctttcgccagctggcgtaatagcgaagaggcccgc accgatcgcccttcccaacagttgcgcagcctgaatggcgcccgctcctttcgctttcttcccttcctttctcgcc acgttcgccggctttccccgtcaagctctaaatcgggggctcccttagggttccgatttagtgctttacggcacc tcgaccccaaaaaacttgatttgggtgatggttcacgtagtgggccatcgccctgatagacggtttttcgcccttt gacgttggagtccacgttctttaatagtggactcttgttccaaactggaacaacactcaaccctatctcgggctat tcttttgatttataagggattttgccgatttcggaaccaccatcaaacaggattttcgcctgctggggcaaaccag cgtggaccgcttgctgcaactctctcagggccaggcggtgaagggcaatcagctgttgcccgtctcactggtgaaa agaaaaaccacccagtacattaaaaacgtccgcaatgtgttattaagttgtctaagcgtcaatttg*tttacacca*

*caatatatactgcca*
(Underlined: 35S promoter; Bold: Sense AtFTB)

SEQ ID NO:53

GAATTCAAATTTTTCGCCAGTTCTAAATATCCGGAAACCTCTTGGGATGCCATTGCCCATCTATCTGTAATTTATT

GACGAAATAGACGAAAAGGAAGGTGGCTCCTATAAAGCACATCATTGCGATAACAGAAAGGCCATTGTTGAAGATA

CCTCTGCTGACATTGGTCCCCAAGTGGAAGCACCACCCCATGAGGAGCACCGTGGAGTAAGAAGACGTTCGAGCCA

CGTCGAAAAAGCAAGTGTGTTGATGTAGTATCTCCATTGACGTAAGGGATGACGCACAATCCAACTATCCATCGCA

AGACCATTGCTCTATATAAGAAAGTTAATATCATTTCGAGTGGCCACGCTGAGCTC<u>GTGGTGGAGAATCTGGGTGC</u>

<u>TTTGACCAACTATACTGGCACAATGAGAGTCCACTTAAACAGTAACATGTGTGATAATGATCTCTACGTTTACCCG</u>

<u>GTTTGTCTCTCAGTCCACCCTCTTGCTCCTGTGCACATAAGAGAATATATTGCTGTAAAGCAATACTGTGAAAAAG</u>

<u>TGGTTCTTGTGCTCTCCACTCATTAATAAATTTATAGGCAATATTTTTAAAATCAGATGAACTGGATTCACTGGTG</u>

<u>CCTTCATGCTCACCACGGCATGTTGCATGACTAGAGGTTCCATCCAAACTTTCTTTTGCTTCAGATACATAAGATA</u>

<u>CCGCAAAAATCTGTGATGTCTCTTCCATCTGTTTGTTGATAATAGAAGATAATCTTTGCAATAGAGCAACAGCACC</u>

<u>TCCCTGCCAAAAGGAATAGCATCCATCCACCAGTTTATTTGTTCTCCCCTGGAATCCACATTCCTTACCTTGTCGG</u>

<u>AATACCACCCAGTCAACTAATCGAGGCAGATCCAAGTGATTAACCTCACCAATCAGAATCATTGTAGCTAATCCAC</u>

<u>AAAAGGTGTACCCACCATGAGCCTCAGAACCAGGCTCACCAGCAATGCCACCCTCATATGTTTGACAGCTTATAAT</u>

<u>GTAGTCTCCAACATTCTGGATCAGCTCATCATCCAAAATGTTCAAAACACTTGCAACAGAAATGGCAGTGTAGCAA</u>

<u>GCTCGAACATCAATTTCACCTTCATCATGCATCCTGAATCCACCATTTGGTTGCTTCATCCGCCGCAGAAACCCAT</u>

<u>ACAGTTTATCTCTATTAATTGATGCCAGGGATTTCTCACCACCCAAAGTAATAAGTGAATTAACAGCAGCATAAGT</u>

<u>TGTGGCAATATGAGGCATCTGGCCTGGTCCCCGGCATATCCACCATTCGGATCCTGGCAACGGTTAAGAAAATCG</u>

<u>ATAGCGTTATCTTCGAGTTCATCATCGACGGATTCTCCCAACAAAGCAATGGAGTGGAAGATCCAGTAGCAGAGCC</u>

<u>AGGGTCGATTAGCGTCCAAAACGGAAAATGCGGAACTGAGATGGCGAAGGCCTTTGGAGACATACTGCATGTGATT</u>

<u>ATCGCGTTGAAGCTCCAACATGAGGGTTTGGGCGTTGCGAGGAATGGTGGC</u>gagctcgaatttccccgatcgttca aacatttggcaataaagtttcttaagattgaatcctgttgccggtcttgcgatgattatcatataatttctgttga attacgttaagcatgtaataattaacatgtaatgcatgacgttatttatgagatgggttttatgattagagtccc gcaattatacatttaatacgcgatagaaaacaaaatatagcgcgcaaactaggataaattatcgcgcgcggtgtca -continued tctatgttactagatcgggaattc
(Upper Case: MuA Promoter; Underlined: Antisense GmFTB; Lower case: NOS terminater)

SEQ ID NO:54

GGAGCCATAGATGCAATTCAATCAAACTGAAATTTCTGCAAGAATCTCAAACACGGAGATCTCAAAGTTTGAAAGA

AAATTTATTTCTTCGACTCAAAACAAACTTACGAAATTTAGGTAGAACTTATATACATTATATTGTAATTTTTTGT

AACAAAATGTTTTTATTATTATTATAGAATTTTACTGGTTAAATTAAAAATGAATAGAAAAGGTGAATTAAGAGGA

GAGAGGAGGTAAACATTTTCTTCTATTTTTTCATATTTTCAGGATAAATTATTGTAAAAGTTTACAAGATTTCCAT

TTGACTAGTGTAAATGAGGAATATTCTCTAGTAAGATCATTATTTCATCTACTTCTTTTATCTTCTACCAGTAGAG

GAATAAACAATATTTAGCTCCTTTGTAAATACAAATTAATTTTCCTTCTTGACATCATTCAATTTTAATTTTACGT

ATAAAATAAAAGATCATACCTATTAGAACGATTAAGGAGAAATACAATTCGAATGAGAAGGATGTGCCGTTTGTTA

TAATAAACAGCCACACGACGTAAACGTAAATGACCACATGATGGGCCAATAGACATGGACCGACTACTAATAATA

GTAAGTTACATTTTAGGATGGAATAAATATCATACCGACATCAGTTTTGAAAGAAAAGGGAAAAAAAGAAAAAATA

AATAAAAGATATACTACCGACATGAGTTCCAAAAAGCAAAAAAAAAGATCAAGCCGACACAGACACGCGTAGAGAG

CAAAATGACTTTGACGTCACACCACGAAAACAGACGCTTCATACGTGTCCCTTTATCTCTCTCAGTCTCTCTATAA

ACTTAGTGAGACCCTCCTCTGTTTTACTCACAAATATGCAAACTAGAAAACAATCATCAGGAATAAAGGGTTTGAT

TACTTCTATTGGAAAG<u>GTGGTGGAGAATCTGGGTGCTTTGACCAACTATACTGGCACAATGAGAGTCCACTTAAAC</u>

<u>AGTAACATGTGTGATAATGATCTCTACGTTTACCCGGTTTGTCTCTCAGTCCACCCTCTTGCTCCTGTGCACATAA</u>

<u>GAGAATATATTGCTGTAAAGCAATACTGTGAAAAAGTGGTTCTTGTGCTCTCCACTCATTAATAAATTTATAGGCA</u>

<u>ATATTTTTAAAATCAGATGAACTGGATTCACTGGTGCCTTCATGCTCACCACGGCATGTTGCATGACTAGAGGTTC</u>

<u>CATCCAAACTTTCTTTTGCTTCAGATACATAAGATACCGCAAAAATCTGTGATGTCTCTTCCATCTGTTTGTTGAT</u>

<u>AATAGAAGATAATCTTTGCAATAGAGCAACAGCACCTCCCTGCCAAAAGGAATAGCATCCATCCACCAGTTTATTT</u>

<u>GTTCTCCCTGGAATCCACATTCCTTACCTTGTCGGAATACCACCCAGTCAACTAATCGAGGCAGATCCAAGTGAT</u>

<u>TAACCTCACCAATCAGAATCATTGTAGCTAATCCACAAAAGGTGTACCCACCATGAGCCTCAGAACCAGGCTCACC</u>

<u>AGCAATGCCACCCTCATATGTTTGACAGCTTATAATGTAGTCTCCAACATTCTGGATCAGCTCATCATCCAAAATG</u>

<u>TTCAAAACACTTGCAACAGAAATGGCAGTGTAGCAAGCTCGAACATCAATTTCACCTTCATCATGCATCCTGAATC</u>

<u>CACCATTTGGTTGCTTCATCCGCCGCAGAAACCCATACAGTTTATCTCTATTAATTGATGCCAGGGATTTCTCACC</u>

<u>ACCCAAAGTAATAAGTGAATTAACAGCAGCATAAGTTGTGGCAATATGAGGCATCTGGCCTGGTCCCCCGGCATAT</u>

<u>CCACCATTCGGATCCTGGCAACGGTTAAGAAAATCGATAGCGTTATCTTCGAGTTCATCATCGACGGATTCTCCCA</u>

<u>ACAAAGCAATGGAGTGGAAGATCCAGTAGCAGAGCCAGGGTCGATTAGCGTCCAAAACGGAAAATGCGGAACTGAG</u>

<u>ATGGCGAAGGCCTTTGGAGACATACTGCATGTGATTATCGCGTTGAAGCTCCAACATGAGGGTTTGGGCGTTGCGA</u>

<u>GGAATGGTGGC</u>gagctcgaatttccccgatcgttcaaacatttggcaataaagtttcttaagattgaatcctgttg ccggtcttgcgatgattatcatataatttctgttgaattacgttaagcatgtaataattaacatgtaatgcatgac gttatttatgagatgggttttatgattagagtcccgcaattatacatttaatacgcgatagaaaacaaaatatag cgcgcaaactaggataaattatcgcgcgcggtgtcatctatgttactagatcgggaattc
(Upper Case: RD29A Promoter; Underlined: Antisense GmFTB; Lower case: NOS)
terminater

SEQ ID NO:55

GAATTCAAATTTTTCGCCAGTTCTAAATATCCGGAAACCTCTTGGGATGCCATTGCCCATCTATCTGTAATTTATT

GACGAAATAGACGAAAAGGAAGGTGGCTCCTATAAAGCACATCATTGCGATAACAGAAAGGCCATTGTTGAAGATA

CCTCTGCTGACATTGGTCCCCAAGTGGAAGCACCACCCCATGAGGAGCACCGTGGAGTAAGAAGACGTTCGAGCCA

CGTCGAAAAAGCAAGTGTGTTGATGTAGTATCTCCATTGACGTAAGGGATGACGCACAATCCAACTATCCATCGCA

AGACCATTGCTCTATATAAGAAAGTTAATATCATTTCGAGTGGCCACGCTGAGCTC<u>GTGGTGGAGAATCTGGGTGC</u>

-continued

<u>TTTGACCAACTATACTGGCACAATGAGAGTCCACTTAAACAGTAACATGTGTGATAATGATCTCTACGTTTACCCG</u>
<u>GTTTGTCTCTCAGTCCACCCTCTTGCTCCTGTGCACATAAGAGAATATATTGCTGTAAAGCAATACTGTGAAAAAG</u>
<u>TGGTTCTTGTGCTCTCCACTCATTAATAAATTTATAGGCAATATTTTTAAAATCAGATGAACTGGATTCACTGGTG</u>
<u>CCTTCATGCTCACCACGGCATGTTGCATGACTAGAGGTTCCATCCAAACTTTCTTTTGCTTCAGATACATAAGATA</u>
<u>CCGCAAAAATCTGTGATGTCTCTTCCATCTGTTTGTTGATAATAGAAGATAATCTTTGCAATAGAGCAACAGCACC</u>
<u>TCCCTGCCAAAAGGAATAGCATCCATCCACCAGTTTATTTGTTCTCCCCTGGAATCCACATTCCTTACCTTGTCGG</u>
<u>AATACCACCCAGTCAACTAATCGAGGCAGATCCAAGTGATTAACCTCACCAATCAGAATCATTGTAGCTAATCCAC</u>
<u>AAAAGGTGTACCCACCATGAGCCTCAGAACCAGGCTCACCAGCAATGCCACCCTCATATGTTTGACAGCTTATAAT</u>
<u>GTAGTCTCCAACATTCTGGATCAGCTCATCATCCAAAATGTTCAAAACACTTGCAACAGAAATGGCAGTGTAGCAA</u>
<u>GCTCGAACATCAATTTCACCTTCATCATGCATCCTGAATCCACCATTTGGTTGCTTCATCCGCCGCAGAAACCCAT</u>
<u>ACAGTTTATCTCTATTAATTGATGCCAGGGATTTCTCACCACCCAAAGTAATAAGTGAATTAACAGCAGCATAAGT</u>
<u>TGTGGCAATATGAGGCATCTGGCCTGGTCCCCCGGCATATCCACCATTCGGATCCTGGCAACGGTTAAGAAAATCG</u>
<u>ATAGCGTTATCTTCGAGTTCATCATCGACGGATTCTCCCAACAAAGCAATGGAGTGGAAGATCCAGTAGCAGAGCC</u>
<u>AGGGTCGATTAGCGTCCAAAACGGAAAATGCGGAACTGAGATGGCGAAGGCCTTTGGAGACATACTGCATGTGATT</u>
<u>ATCGCGTTGAAGCTCCAACATGAGGGTTTGGGCGTTGCGAGGAATGGTGGC</u>GGTGAGGTTAATCACTTGGATCTGC
CTCGATTAGTTGACTGGGTGGTATTCCGACAAGGTAAGGAATGTGGATTCCAGGGGAGAACAAATAAACTGGTGGA
TGGATGCTATTCCTTTTGGCAGGGAGGTGCTGTTGCTCTATTGCAAAGATTATCTTCTATTATCAACAAACAGATG
GAAGAGACATCACAGATTTTTGCGGTATCTTATGTATCTGAAGCAAAAGAAAGTTTGGATGGAACCTCTAGTCATG
CAACATGCCGTGGTGAGCATGAAGGCACCAGTGAATCCAGTTCATCTGATTTTAAAAATATTGCCTATAAATTTAT
TAATGAGTGGAGAGCACAAGAACCACTTTTTCACAGTATTGCTTTACAGCAATATATTCTCTTATGTGCACAGGAG
CAAGAGGGTGGACTGAGAGACAAACCGGGTAAACGTAGAGATCATTATCACACATGTTACTGTTTAAGTGGACTCT
CATTGTGCCAGTATAGTTGGTCAAAGCACCCAGATTCTCCACCAgagctcgaatttccccgatcgttcaaacatt
tggcaataaagtttcttaagattgaatcctgttgccggtcttgcgatgattatcatataatttctgttgaattacg
ttaagcatgtaataattaacatgtaatgcatgacgttatttatgagatgggttttttatgattagagtcccgcaatt
atacatttaatacgcgatagaaaacaaaatatagcgcgcaaactaggataaattatcgcgcgcggtgtcatctatg
ttactagatcgggaattc
(Upper Case: MuA Promoter; Underlined: Antisense GmFTB; Bold: Sense GmFTB;
Lower case: NOS terminater)

SEQ ID NO:56
GGAGCCATAGATGCAATTCAATCAAACTGAAATTTCTGCAAGAATCTCAAACACGGAGATCTCAAAGTTTGAAAGA
AAATTTATTTCTTCGACTCAAAACAAACTTACGAAATTTAGGTAGAACTTATATACATTATATTGTAATTTTTTGT
AACAAAATGTTTTTATTATTATTATAGAATTTTACTGGTTAAATTAAAAATGAATAGAAAAGGTGAATTAAGAGGA
GAGAGGAGGTAAACATTTTCTTCTATTTTTTCATATTTTCAGGATAAATTATTGTAAAAGTTTACAAGATTTCCAT
TTGACTAGTGTAAATGAGGAATATTCTCTAGTAAGATCATTATTTCATCTACTTCTTTTATCTTCTACCAGTAGAG
GAATAAACAATATTTAGCTCCTTTGTAAATACAAATTAATTTTCCTTCTTGACATCATTCAATTTTAATTTTACGT
ATAAAATAAAAGATCATACCTATTAGAACGATTAAGGAGAAATACAATTCGAATGAGAAGGATGTGCCGTTTGTTA
TAATAAACAGCCACACGACGTAAACGTAAAATGACCACATGATGGGCCAATAGACATGGACCGACTACTAATAATA
GTAAGTTACATTTTAGGATGGAATAAATATCATACCGACATCAGTTTTGAAAGAAAAGGGAAAAAAAGAAAAAATA
AATAAAAGATATACTACCGACATGAGTTCCAAAAAGCAAAAAAAAAGATCAAGCCGACACAGACACGCGTAGAGAG
CAAAATGACTTTGACGTCACACCACGAAAACAGACGCTTCATACGTGTCCCTTTATCTCTCTCAGTCTCTCTATAA
ACTTAGTGAGACCCTCCTCTGTTTTACTCACAAATATGCAAACTAGAAAACAATCATCAGGAATAAAGGGTTTGAT

-continued

TACTTCTATTGGAAAG<u>GTGGTGGAGAATCTGGGTGCTTTGACCAACTATACTGGCACAATGAGAGTCCACTTAAAC</u>

<u>AGTAACATGTGTGATAATGATCTCTACGTTTACCCGGTTTGTCTCTCAGTCCACCCTCTTGCTCCTGTGCACATAA</u>

<u>GAGAATATATTGCTGTAAAGCAATACTGTGAAAAAGTGGTTCTTGTGCTCTCCACTCATTAATAAATTTATAGGCA</u>

<u>ATATTTTTAAAATCAGATGAACTGGATTCACTGGTGCCTTCATGCTCACCACGGCATGTTGCATGACTAGAGGTTC</u>

<u>CATCCAAACTTTCTTTTGCTTCAGATACATAAGATACCGCAAAAATCTGTGATGTCTCTTCCATCTGTTTGTTGAT</u>

<u>AATAGAAGATAATCTTTGCAATAGAGCAACAGCACCTCCCTGCCAAAAGGAATAGCATCCATCCACCAGTTTATTT</u>

<u>GTTCTCCCCTGGAATCCACATTCCTTACCTTGTCGGAATACCACCCAGTCAACTAATCGAGGCAGATCCAAGTGAT</u>

<u>TAACCTCACCAATCAGAATCATTGTAGCTAATCCACAAAAGGTGTACCCACCATGAGCCTCAGAACCAGGCTCACC</u>

<u>AGCAATGCCACCCTCATATGTTTGACAGCTTATAATGTAGTCTCCAACATTCTGGATCAGCTCATCATCCAAAATG</u>

<u>TTCAAAACACTTGCAACAGAAATGGCAGTGTAGCAAGCTCGAACATCAATTTCACCTTCATCATGCATCCTGAATC</u>

<u>CACCATTTGGTTGCTTCATCCGCCGCAGAAACCCATACAGTTTATCTCTATTAATTGATGCCAGGGATTTCTCACC</u>

<u>ACCCAAAGTAATAAGTGAATTAACAGCAGCATAAGTTGTGGCAATATGAGGCATCTGGCCTGGTCCCCCGGCATAT</u>

<u>CCACCATTCGGATCCTGGCAACGGTTAAGAAAATCGATAGCGTTATCTTCGAGTTCATCATCGACGGATTCTCCCA</u>

<u>ACAAAGCAATGGAGTGGAAGATCCAGTAGCAGAGCCAGGGTCGATTAGCGTCCAAAACGGAAAATGCGGAACTGAG</u>

<u>ATGGCGAAGGCCTTTGGAGACATACTGCATGTGATTATCGCGTTGAAGCTCCAACATGAGGGTTTGGGCGTTGCGA</u>

<u>GGAATGGTGGC</u>GGTGAGGTTAATCACTTGGATCTGCCTCGATTAGTTGACTGGGTGGTATTCCGACAAGGTAAGGA

ATGTGGATTCCAGGGGAGAACAAATAAACTGGTGGATGGATGCTATTCCTTTTGGCAGGGAGGTGCTGTTGCTCTA

TTGCAAAGATTATCTTCTATTATCAACAAACAGATGGAAGAGACATCACAGATTTTTGCGGTATCTTATGTATCTG

AAGCAAAAGAAAGTTTGGATGGAACCTCTAGTCATGCAACATGCCGTGGTGAGCATGAAGGCACCAGTGAATCCAG

TTCATCTGATTTTAAAAATATTGCCTATAAATTTATTAATGAGTGGAGAGCACAAGAACCACTTTTTCACAGTATT

GCTTTACAGCAATATATTCTCTTATGTGCACAGGAGCAAGAGGGTGGACTGAGAGACAAACCGGGTAAACGTAGAG

ATCATTATCACACATGTTACTGTTTAAGTGGACTCTCATTGTGCCAGTATAGTTGGTCAAAGCACCCAGATTCTCC

ACCACgagctcgaatttccccgatcgttcaaacatttggcaataaagtttcttaagattgaatcctgttgccggtc ttgcgatgattatcatataatttctgttgaattacgttaagcatgtaataattaacatgtaatgcatgacgttatt tatgagatgggttttatgattagagtcccgcaattatacatttaatacgcgatagaaaacaaaatataggccgca aactaggataaattatcgcgcgcggtgtcatctatgttactagatcgggaattc
(Upper Case: RD29A Promoter; Underlined: Antisense GmFTB; Bold: Sense GmFTB;
Lower case: NOS terminater)

SEQ ID NO:57
GAATTCAAATTTTTCGCCAGTTCTAAATATCCGGAAACCTCTTGGGATGCCATTGCCCATCTATCTGTAATTTATT

GACGAAATAGACGAAAAGGAAGGTGGCTCCTATAAAGCACATCATTGCGATAACAGAAAGGCCATTGTTGAAGATA

CCTCTGCTGACATTGGTCCCCAAGTGGAAGCACCACCCCATGAGGAGCACCGTGGAGTAAGAAGACGTTCGAGCCA

CGTCGAAAAAGCAAGTGTGTTGATGTAGTATCTCCATTGACGTAAGGGATGACGCACAATCCAACTATCCATCGCA

AGACCATTGCTCTATATAAGAAAGTTAATATCATTTCGAGTGGCCACGCTGAGCTC<u>GGATGGATTGGCTCCAGCAA</u>

<u>ATTAGAGTACGGTCCAAGCACATGCTGAGGTAATGGGCACGAACCAGTATCAGTCATGGCACTGTACTGGCTAACT</u>

<u>GCGAGGCCACTGAGGCAGTAGCATGAATGATAGTGATCTCTGTTCTTTCCAGGCTTATCCCTCAAGCCTCCCTCTA</u>

<u>GTACCTGAGAACAAAGTAGGATGTATTGTTGCAGGGCAATGTTATGGAAGAGTGGGCCAATTTGGTTGCTCTGTTG</u>

<u>TATAAAATCAAATCCAAACTTCGCATAGTCCACAGCAGAGGAAGACTTATTCGCGGTGCACCCATATGAACTGGTG</u>

<u>CTGCAGGCATCCTCTCCTGATGGCCTTTTGCAGGAATACGAGGACCTCAATTGCTTATCAACAATCGTAATTAACT</u>

<u>TTTGTGTGAAAGCAATGGCAGCTCCCTGCCAAAAGGAGTAGCAACCATCAACCAATTTATTAGTTCGTCCTTGAAA</u>

<u>TCCGCATTCCACTCCTTGACGAAAAGCCACCCAGCCAATCAAACTAGGCAAGTCAACTTTCTCTGCCTCATTAAGC</u>

<u>AGGATCAAAGCAGCCAATCCACAGAATGTATACCCACCATGTGCTTCAGCATAAGGCTCCCCAGCAATACCACCTT</u>

-continued

<u>CATAAGTTTGACATCTTGCTATGTAGTCGCCTACACCTTTTGCCAGTTTAAAATCAAGAATATTCACAAGGCTGGC</u>

<u>AACCGATATAGCGGTGTAGGAAGCACGGACATCAATTTCGCCACCATCATGCATTCTGAAAGCACCTGATACATCT</u>

<u>TTCATCTGCAGCATAAAATTGTACAGGTTGCCCCTATTGATTGATGACAATGCTCTTTCGCTCCCTATTGTCACAA</u>

<u>GTGTATTTACAGCAGCATAAGTCGTAGCTAGGTGAGGCAACTGTCCAGGTCCACCACTATATCCACCATCTTTATC</u>

<u>CTGACATCGAGCTAAGAAGTCTATGATATCATTCTCAAGATCATCATCAAGTGCTTCATCCAGCAAAGCAAGTGGA</u>

<u>TGAACCATCCAGTAGCATAGCCAAGGGCGATTGGCATCTAGAACATGAAAGGCTGGTCCCATATGCCTCAGCCCAG</u>

<u>GCGTCAGATACTCGATATGCTGATCACGCCACGACTCTAGCATGATGGATTTCGTGTTGGGCGCGGCCCCGAAGAG</u>

<u>GGAGCGGTAGATGTCGCCAACCCTGGCCTCCACCTTCATCTGCTCCACCTGCGTCACCGTGAGCCTCGGTAGGTCG</u>

<u>GGATCCGCC</u>gagctcgaatttccccgatcgttcaaacatttggcaataaagtttcttaagattgaatcctgttgcc ggtcttgcgatgattatcatataatttctgttgaattacgttaagcatgtaataattaacatgtaatgcatgacgt tatttatgagatgggttttatgattagagtcccgcaattatacatttaatacgcgatagaaaacaaaatatagcg cgcaaactaggataaattatcgcgcgcggtgtcatctatgttactagatcgggaattc
(Upper Case: MuA Promoter; Underlined: Antisense Zea maize-FTB; Lower
case: NOS terminator)

SEQ ID NO:58

GAATTCAAATTTTTCGCCAGTTCTAAATATCCGGAAACCTCTTGGGATGCCATTGCCCATCTATCTGTAATTTATT

GACGAAATAGACGAAAAGGAAGGTGGCTCCTATAAAGCACATCATTGCGATAACAGAAAGGCCATTGTTGAAGATA

CCTCTGCTGACATTGGTCCCCAAGTGGAAGCACCACCCCATGAGGAGCACCGTGGAGTAAGAAGACGTTCGAGCCA

CGTCGAAAAAGCAAGTGTGTTGATGTAGTATCTCCATTGACGTAAGGGATGACGCACAATCCAACTATCCATCGCA

AGACCATTGCTCTATATAAGAAAGTTAATATCATTTCGAGTGGCCACGCTGAGCTC<u>GGATGGATTGGCTCCAGCAA</u>

<u>ATTAGAGTACGGTCCAAGCACATGCTGAGGTAATGGGCACGAACCAGTATCAGTCATGGCACTGTACTGGCTAACT</u>

<u>GCGAGGCCACTGAGGCAGTAGCATGAATGATAGTGATCTCTGTTCTTTCCAGGCTTATCCCTCAAGCCTCCCTCTA</u>

<u>GTACCTGAGAACAAAGTAGGATGTATTGTTGCAGGGCAATGTTATGGAAGAGTGGGCCAATTTGGTTGCTCTGTTG</u>

<u>TATAAAATCAAATCCAAACTTCGCATAGTCCACAGCAGAGGAAGACTTATTCGCGGTGCACCCATATGAACTGGTG</u>

<u>CTGCAGGCATCCTCTCCTGATGGCCTTTTGCAGGAATACGAGGACCTCAATTGCTTATCAACAATCGTAATTAACT</u>

<u>TTTGTGTGAAAGCAATGGCAGCTCCCTGCCAAAAGGAGTAGCAACCATCAACCAATTTATTAGTTCGTCCTTGAAA</u>

<u>TCCGCATTCCACTCCTTGACGAAAAGCCACCCAGCCAATCAAACTAGGCAAGTCAACTTTCTCTGCCTCATTAAGC</u>

<u>AGGATCAAAGCAGCCAATCCACAGAATGTATACCCACCATGTGCTTCAGCATAAGGCTCCCCAGCAATACCACCTT</u>

<u>CATAAGTTTGACATCTTGCTATGTAGTCGCCTACACCTTTTGCCAGTTTAAAATCAAGAATATTCACAAGGCTGGC</u>

<u>AACCGATATAGCGGTGTAGGAAGCACGGACATCAATTTCGCCACCATCATGCATTCTGAAAGCACCTGATACATCT</u>

<u>TTCATCTGCAGCATAAAATTGTACAGGTTGCCCCTATTGATTGATGACAATGCTCTTTCGCTCCCTATTGTCACAA</u>

<u>GTGTATTTACAGCAGCATAAGTCGTAGCTAGGTGAGGCAACTGTCCAGGTCCACCACTATATCCACCATCTTTATC</u>

<u>CTGACATCGAGCTAAGAAGTCTATGATATCATTCTCAAGATCATCATCAAGTGCTTCATCCAGCAAAGCAAGTGGA</u>

<u>TGAACCATCCAGTAGCATAGCCAAGGGCGATTGGCATCTAGAACATGAAAGGCTGGTCCCATATGCCTCAGCCCAG</u>

<u>GCGTCAGATACTCGATATGCTGATCACGCCACGACTCTAGCATGATGGATTTCGTGTTGGGCGCGGCCCCGAAGAG</u>

<u>GGAGCGGTAGATGTCGCCAACCCTGGCCTCCACCTTCATCTGCTCCACCTGCGTCACCGTGAGCCTCGGTAGGTCG</u>

<u>GGATCCGCC</u>ggatccGCTGGGGAGCCTTATGCTGAAGCACATGGTGGGTATACATTCTGTGGATTGGCTGCTTTGA

TCCTGCTTAATGAGGCAGAGAAAGTTGACTTGCCTAGTTTGATTGGCTGGGTGGCTTTTCGTCAAGGAGTGGAATG

CGGATTTCAAGGACGAACTAATAAATTGGTTGATGGTTGCTACTCCTTTTGGCAGGGAGCTGCCATTGCTTTCACA

CAAAAGTTAATTACGATTGTTGATAAGCAATTGAGGTCCTCGTATTCCTGCAAAAGGCCATCAGGAGAGGATGCCT

GCAGCACCAGTTCATATGGGTGCACCGCGAATAAGTCTTCCTCTGCTGTGGACTATGCGAAGTTTGGATTTGATTT

-continued

```
TATACAACAGAGCAACCAAATTGGCCCACTCTTCCATAACATTGCCCTGCAACAATACATCCTACTTTGTTCTCAG

GTACTAGAGGGAGGCTTGAGGGATAAGCCTGGAAAGAACAGAGATCACTATCATTCATGCTACTGCCCTCAGTGGCC

TCGCAGTTAGCCAGTACAGTGCCATGACTGATACTGGTTCGTGCCCATTACCTCAGCATGTGCTTGGACCGTACTC

TAATTTGCTGGAGCCAATCCATCCaagcttgaatttccccgatcgttcaaacatttggcaataaagtttcttaaga ttgaatcctgttgccggtcttgcgatgattatcatataatttctgttgaattacgttaagcatgtaataattaaca tgtaatgcatgacgttatttatgagatgggttttttatgattagagtcccgcaattatacatttaatacgcgataga aaacaaaatatagcgcgcaaactaggataaattatcgcgcgcggtgtcatctatgttactagatcggaagctt
(Upper Case: MuA Promoter; Underlined: Antisense Zea maize-FTB; Bold:
Sense Zea maize-FTB; Lower case: NOS terminater)
```

Example 7

PCR Analysis of Putative Transgenic Plants

To verify that the putative transgenic plants carried the gene of interest PCR analysis was performed. Genomic DNA was isolated and PCR run according to standard protocols and conditions which are known to one of skill in the art. A typical reaction was performed in a volume of 25 µl and primer pairs used were dependent on the gene and promoter combination of the particular construct (Table 12).

Figure 15:
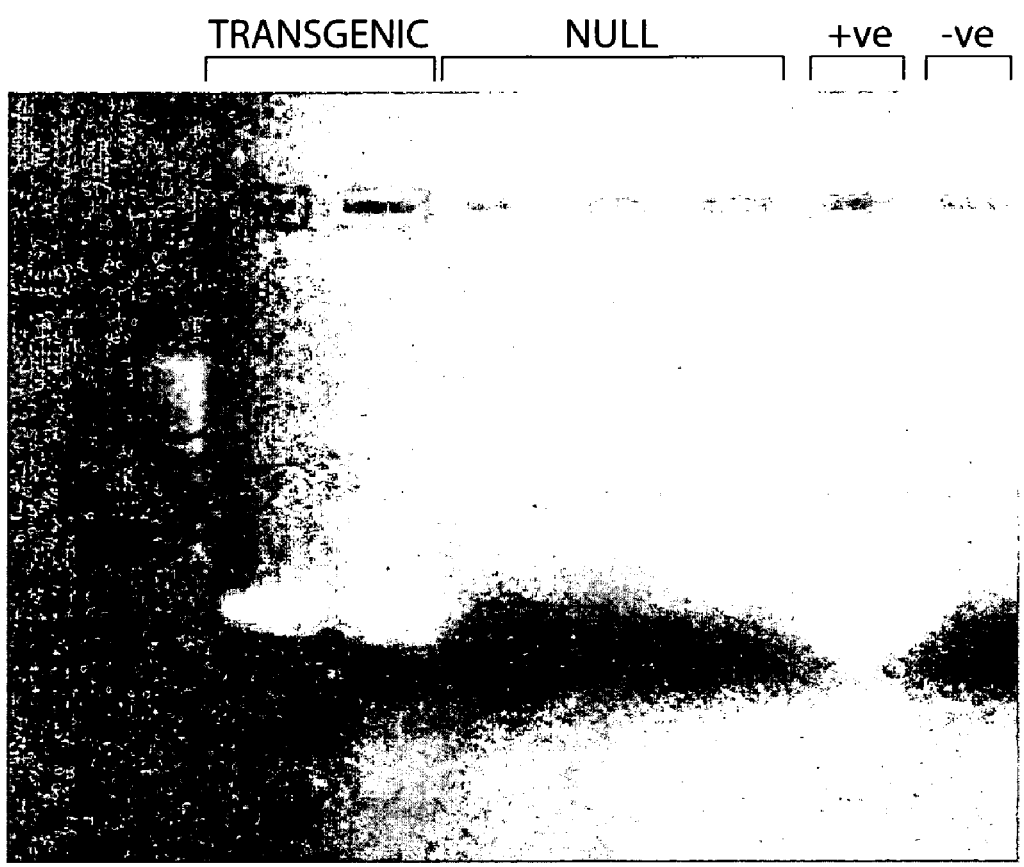
FIG. 15 is a representitive illustration of gel electrophoresis analysis of PCR products in an assay to detect transgenic lines of *Brassica napus*.

Putative transgenic *Brassica napus* plants were screened using the primer combinations detailed in the table below. A representative gel showing PCR analysis results is shown in FIG. 15 which represents transgenic plants carrying the pRD29A-anti-FTA construct. Transformants were confirmed in an analogous manner for each species and construct transformation done.

TABLE 12

| Construct Name | Primer Name | Primer Sequence (5'-3') |
|---|---|---|
| 35S-antiFTA | SEQ ID NO:10 | GCCGACAGTGGTCCCAAAGATGG |
| | SEQ ID NO:11 | AAAGGATCCTCAAATTGCTGCCACTGTAAT |
| rd29A-antiFTA | SEQ ID NO:12 | AAACCCGGGATGAATTTCGACGAGAACGTG |
| | SEQ ID NO:13 | GCAAGACCGGCAACAGGA |
| rd29B-antiFTA | SEQ ID NO:14 | TTTAAGCTTGACAGAAACAGTCAGCGAGAC |
| | SEQ ID NO:11 | AAACCCGGGATGAATTTCGACGAGAACGTG |
| 35S-DA-FTA | SEQ ID NO:15 | GCTCTTCCTCCATGCCCA |
| | SEQ ID NO:13 | GCAAGACCGGCAACAGGA |
| rd29A-DA-FTA | SEQ ID NO:16 | TTTAAGCTTGGAGCCATAGATGCAATTCAA |
| | SEQ ID NO:17 | CGGGCATTAGGAGGATGGGAA |
| 35S-HP-FTB | SEQ ID NO:10 | GCCGACAGTGGTCCCAAAGATGG |
| | SEQ ID NO:18 | GTCCGGAATTCCCGGGTC |
| rd29A-HP-FTB | SEQ ID NO:16 | TTTAAGCTTGGAGCCATAGATGCAATTCAA |
| | SEQ ID NO:18 | GTCCGGAATTCCCGGGTC |

Example 8

Southern Analysis

Figure 2:
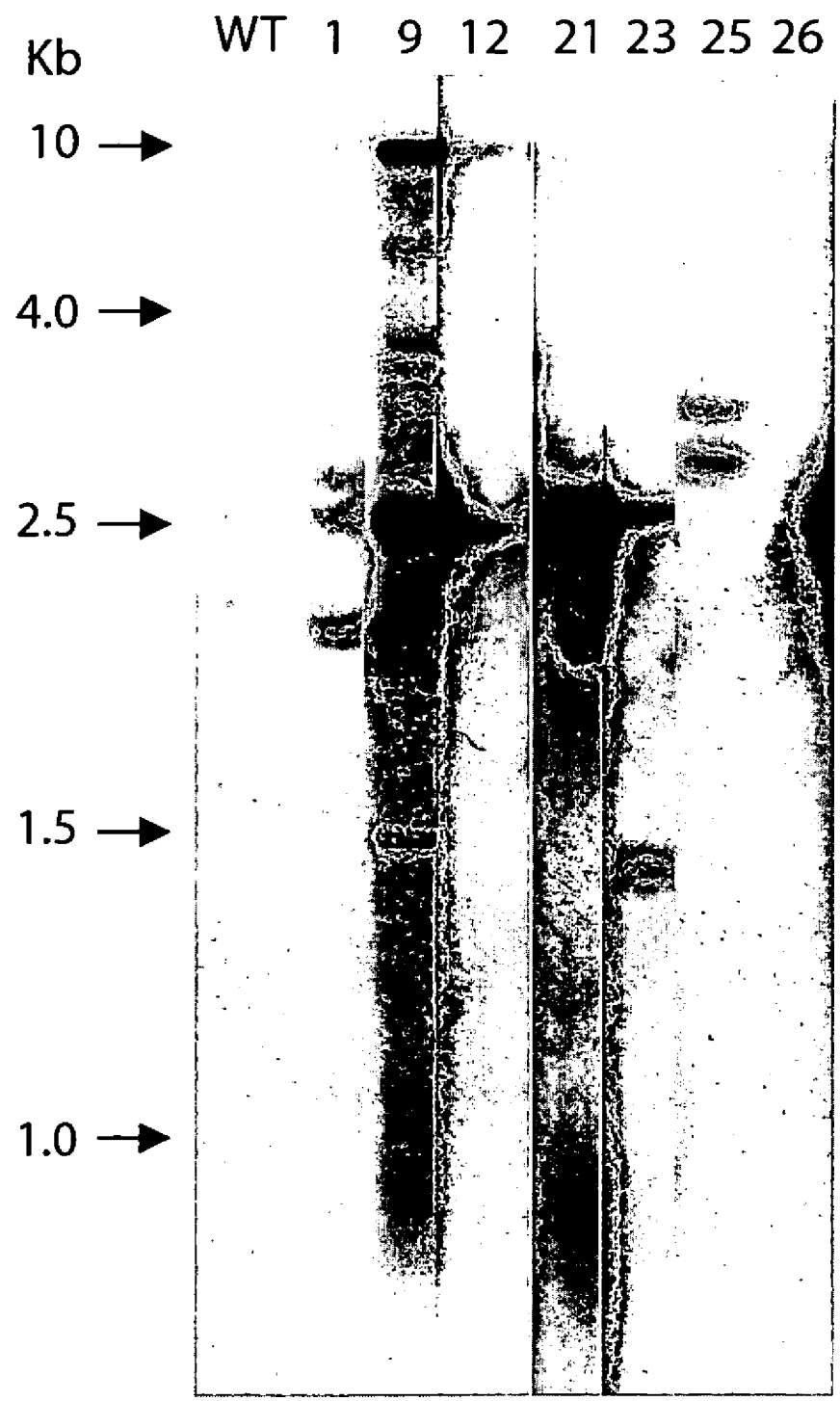
FIG. 2 is an illustration of genomic Southern hybridization analysis of anti-FTA transgenic *Arabidopsis thaliana*.

Genomic Southern analysis of anti-FTA transgenic *Arabidopsis thaliana*. The numbers indicate the line numbers. Five micrograms of genomic DNA of T1 plants was digested with HindIII (a unique site in the T-DNA plasmid) and separated in a 0.8% agarose gel. The NPTII coding region was used as the probe for radio-labeling. FIG. 2 shows a typical result from Southern analysis indicating the presence of the transgene.

Example 9

Northern Blots of Antisense FTA Lines

Figure 3A:
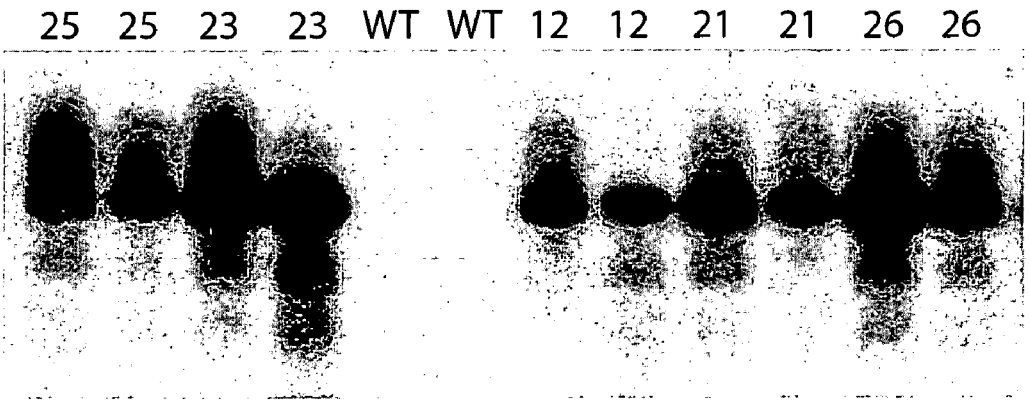
FIG. 3 is an illustration of Northern analysis of five 35S-anti-FTA *Arabidopsis thaliana* lines (T3 plants).
Figure 3B:
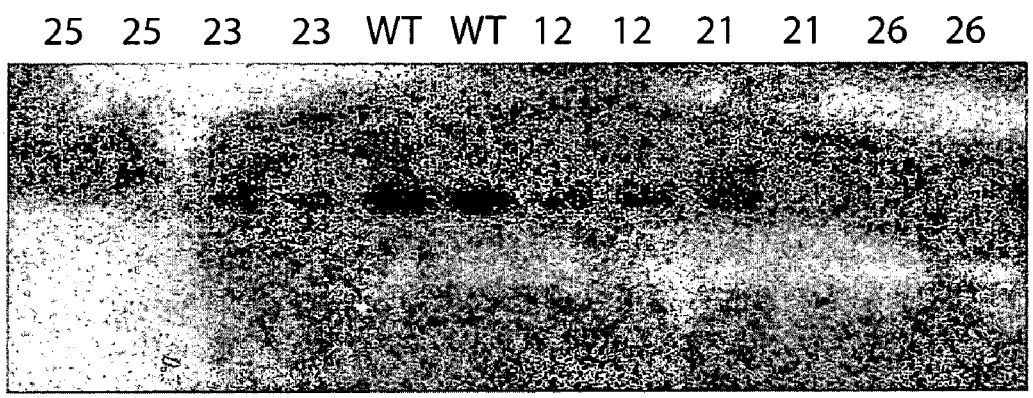
Figure 3C:
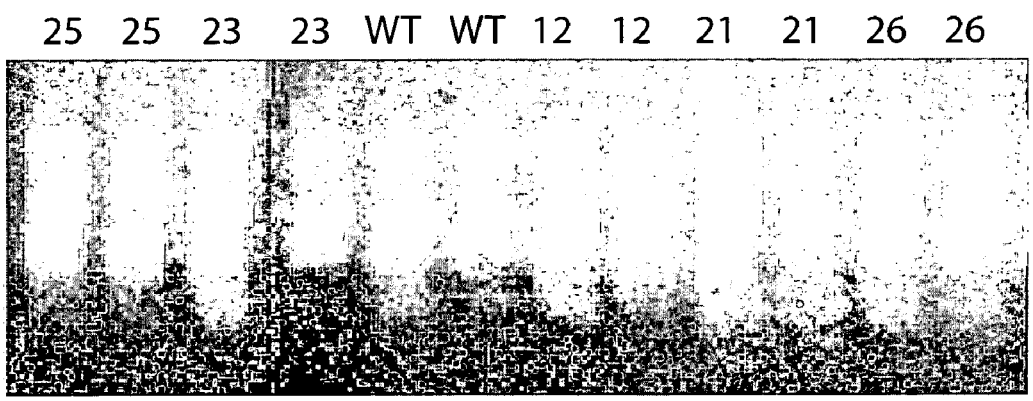

RNA was isolated from developing leaf tissue of five 35S-anti-FTA *Arabidopsis thaliana* lines (T3 plants). The blot was first probed with $P^{32}$ labeled, single-stranded sense transcript of FTA (FIG. 3 panel A) which detects antisense transcript, then stripped and re-probed with the single-stranded anti-sense transcript of FTA (FIG. 3 panel B) that detects the sense transcript. FIG. 3 panel C shows the ethidium bromide stained gel for the blot. Approximately 5 µg of total RNA was loaded into each lane. FIG. 3 indicates the accumulation of the transgene anti-sense transcript and a reduction in the sense transcript in transgenic plants.

Example 10

Western Blot Antisense FTA Lines with Anti-FT-α Antibodies

Figure 4:
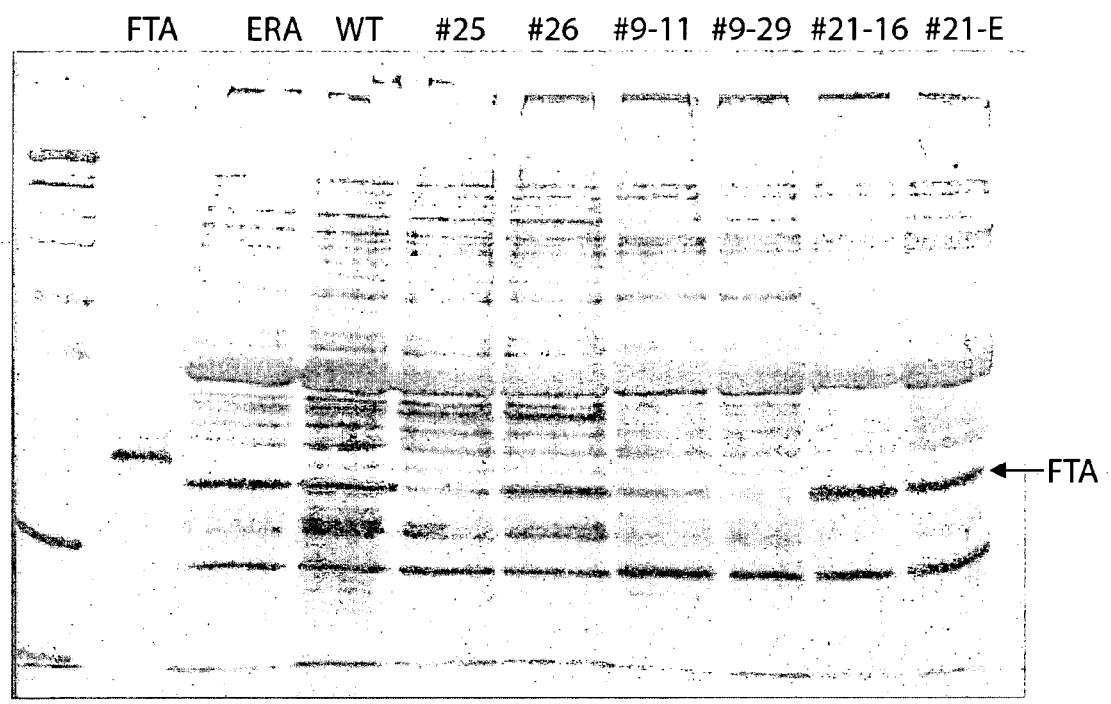
FIG. 4 shows a Western expression analysis using anti-FTA antibodies to detect the FTA polypeptides.

The antibodies produced according to the methods of Example 19 were used to analyze protein extracts from transgenic plants on western blots. Lane 1 of FIG. 4 is a molecular weight standard, lane 2 purified FTA protein, lanes 3–10 are protein extracts from the ERA1 mutant, wild type, and 4 lines of transgenic *Arabidopsis thaliana*. FIG. 4 illustrates the reduction of detectable FTA protein in transgenic lines.

Example 11

ABA Sensitivity of Transgenic Seedlings

Figure 5:
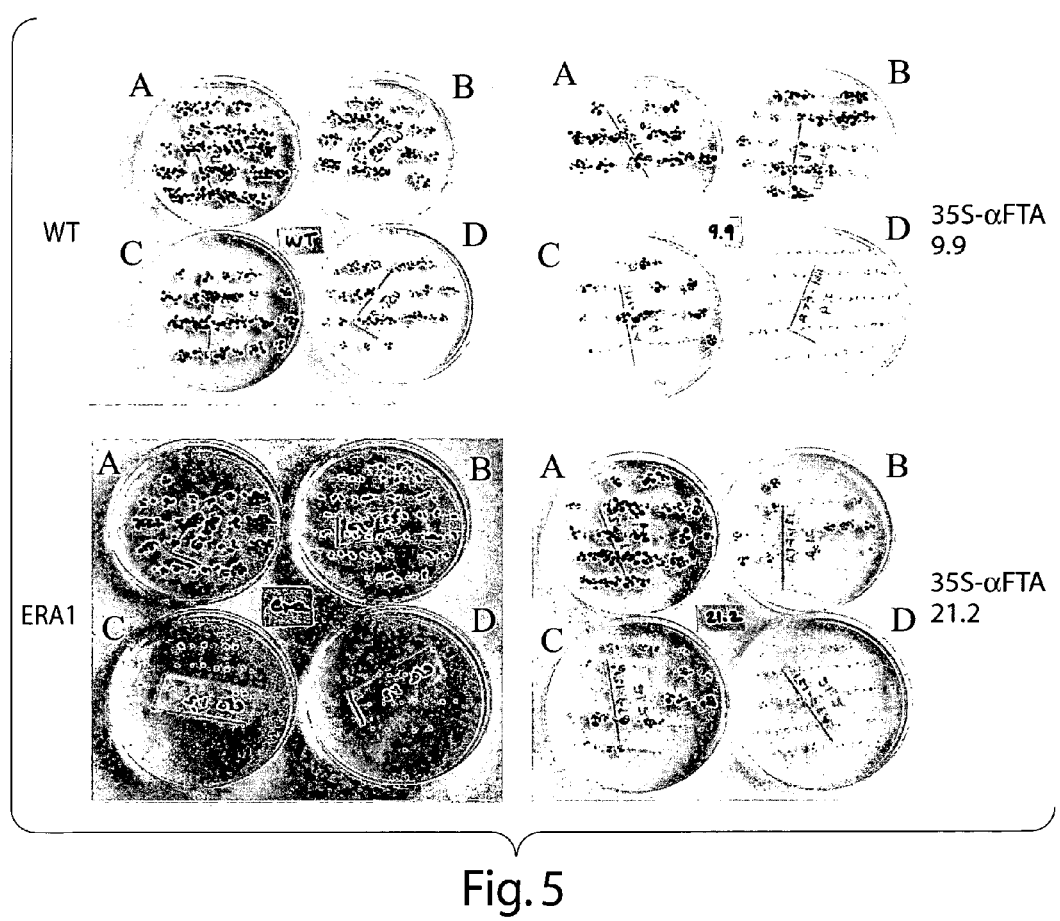
FIG. 5 is a set of photographs showing ABA effects on seedling growth and development. FTA Antisense transgenic seedlings exhibit enhanced ABA sensitivity.

Seeds of wild type Columbia, era1-2 and T3 homozygous seeds of two antisense, drought tolerant lines of 35S-antisense-FTA were plated on minimum medium (½ MS) supplemented with no ABA (A), 0.3 µM (B), 0.5 µM (C) or 1.0 µM ABA (D). Plates were chilled for 3 days in 4° C. in the dark, and incubated for 11 days at 22° C. with 24 hour continuous light. era1 and transgenic lines were more inhibited in germination than wild type plants. Results are shown in FIG. 5.

Figure 6A:
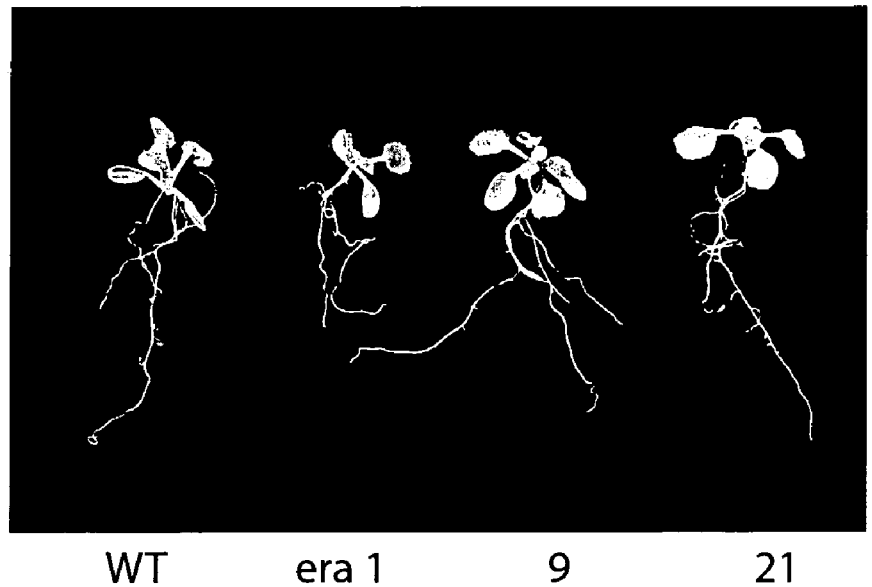
FIG. 6 shows the effect of ABA on seedling growth and development.
Figure 6B:

Twelve day old seedling phenotypes of wild type Columbia, era1–2 and two drought tolerant 35S-antisense-FTA lines (9.9 & 21.2) in minimum medium without (A) or with (B) 1 µM ABA. FIG. 6 shows the reduced root growth and development of era1 and transgenic lines relative to wild type plants. The 35S-antisense-FTA lines show reduced root growth, similar to the era1 mutant, in response to ABA.

A transgenic *Brassica napus* line carrying the 35S-antisense-FTA construct was assessed for ABA sensitivity. At about 10 µm an effect was observed showing reduced seedling development and vigor at the cotyledon and first leaf stage, thereby indicating an increased sensitivity to ABA ABA sensitivity is assessed in all transgenic plants engineered to have reduced or increased FTA or FTB expression or activity by the methods above. The ABA concentration used varies depending upon the species under examination.

Example 12

Drought Experiment

To assess the response of plants under water stress or drought one can expose plants to various situations. For example, the plant can be removed from soil or media and placed on paper towel for a period of time, such as 4 hours, then returned to a plate to continue growth and development. Survival and vigour can be assessed.

Figure 7:
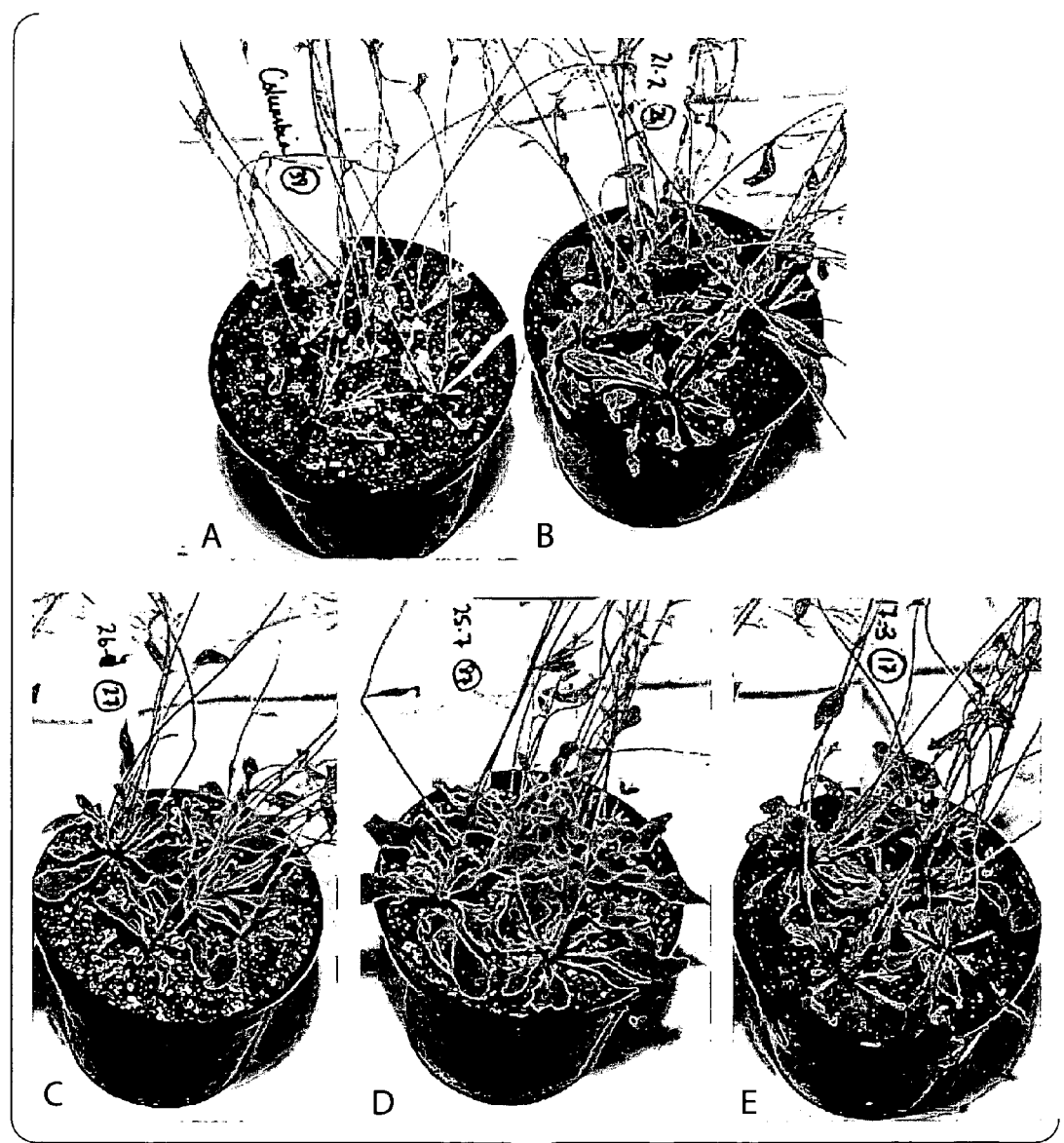
FIG. 7 shows photographs of wild type Columbia (A) and four antisense FTA transgenic lines (B, C, D, E) of *Arabidopsis thaliana* after 8 days without watering.

Alternatively one can impose a water stress in such a way as to more closely resemble a field situation by withholding water for a period of time, such as up to 6 days. Plants were grown five plants per four inch pot, in a replicated water-stress experiment. All pots were filled with equal amounts of homogeneous premixed and wetted soil. Growth conditions were 16 hour daylight (150–200 µmol/m²/s) at 22° C. and 70% relative humidity. On the day that the first flower opened drought treatment was initiated first by equalizing the soil water content in each pot on a weight basis and then cessation of watering. At the end of the water stress treatment plants were typically either harvested for biomass data or re-watered to complete the life cycle and determination of biomass and yield data. Physiological parameters have been assessed under stressed and optimal conditions, for example, shoot and root biomass accumulation, soil water content, water loss alone or as a function of parameters such as biomass, seed yield, and leaf number and leaf area. FIG. 7 shows photographs of wild type Columbia (A) and four 35S-antisense-FTA transgenic *Arabidopsis thaliana* lines (B, C, D, E) after 8 days of water stress treatment. The control plant is visibly stressed and less healthy. This experiment has been conducted on transgenic lines containing vectors described by SEQ ID NO: 4, 40–58.

Drought or water stress tolerance is assessed in all transgenic plants engineered to have reduced or increased FTA or FTB expression or activity by the described methods.

Example 13

Figure 10:
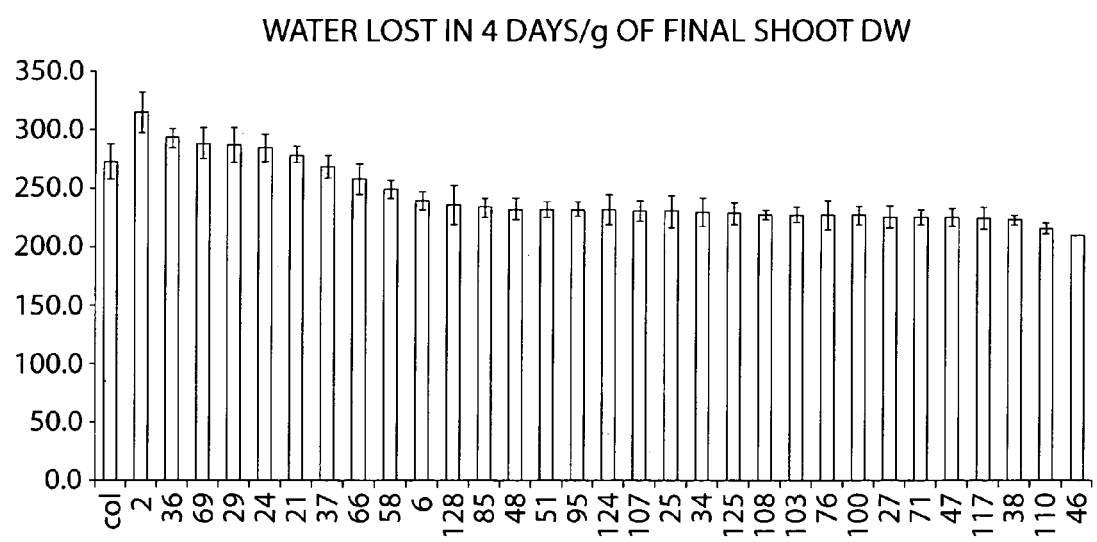
FIG. 10 is an illustration of transgenic performance during water stress.

Analysis of Water Loss in *Arabidopsis thaliana* pRD29A-DA-FTA Lines During Drought Stress Plants were grown 5 plants per 4 inch pot and 6 pots per line. When the plants had grown to the first flower stage drought treatment was initiated as described in Example 12. Pots were weighed daily and at the end of the 7 day drought treatment all plants were harvested for shoot fresh weight and dry weight determinations. FIG. 10 shows the water loss on a per shoot dry weight basis at 4 days of water stress treatment. Of the 31 lines examined in this experiment 25 showed lower water loss relative to the Columbia wild type, 22 of which were statistically significant. All lines had been assessed for ABA sensitivity as described in Example 6, increased ABA sensitivity ($ABA^S$) also correlated with a decreased water loss during drought treatment. Those lines determined to have wild type ABA sensitivity ($ABA^{WT}$) were the same 6 lines (lines 2, 36, 69, 29, 24, 21) that did not show a reduced water loss compared to wild type.

The above experiment was repeated using two $ABA^S$ lines, one $ABA^{WT}$ line and a Columbia control. Plants were harvested after 2, 4 and 6 days of water stress treatment for shoot dry weight determinations. $ABA^S$ transgenics had greater leaf and shoot biomass, greater soil water contents and lower water loss per shoot dry weight when compared to the $ABA^{WT}$ or Columbia controls. Results were consistent at all three harvest stages.

The data shown in this example was obtained using transgenic plants carrying the pRD29A-DA-FTA construct. The experiment has also been conducted on lines carrying variations of this construct such as 35S-DA-FTA, pRD29A-antisense-FTA or 35S-antisense-FTA, with similar water stress tolerant trends observed. Soil water loss is assessed in all transgenic plants engineered to have reduced or increased FTA or FTB expression or activity by the described methods.

Example 14

Figure 11:
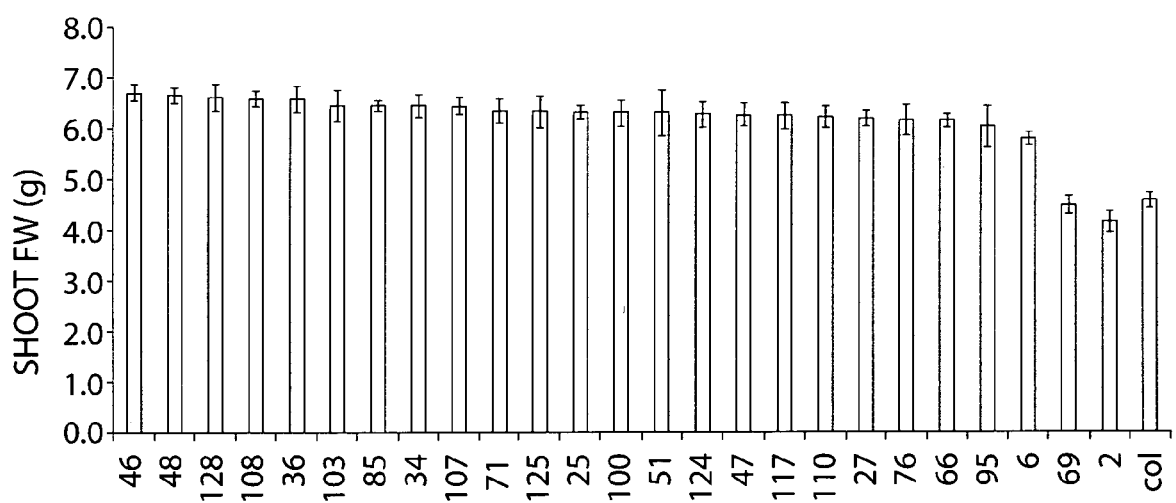
FIG. 11 is an illustration of shoot fresh weight, or biomass accumulation, after 6 days of water stress treatment and 6 days recovery time.

Analysis of Shoot Fresh Weight in *Arabidopsis thaliana* pRD29A-DA-FTA Lines During Drought Stress Plants were grown 5 plants per 4 inch pot and 8 pots per line. When the plants had grown to the first flower stage drought treatment was initiated as described in Example 12. Plants were re-watered after 6 days drought treatment and allowed to recover for an additional 6 days. Plants were harvested and shoot fresh weights determined. FIG. 11 shows the shoot fresh weights. This experiment consisted of 25 transgenic lines, 2 of which are $ABA^{WT}$ (line 2 and 69) and a Columbia wild type control. All 23 $ABA^S$ transgenic lines had statistically significant greater shoot fresh weights, on average 44% greater.

The data shown in this example was obtained using transgenic plants carrying the pRD29A-DA-FTA construct.

The experiment has been conducted on lines carrying variations of this construct such as 35S-DA-FTA, pRD29A-antisense-FTA or 35S-antisense-FTA, with similar trends observed.

Example 15

Analysis of Seed Yield in *Arabidopsis thaliana* pRD29A-DA-FTA Lines During Drought Stress and Under Optimal Conditions Plants were grown 1 plant per 4 inch pot. When the plants had grown to the first flower stage drought treatment was initiated as described in Example 12. Plants were re-watered after 6 days drought treatment and allowed to grow to maturity. The optimal group was not exposed to the drought treatment.

Figure 12:
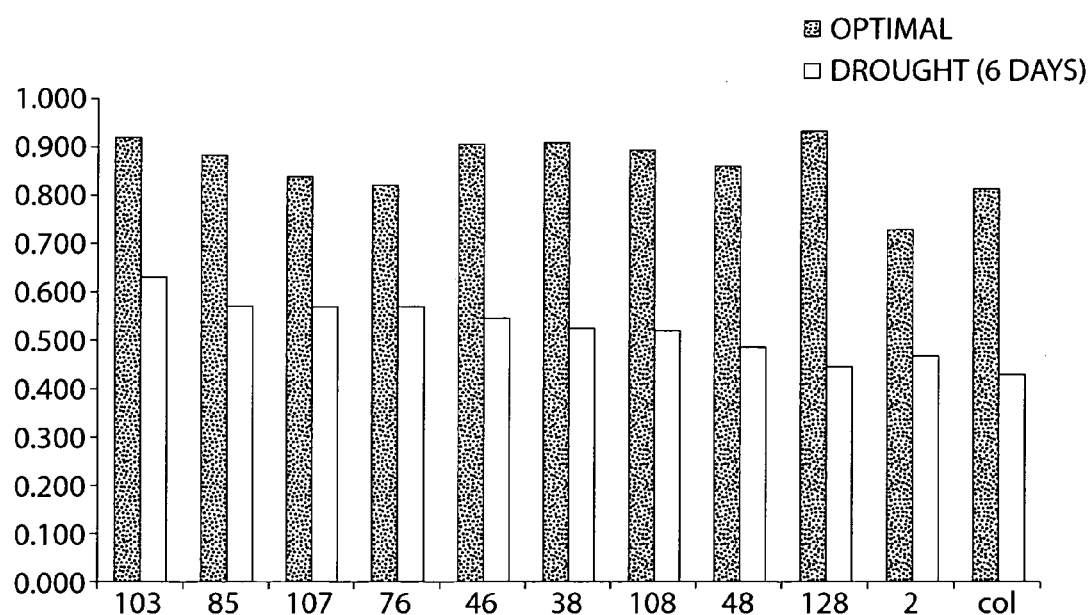
FIG. 12 is an illustration of seed yield (grams) obtained under optimal conditions or following a 6 day water stress treatment.

Yield analysis indicates that although drought treatment results in decreased yields, the transgenics do not suffer as severely as controls and maintain a productivity advantage (FIG. 12) as shown previously in Experiment 14. Comparison of the yields produced by the $ABA^S$ transgenics versus the control plants show that a 15% greater yield was obtained under optimal conditions and a 20% increase under drought conditions. In the drought treatment group 8 of 9 transgenic lines showed greater yield than controls. Expression of yield of each line obtained under drought treatment as a percentage of its performance under optimum conditions indicates that 8 of 9 $ABA^S$ lines outperformed the control line while 4 of 9 out performed the $ABA^{WT}$ controls.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 16

Figure 13:
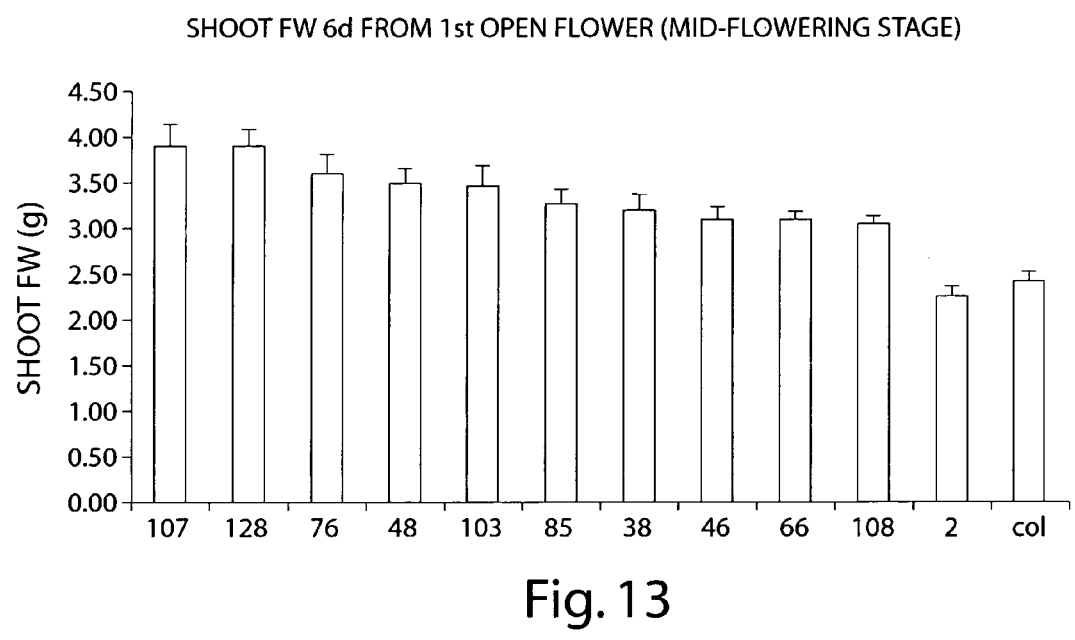
FIG. 13 is an illustration of vegitative growth under optimal conditions, shown is shoot fresh weight 6 days after the first flower opened.

Analysis of Vegetative Growth in *Arabidopsis thaliana* pRD29A-DA-FTA Lines Under Optimum Growth Conditions Plants were grown 1 plant per 3 inch pot and 8 pots per line. Plants were harvested at three stages and fresh weights determined. Vegetative stage was defined as 14 day old seedlings, bolting stage as the appearance of first flower (19–21 day seedlings) and mid-flowering as 6 days from first flower. At each of the above stages respectively 7, 8 and 10 of the 10 $ABA^S$ transgenic lines tested showed statistically greater shoot fresh weight biomass than the control plants (FIG. 13). One Columbia line and an $ABA^{WT}$ (line 2) line were used as the control group. Additionally, there was a statistically significant trend for the transgenic lines to have an increased number of rosette leaves.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 17

Figure 14:
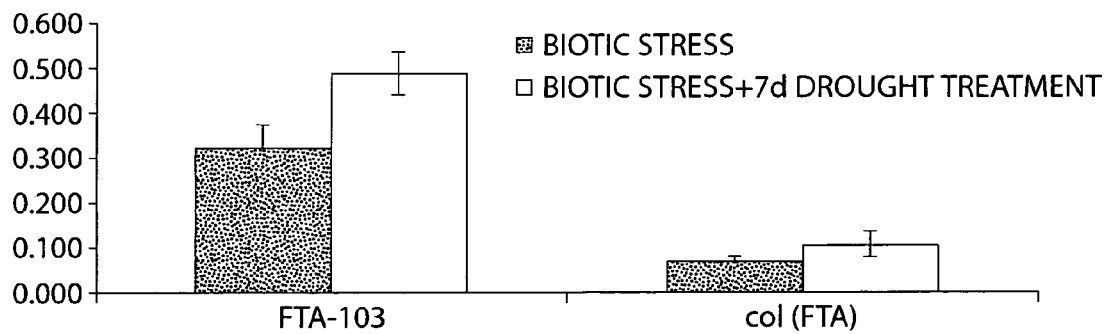
FIG. 14 is an illustration of the effect of a biotic stress coupled with drought stress treatment on seed yield.

Analysis of *Arabidopsis thaliana* pRD29A-DA-FTA Lines Under Drought Treatment and Biotic Stress Plants were grown 1 plant per 4 inch pot and 8 pots. When the plants had grown to the first flower stage drought treatment was initiated as described in Example 12. Plants were re-watered after 7 days drought treatment and allowed to grow to maturity. One Columbian control line (col) and one transgenic line were evaluated. Analysis of seed yield indicated less than normal yields, approximately 12% of expected optimal yield. It was determined that the soil used contained a fungal contaminant that was responsible for the reduced yields as the biotic stress could be negated by sterilization of the soil prior to use. This biotic stress was less severe in the transgenic line compared to the control which had a yield 22% of the transgenic line. In the drought treatment groups of plants the biotic stress was reduced however, transgenics outperformed controls by nearly 4.5 fold (FIG. 14).

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 18

Analysis of *Arabidopsis thaliana* pRD29A-DA-FTA Lines for Stomatal Number

The number of stomata on both the upper and lower surface of the leaf was assessed on two transgenic lines and a wild type Columbia control. Nail polish imprints were made of both upper and lower leaf surfaces of the fifth leaf, plants were at the early flowering stage. No differences in stoma density were observed.

The data shown in this example was obtained using transgenic plants carrying the pRD29A-DA-FTA construct. The experiment has been conducted on lines carrying variations of this construct such as 35S-DA-FTA, pRD29A-antisense-FTA or 35S-antisense-FTA, with similar trends observed.

Example 19

Production of Polyclonal Antibodies Against FT-A and FT-B

The isolated *Arabidopsis thaliana* FT sequences were cloned into the *E. coli* expression vector derived from pET11D. To generate the Histidine tagged FT-B construct the *Arabidopsis thaliana* FT-B clone and pET vector were digested with BamHI and ligated together. Restriction digests were performed to verify the orientation of the insert. To produce the FT-A construct the *Arabidopsis thaliana* FT-A clone and pET vector were digested with BamHI and EcoRI and subsequently ligated together. The resultant plasmids directed the expression of fusion proteins containing 6 consecutive histidine residues at the N-termini of AtFTA and AtFTB. The fusion proteins were expressed in the bacterial host BL21(DE3) and purified using Hi-Trap chelating chromatography as described by the manufacturer (Pharmacia). The soluble fraction of the crude bacterial extract containing the His-FT fusion proteins were loaded to a Hi-Trap column (1.5 cm×2.0 cm), and the proteins eluted with a 200 ml linear gradient of 0.0 to 0.3 M imidazole in column buffer (25 mM Tris-HCl, pH 7.5, 1 mM DTT). Fractions containing purified His-FT proteins were pooled, desalted and concentrated with a Centriprep-30 concentrator (Amicon). All purification steps were carried out at 4° C. To generate an antibody, the purified fusion protein was further separated by SDS/PAGE and the Coomassie stained band corresponding to the fusion protein was excised. Protein was eluted from the gel slice by electroelution and then emulsified in Ribi adjuvant (Ribi Immunochem) to a final volume of 1 ml. His-AtFTA or His-AtFTB (250 µg) were injected into a 3 kg New Zealand rabbit on day 1 and booster injections given on day 21 and day 35 with 200 µg of the protein. High-titer antisera were obtained one week after the final injection. These antibodies were used in the western analysis of example 10, FIG. 4.

Example 20

Screening for Related Genes

The transgenic plants of the invention can be used to identify genes which interact with the genes of the present invention. One can make use of the transgenic plants of the invention to screen for related genes, for example, suppressors, enhancers or modulators of gene expression or activity can be identified through genetic screening protocols. By way of example, a mutant library can be generated using the transgenic plants of the invention as the genetic background. Various methods are available and would be known to one of skill in the art. For example, chemical mutagens such as EMS can be used to induce point mutations in the genome, fast neutron irradiation of seeds can result in deletion mutations, T-DNA libraries can be produced that inactivate genes through insertional effects or activation tagging methods can be used to produce libraries with up-regulated genes. Analysis of these types of libraries can identify genes which rescue or modulate the phenotypes observed in the transgenic plants of the present invention.

What is claimed is:

1. An isolated nucleic acid molecule comprising the nucleic acid sequence of SEQ ID NO: 1.

2. An isolated nucleic acid molecule encoding a polypeptide comprising the amino acid sequence of SEQ ID NO: 5.

3. An isolated nucleic acid molecule comprising the nucleic acid sequence of SEQ ID NO: 2, or 3 wherein said nucleic acid inhibits farnesyl transferase expression or activity.

4. An isolated nucleic acid molecule comprising the nucleic acid sequence of SEQ ID NO: 4, SEQ ID NO:40, SEQ ID NO:41, SEQ ID NO:42, or SEQ ID NO:43.

5. A vector comprising the nucleic acid molecule of claim 1.

6. The vector of claim 5, further comprising a promoter operably linked to said nucleic acid molecule.

7. A cell comprising the vector of claim 6.

8. A vector comprising the nucleic acid molecule of claim 3.

9. The vector of claim 8, further comprising a promoter operably linked to said nucleic acid molecule.

10. A cell comprising the vector of claim 8.

* * * * *

SEQUENCE LISTING

<160> NUMBER OF SEQ ID NOS: 90

<210> SEQ ID NO 1
<211> LENGTH: 999
<212> TYPE: DNA
<213> ORGANISM: Arabidopsis thaliana

<400> SEQUENCE: 1

```
aaacccggga tgaatttcga cgagaccgtg ccactgagcc aacgattgga gtggtcagac        60
gtggtcccat tgactcagga cgatggtccg aatccagtgg tgccaattgc ctacaaggaa       120
gagttccgcg agactatgga ttacttccgt gcgatttact tttccgacga gcgatctcct       180
cgcgcactac gactcacgga agaaaccctc ctcttaaact ccggcaacta cacagtgtgg       240
catttcaggc gcctagtact cgaggccctt aatcacgact tgtttgaaga actcgagttc       300
atcgaacgca ttgctgagga taactctaag aactaccaac tgtggcatca tcggcgatgg       360
gttgcagaga aactgggtcc tgatgttgca gggagagaac ttgaatttac ccgtagagta       420 cttttcacttg atgccaaaca ttatcatgct tggtcacata ggcagtggac actacgggca       480
ttaggaggat gggaagatga gctcgattac tgtcacgagc tccttgaagc tgacgtcttt       540
aacaattccg cctggaatca gaggtattat gtcatcaccc aatctccttt gttgggaggc       600
ctagaagcca tgagagaatc tgaagtaagc tacacaatca aagccatttt aaccaatcct       660
gcaaacgaga gctcatggcg atacctaaaa gcgctttaca aagacgacaa agaatcctgg       720
attagtgatc caagtgtttc ctcagtctgt ttgaatgttc tatcccgcac agattgcttc       780
catggattcg ctctgagcac cctttttggat cttctatgtg atggactgag accaaccaac       840
gagcataaag actcagtgag agctctagct aatgaagaac cagagactaa cttggccaat       900
ttggtgtgta ctattcttgg tcgtgtagat cctataagag ctaactattg ggcatggagg       960
aagagcaaga ttacagtggc agcaatttga ggatccttt                              999
```

<210> SEQ ID NO 2
<211> LENGTH: 999
<212> TYPE: DNA

<213> ORGANISM: Artificial Sequence
<220> FEATURE:
<223> OTHER INFORMATION: Description of Artificial Sequence: Compliment to SEQID:1

<400> SEQUENCE: 2

```
aaaggatcct caaattgctg ccactgtaat cttgctcttc ctccatgccc aatagttagc      60
tcttatagga tctacacgac caagaatagt acacaccaaa ttggccaagt tagtctctgg     120
ttcttcatta gctagagctc tcactgagtc tttatgctcg ttggttggtc tcagtccatc     180
acatagaaga tccaaagggt gctcagagc gaatccatgg aagcaatctg tgcgggatag     240
aacattcaaa cagactgagg aaacacttgg atcactaatc caggattctt tgtcgtcttt     300
gtaaagcgct tttaggtatc gccatgagct ctcgtttgca ggattggtta aaatggcttt     360
gattgtgtag cttacttcag attctctcat ggcttctagg cctcccaaca aggagattg      420
ggtgatgaca taatacctct gattccaggc ggaattgtta aagacgtcag cttcaaggag     480
ctcgtgacag taatcgagct catcttccca tcctcctaat gcccgtagtg tccactgcct     540
atgtgaccaa gcatgataat gtttggcatc aagtgaaagt actctacggg taaattcaag     600
ttctctccct gcaacatcag gacccagttt ctctgcaacc catcgccgat gatgccacag     660
ttggtagttc ttagagttat cctcagcaat gcgttcgatg aactcgagtt cttcaaacaa     720
gtcgtgatta agggcctcga gtactaggcg cctgaaatgc cacactgtgt agttgccgga     780
gtttaagagg agggtttctt ccgtgagtcg tagtgcgcga ggagatcgct cgtcggaaaa     840
gtaaatcgca cggaagtaat ccatagtctc gcggaactct tccttgtagg caattggcac     900
cactggattc ggaccatcgt cctgagtcaa tgggaccacg tctgaccact ccaatcgttg     960
gctcagtggc acggtctcgt cgaaattcat cccgggttt                            999
```

<210> SEQ ID NO 3
<211> LENGTH: 989
<212> TYPE: DNA
<213> ORGANISM: Artificial Sequence
<220> FEATURE:
<223> OTHER INFORMATION: Description of Artificial Sequence: Sequence of SEQID NO:1 ligated

<400> SEQUENCE: 3

```
gatcctcaaa ttgctgccac tgtaatcttg ctcttcctcc atgcccaata gttagctctt      60
ataggatcta cacgaccaag aatagtacac accaaattgg ccaagttagt ctctggttct     120
tcattagcta gagctctcac tgagtctttca tgctcgttgg ttggtctcag tccatcacat     180
agaagatcca aagggtgct cagagcgaat ccatggaagc aatctgtgcg ggatagaaca     240
ttcaaacaga ctgaggaaac acttggatca ctaatccagg attctttgtc gtctttgtaa     300
agcgctttta ggtatcgcca tgagctctcg tttgcaggat tggttaaaat ggctttgatt     360
gtgtagctta cttcagattc tctcatggct tctaggcctc ccaacaaagg agattgggtg     420
atgacataat acctctgatt ccaggcggaa ttgttaaaga cgtcagcttc aaggagctcg     480
tgacagtaat cgagctcatc ttcccatcct cctaatgccc gtagtgtcca ctgcctatgt     540
gaccaagcat gataatgttt ggcatcaagt gaaagtactc tacgggtaaa ttcaagttct     600
ctccctgcaa catcaggacc cagtttctct gcaacccatc gccgatgatg ccacagttgg     660
tagttcttag agttatcctc agcaatgcgt tcgatgaact cgagttcttc aaacaagtcg     720
tgattaaggg cctcgagtac taggcgcctg aaatgccaca ctgtgtagtt gccggagttt     780
aagaggaggg tttcttccgt gagtcgtagt gcgcgaggag atcgctcgtc ggaaaagtaa     840
```

-continued

| | |
|---|---|
| atcgcacgga agtaatccat agtctcgcgg aactcttcct tgtaggcaat tggcaccact | 900 |
| ggattcggac catcgtcctg agtcaatggg accacgtctg accactccaa tcgttggctc | 960 |
| agtggcacgg tctcgtcgaa attcatccc | 989 |

<210> SEQ ID NO 4
<211> LENGTH: 5250
<212> TYPE: DNA
<213> ORGANISM: Artificial Sequence
<220> FEATURE:
<223> OTHER INFORMATION: Description of Artificial Sequence: Plasmid
    pBI121-35S-anti-AtFTA sequence

<400> SEQUENCE: 4

| | |
|---|---|
| gtttacccgc caatatatcc tgtcaaacac tgatagttta aactgaaggc gggaaacgac | 60 |
| aatctgatca tgagcggaga attaagggag tcacgttatg accccgccg atgacgcggg | 120 |
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt cccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttttgt caagaccgac | 540 |
| ctgtccggtg ccctgaatga actgcaggac gaggcagcgc ggctatcgtg gctggccacg | 600 |
| acgggcgttc cttgcgcagc tgtgctcgac gttgtcactg aagcgggaag ggactggctg | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |
| ggcggcgaat gggctgaccg cttcctcgtg ctttacggta tcgccgctcc cgattcgcag | 1140 |
| cgcatcgcct tctatcgcct tcttgacgag ttcttctgag cgggactctg gggttcgaaa | 1200 |
| tgaccgacca agcgacgccc aacctgccat cacgagattt cgattccacc gccgccttct | 1260 |
| atgaaaggtt gggcttcgga atcgttttcc gggacgccgg ctggatgatc ctccagcgcg | 1320 |
| gggatctcat gctggagttc ttcgcccacg ggatctctgc ggaacaggcg gtcgaaggtg | 1380 |
| ccgatatcat tacgacagca acggccgaca agcacaacgc cacgatcctg agcgacaata | 1440 |
| tgatcgggcc cggcgtccac atcaacggcg tcggcggcga ctgcccaggc aagaccgaga | 1500 |
| tgcaccgcga tatcttgctg cgttcggata ttttcgtgga gttcccgcca cagacccgga | 1560 |
| tgatccccga tcgttcaaac atttggcaat aaagtttctt aagattgaat cctgttgccg | 1620 |
| gtcttgcgat gattatcata taatttctgt tgaattacgt taagcatgta ataattaaca | 1680 |
| tgtaatgcat gacgttattt atgagatggg ttttttatgat tagagtcccg caattataca | 1740 |
| tttaatacgc gatagaaaac aaaatatagc gcgcaaacta ggataaatta tcgcgcgcgg | 1800 |
| tgtcatctat gttactagat cgggcctcct gtcaatgctg gcggcggctc tggtggtggt | 1860 |

```
tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata aggggctat gaccgaaaat gccgatgaaa acgcgctaca gtctgacgct     2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagcccaca    2520
gatggttaga gaggcttacg cagcaggtct catcaagacg atctacccga gcaataatct    2580
ccaggaaatc aaataccttc caagaaggt taaagatgca gtcaaaagat tcaggactaa     2640
ctgcatcaag aacacagaga aagatatatt tctcaagatc agaagtacta ttccagtatg    2700
gacgattcaa ggcttgcttc acaaaccaag gcaagtaata gagattggag tctctaaaaa    2760
ggtagttccc actgaatcaa aggccatgga gtcaaagatt caaatagagg acctaacaga    2820
actcgccgta aagactggcg aacagttcat acagagtctc ttacgactca atgacaagaa    2880
gaaaatcttc gtcaacatgg tggagcacga cacacttgtc tactccaaaa atatcaaaga    2940
tacagtctca gaagaccaaa gggcaattga acttttcaa caaagggtaa tatccggaaa     3000
cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggacccc acccacgagg agcatcgtgg aaaaagaaga     3180
cgttccaacc acgtcttcaa agcaagtgga ttgatgtgat atctccactg acgtaaggga    3240
tgacgcacaa tcccactatc cttcgcaaga cccttcctct atataaggaa gttcatttca    3300
tttggagaga acacggggga ctctagagga tcctcaaatt gctgccactg taatcttgct    3360
cttcctccat gcccaatagt tagctcttat aggatctaca cgaccaagaa tagtacacac    3420
caaattggcc aagttagtct ctggttcttc attagctaga gctctcactg agtctttatg    3480
ctcgttggtt ggtctcagtc catcacatag aagatccaaa agggtgctca gagcgaatcc    3540
atggaagcaa tctgtgcggg atagaacatt caaacagact gaggaaacac ttggatcact    3600
aatccaggat tcttttgtcgt ctttgtaaag cgcttttagg tatcgccatg agctctcgtt    3660
tgcaggattg gttaaaatgg ctttgattgt gtagcttact tcagattctc tcatggcttc    3720
taggcctccc aacaaaggag attgggtgat gacataatac ctctgattcc aggcggaatt    3780
gttaaagacg tcagcttcaa ggagctcgtg acagtaatcg agctcatctt cccatcctcc    3840
taatgcccgt agtgtccact gcctatgtga ccaagcatga taatgtttgg catcaagtga    3900
aagtactcta cgggtaaatt caagttctct ccctgcaaca tcaggaccca gtttctctgc    3960
aacccatcgc cgatgatgcc acagttggta gttcttagag ttatcctcag caatgcgttc    4020
gatgaactcg agttcttcaa acaagtcgtg attaagggcc tcgagtacta ggcgcctgaa    4080
atgccacact gtgtagttgc cggagtttaa gaggagggtt tcttccgtga gtcgtagtgc    4140
gcgaggagat cgctcgtcgg aaaagtaaat cgcacggaag taatccatag tctcgcggaa    4200
```

```
ctcttccttg taggcaattg gcaccactgg attcggacca tcgtcctgag tcaatgggac      4260
cacgtctgac cactccaatc gttggctcag tggcacggtc tcgtcgaaat tcatcccctc      4320
gaatttcccc gatcgttcaa acatttggca ataaagtttc ttaagattga atcctgttgc      4380
cggtcttgcg atgattatca tataatttct gttgaattac gttaagcatg taataattaa      4440
catgtaatgc atgacgttat ttatgagatg ggtttttatg attagagtcc cgcaattata      4500
catttaatac gcgatagaaa acaaaatata gcgcgcaaac taggataaat tatcgcgcgc      4560
ggtgtcatct atgttactag atcgggaatt cactggccgt cgttttacaa cgtcgtgact      4620
gggaaaaccc tggcgttacc caacttaatc gccttgcagc acatcccct ttcgccagct       4680 ggcgtaatag cgaagaggcc cgcaccgatc gcccttccca acagttgcgc agcctgaatg      4740
gcgcccgctc ctttcgcttt cttcccttcc tttctcgcca cgttcgccgg ctttccccgt      4800
caagctctaa atcgggggct ccctttaggg ttccgattta gtgctttacg cacctcgac       4860 cccaaaaaac ttgatttggg tgatggttca cgtagtgggc catcgccctg atagacggtt      4920
tttcgccctt tgacgttgga gtccacgttc tttaatagtg gactcttgtt ccaaactgga      4980
acaacactca accctatctc gggctattct tttgatttat aagggatttt gccgatttcg      5040
gaaccaccat caaacaggat tttcgcctgc tggggcaaac cagcgtggac cgcttgctgc      5100
aactctctca gggccaggcg gtgaagggca atcagctgtt gcccgtctca ctggtgaaaa      5160
gaaaaaccac cccagtacat aaaaacgtc cgcaatgtgt tattaagttg tctaagcgtc       5220
aatttgttta caccacaata tatcctgcca                                       5250
```

<210> SEQ ID NO 5
<211> LENGTH: 326
<212> TYPE: PRT
<213> ORGANISM: Arabidopsis thaliana

<400> SEQUENCE: 5

```
Met Asn Phe Asp Glu Thr Val Pro Leu Ser Gln Arg Leu Glu Trp Ser
 1               5                  10                  15

Asp Val Val Pro Leu Thr Gln Asp Asp Gly Pro Asn Pro Val Val Pro
             20                  25                  30

Ile Ala Tyr Lys Glu Glu Phe Arg Glu Thr Met Asp Tyr Phe Arg Ala
         35                  40                  45

Ile Tyr Phe Ser Asp Glu Arg Ser Pro Arg Ala Leu Arg Leu Thr Glu
     50                  55                  60

Glu Thr Leu Leu Leu Asn Ser Gly Asn Tyr Thr Val Trp His Phe Arg
 65                  70                  75                  80

Arg Leu Val Leu Glu Ala Leu Asn His Asp Leu Phe Glu Glu Leu Glu
                 85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Arg Glu Leu Glu Phe Thr Arg Arg Val Leu Ser Leu Asp Ala Lys His
    130                 135                 140

Tyr His Ala Trp Ser His Arg Gln Trp Thr Leu Arg Ala Leu Gly Gly
145                 150                 155                 160

Trp Glu Asp Glu Leu Asp Tyr Cys His Glu Leu Leu Glu Ala Asp Val
                165                 170                 175

Phe Asn Asn Ser Ala Trp Asn Gln Arg Tyr Tyr Val Ile Thr Gln Ser
            180                 185                 190
```

Pro Leu Leu Gly Gly Leu Glu Ala Met Arg Glu Ser Glu Val Ser Tyr
            195                 200                 205

Thr Ile Lys Ala Ile Leu Thr Asn Pro Ala Asn Glu Ser Ser Trp Arg
        210                 215                 220

Tyr Leu Lys Ala Leu Tyr Lys Asp Asp Lys Glu Ser Trp Ile Ser Asp
225                 230                 235                 240

Pro Ser Val Ser Val Cys Leu Asn Val Leu Ser Arg Thr Asp Cys
            245                 250                 255

Phe His Gly Phe Ala Leu Ser Thr Leu Leu Asp Leu Leu Cys Asp Gly
            260                 265                 270

Leu Arg Pro Thr Asn Glu His Lys Asp Ser Val Arg Ala Leu Ala Asn
        275                 280                 285

Glu Glu Pro Glu Thr Asn Leu Ala Asn Leu Val Cys Thr Ile Leu Gly
290                 295                 300

Arg Val Asp Pro Ile Arg Ala Asn Tyr Trp Ala Trp Arg Lys Ser Lys
305                 310                 315                 320

Ile Thr Val Ala Ala Ile
            325

<210> SEQ ID NO 6
<211> LENGTH: 822
<212> TYPE: DNA
<213> ORGANISM: Brassica napus

<400> SEQUENCE: 6
atggattact tccgtgcgat ttacttctcc gacgagcgtt ctgctcgcgc gctgcgactc     60
acggaagaag ctctccgctt aaactcgggc aactacaccg tgtggcactt cgggcgctta    120
gtactcgagg agcttaataa cgacttgtat gaagagctca agttcatcga aagcattgct    180
gaggataact ctaagaacta ccagttgtgg catcatcgac gatgggtcgc agagaaactg    240
ggtcctgatg ttgcaggaaa ggaacttgag tttactcgga gggtactatc acttgatgcc    300
aagcattatc atgcttggtc acataggcag tgggcgctac aagcattagg aggatgggaa    360
aatgagctta actactgcca cgagctcctt gaagctgacg tctttaacaa ctctgcatgg    420
aatcagaggt attacgttat aactagatca ccttcgttgg gaggcctaga agccatgaga    480
gaatctgaag taagctacac agtcaaagcc attttagcaa atcccgggaa cgagagctct    540
tggaggtacc tgaaagccct ttacaaagac gacacagagt cttggattag tgatccaagt    600
gtttcctcag tctgtttgaa agttctctca cgcgcggact gcttccatgg attcgctctg    660
agcacccttt tggatcttct gtgcgatggg ttgagaccaa ccaacgagca tagagactcg    720
gtgaaagctc tagctaatga agaaccagag actaacttgg ccaatttggt tgtgtaccatt    780 ctgtgtcgtg ttgatccaat aagagctaac tattgggcat gg                       822

<210> SEQ ID NO 7
<211> LENGTH: 276
<212> TYPE: PRT
<213> ORGANISM: Brassica napus

<400> SEQUENCE: 7

Met Asp Tyr Phe Arg Ala Ile Tyr Phe Ser Asp Glu Arg Ser Ala Arg
1               5                  10                  15

Ala Leu Arg Leu Thr Glu Glu Ala Leu Arg Leu Asn Ser Gly Asn Tyr
            20                  25                  30

Thr Val Trp His Phe Gly Arg Leu Val Leu Glu Glu Leu Asn Asn Asp

```
                    35                  40                  45
Leu Tyr Glu Glu Leu Lys Phe Ile Glu Ser Ile Ala Glu Asp Asn Ser
     50                  55                  60

Lys Asn Tyr Gln Leu Trp His His Arg Arg Trp Val Ala Glu Lys Leu
 65                  70                  75                  80

Gly Pro Asp Val Ala Gly Leu Glu Lys Glu Phe Thr Arg Arg Val Leu
                 85                  90                  95

Ser Leu Asp Ala Lys His Tyr His Ala Trp Ser His Arg Gln Trp Ala
                100                 105                 110

Leu Gln Ala Leu Gly Gly Trp Glu Asn Glu Leu Asn Tyr Cys His Glu
            115                 120                 125

Leu Leu Glu Ala Asp Val Phe Asn Asn Ser Ala Trp Asn Gln Arg Tyr
        130                 135                 140

Tyr Val Ile Thr Arg Ser Pro Ser Leu Gly Gly Leu Glu Ala Met Arg
145                 150                 155                 160

Glu Ser Glu Val Ser Tyr Thr Val Lys Ala Ile Leu Ala Asn Pro Gly
                165                 170                 175

Asn Glu Ser Ser Trp Arg Tyr Leu Lys Ala Leu Tyr Lys Asp Asp Thr
            180                 185                 190

Glu Ser Trp Ile Ser Asp Pro Ser Val Ser Ser Val Cys Leu Lys Val
        195                 200                 205

Leu Ser Arg Ala Asp Cys Phe His Gly Phe Ala Leu Ser Thr Leu Leu
    210                 215                 220

Asp Leu Leu Cys Asp Gly Leu Arg Pro Thr Asn Glu His Arg Asp Ser
225                 230                 235                 240

Val Lys Ala Leu Ala Asn Glu Glu Pro Glu Thr Asn Leu Ala Asn Leu
                245                 250                 255

Val Cys Thr Ile Leu Cys Arg Val Asp Pro Ile Arg Ala Asn Tyr Trp
            260                 265                 270

Ala Trp Lys Leu
        275

<210> SEQ ID NO 8
<211> LENGTH: 1110
<212> TYPE: DNA
<213> ORGANISM: Brassica napus

<400> SEQUENCE: 8
tggctttgtt actggattct tcattcaatt gctttgcttg gggagtctgt ggatgatgac      60
ttagaaaaca atgcaatcga ttttcttgga cgttgccagg gttctgatgg tggatatggt     120
ggtggtcctg gccaacttcc acatcttgca acaagttatg ctgcagtgaa tacacttgtt     180
actttaggag gtgagaaagc cttctcttca attaacagag aacaaatggc ttgtttctta     240
agacgaatga aggatacaaa tggaggtttc aggatgcata atatgggaga atagatgtg      300 cgagcgtgct acactgcgat tttgattgca agcatcctga acattgtgga tgatgaactc     360
acccgcggct taggagatta catttttgagt tgccaaactt atgaaggtgg cattggaggg    420
gaacctggct ccgaagctca tggtgggtac acgtactgtg ggttggctac tatgatttta    480
atcaatgaag tcgaccgctt gaatttggat tcgttaatga attgggttgt acatcgacaa     540
ggagtagaaa tggattccca aggtaggacg aacaaattgg tcgacggttg ctacacgttt     600
tggcaggcag ccccctgtgt tctactacag cgatttttttt catcccagga tatggcacct    660
catggatcat catcacatat gtcacaaggg acagatgaag atcacgagga acatggtcat    720
```

|  |  |  |  |  |
|---|---|---|---|---|
| gatgaagatg | atcctgaaga | cagtgatgaa | gatgattctg | atgaggatag cgatgaagat | 780 |
| tcagggaatg | gtcaccaagt | tcatcatacg | tctacctaca | ttgacaggag aattcaacct | 840 |
| gtttttgata | gcctcggctt | gcaaagatat | gtgctcttgt | gctctcaggt tgctgatggt | 900 |
| ggattcagag | acaagctgag | gaaacccgt | gacttctacc | acacatgtta ctgcctaagc | 960 |
| ggtctttccg | tggctcaaca | cgcttggtca | aagacgagg | acactcctcc tttgactcgt | 1020 |
| gacattttgg | gtggctacgc | aaaccacctt | gaacctgttc | acctcctcca caacattgtc | 1080 |
| ttggatcggt | attatgaagc | ttctagattt |  |  | 1110 |

<210> SEQ ID NO 9
<211> LENGTH: 370
<212> TYPE: PRT
<213> ORGANISM: Brassica napus

<400> SEQUENCE: 9

Trp Leu Cys Tyr Trp Ile Leu His Ser Ile Ala Leu Leu Gly Glu Ser
  1               5                  10                  15

Val Asp Asp Leu Glu Asn Asn Ala Ile Asp Phe Leu Gly Arg Cys
             20                  25                  30

Gln Gly Ser Asp Gly Gly Tyr Gly Gly Pro Gly Gln Leu Pro His
         35                  40                  45

Leu Ala Thr Ser Tyr Ala Ala Val Asn Thr Leu Val Thr Leu Gly Gly
     50                  55                  60

Glu Lys Ala Phe Ser Ser Ile Asn Arg Glu Gln Met Ala Cys Phe Leu
 65                  70                  75                  80

Arg Arg Met Lys Asp Thr Asn Gly Gly Phe Arg Met His Asn Met Gly
                 85                  90                  95

Glu Ile Asp Val Arg Ala Cys Tyr Thr Ala Ile Leu Ile Ala Ser Ile
            100                 105                 110

Leu Asn Ile Val Asp Asp Glu Leu Thr Arg Gly Leu Gly Asp Tyr Ile
        115                 120                 125

Leu Ser Cys Gln Thr Tyr Glu Gly Gly Ile Gly Gly Glu Pro Gly Ser
    130                 135                 140

Glu Ala His Gly Gly Tyr Thr Tyr Cys Gly Leu Ala Thr Met Ile Leu
145                 150                 155                 160

Ile Asn Glu Val Asp Arg Leu Asn Leu Asp Ser Leu Met Asn Trp Val
                165                 170                 175

Val His Arg Gln Gly Val Glu Met Gly Phe Gln Gly Arg Thr Asn Lys
            180                 185                 190

Leu Val Asp Gly Cys Tyr Thr Phe Trp Gln Ala Ala Pro Cys Val Leu
        195                 200                 205

Leu Gln Arg Phe Phe Ser Ser Gln Asp Met Ala Pro His Gly Ser Ser
    210                 215                 220

Ser His Met Ser Gln Gly Thr Asp Glu Asp His Glu Glu His Gly His
225                 230                 235                 240

Asp Glu Asp Asp Pro Glu Asp Ser Asp Glu Asp Ser Asp Glu Asp
                245                 250                 255

Ser Asp Glu Asp Ser Gly Asn Gly His Gln Val His His Thr Ser Thr
            260                 265                 270

Tyr Ile Asp Arg Arg Ile Gln Pro Val Phe Asp Ser Leu Gly Leu Gln
        275                 280                 285

Arg Tyr Val Leu Leu Cys Ser Gln Val Ala Asp Gly Gly Phe Arg Asp
    290                 295                 300

```
Lys Leu Arg Lys Pro Arg Asp Phe Tyr His Thr Cys Tyr Cys Leu Ser
305                 310                 315                 320

Gly Leu Ser Val Ala Gln His Ala Trp Ser Lys Asp Glu Asp Thr Pro
                325                 330                 335

Pro Leu Thr Arg Asp Ile Leu Gly Gly Tyr Ala Asn His Leu Glu Pro
            340                 345                 350

Val His Leu Leu His Asn Ile Leu Val Asp Arg Tyr Tyr Glu Ala Ser
        355                 360                 365

Arg Phe
    370

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: PCR Primer

<400> SEQUENCE: 10
gccgacagtg gtcccaaaga tgg                                          23

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 11
aaaggatcct caaattgctg ccactgtaat                                   30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 12
aaacccggga tgaatttcga cgagaacgtg                                   30

<210> SEQ ID NO 13
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 13
gcaagaccgg caacagga                                                18

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 14
tttaagcttg acagaaacag tcagcgagac                                   30

<210> SEQ ID NO 15
<211> LENGTH: 18
<212> TYPE: DNA
```

```
<213> ORGANISM: Artificial Sequence
<220> FEATURE:
<223> OTHER INFORMATION: Description of Artificial Sequence: PCR Primer

<400> SEQUENCE: 15
gctcttcctc catgccca                                                     18

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: PCR Primer

<400> SEQUENCE: 16
tttaagcttg gagccataga tgcaattcaa                                        30

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: PCR Primer

<400> SEQUENCE: 17
cgggcattag gaggatggga a                                                 21

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 18
gtccggaatt cccgggtc                                                     18

<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: PCR Primer

<400> SEQUENCE: 19
ggatccatgg attacttccg tgcgatttac ttctcc                                 36

<210> SEQ ID NO 20
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 20
aaaaagcttc catgcccaat agttagctct tattggatc                              39

<210> SEQ ID NO 21
<211> LENGTH: 38
<212> TYPE: DNA
<213> ORGANISM: Artificial Sequence
<220> FEATURE:
<223> OTHER INFORMATION: Description of Artificial Sequence: PCR Primer

<400> SEQUENCE: 21
aaaaagcttt ggctttgtta ctggattctt cattcaat                               38
```

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: PCR Primer

<400> SEQUENCE: 22
aaatctagaa gcttcataat accgatccaa gacaatgtt                    39

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 23
aaaggatcca tggaatctgg gtctagcga                               29

<210> SEQ ID NO 24
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 24
aaatctagaa ggaagtctgc tcttgcgc                                28

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence: PCR Primer

<400> SEQUENCE: 25
aaatctagag ccaccattcc tcgcaacg                                28

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence: PCR Primer

<400> SEQUENCE: 26
aaagagctcg tggtggagaa tctgggtgc                               29

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: PCR Primer

<400> SEQUENCE: 27
ggcggatccc gacctaccga gg                                      22

<210> SEQ ID NO 28
<211> LENGTH: 29
<212> TYPE: DNA
<213> ORGANISM: Artificial Sequence
<220> FEATURE:

<223> OTHER INFORMATION: Description of Artificial Sequence: PCR Primer

<400> SEQUENCE: 28
aaagagctcg tggatggatt ggctccagc    29

<210> SEQ ID NO 29
<211> LENGTH: 822
<212> TYPE: DNA
<213> ORGANISM: Artificial Sequence
<220> FEATURE:
<223> OTHER INFORMATION: Description of Artificial Sequence: Compliment
      of SEQ ID NO: 6

<400> SEQUENCE: 29

```
ccatgcccaa tagttagctc ttattggatc aacacgacac agaatggtac acaccaaatt      60
ggccaagtta gtctctggtt cttcattagc tagagctttc accgagtctc tatgctcgtt     120
ggttggtctc aacccatcgc acagaagatc aaaagggtg ctcagagcga atccatggaa      180
gcagtccgcg cgtgagagaa ctttcaaaca gactgaggaa acacttggat cactaatcca     240
agactctgtg tcgtctttgt aaagggcttt caggtacctc caagagctct cgttcccggg     300
atttgctaaa atggctttga ctgtgtagct tacttcagat tctctcatgg cttctaggcc     360
tcccaacgaa ggtgatctag ttataacgta atacctctga ttccatgcag agttgttaaa     420
gacgtcagct tcaaggagct cgtggcagta gttaagctca ttttcccatc ctcctaatgc     480
ttgtagcgcc cactgcctat gtgaccaagc atgataatgc ttggcatcaa gtgatagtac     540
cctccgagta aactcaagtt cctttcctgc aacatcagga cccagtttct ctgcgaccca     600
tcgtcgatga tgccacaact ggtagttctt agagttatcc tcagcaatgc tttcgatgaa     660
cttgagctct tcatacaagt cgttattaag ctcctcgagt actaagcgcc cgaagtgcca     720
cacggtgtag ttgcccgagt ttaagcggag agcttcttcc gtgagtcgca gcgcgcgagc     780
agaacgctcg tcggagaagt aaatcgcacg gaagtaatcc at                         822
```

<210> SEQ ID NO 30
<211> LENGTH: 1110
<212> TYPE: DNA
<213> ORGANISM: Artificial Sequence
<220> FEATURE:
<223> OTHER INFORMATION: Description of Artificial Sequence: Compliment
      to Seq Id No:8

<400> SEQUENCE: 30

```
aaatctagaa gcttcataat accgatccaa gacaatgttg tggaggaggt gaacaggttc      60
aaggtggttt gcgtagccac ccaaaatgtc acgagtcaaa ggaggagtgt cctcgtcttt     120
tgaccaagcg tgttgagcca cggaaagacc gcttaggcag taacatgtgt ggtagaagtc     180
acggggtttc ctcagcttgt ctctgaatcc accatcagca acctgagagc acaagagcac     240
atatctttgc aagccgaggc tatcaaaaac aggttgaatt ctcctgtcaa tgtaggtaga     300
cgtatgatga acttggtgac cattccctga atcttcatcg ctatcctcat cagaatcatc     360
ttcatcactg tcttcaggat catcttcatc atgaccatgt tcctcgtgat cttcatctgt     420
cccttgtgac atatgtgatg atgatccatg aggtgccata tcctgggatg aaaaaaatcg     480
ctgtagtaga acacaggggg ctgcctgcca aaacgtgtag caaccgtcga ccaatttgtt     540
cgtcctacct tggaatccca tttctactcc ttgtcgatgt acaacccaat tcattaacga     600
atccaaattc aagcggtcga cttcattgat taaaatcata gtagccaacc cacagtacgt     660
gtacccacca tgagcttcgg agccaggttc ccctccaatg ccaccttcat aagtttggca     720
```

-continued

```
actcaaaatg taatctccta agccgcgggt gagttcatca tccacaatgt tcaggatgct      780
tgcaatcaaa atcgcagtgt agcacgctcg cacatctatt tctcccatat tatgcatcct      840
gaaacctcca tttgtatcct tcattcgtct taagaaacaa gccatttgtt ctctgttaat      900
tgaagagaag gctttctcac ctcctaaagt aacaagtgta ttcactgcag cataacttgt      960
tgcaagatgt ggaagttggc caggaccacc accatatcca ccatcagaac cctggcaacg     1020
tccaagaaaa tcgattgcat tgtttctaa gtcatcatcc acagactccc caagcaaagc      1080
aattgaatga agaatccagt aacaaagcca                                       1110
```

<210> SEQ ID NO 31
<211> LENGTH: 1041
<212> TYPE: DNA
<213> ORGANISM: Glycine max
<220> FEATURE:
<221> NAME/KEY: misc_feature
<222> LOCATION: (360)...(360)
<223> OTHER INFORMATION: Wherein "n" is A, T, C or G

<400> SEQUENCE: 31

```
atggaatctg ggtctagcga aggagaagag gtgcagcaac gcgtgccgtt gagggagaga       60
gtggagtggt cagatgttac tccggttcct caaaacgacg gccctaaccc tgtcgttccg      120
atccagtaca ctgaagagtt ttccgaagtt atggattact ttcgcgccgt ttacctcacc      180
gatgaacgct cccctcgcgc cctcgctctc acagccgaag ccgttcaatt caactccggc      240
aactacactg tgtggcattt ccgacggttg ttacttgagt cgctaaaagt cgacttgaac      300
gatgaactgg agtttgtgga gcgtatggcc gctggaaatt ctaaaaatta tcagatgtgn      360
atgttctgta ggcatcctag acgatgggtt gccgagaagt taggtcctga agctagaaac      420
aatgagctcg agttcaccaa aaagatactg tccgttgatg ccaaacatta tcatgcatgg      480
tctcatagac agtgggctct tcaaacacta ggaggatggg aagatgaact taattattgc      540
acagaactac ttaaagaaga cattttttaac aattctgctt ggaatcagag atattttgtc      600
ataacaaggt ctcctttctt gggggggccta aaagctatga gagagtctga agtgctttac      660
accatcgaag ccattatagc ctaccctgaa atgaaagct cgtggagata tctacgagga       720
ctttataaag gtgaaactac ttcatgggta atgatcctc aagtttcttc agtatgctta      780
aagattttga gaactaagag caactacgtg tttgctctta gcactatttt agatcttata      840
tgctttggtt atcaaccaaa tgaagacatt agagatgcca ttgacgcctt aaagaccgca      900
gatatggata acaagatttt agatgatgat gagaaagggg aacaacaaaa tttaaatata      960
gcacgaaata tttgttctat cctaaaacaa gttgatccaa ttagaaccaa ctattggatt     1020
tggcgcaaga gcagacttcc t                                                1041
```

<210> SEQ ID NO 32
<211> LENGTH: 1041
<212> TYPE: DNA
<213> ORGANISM: Artificial Sequence
<220> FEATURE:
<223> OTHER INFORMATION: Description of Artificial Sequence: Compliment to Seq Id No: 31
<220> FEATURE:
<221> NAME/KEY: misc_feature
<222> LOCATION: (682)..(682)
<223> OTHER INFORMATION: Wherein "n" is A, T, C or G

<400> SEQUENCE: 32

```
aggaagtctg ctcttgcgcc aaatccaata gttggttcta attggatcaa cttgttttag       60
```

-continued

```
gatagaacaa atatttcgtg ctatatttaa attttgttgt tcccctttct catcatcatc      120
taaatcttgt ttatccatat ctgcggtctt taaggcgtca atggcatctc taatgtcttc      180
atttggttga taaccaaagc atataagatc taaaatagtg ctaagagcaa acacgtagtt      240
gctcttagtt ctcaaaatct ttaagcatac tgaagaaact tgaggatcat ttacccatga      300
agtagtttca cctttataaa gtcctcgtag atatctccac gagctttcat tttcagggta      360
ggctataatg gcttcgatgg tgtaaagcac ttcagactct ctcatagctt ttaggccccc      420
caagaaagga gaccttgtta tgacaaaata tctctgattc caagcagaat tgttaaaaat      480
gtcttcttta agtagttctg tgcaataatt aagttcatct tcccatcctc ctagtgtttg      540
aagagcccac tgtctatgag accatgcatg ataatgtttg gcatcaacgg acagtatctt      600
tttggtgaac tcgagctcat tgtttctagc ttcaggacct aacttctcgg caacccatcg      660
tctaggatgc ctacagaaca tncacatctg ataatttta gaatttccag cggccatacg      720
ctccacaaac tccagttcat cgttcaagtc gactttagc gactcaagta acaaccgtcg      780
gaaatgccac acagtgtagt tgccggagtt gaattgaacg gcttcggctg tgagagcgag      840
ggcgcgaggg gagcgttcat cggtgaggta acggcgcga aagtaatcca taacttcgga      900
aaactcttca gtgtactgga tcggaacgac agggttaggg ccgtcgtttt gaggaaccgg      960
agtaacatct gaccactcca ctctctccct caacggcacg cgttgctgca cctcttctcc     1020
ttcgctagac ccagattcca t                                              1041
```

<210> SEQ ID NO 33
<211> LENGTH: 347
<212> TYPE: PRT
<213> ORGANISM: Glycine max
<220> FEATURE:
<221> NAME/KEY: VARIANT
<222> LOCATION: (120)...(120)
<223> OTHER INFORMATION: Wherein "Xaa" is any amino acid

<400> SEQUENCE: 33

```
Met Glu Ser Gly Ser Ser Glu Gly Glu Glu Val Gln Gln Arg Val Pro
  1               5                  10                  15

Leu Arg Glu Arg Val Glu Trp Ser Asp Val Thr Pro Val Pro Gln Asn
             20                  25                  30

Asp Gly Pro Asn Pro Val Val Pro Ile Gln Tyr Thr Glu Glu Phe Ser
         35                  40                  45

Glu Val Met Asp Tyr Phe Arg Ala Val Tyr Leu Thr Asp Glu Arg Ser
     50                  55                  60

Pro Arg Ala Leu Ala Leu Thr Ala Glu Ala Val Gln Phe Asn Ser Gly
 65                  70                  75                  80

Asn Tyr Thr Val Trp His Phe Arg Arg Leu Leu Leu Glu Ser Leu Lys
                 85                  90                  95

Val Asp Leu Asn Asp Glu Leu Glu Phe Val Glu Arg Met Ala Ala Gly
            100                 105                 110

Asn Ser Lys Asn Tyr Gln Met Xaa Met Phe Cys Arg His Pro Arg Arg
        115                 120                 125

Trp Val Ala Glu Lys Leu Gly Pro Glu Ala Arg Asn Asn Glu Leu Glu
    130                 135                 140

Phe Thr Lys Lys Ile Leu Ser Val Asp Ala Lys His Tyr His Ala Trp
145                 150                 155                 160

Ser His Arg Gln Trp Ala Leu Gln Thr Leu Gly Gly Trp Glu Asp Glu
                165                 170                 175
```

| | | | | | | | | | | | |
|---|---|---|---|---|---|---|---|---|---|---|---|
|Leu|Asn|Tyr|Cys|Thr|Glu|Leu|Leu|Lys|Glu|Asp|Ile|Phe|Asn|Asn|Ser|
| | |180| | | | |185| | | | |190| | | |

| | | | | | | | | | | | | | | | |
|---|---|---|---|---|---|---|---|---|---|---|---|---|---|---|---|
|Ala|Trp|Asn|Gln|Arg|Tyr|Phe|Val|Ile|Thr|Arg|Ser|Pro|Phe|Leu|Gly|
| | |195| | | | |200| | | | |205| | | |

| | | | | | | | | | | | | | | | |
|---|---|---|---|---|---|---|---|---|---|---|---|---|---|---|---|
|Gly|Leu|Lys|Ala|Met|Arg|Glu|Ser|Glu|Val|Leu|Tyr|Thr|Ile|Glu|Ala|
| | |210| | | | |215| | | | |220| | | |

| | | | | | | | | | | | | | | | |
|---|---|---|---|---|---|---|---|---|---|---|---|---|---|---|---|
|Ile|Ile|Ala|Tyr|Pro|Glu|Asn|Glu|Ser|Ser|Trp|Arg|Tyr|Leu|Arg|Gly|
|225| | | |230| | | |235| | | |240| | | |

| | | | | | | | | | | | | | | | |
|---|---|---|---|---|---|---|---|---|---|---|---|---|---|---|---|
|Leu|Tyr|Lys|Gly|Glu|Thr|Thr|Ser|Trp|Val|Asn|Asp|Pro|Gln|Val|Ser|
| | | |245| | | | |250| | | | |255| | |

| | | | | | | | | | | | | | | | |
|---|---|---|---|---|---|---|---|---|---|---|---|---|---|---|---|
|Ser|Val|Cys|Leu|Lys|Ile|Leu|Arg|Thr|Lys|Ser|Asn|Tyr|Val|Phe|Ala|
| | | |260| | | | |265| | | | |270| | |

| | | | | | | | | | | | | | | | |
|---|---|---|---|---|---|---|---|---|---|---|---|---|---|---|---|
|Leu|Ser|Thr|Ile|Leu|Asp|Leu|Ile|Cys|Phe|Gly|Tyr|Gln|Pro|Asn|Glu|
| | | |275| | | | |280| | | | |285| | |

| | | | | | | | | | | | | | | | |
|---|---|---|---|---|---|---|---|---|---|---|---|---|---|---|---|
|Asp|Ile|Arg|Asp|Ala|Ile|Asp|Ala|Leu|Lys|Thr|Ala|Asp|Met|Asp|Lys|
| | | |290| | | | |295| | | | |300| | |

| | | | | | | | | | | | | | | | |
|---|---|---|---|---|---|---|---|---|---|---|---|---|---|---|---|
|Gln|Asp|Leu|Asp|Asp|Glu|Lys|Gly|Glu|Gln|Gln|Asn|Leu|Asn|Ile|
|305| | | |310| | | |315| | | |320| | | |

| | | | | | | | | | | | | | | | |
|---|---|---|---|---|---|---|---|---|---|---|---|---|---|---|---|
|Ala|Arg|Asn|Ile|Cys|Ser|Ile|Leu|Lys|Gln|Val|Asp|Pro|Ile|Arg|Thr|
| | | |325| | | | |330| | | | |335| | |

| | | | | | | | |
|---|---|---|---|---|---|---|---|
|Asn|Tyr|Trp|Ile|Trp|Arg|Lys|Ser|Arg|Leu|Pro|
| | | |340| | | | |345| | |

<210> SEQ ID NO 34
<211> LENGTH: 1135
<212> TYPE: DNA
<213> ORGANISM: Glycine max

<400> SEQUENCE: 34

```
gccaccattc ctcgcaacgc ccaaaccctc atgttggagc ttcaacgcga taatcacatg      60
cagtatgtct ccaaaggcct tcgccatctc agttccgcat tttccgtttt ggacgctaat     120
cgaccctggc tctgctactg gatcttccac tccattgctt tgttgggaga atccgtcgat     180
gatgaactcg aagataacgc tatcgatttt cttaaccgtt gccaggatcc gaatggtgga     240
tatgccgggg gaccaggcca gatgcctcat attgccacaa cttatgctgc tgttaattca     300
cttattactt tgggtggtga gaaatccctg gcatcaatta atagagataa actgtatggg     360
tttctgcggc ggatgaagca accaaatggt ggattcagga tgcatgatga aggtgaaatt     420
gatgttcgag cttgctacac tgccatttct gttgcaagtg ttttgaacat tttggatgat     480
gagctgatcc agaatgttgg agactacatt ataagctgtc aaacatatga gggtggcatt     540
gctggtgagc ctggttctga ggctcatggt gggtacacct tttgtggatt agctacaatg     600
attctgattg gtgaggttaa tcacttggat ctgcctcgat tagttgactg ggtggtattc     660
cgacaaggta aggaatgtgg attccagggg agaacaaata aactggtgga tggatgctat     720
tccttttggc agggaggtgc tgttgctcta ttgcaaagat tatcttctat tatcaacaaa     780
cagatggaag agacatcaca gattttgcg gtatcttatg tatctgaagc aaaagaaagt     840
ttggatggaa cctctagtca tgcaacatgc cgtggtgagc atgaaggcac cagtgaatcc     900
agttcatctg attttaaaaa tattgcctat aaatttatta atgagtggag agcacaagaa     960
ccactttttc acagtattgc tttacagcaa tatattctct tatgtgcaca ggagcaagag    1020
ggtggactga gagacaaacc gggtaaacgt agagatcatt atcacacatg ttactgttta    1080
agtggactct cattgtgcca gtatagttgg tcaaagcacc cagattctcc accac         1135
```

<210> SEQ ID NO 35
<211> LENGTH: 1135
<212> TYPE: DNA
<213> ORGANISM: Artificial Sequence
<220> FEATURE:
<223> OTHER INFORMATION: Description of Artificial Sequence: Compliment to Seq Id No: 34

<400> SEQUENCE: 35

```
gtggtggaga atctgggtgc tttgaccaac tatactggca caatgagagt ccacttaaac      60
agtaacatgt gtgataatga tctctacgtt tacccggttt gtctctcagt ccaccctctt     120
gctcctgtgc acataagaga atatattgct gtaaagcaat actgtgaaaa agtggttctt     180
gtgctctcca ctcattaata aatttatagg caatattttt aaaatcagat gaactggatt     240
cactggtgcc ttcatgctca ccacggcatg ttgcatgact agaggttcca tccaaacttt     300
cttttgcttc agatacataa gataccgcaa aaatctgtga tgtctcttcc atctgtttgt     360
tgataataga agataatctt tgcaatagag caacagcacc tccctgccaa aaggaatagc     420
atccatccac cagtttattt gttctcccct ggaatccaca ttccttacct tgtcggaata     480
ccacccagtc aactaatcga ggcagatcca agtgattaac ctcaccaatc agaatcattg     540
tagctaatcc acaaaaggtg tacccaccat gagcctcaga accaggctca ccagcaatgc     600
caccctcata tgtttgacag cttataatgt agtctccaac attctggatc agctcatcat     660
ccaaaatgtt caaacacttt gcaacagaaa tggcagtgta gcaagctcga acatcaattt     720
caccttcatc atgcatcctg aatccaccat ttggttgctt catccgccgc agaaacccat     780
acagtttatc tctattaatt gatgccaggg atttctcacc acccaaagta ataagtgaat     840
taacagcagc ataagttgtg gcaatatgag gcatctggcc tggtcccccg gcatatccac     900
cattcggatc ctggcaacgg ttaagaaaat cgatagcgtt atcttcgagt tcatcatcga     960
cggattctcc caacaaagca atggagtgga agatccagta gcagagccag ggtcgattag    1020
cgtccaaaac ggaaaatgcg gaactgagat ggcgaaggcc tttggagaca tactgcatgt    1080
gattatcgcg ttgaagctcc aacatgaggg tttgggcgtt gcgaggaatg gtggc        1135
```

<210> SEQ ID NO 36
<211> LENGTH: 378
<212> TYPE: PRT
<213> ORGANISM: Glycine max

<400> SEQUENCE: 36

```
Ala Thr Ile Pro Arg Asn Ala Gln Thr Leu Met Leu Glu Leu Gln Arg
  1               5                  10                  15

Asp Asn His Met Gln Tyr Val Ser Lys Gly Leu Arg His Leu Ser Ser
             20                  25                  30

Ala Phe Ser Val Leu Asp Ala Asn Arg Pro Trp Leu Cys Tyr Trp Ile
         35                  40                  45

Phe His Ser Ile Ala Leu Leu Gly Glu Ser Val Asp Asp Glu Leu Glu
     50                  55                  60

Asp Asn Ala Ile Asp Phe Leu Asn Arg Cys Gln Asp Pro Asn Gly Gly
 65                  70                  75                  80

Tyr Ala Gly Gly Pro Gly Gln Met Pro His Ile Ala Thr Thr Tyr Ala
                 85                  90                  95

Ala Val Asn Ser Leu Ile Thr Leu Gly Gly Glu Lys Ser Leu Ala Ser
            100                 105                 110
```

-continued

```
Ile Asn Arg Asp Lys Leu Tyr Gly Phe Leu Arg Arg Met Lys Gln Pro
        115                 120                 125

Asn Gly Gly Phe Arg Met His Asp Glu Gly Glu Ile Asp Val Arg Ala
130                 135                 140

Cys Tyr Thr Ala Ile Ser Val Ala Ser Val Leu Asn Ile Leu Asp Asp
145                 150                 155                 160

Glu Leu Ile Gln Asn Val Gly Asp Tyr Ile Ile Ser Cys Gln Thr Tyr
                165                 170                 175

Glu Gly Gly Ile Ala Gly Glu Pro Ser Glu Ala His Gly Gly Tyr
            180                 185                 190

Thr Phe Cys Gly Leu Ala Thr Met Ile Leu Ile Gly Glu Val Asn His
        195                 200                 205

Leu Asp Leu Pro Arg Leu Val Asp Trp Val Val Phe Arg Gln Gly Lys
    210                 215                 220

Glu Cys Gly Phe Gln Gly Arg Thr Asn Lys Leu Val Asp Gly Cys Tyr
225                 230                 235                 240

Ser Phe Trp Gln Gly Gly Ala Val Ala Leu Leu Gln Arg Leu Ser Ser
                245                 250                 255

Ile Ile Asn Lys Gln Met Glu Glu Thr Ser Gln Ile Phe Ala Val Ser
            260                 265                 270

Tyr Val Ser Glu Ala Lys Glu Ser Leu Asp Gly Thr Ser Ser His Ala
        275                 280                 285

Thr Cys Arg Gly Glu His Glu Gly Thr Ser Glu Ser Ser Ser Asp
    290                 295                 300

Phe Lys Asn Ile Ala Tyr Lys Phe Ile Asn Glu Trp Arg Ala Gln Glu
305                 310                 315                 320

Pro Leu Phe His Ser Ile Ala Leu Gln Gln Tyr Ile Leu Leu Cys Ala
                325                 330                 335

Gln Glu Gln Glu Gly Gly Leu Arg Asp Lys Pro Gly Lys Arg Arg Asp
            340                 345                 350

His Tyr His Thr Cys Tyr Cys Leu Ser Gly Leu Ser Leu Cys Gln Tyr
        355                 360                 365

Ser Trp Ser Lys His Pro Asp Ser Pro Pro
    370                 375

<210> SEQ ID NO 37
<211> LENGTH: 1245
<212> TYPE: DNA
<213> ORGANISM: Zea Maize

<400> SEQUENCE: 37
ggcggatccc gacctaccga ggctcacggt gacgcaggtg gagcagatga aggtggaggc      60
cagggttggc gacatctacc gctccctctt cggggccgcg cccaacacga aatccatcat     120
gctagagctg tggcgtgatc agcatatcga gtatctgacg cctgggctga ggcatatggg     180
accagccttt catgttctag atgccaatcg cccttggcta tgctactgga tggttcatcc     240
acttgctttg ctggatgaag cacttgatga tgatcttgag aatgatatca tagacttctt     300
agctcgatgt caggataaag atggtggata tagtggtgga cctggacagt tgcctcacct     360
agctacgact tatgctgctg taaatacact tgtgacaata gggagcgaaa gagcattgtc     420
atcaatcaat aggggcaacc tgtacaattt tatgctgcag atgaaagatg tatcaggtgc     480
tttcagaatg catgatggtg gcgaaattga tgtccgtgct cctacaccg ctatatcggt      540 tgccagcctt gtgaatattc ttgattttaa actggcaaaa ggtgtaggcg actacatagc     600
```

|  |  |
|---|---|
| aagatgtcaa acttatgaag gtggtattgc tggggagcct tatgctgaag cacatggtgg | 660 |
| gtatacattc tgtggattgg ctgctttgat cctgcttaat gaggcagaga aagttgactt | 720 |
| gcctagtttg attggctggg tggcttttcg tcaaggagtg gaatgcggat ttcaaggacg | 780 |
| aactaataaa ttggttgatg gttgctactc cttttggcag ggagctgcca ttgctttcac | 840 |
| acaaaagtta attacgattg ttgataagca attgaggtcc tcgtattcct gcaaaaggcc | 900 |
| atcaggagag gatgcctgca gcaccagttc atatgggtgc accgcgaata agtcttcctc | 960 |
| tgctgtggac tatgcgaagt ttggatttga ttttatacaa cagagcaacc aaattggccc | 1020 |
| actcttccat aacattgccc tgcaacaata catcctactt tgttctcagg tactagaggg | 1080 |
| aggcttgagg gataagcctg gaaagaacag agatcactat cattcatgct actgcctcag | 1140 |
| tggcctcgca gttagccagt acagtgccat gactgatact ggttcgtgcc cattacctca | 1200 |
| gcatgtgctt ggaccgtact ctaatttgct ggagccaatc catcc | 1245 |

<210> SEQ ID NO 38
<211> LENGTH: 1245
<212> TYPE: DNA
<213> ORGANISM: Artificial Sequence
<220> FEATURE:
<223> OTHER INFORMATION: Description of Artificial Sequence: Compliment to Seq Id No: 37

<400> SEQUENCE: 38

|  |  |
|---|---|
| ggatggattg gctccagcaa attagagtac ggtccaagca catgctgagg taatgggcac | 60 |
| gaaccagtat cagtcatggc actgtactgg ctaactgcga ggccactgag gcagtagcat | 120 |
| gaatgatagt gatctctgtt ctttccaggc ttatccctca agcctccctc tagtacctga | 180 |
| gaacaaagta ggatgtattg ttgcagggca atgttatgga agagtgggcc aatttggttg | 240 |
| ctctgttgta taaaatcaaa tccaaacttc gcatagtcca cagcagagga agacttattc | 300 |
| gcggtgcacc catatgaact ggtgctgcag gcatcctctc ctgatggcct tttgcaggaa | 360 |
| tacgaggacc tcaattgctt atcaacaatc gtaattaact tttgtgtgaa agcaatggca | 420 |
| gctccctgcc aaaaggagta gcaaccatca accaatttat tagttcgtcc ttgaaatccg | 480 |
| cattccactc cttgacgaaa agccacccag ccaatcaaac taggcaagtc aactttctct | 540 |
| gcctcattaa gcaggatcaa agcagccaat ccacagaatg tatacccacc atgtgcttca | 600 |
| gcataaggct ccccagcaat accaccttca taagtttgac atcttgctat gtagtcgcct | 660 |
| acacctttg ccagtttaaa atcaagaata ttcacaaggc tggcaaccga tatagcggtg | 720 |
| taggaagcac ggacatcaat ttcgccacca tcatgcattc tgaaagcacc tgatacatct | 780 |
| ttcatctgca gcataaaatt gtacaggttg cccctattga ttgatgacaa tgctctttcg | 840 |
| ctccctattg tcacaagtgt atttacagca gcataagtcg tagctaggtg aggcaactgt | 900 |
| ccaggtccac cactatatcc accatcttta tcctgcatc gagctaagaa gtctatgata | 960 |
| tcattctcaa gatcatcatc aagtgcttca tccagcaaag caagtggatg aaccatccag | 1020 |
| tagcatagcc aagggcgatt ggcatctaga acatgaaagg ctggtcccat atgcctcagc | 1080 |
| ccaggcgtca gatactcgat atgctgatca cgccacagct ctagcatgat ggatttcgtg | 1140 |
| ttgggcgcgg ccccgaagag ggagcggtag atgtcgccaa ccctggcctc caccttcatc | 1200 |
| tgctccacct gcgtcaccgt gagcctcggt aggtcgggat ccgcc | 1245 |

<210> SEQ ID NO 39
<211> LENGTH: 414
<212> TYPE: PRT

-continued

<213> ORGANISM: Zea Maize

<400> SEQUENCE: 39

```
Ala Asp Pro Asp Leu Pro Arg Leu Thr Val Thr Gln Val Glu Gln Met
1               5                   10                  15

Lys Val Glu Ala Arg Val Gly Asp Ile Tyr Arg Ser Leu Phe Gly Ala
            20                  25                  30

Ala Pro Asn Thr Lys Ser Ile Met Leu Glu Leu Trp Arg Asp Gln His
        35                  40                  45

Ile Glu Tyr Leu Thr Pro Gly Leu Arg His Met Gly Pro Ala Phe His
    50                  55                  60

Val Leu Asp Ala Asn Arg Pro Trp Leu Cys Tyr Trp Met Val His Pro
65                  70                  75                  80

Leu Ala Leu Leu Asp Glu Ala Leu Asp Asp Leu Glu Asn Asp Ile
                85                  90                  95

Ile Asp Phe Leu Ala Arg Cys Gln Asp Lys Asp Gly Gly Tyr Ser Gly
                100                 105                 110

Gly Pro Gly Gln Leu Pro His Leu Ala Thr Thr Tyr Ala Ala Val Asn
            115                 120                 125

Thr Leu Val Thr Ile Gly Ser Glu Arg Ala Leu Ser Ser Ile Asn Arg
130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
                180                 185                 190

Lys Gly Val Gly Asp Tyr Ile Ala Arg Cys Gln Thr Tyr Glu Gly Gly
            195                 200                 205

Ile Ala Gly Glu Pro Tyr Ala Glu Ala His Gly Gly Tyr Thr Phe Cys
    210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
                260                 265                 270

Gln Gly Ala Ala Ile Ala Phe Thr Gln Lys Leu Ile Thr Ile Val Asp
            275                 280                 285

Lys Gln Leu Arg Ser Ser Tyr Ser Cys Lys Arg Pro Ser Gly Glu Asp
    290                 295                 300

Ala Cys Ser Thr Ser Ser Tyr Gly Cys Thr Ala Asn Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
    370                 375                 380

Ser Gln Tyr Ser Ala Met Thr Asp Thr Gly Ser Cys Pro Leu Pro Gln
385                 390                 395                 400
```

-continued

His Val Gly Pro Tyr Ser Asn Leu Leu Glu Pro Ile His
           405                              410

<210> SEQ ID NO 40
<211> LENGTH: 5247
<212> TYPE: DNA
<213> ORGANISM: Artificial Sequence
<220> FEATURE:
<223> OTHER INFORMATION: Description of Artificial Sequence: Plasmid
     pBI121-35S-AtFTA

<400> SEQUENCE: 40

```
gtttaccogc caatatatcc tgtcaaacac tgatagttta aactgaaggc gggaaacgac      60
aatctgatca tgagcggaga attaagggag tcacgttatg accccgccg atgacgcggg     120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg gatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgcccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg ttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aagatggca   1980
```

```
aacgctaata agggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcaccttTaa tgaataattt ccgtcaatat    2220
ttaccttccc tccctcaatc ggttgaatgt cgccctTttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagcccaca    2520
gatggttaga gaggcttacg cagcaggtct catcaagacg atctacccga gcaataatct    2580
ccaggaaatc aaataccttc caagaaggt taaagatgca gtcaaaagat tcaggactaa    2640
ctgcatcaag aacacagaga aagatatatt tctcaagatc agaagtacta ttccagtatg    2700
gacgattcaa ggcttgcttc acaaaccaag gcaagtaata gagattggag tctctaaaaa    2760
ggtagttccc actgaatcaa aggccatgga gtcaaagatt caaatagagg acctaacaga    2820
actcgccgta aagactggcg aacagttcat acagagtctc ttacgactca atgacaagaa    2880
gaaaatcttc gtcaacatgg tggagcacga cacacttgtc tactccaaaa atatcaaaga    2940
tacagtctca gaagaccaaa gggcaattga acttttcaa caagggtaa tatccggaaa    3000 cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggacccc acccacgagg agcatcgtgg aaaaagaaga    3180
cgttccaacc acgtcttcaa agcaagtgga ttgatgtgat atctccactg acgtaaggga    3240
tgacgcacaa tcccactatc cttcgcaaga cccttcctct atataaggaa gttcatttca    3300
tttggagaga acacggggga ctctagagga tccatgaatt tcgacgagac cgtgccactg    3360
agccaacgat tggagtggtc agacgtggtc ccattgactc aggacgatgg tccgaatcca    3420
gtggtgccaa ttgcctacaa ggaagagttc cgcgagacta tggattactt ccgtgcgatt    3480
tacttttccg acgagcgatc tcctcgcgca ctacgactca cggaagaaac cctcctctta    3540
aactccggca actacacagt gtggcatttc aggcgcctag tactcgaggc ccttaatcac    3600
gacttgtttg aagaactcga gttcatcgaa cgcattgctg aggataactc taagaactac    3660
caactgtggc atcatcggcg atgggttgca gagaaactgg gtcctgatgt tgcagggaga    3720
gaacttgaat ttacccgtag agtactttca cttgatgcca acattatca tgcttggtca    3780 cataggcagt ggacactacg ggcattagga ggatgggaag atgagctcga ttactgtcac    3840
gagctccttg aagctgacgt ctttaacaat tccgcctgga atcagaggta ttatgtcatc    3900
acccaatctc ctttgttggg aggcctagaa gccatgagag aatctgaagt aagctacaca    3960
atcaaagcca ttttaaccaa tcctgcaaac gagagctcat ggcgatacct aaaagctctt    4020
tacaaagacg acaaagaatc ctggattagt gatccaagtg tttcctcagt ctgtttgaat    4080
gttctatccc gcacagattg cttccatgga ttcgctctga gcacccttTt ggatcttcta    4140
tgtgatggac tgagaccaac caacgagcat aaagactcag tgagagctct agctaatgaa    4200
gaaccagaga ctaacttggc caatttggtg tgtactattc ttggtcgtgt agatcctgta    4260
agagctaact attgggcatg gaggaagagc aagattacag tggcagcaat ttgactcgaa    4320
```

```
tttccccgat cgttcaaaca tttggcaata aagtttctta agattgaatc ctgttgccgg    4380
tcttgcgatg attatcatat aatttctgtt gaattacgtt aagcatgtaa taattaacat    4440
gtaatgcatg acgttattta tgagatgggt ttttatgatt agagtcccgc aattatacat    4500
ttaatacgcg atagaaaaca aaatatagcg cgcaaactag gataaattat cgcgcgcggt    4560
gtcatctatg ttactagatc gggaattcac tggccgtcgt tttacaacgt cgtgactggg    4620
aaaaccctgg cgttacccaa cttaatcgcc ttgcagcaca tccccctttc gccagctggc    4680
gtaatagcga agaggcccgc accgatcgcc cttcccaaca gttgcgcagc ctgaatggcg    4740
cccgctcctt tcgctttctt cccttccttt ctcgccacgt tcgccggctt tccccgtcaa    4800
gctctaaatc gggggctccc tttagggttc cgatttagtg ctttacggca cctcgacccc    4860
aaaaaacttg atttgggtga tggttcacgt agtgggccat cgccctgata gacgttttt    4920 cgcccttga cgttggagtc cacgttcttt aatagtggac tcttgttcca aactggaaca    4980
acactcaacc ctatctcggg ctattctttt gatttataag ggattttgcc gatttcggaa    5040
ccaccatcaa acaggatttt cgcctgctgg ggcaaaccag cgtggaccgc ttgctgcaac    5100
tctctcaggg ccaggcggtg aagggcaatc agctgttgcc cgtctcactg gtgaaaagaa    5160
aaaccacccc agtacattaa aaacgtccgc aatgtgttat taagttgtct aagcgtcaat    5220
ttgtttacac cacaatatat cctgcca                                        5247
```

<210> SEQ ID NO 41
<211> LENGTH: 5373
<212> TYPE: DNA
<213> ORGANISM: Artificial Sequence
<220> FEATURE:
<223> OTHER INFORMATION: Description of Artificial Sequence: Plasmid
      pBI121-rd29A-anti-AtFTA sequence

<400> SEQUENCE: 41

```
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttttgt caagaccgac    540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
```

```
ggcggcgaat gggctgaccg cttcctcgtg ctttacggta tcgccgctcc cgattcgcag    1140
cgcatcgcct tctatcgcct tcttgacgag ttcttctgag cgggactctg ggttcgaaa     1200 tgaccgacca agcgacgccc aacctgccat cacgagattt cgattccacc gccgccttct    1260
atgaaaggtt gggcttcgga atcgtttttcc gggacgccgg ctggatgatc ctccagcgcg   1320
gggatctcat gctggagttc ttcgcccacg ggatctctgc ggaacaggcg gtcgaaggtg    1380
ccgatatcat tacgacagca acggccgaca agcacaacgc cacgatcctg agcgacaata    1440
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg tttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata agggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagggagcc    2520
atagatgcaa ttcaatcaaa ctgaaatttc tgcaagaatc tcaaacacgg agatctcaaa    2580
gtttgaaaga aaatttattt cttcgactca aaacaaactt acgaaattta ggtagaactt    2640
atatacatta tattgtaatt ttttgtaaca aaatgttttt attattatta tagaatttta    2700
ctggttaaat taaaaatgaa tagaaaaggt gaattaagag gagagaggag gtaaacattt    2760 tcttctatt tttcatattt tcaggataaa ttattgtaaa agtttacaag atttccattt      2820
gactagtgta aatgaggaat attctctagt aagatcatta tttcatctac ttcttttatc    2880
ttctaccagt agaggaataa acaatattta gctccttgt aaatacaaat taatttttcct    2940 tcttgacatc attcaatttt aattttacgt ataaaataaa agatcatacc tattagaacg    3000
attaaggaga aatacaattc gaatgagaag gatgtgccgt tgttataat aaacagccac      3060 acgacgtaaa cgtaaaatga ccacatgatg ggccaataga catggaccga ctactaataa    3120
tagtaagtta cattttagga tggaataaat atcataccga catcagtttt gaaagaaaag    3180
ggaaaaaaag aaaaaataaa taaagatat actaccgaca tgagttccaa aaagcaaaaa     3240 aaagatcaa gccgacacag acacgcgtag agagcaaaat gactttgacg tcacaccacg     3300
aaaacagacg cttcatacgt gtcccttat ctctctcagt ctctctataa acttagtgag      3360
accctcctct gttttactca caaatatgca aactagaaaa caatcatcag gaataaaggg     3420
tttgattact tctattggaa agactctaga ggatcctcaa attgctgcca ctgtaatctt    3480
```

-continued

```
gctcttcctc catgcccaat agttagctct tataggatct acacgaccaa gaatagtaca    3540
caccaaattg gccaagttag tctctggttc ttcattagct agagctctca ctgagtcttt    3600
atgctcgttg gttggtctca gtccatcaca tagaagatcc aaaagggtgc tcagagcgaa    3660
tccatggaag caatctgtgc gggatagaac attcaaacag actgaggaaa cacttggatc    3720
actaatccag gattctttgt cgtctttgta aagcgctttt aggtatcgcc atgagctctc    3780
gtttgcagga ttggttaaaa tggctttgat tgtgtagctt acttcagatt ctctcatggc    3840
ttctaggcct cccaacaaag gagattgggt gatgacataa tacctctgat tccaggcgga    3900
attgttaaag acgtcagctt caaggagctc gtgacagtaa tcgagctcat cttcccatcc    3960
tcctaatgcc cgtagtgtcc actgcctatg tgaccaagca tgataatgtt tggcatcaag    4020
tgaaagtact ctacgggtaa attcaagttc tctccctgca acatcaggac ccagtttctc    4080
tgcaacccat cgccgatgat gccacagttg gtagttctta gagttatcct cagcaatgcg    4140
ttcgatgaac tcgagttctt caaacaagtc gtgattaagg gcctcgagta ctaggcgcct    4200
gaaatgccac actgtgtagt tgccggagtt aagaggagg gtttcttccg tgagtcgtag    4260
tgcgcgagga gatcgctcgt cggaaaagta atcgcacgg aagtaatcca tagtctcgcg    4320
gaactcttcc ttgtaggcaa ttggcaccac tggattcgga ccatcgtcct gagtcaatgg    4380
gaccacgtct gaccactcca atcgttggct cagtggcacg gtctcgtcga aattcatccc    4440
ctcgaatttc cccgatcgtt caaacatttg gcaataaagt ttcttaagat tgaatcctgt    4500
tgccggtctt gcgatgatta tcatataatt tctgttgaat tacgttaagc atgtaataat    4560
taacatgtaa tgcatgacgt tatttatgag atgggttttt atgattagag tcccgcaatt    4620
atacatttaa tacgcgatag aaaacaaaat atagcgcgca aactaggata aattatcgcg    4680
cgcggtgtca tctatgttac tagatcggga attcactggc cgtcgtttta caacgtcgtg    4740
actgggaaaa ccctggcgtt acccaactta atcgccttgc agcacatccc ctttcgcca    4800 gctggcgtaa tagcgaagag gcccgcaccg atcgcccttc ccaacagttg cgcagcctga    4860
atggcgcccg ctccttcgc tttcttccct cctttctcg ccacgttcgc cggctttccc    4920
cgtcaagctc taaatcgggg gctcccttta gggttccgat ttagtgcttt acggcacctc    4980
gaccccaaaa aacttgattt gggtgatggt tcacgtagtg ggccatcgcc ctgatagacg    5040
gtttttcgcc ctttgacgtt ggagtccacg ttctttaata gtggactctt gttccaaact    5100
ggaacaacac tcaaccctat ctcgggctat tcttttgatt tataagggat tttgccgatt    5160
tcggaaccac catcaaacag gattttcgcc tgctgggca aaccagcgtg gaccgcttgc    5220
tgcaactctc tcagggccag gcggtgaagg gcaatcagct gttgcccgtc tcactggtga    5280
aaagaaaaac caccccagta cattaaaaac gtccgcaatg tgttattaag ttgtctaagc    5340
gtcaatttgt ttacaccaca atatatcctg cca                                5373
```

```
<210> SEQ ID NO 42
<211> LENGTH: 6285
<212> TYPE: DNA
<213> ORGANISM: Artificial Sequence
<220> FEATURE:
<223> OTHER INFORMATION: Description of Artificial Sequence: Plasmid
      pBI121-35S-DA-AtFTA

<400> SEQUENCE: 42
```

```
gtttacccgc caatatatcc tgtcaaacac tgatagttta aactgaaggc gggaaacgac     60
aatctgatca tgagcggaga attaagggag tcacgttatg accccgccg atgacgcggg     120
```

-continued

| | |
|---|---|
| acaagccgtt ttacgtttgg aactgacaga accgcaacgt tgaaggagcc actcagccgc | 180 |
| gggtttctgg agtttaatga gctaagcaca tacgtcagaa accattattg cgcgttcaaa | 240 |
| agtcgcctaa ggtcactatc agctagcaaa tatttcttgt caaaaatgct ccactgacgt | 300 |
| tccataaatt cccctcggta tccaattaga gtctcatatt cactctcaat ccaaataatc | 360 |
| tgcaccggat ctggatcgtt tcgcatgatt gaacaagatg gattgcacgc aggttctccg | 420 |
| gccgcttggg tggagaggct attcggctat gactgggcac aacagacaat cggctgctct | 480 |
| gatgccgccg tgttccggct gtcagcgcag gggcgcccgg ttcttttgt caagaccgac | 540 |
| ctgtccggtg ccctgaatga actgcaggac gaggcagcgc ggctatcgtg ctggccacg | 600 |
| acgggcgttc cttgcgcagc tgtgctcgac gttgtcactg aagcgggaag ggactggctg | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |
| ggcggcgaat gggctgaccg cttcctcgtg ctttacggta tcgccgctcc cgattcgcag | 1140 |
| cgcatcgcct tctatcgcct tcttgacgag ttcttctgag cgggactctg ggttcgaaa | 1200 |
| tgaccgacca agcgacgccc aacctgccat cacgagattt cgattccacc gccgccttct | 1260 |
| atgaaaggtt gggcttcgga atcgttttcc gggacgccgg ctggatgatc ctccagcgcg | 1320 |
| gggatctcat gctggagttc ttcgcccacg gatctctgc ggaacaggcg gtcgaaggtg | 1380 |
| ccgatatcat tacgacagca acggccgaca agcacaacgc cacgatcctg agcgacaata | 1440 |
| tgatcgggcc cggcgtccac atcaacggcg tcggcggcga ctgcccaggc aagaccgaga | 1500 |
| tgcaccgcga tatcttgctg cgttcggata ttttcgtgga gttcccgcca cagacccgga | 1560 |
| tgatccccga tcgttcaaac atttggcaat aaagtttctt aagattgaat cctgttgccg | 1620 |
| gtcttgcgat gattatcata taatttctgt tgaattacgt taagcatgta ataattaaca | 1680 |
| tgtaatgcat gacgttattt atgagatggg tttttatgat tagagtcccg caattataca | 1740 |
| tttaatacgc gatagaaaac aaaatatagc gcgcaaacta ggataaatta tcgcgcgcgg | 1800 |
| tgtcatctat gttactagat cgggcctcct gtcaatgctg gcggcggctc tggtggtggt | 1860 |
| tctggtggcg gctctgaggg tggtggctct gagggtggcg gttctgaggg tggcggctct | 1920 |
| gagggaggcg gttccggtgg tggctctggt tccggtgatt tgattatga aagatggca | 1980 |
| aacgctaata aggggctat gaccgaaaat gccgatgaaa acgcgctaca gtctgacgct | 2040 |
| aaaggcaaac ttgattctgt cgctactgat tacggtgctg ctatcgatgg tttcattggt | 2100 |
| gacgtttccg gccttgctaa tggtaatggt gctactggtg attttgctgg ctctaattcc | 2160 |
| caaatggctc aagtcggtga cggtgataat tcacctttaa tgaataattt ccgtcaatat | 2220 |
| ttaccttccc tccctcaatc ggttgaatgt cgcccttttg tctttggccc aatacgcaaa | 2280 |
| ccgcctctcc ccgcgcgttg gccgattcat taatgcagct ggcacgacag gtttcccgac | 2340 |
| tggaaagcgg gcagtgagcg caacgcaatt aatgtgagtt agctcactca ttaggcaccc | 2400 |
| caggctttac actttatgct tccggctcgt atgttgtgtg gaattgtgag cggataacaa | 2460 |

-continued

```
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaataccttc caagaaggt taaagatgca gtcaaagat tcaggactaa    2640 ctgcatcaag aacacagaga agatatatt tctcaagatc agaagtacta ttccagtatg   2700
gacgattcaa ggcttgcttc acaaaccaag gcaagtaata gagattggag tctctaaaaa  2760
ggtagttccc actgaatcaa aggccatgga gtcaaagatt caaatagagg acctaacaga  2820
actcgccgta aagactggcg aacagttcat acagagtctc ttacgactca atgacaagaa  2880
gaaaatcttc gtcaacatgg tggagcacga cacacttgtc tactccaaaa atatcaaaga  2940
tacagtctca gaagaccaaa gggcaattga acttttcaa caaagggtaa tatccggaaa   3000
cctcctcgga ttccattgcc cagctatctg tcactttatt gtgaagatag tggaaaagga  3060
aggtggctcc tacaaatgcc atcattgcga taaaggaaag gccatcgttg aagatgcctc  3120
tgccgacagt ggtcccaaag atggaccccc acccacgagg agcatcgtgg aaaaagaaga  3180
cgttccaacc acgtcttcaa agcaagtgga ttgatgtgat atctccactg acgtaaggga  3240
tgacgcacaa tcccactatc cttcgcaaga cccttcctct atataaggaa gttcatttca  3300
tttggagaga cacggggga ctctagagga tcctcgctct tcctccatgc caatagtta   3360 gctcttacag gatctacacg accaagaata gtacacacca aattggccaa gttagtctct  3420
ggttcttcat tagctagagc tctcactgag tctttatgct cgttggttgg tctcagtcca  3480
tcacatagaa gatccaaaag ggtgctcaga gcgaatccat ggaagcaatc tgtgcgggat  3540
agaacattca aacagactga ggaaacactt ggatcactaa tccaggattc tttgtcgtct  3600
ttgtaaagag cttttaggta tcgccatgag ctctcgtttg caggattggt taaaatggct  3660
ttgattgtgt agcttacttc agattctctc atggcttcta ggcctcccaa caaaggagat  3720
tgggtgatga cataatacct ctgattccag gcggaattgt taaagacgtc agcttcaagg  3780
agctcgtgac agtaatcgag ctcatcttcc catcctccta atgcccggag gatccccatc  3840
tacccgcttc gcgtcggcat ccggtcagtg gcagtgaagg gcgaacagtt cctgattaac  3900
cacaaaccgt tctactttac tggctttggt cgtcatgaag atgcggactt gcgtggcaaa  3960
ggattcgata acgtgctgat ggtgcacgac cacgcattaa tggactggat tggggccaac  4020
tcctaccgta cctcgcatta cccttacgct gaagagatgc tcgactgggc agatgaacat  4080
ggcatcgtgg tgattgatga aactgctgct gtcggctttt cgctctcttt aggcattggt  4140
ttcgaagcgg gcaacaagcc gaaagaactg tacagcgaag aggcagtcaa cggggaaact  4200
cagcaagcgc acttacaggc gattaaagag ctgatagcgc gtgacaaaaa ccacccaagc  4260
gtggtgatgt ggagtattgc caacgaaccg gatacccgtc gcaaggtgc acgggaatat   4320 ttcgcgccac tggcggaagc aacgcgtaaa ctcgacccga cgcgtccgat cacctgcgtc  4380
aatgtaatgt tctgcgacgc tcacaccgat accatcagca atctctttga tgtgctgtgc  4440
ctgaaccgtt attacggatg gtatgtccaa gcggcgatt tggaaacggc agagaaggta   4500 ctggaaaag aacttctggc ctggcaggag aaactgtaca ccgacatgtg gagtgaagag   4560
tatcagtgtg catggctgga tatgtatcac cgcgtctttg atcgcgtcag cgccgtcgtc  4620
ggtgaacagg tatggaattt cgccgatttt gcgacctcgc aaggcatatt gcgcgttggc  4680
ggtaacaaga aagggatctt cactcgcgac cgcaaaccga gtcggcggc ttttctgctg    4740 caaaaacgct ggactggcat gaacttcggt gaaaaccgc agcagggagg caaacaatga   4800
atcaacaact ctcctggcgc accatcgtcg gctacagcct cgggaattgc taccgagctc  4860
```

```
gctcttcctc catgcccaat agttagctct tacaggatct acacgaccaa gaatagtaca    4920
caccaaattg gccaagttag tctctggttc ttcattagct agagctctca ctgagtcttt    4980
atgctcgttg gttggtctca gtccatcaca tagaagatcc aaaagggtgc tcagagcgaa    5040
tccatggaag caatctgtgc gggatagaac attcaaacag actgaggaaa cacttggatc    5100
actaatccag gattctttgt cgtctttgta aagagctttt aggtatcgcc atgagctctc    5160
gtttgcagga ttggttaaaa tggctttgat tgtgtagctt acttcagatt ctctcatggc    5220
ttctaggcct cccaacaaag gagattgggt gatgacataa tacctctgat tccaggcgga    5280
attgttaaag acgtcagctt caaggagctc gtgacagtaa tcgagctcat cttcccatcc    5340
tcctaatgcc cgctcgaatt tccccgatcg ttcaaacatt tggcaataaa gtttcttaag    5400
attgaatcct gttgccggtc ttgcgatgat tatcatataa tttctgttga attacgttaa    5460
gcatgtaata attaacatgt aatgcatgac gttatttatg agatgggttt ttatgattag    5520
agtcccgcaa ttatacattt aatacgcgat agaaaacaaa atatagcgcg caaactagga    5580
taaattatcg cgcgcggtgt catctatgtt actagatcgg gaattcactg gccgtcgttt    5640
tacaacgtcg tgactgggaa acccctggcg ttacccaact taatcgcctt gcagcacatc    5700
cccctttcgc cagctggcgt aatagcgaag aggcccgcac cgatcgccct tcccaacagt    5760
tgcgcagcct gaatggcgcc cgctcctttc gctttcttcc cttcctttct cgccacgttc    5820
gccggctttc cccgtcaagc tctaaatcgg ggctcccctt tagggttccg atttagtgct    5880
ttacggcacc tcgaccccaa aaaacttgat ttgggtgatg gttcacgtag tgggccatcg    5940
ccctgataga cggttttttcg ccctttgacg ttggagtcca cgttctttaa tagtggactc    6000
ttgttccaaa ctggaacaac actcaaccct atctcgggct attcttttga tttataaggg    6060
attttgccga tttcggaacc accatcaaac aggattttcg cctgctgggg caaaccagcg    6120
tggaccgctt gctgcaactc tctcagggcc aggcggtgaa gggcaatcag ctgttgcccg    6180
tctcactggt gaaaagaaaa accaccccag tacattaaaa acgtccgcaa tgtgttatta    6240
agttgtctaa gcgtcaattt gtttacacca caatatatcc tgcca                    6285
```

<210> SEQ ID NO 43
<211> LENGTH: 6409
<212> TYPE: DNA
<213> ORGANISM: Artificial Sequence
<220> FEATURE:
<223> OTHER INFORMATION: Description of Artificial Sequence: Plasmid
      pBI121-RD29A-DA-AtFTA

<400> SEQUENCE: 43

```
gtttaccccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagccgc     180
gggtttctgg agtttaatga gctaagcaca tacgtcagaa accattattg cgcgttcaaa     240
agtcgcctaa ggtcactatc agctagcaaa tatttcttgt caaaaatgct ccactgacgt     300
tccataaatt cccctcggta tccaattaga gtctcatatt cactctcaat ccaaataatc     360
tgcaccggat ctggatcgtt tcgcatgatt gaacaagatg gattgcacgc aggttctccg     420
gccgcttggg tggagaggct attcggctat gactgggcac aacagacaat cggctgctct     480
gatgccgccg tgttccggct gtcagcgcag ggcgcccgg ttcttttttgt caagaccgac     540 ctgtccggtg ccctgaatga actgcaggac gaggcagcgc ggctatcgtg gctggccacg     600
```

-continued

| | |
|---|---|
| acgggcgttc cttgcgcagc tgtgctcgac gttgtcactg aagcgggaag ggactggctg | 660 |
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |
| ggcggcgaat gggctgaccg cttcctcgtg ctttacggta tcgccgctcc cgattcgcag | 1140 |
| cgcatcgcct tctatcgcct tcttgacgag ttcttctgag cgggactctg gggttcgaaa | 1200 |
| tgaccgacca agcgacgccc aacctgccat cacgagattt cgattccacc gccgccttct | 1260 |
| atgaaaggtt gggcttcgga atcgttttcc gggacgccgg ctggatgatc ctccagcgcg | 1320 |
| gggatctcat gctggagttc ttcgcccacg gatctctgc ggaacaggcg gtcgaaggtg | 1380 |
| ccgatatcat tacgacagca acggccgaca agcacaacgc cacgatcctg agcgacaata | 1440 |
| tgatcgggcc cggcgtccac atcaacggct cggcggcga ctgcccaggc aagaccgaga | 1500 |
| tgcaccgcga tatcttgctg cgttcggata ttttcgtgga gttcccgcca cagacccgga | 1560 |
| tgatccccga tcgttcaaac atttggcaat aaagtttctt aagattgaat cctgttgccg | 1620 |
| gtcttgcgat gattatcata taatttctgt tgaattacgt taagcatgta ataattaaca | 1680 |
| tgtaatgcat gacgttattt atgagatggg tttttatgat tagagtcccg caattataca | 1740 |
| tttaatacgc gatagaaaac aaaatatagc gcgcaaacta ggataaatta tcgcgcgcgg | 1800 |
| tgtcatctat gttactagat cgggcctcct gtcaatgctg gcggcggctc tggtggtggt | 1860 |
| tctggtggcg gctctgaggg tggtggctct gagggtggcg gttctgaggg tggcggctct | 1920 |
| gagggaggcg gttccggtgg tggctctggt tccggtgatt ttgattatga aaagatggca | 1980 |
| aacgctaata agggggctat gaccgaaaat gccgatgaaa acgcgctaca gtctgacgct | 2040 |
| aaaggcaaac ttgattctgt cgctactgat tacggtgctg ctatcgatgg tttcattggt | 2100 |
| gacgtttccg gccttgctaa tggtaatggt gctactggtg attttgctgg ctctaattcc | 2160 |
| caaatggctc aagtcggtga cggtgataat tcacctttaa tgaataattt ccgtcaatat | 2220 |
| ttaccttccc tccctcaatc ggttgaatgt cgccctttg tctttggccc aatacgcaaa | 2280 |
| ccgcctctcc ccgcgcgttg gccgattcat taatgcagct ggcacgacag gtttcccgac | 2340 |
| tggaaagcgg gcagtgagcg caacgcaatt aatgtgagtt agctcactca ttaggcaccc | 2400 |
| caggctttac actttatgct tccggctcgt atgttgtgtg gaattgtgag cggataacaa | 2460 |
| tttcacacag gaaacagcta tgaccatgat tacgccaagc ttgcatgcct gcagggagcc | 2520 |
| atagatgcaa ttcaatcaaa ctgaaatttc tgcaagaatc tcaaacacgg agatctcaaa | 2580 |
| gtttgaaaga aaatttattt cttcgactca aacaaactt acgaaattta ggtagaactt | 2640 |
| atatacatta tattgtaatt ttttgtaaca aaatgttttt attattatta tagaattta | 2700 |
| ctggttaaat taaaatgaa tagaaaaggt gaattaagag gagagaggag gtaaacattt | 2760 |
| tcttctattt tttcatattt tcaggataaa ttattgtaaa agtttacaag atttccattt | 2820 |
| gactagtgta aatgaggaat attctctagt aagatcatta tttcatctac ttcttttatc | 2880 |
| ttctaccagt agaggaataa acaatattta gctcctttgt aaatacaaat taattttcct | 2940 |

-continued

```
tcttgacatc attcaattttt aattttacgt ataaaataaa agatcatacc tattagaacg    3000
attaaggaga aatacaattc gaatgagaag gatgtgccgt ttgttataat aaacagccac    3060
acgacgtaaa cgtaaaatga ccacatgatg ggccaataga catggaccga ctactaataa    3120
tagtaagtta cattttagga tggaataaat atcataccga catcagtttt gaaagaaaag    3180
ggaaaaaaag aaaaaataaa taaaagatat actaccgaca tgagttccaa aaagcaaaaa    3240
aaaagatcaa gccgacacag acacgcgtag agagcaaaat gactttgacg tcacaccacg    3300
aaaacagacg cttcatacgt gtccctttat ctctctcagt ctctctataa acttagtgag    3360
accctcctct gttttactca caaatatgca aactagaaaa caatcatcag gaataaaggg    3420
tttgattact tctattggaa aggactctag aggatcctcg ctcttcctcc atgcccaata    3480
gttagctctt acaggatcta cacgaccaag aatagtacac accaaattgg ccaagttagt    3540
ctctggttct tcattagcta gagctctcac tgagtcttta tgctcgttgg ttggtctcag    3600
tccatcacat agaagatcca aaagggtgct cagagcgaat ccatggaagc aatctgtgcg    3660
ggatagaaca ttcaaacaga ctgaggaaac acttggatca ctaatccagg attctttgtc    3720
gtctttgtaa agagctttta ggtatcgcca tgagctctcg tttgcaggat tggttaaaat    3780
ggctttgatt gtgtagctta cttcagattc tctcatggct tctaggcctc ccaacaaagg    3840
agattgggtg atgacataat acctctgatt ccaggcggaa ttgttaaaga cgtcagcttc    3900
aaggagctcg tgacagtaat cgagctcatc ttcccatcct cctaatgccc ggaggatccc    3960
catctacccg cttcgcgtcg gcatccggtc agtggcagtg aagggcgaac agttcctgat    4020
taaccacaaa ccgttctact ttactggctt tggtcgtcat gaagatgcgg acttgcgtgg    4080
caaaggattc gataacgtgc tgatggtgca cgaccacgca ttaatggact ggattggggc    4140
caactcctac cgtacctcgc attaccctta cgctgaagag atgctcgact gggcagatga    4200
acatggcatc gtggtgattg atgaaactgc tgctgtcggc ttttcgctct ctttaggcat    4260
tggtttcgaa gcgggcaaca agccgaaaga actgtacagc gaagaggcag tcaacgggga    4320
aactcagcaa gcgcacttac aggcgattaa agagctgata gcgcgtgaca aaaaccaccc    4380
aagcgtggtg atgtggagta ttgccaacga accggatacc cgtccgcaag gtgcacggga    4440
atatttcgcg ccactggcgg aagcaacgcg taaactcgac ccgacgcgtc cgatcacctg    4500
cgtcaatgta atgttctgcg acgctcacac cgataccatc agcgatctct ttgatgtgct    4560
gtgcctgaac cgttattacg gatggtatgt ccaaagcggc gatttggaaa cggcagagaa    4620
ggtactggaa aaagaacttc tggcctggca ggagaaactg tacaccgaca tgtggagtga    4680
agagtatcag tgtgcatggc tggatatgta tcaccgcgtc tttgatcgcg tcagcgccgt    4740
cgtcggtgaa caggtatgga atttcgccga ttttgcgacc tcgcaaggca tattgcgcgt    4800
tggcggtaac aagaaaggga tcttcactcg cgaccgcaaa ccgaagtcgg cggcttttct    4860
gctgcaaaaa cgctggactg gcatgaactt cggtgaaaaa ccgcagcagg gaggcaaaca    4920
atgaatcaac aactctcctg gcgcaccatc gtcggctaca gcctcgggaa ttgctaccga    4980
gctcgctctt cctccatgcc caatagttag ctcttacagg atctacacga ccaagaatag    5040
tacacaccaa attggccaag ttagtctctg gttcttcatt agctagagct ctcactgagt    5100
ctttatgctc gttggttggt ctcagtccat cacatagaag atccaaaagg gtgctcagag    5160
cgaatccatg gaagcaatct gtgcgggata gaacattcaa acagactgag gaaacacttg    5220
gatcactaat ccaggattct ttgtcgtctt tgtaaagagc ttttaggtat cgccatgagc    5280
tctcgtttgc aggattggtt aaaatggctt tgattgtgta gcttacttca gattctctca    5340
```

-continued

```
tggcttctag gcctcccaac aaaggagatt gggtgatgac ataataccte tgattccagg    5400 cggaattgtt aaagacgtca gcttcaagga gctcgtgaca gtaatcgagc tcatcttccc    5460
atcctcctaa tgcccgctcg aatttccccg atcgttcaaa catttggcaa taaagtttct    5520
taagattgaa tcctgttgcc ggtcttgcga tgattatcat ataatttctg ttgaattacg    5580
ttaagcatgt aataattaac atgtaatgca tgacgttatt tatgagatgg gtttttatga    5640
ttagagtccc gcaattatac atttaatacg cgatagaaaa caaaatatag cgcgcaaact    5700
aggataaatt atcgcgcgcg tgtcatcta tgttactaga tcgggaattc actggccgtc    5760
gttttacaac gtcgtgactg ggaaaaccct ggcgttaccc aacttaatcg ccttgcagca    5820
catccccctt tcgccagctg gcgtaatagc gaagaggccc gcaccgatcg cccttcccaa    5880
cagttgcgca gcctgaatgg cgcccgctcc tttcgctttc ttcccttcct ttctcgccac    5940
gttcgccggc tttccccgtc aagctctaaa tcggggctc cctttagggt tccgatttag    6000
tgctttacgg cacctcgacc ccaaaaaact tgatttgggt gatggttcac gtagtgggcc    6060
atcgccctga tagacggttt ttcgcccttt gacgttggag tccacgttct ttaatagtgg    6120
actcttgttc caaactggaa caacactcaa ccctatctcg ggctattctt ttgatttata    6180
agggattttg ccgatttcgg aaccaccatc aaacaggatt ttcgcctgct ggggcaaacc    6240
agcgtggacc gcttgctgca actctctcag ggccaggcgg tgaagggcaa tcagctgttg    6300
cccgtctcac tggtgaaaag aaaaaccacc ccagtacatt aaaaacgtcc gcaatgtgtt    6360
attaagttgt ctaagcgtca atttgtttac accacaatat atcctgcca                6409
```

<210> SEQ ID NO 44
<211> LENGTH: 1254
<212> TYPE: DNA
<213> ORGANISM: Artificial Sequence
<220> FEATURE:
<223> OTHER INFORMATION: Description of Artificial Sequence: Plasmid MuA-anti-GmFTA

<400> SEQUENCE: 44

```
gaattcaaat ttttcgccag ttctaaatat ccggaaacct cttgggatgc cattgcccat      60
ctatctgtaa tttattgacg aaatagacga aaaggaaggt ggctcctata aagcacatca     120
ttgcgataac agaaaggcca ttgttgaaga tacctctgct gacattggtc cccaagtgga     180
agcaccaccc catgaggagc accgtggagt aagaagacgt tcgagccacg tcgaaaaagc     240
aagtgtgttg atgtagtatc tccattgacg taagggatga cgcacaatcc aactatccat     300
cgcaagacca ttgctctata taagaaagtt aatatcattt cgagtggcca cgctgagctc     360
aggaagtctg ctcttgcgcc aaatccaata gttggttcta attggatcaa cttgttttag     420
gatagaacaa atatttcgtg ctatatttaa attttgttgt tccccttct catcatcatc     480 taaatcttgt ttatccatat ctgcggtctt taaggcgtca atggcatctc taatgtcttc     540
atttggttga taaccaaagc atataagatc taaaatagtg ctaagagcaa acacgtagtt     600
gctcttagtt ctcaaaatct ttaagcatac tgaagaaact tgaggatcat ttacccatga     660
agtagtttca ccttttataaa gtcctcgtag atatctccac gagctttcat tttcagggta     720
ggctataatg gcttcgatgg tgtaaagcac ttcagactct tcatagctt ttaggccccc     780 caagaaagga gaccttgtta tgacaaaata tctctgattc caagcagaat tgttaaaaat     840
gtcttcttta agtagttctg tgcaataatt aagttcatct tcccatcctc ctagtgtttg     900
aagagcccac tgtctatgag accatgcatg ataatgtttg gcatcaacgg acagtatctt     960
```

-continued

```
tttggtgaac tcgagctgag ctcgaatttc cccgatcgtt caaacatttg gcaataaagt   1020
ttcttaagat tgaatcctgt tgccggtctt gcgatgatta tcatataatt tctgttgaat   1080
tacgttaagc atgtaataat taacatgtaa tgcatgacgt tatttatgag atgggttttt   1140
atgattagag tcccgcaatt atacatttaa tacgcgatag aaaacaaaat atagcgcgca   1200
aactaggata aattatcgcg cgcggtgtca tctatgttac tagatcggga attc         1254
```

<210> SEQ ID NO 45
<211> LENGTH: 1822
<212> TYPE: DNA
<213> ORGANISM: Artificial Sequence
<220> FEATURE:
<223> OTHER INFORMATION: Description of Artificial Sequence: Plasmid
      RD29A-anti-GmFTA

<400> SEQUENCE: 45

```
ggagccatag atgcaattca atcaaactga aatttctgca agaatctcaa acacggagat     60
ctcaaagttt gaaagaaaat ttatttcttc gactcaaaac aaacttacga aatttaggta    120
gaacttatat acattatatt gtaatttttt gtaacaaaat gttttttatta ttattataga   180 atttttactgg ttaaattaaa aatgaataga aaaggtgaat taagaggaga gaggaggtaa   240 acatttctt ctattttttc atattttcag gataaattat tgtaaaagtt tacaagattt    300
ccatttgact agtgtaaatg aggaatattc tctagtaaga tcattatttc atctacttct   360
tttatcttct accagtagag gaataaacaa tatttagctc ctttgtaaat acaaattaat   420
tttccttctt gacatcattc aattttaatt ttacgtataa aataaaagat catacctatt   480
agaacgatta aggagaaata caattcgaat gagaaggatg tgccgtttgt tataataaac   540
agccacacga cgtaaacgta aaatgaccac atgatgggcc aatagacatg gaccgactac   600
taataatagt aagttacatt ttaggatgga ataaatatca taccgacatc agttttgaaa   660
gaaaagggaa aaaagaaaa aataaataaa agatatacta ccgacatgag ttccaaaaag   720
caaaaaaaaa gatcaagccg acacagacac gcgtagagag caaaatgact ttgacgtcac   780
accacgaaaa cagacgcttc atacgtgtcc ctttatctct ctcagtctct ctataaactt   840
agtgagaccc tcctctgttt tactcacaaa tatgcaaact agaaacaat catcaggaat    900 aaagggtttg attacttcta ttggaaagag gaagtctgct cttgcgccaa atccaatagt   960
tggttctaat tggatcaact tgttttagga tagaacaaat atttcgtgct atatttaaat  1020
tttgttgttc ccctttctca tcatcatcta atcttgtttt atccatatct gcggtcttta  1080
aggcgtcaat ggcatctcta atgtcttcat ttggttgata accaaagcat ataagatcta  1140
aaatagtgct aagagcaaac acgtagttgc tcttagttct caaaatcttt aagcatactg  1200
aagaaacttg aggatcattt acccatgaag tagtttcacc tttataaagt cctcgtagat  1260
atctccacga gctttcattt tcagggtagg ctataatggc ttcgatggtg taaagcactt  1320
cagactctct catagctttt aggccccccca agaaaggaga ccttgttatg acaaaatatc  1380
tctgattcca agcagaattg ttaaaaatgt cttctttaag tagttctgtg caataattaa  1440
gttcatcttc ccatcctcct agtgtttgaa gagcccactg tctatgagac catgcatgat  1500
aatgtttggc atcaacggac agtatctttt tggtgaactc gagctgagct cgaatttccc  1560
cgatcgttca aacatttggc aataaagttt cttaagattg aatcctgttg ccggtcttgc  1620
gatgattatc atataatttc tgttgaatta cgttaagcat gtaataatta acatgtaatg  1680
catgacgtta tttatgagat gggttttat gattagagtc ccgcaattat acatttaata  1740
```

```
cgcgatagaa acaaaatat agcgcgcaaa ctaggataaa ttatcgcgcg cggtgtcatc      1800
tatgttacta gatcgggaat tc                                             1822

<210> SEQ ID NO 46
<211> LENGTH: 1570
<212> TYPE: DNA
<213> ORGANISM: Artificial Sequence
<220> FEATURE:
<223> OTHER INFORMATION: Description of Artificial Sequence: Plasmid
      MuA-HP-GmFTA-Nos-Term

<400> SEQUENCE: 46
gaattcaaat ttttcgccag ttctaaatat ccggaaacct cttgggatgc cattgcccat     60
ctatctgtaa tttattgacg aaatagacga aaggaaggt ggctcctata agcacatca     120 ttgcgataac agaaaggcca ttgttgaaga tacctctgct gacattggtc cccaagtgga    180
agcaccaccc catgaggagc accgtggagt aagaagacgt cgagccacg tcgaaaaagc    240 aagtgtgttg atgtagtatc tccattgacg taagggatga cgcacaatcc aactatccat    300
cgcaagacca ttgctctata taagaaagtt aatatcattt cgagtggcca cgctgagctc    360
aggaagtctg ctcttgcgcc aaatccaata gttggttcta attggatcaa cttgttttag    420
gatagaacaa atatttcgtg ctatatttaa attttgttgt tcccctttct catcatcatc    480
taaatcttgt ttatccatat ctgcggtctt aaggcgtca atggcatctc taatgtcttc    540
atttggttga taaccaaagc atataagatc taaaatagtg ctaagagcaa acacgtagtt    600
gctcttagtt ctcaaaatct ttaagcatac tgaagaaact tgaggatcat ttacccatga    660
agtagtttca cctttataaa gtcctcgtag atatctccac gagctttcat tttcagggta    720
ggctataatg gcttcgatgg tgtaaagcac ttcagactct ctcatagctt ttaggccccc    780
caagaaagga gaccttgtta tgacaaaata tctctgattc caagcagaat tgttaaaaat    840
gtcttcttta agtagttctg tgcaataatt aagttcatct tcccatcctc ctagtgtttg    900
aagagcccac tgtctatgag accatgcatg ataatgtttg gcatcaacgg acagtatctt    960
tttggtgaac tcgagcttaa aggtgaaact acttcatggg taaatgatcc tcaagtttct   1020
tcagtatgct taaagatttt gagaactaag agcaactacg tgtttgctct tagcactatt   1080
ttagatctta tatgctttgg ttatcaacca aatgaagaca ttagagatgc cattgacgcc   1140
ttaaagaccg cagatatgga taaacaagat ttagatgatg atgagaaagg ggaacaacaa   1200
aatttaaata tagcacgaaa tatttgttct atcctaaaac aagttgatcc aattagaacc   1260
aactattgga tttggcgcaa gagcagactt cctgagctcg aatttccccg atcgttcaaa   1320
catttggcaa taaagtttct taagattgaa tcctgttgcc ggtcttgcga tgattatcat   1380
ataatttctg ttgaattacg ttaagcatgt aataattaac atgtaatgca tgacgttatt   1440
tatgagatgg gttttatga ttagagtccc gcaattatac atttaatacg cgatagaaaa   1500
caaaatatag cgcgcaaact aggataaatt atcgcgcgcg gtgtcatcta tgttactaga   1560
tcgggaattc                                                          1570

<210> SEQ ID NO 47
<211> LENGTH: 2138
<212> TYPE: DNA
<213> ORGANISM: Artificial Sequence
<220> FEATURE:
<223> OTHER INFORMATION: Description of Artificial Sequence: Plasmid
      RD29AP-HP-GmFTA-Nos-Term
```

-continued

<400> SEQUENCE: 47

```
ggagccatag atgcaattca atcaaactga aatttctgca agaatctcaa acacggagat      60
ctcaaagttt gaaagaaaat ttatttcttc gactcaaaac aaacttacga aatttaggta     120
gaacttatat acattatatt gtaatttttt gtaacaaaat gtttttatta ttattataga    180
attttactgg ttaaattaaa aatgaataga aaggtgaat taagaggaga gaggaggtaa     240
acattttctt ctattttttc atattttcag gataaattat tgtaaaagtt tacaagattt     300
ccatttgact agtgtaaatg aggaatattc tctagtaaga tcattatttc atctacttct     360
tttatcttct accagtagag gaataaacaa tatttagctc ctttgtaaat acaaattaat     420
tttccttctt gacatcattc aatttaatt ttacgtataa aataaaagat catacctatt      480
agaacgatta aggagaaata caattcgaat gagaaggatg tgccgtttgt tataataaac     540
agccacacga cgtaaacgta aaatgaccac atgatgggcc aatagacatg gaccgactac     600
taataatagt aagttacatt ttaggatgga ataaatatca taccgacatc agttttgaaa     660
gaaaagggaa aaaagaaaa aataaataaa agatatacta ccgacatgag ttccaaaaag     720
caaaaaaaaa gatcaagccg acacagacac gcgtagagag caaaatgact ttgacgtcac     780
accacgaaaa cagacgcttc atacgtgtcc ctttatctct ctcagtctct ctataaactt    840
agtgagaccc tcctctgttt tactcacaaa tatgcaaact agaaacaat catcaggaat     900
aaagggtttg attacttcta ttggaaagag gaagtctgct cttgcgccaa atccaatagt    960
tggttctaat tggatcaact tgttttagga tagaacaaat atttcgtgct atatttaaat    1020
tttgttgttc ccctttctca tcatcatcta aatcttgttt atccatatct gcggtcttta    1080
aggcgtcaat ggcatctcta atgtcttcat ttggttgata accaaagcat ataagatcta    1140
aaatagtgct aagagcaaac acgtagttgc tcttagttct caaaatcttt aagcatactg    1200
aagaaacttg aggatcattt acccatgaag tagtttcacc tttataaagt cctcgtagat    1260
atctccacga gctttcattt tcagggtagg ctataatggc ttcgatggtg taaagcactt    1320
cagactctct catagctttt aggcccccca agaaaggaga ccttgttatg acaaaatatc    1380
tctgattcca agcagaattg ttaaaaatgt cttctttaag tagttctgtg caataattaa    1440
gttcatcttc ccatcctcct agtgtttgaa gagcccactg tctatgagac catgcatgat    1500
aatgtttggc atcaacggac agtatctttt tggtgaactc gagcttaaag gtgaaactac    1560
ttcatgggta aatgatcctc aagtttcttc agtatgctta agattttga gaactaagag    1620
caactacgtg tttgctctta gcactatttt agatcttata tgctttggtt atcaaccaaa    1680
tgaagacatt agagatgcca ttgacgcctt aaagaccgca gatatggata acaagatttt    1740
agatgatgat gagaaagggg aacaacaaaa tttaaatata gcacgaaata tttgttctat    1800
cctaaaacaa gttgatccaa ttagaaccaa ctattggatt tggcgcaaga gcagacttcc    1860
tgagctcgaa tttccccgat cgttcaaaca tttggcaata aagtttctta agattgaatc    1920
ctgttgccgg tcttgcgatg attatcatat aatttctgtt gaattacgtt aagcatgtaa    1980
taattaacat gtaatgcatg acgttattta tgagatgggt ttttatgatt agagtcccgc    2040
aattatacat ttaatacgcg atagaaaaca aaatatagcg cgcaaactag gataaattat    2100
cgcgcgcggt gtcatctatg ttactagatc gggaattc                            2138
```

<210> SEQ ID NO 48
<211> LENGTH: 5511
<212> TYPE: DNA
<213> ORGANISM: Artificial Sequence
<220> FEATURE:
<223> OTHER INFORMATION: Description of Artificial Sequence: Plasmid
      pBI121-35S-Anti-AtFTB

<400> SEQUENCE: 48

```
gtttacccgc caatatatcc tgtcaaacac tgatagttta aactgaaggc gggaaacgac     60
aatctgatca tgagcggaga attaagggag tcacgttatg accccgccg atgacgcggg    120
acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaaataatc    360
tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac    540
ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
ctattgggcg aagtgccggg gcaggatctc ctgtcatctc accttgctcc tgccgagaaa    720
gtatccatca tggctgatgc aatgcggcgg ctgcatacgc ttgatccggc tacctgccca    780
ttcgaccacc aagcgaaaca tcgcatcgag cgagcacgta ctcggatgga agccggtctt    840
gtcgatcagg atgatctgga cgaagagcat caggggctcg cgccagccga actgttcgcc    900
aggctcaagg cgcgcatgcc cgacggcgat gatctcgtcg tgacccatgg cgatgcctgc    960
ttgccgaata tcatggtgga aaatggccgc ttttctggat tcatcgactg tggccggctg   1020
ggtgtggcgg accgctatca ggacatagcg ttggctaccc gtgatattgc tgaagagctt   1080
ggcggcgaat gggctgaccg cttcctcgtg ctttacggta tcgccgctcc cgattcgcag   1140
cgcatcgcct tctatcgcct tcttgacgag ttcttctgag cgggactctg gggttcgaaa   1200
tgaccgacca agcgacgccc aacctgccat cacgagattt cgattccacc gccgccttct   1260
atgaaaggtt gggcttcgga atcgttttcc gggacgccgg ctggatgatc ctccagcgcg   1320
gggatctcat gctggagttc ttcgcccacg gatctctgc ggaacaggcg gtcgaaggtg   1380
ccgatatcat tacgacagca acggccgaca agcacaacgc cacgatcctg agcgacaata   1440
tgatcgggcc cggcgtccac atcaacggcg tcggcggcga ctgccaggc aagaccgaga   1500
tgcaccgcga tatcttgctg cgttcggata ttttcgtgga gttcccgcca cagacccgga   1560
tgatccccga tcgttcaaac atttggcaat aaagtttctt aagattgaat cctgttgccg   1620
gtcttgcgat gattatcata taatttctgt tgaattacgt taagcatgta ataattaaca   1680
tgtaatgcat gacgttattt atgagatggg ttttatgat tagagtcccg caattataca   1740
tttaatacgc gatagaaaac aaaatatagc gcgcaaacta ggataaatta tcgcgcgcgg   1800
tgtcatctat gttactagat cgggcctcct gtcaatgctg gcggcggctc tggtggtggt   1860
tctggtggcg gctctgaggg tggtggctct gagggtggcg gttctgaggg tggcggctct   1920
gagggaggcg gttccggtgg tggctctggt tccggtgatt ttgattatga aagatggca   1980
aacgctaata aggggctat gaccgaaaat gccgatgaaa acgcgctaca gtctgacgct   2040
aaaggcaaac ttgattctgt cgctactgat tacggtgctg ctatcgatgg tttcattggt   2100
gacgtttccg gccttgctaa tggtaatggt gctactggtg attttgctgg ctctaattcc   2160
caaatggctc aagtcggtga cggtgataat tcacctttaa tgaataattt ccgtcaatat   2220
```

-continued

| | |
|---|---|
| ttaccttccc tccctcaatc ggttgaatgt cgcccttttg tctttggccc aatacgcaaa | 2280 |
| ccgcctctcc ccgcgcgttg gccgattcat taatgcagct ggcacgacag gtttcccgac | 2340 |
| tggaaagcgg gcagtgagcg caacgcaatt aatgtgagtt agctcactca ttaggcaccc | 2400 |
| caggctttac actttatgct tccggctcgt atgttgtgtg gaattgtgag cggataacaa | 2460 |
| tttcacacag gaaacagcta tgaccatgat tacgccaagc ttgcatgcct gcagcccaca | 2520 |
| gatggttaga gaggcttacg cagcaggtct catcaagacg atctacccga gcaataatct | 2580 |
| ccaggaaatc aaataccttc caagaaggt taaagatgca gtcaaagat tcaggactaa | 2640 |
| ctgcatcaag aacacagaga agatatatt tctcaagatc agaagtacta ttccagtatg | 2700 |
| gacgattcaa ggcttgcttc acaaaccaag gcaagtaata gagattggag tctctaaaaa | 2760 |
| ggtagttccc actgaatcaa aggccatgga gtcaaagatt caaatagagg acctaacaga | 2820 |
| actcgccgta aagactggcg aacagttcat acagagtctc ttacgactca atgacaagaa | 2880 |
| gaaaatcttc gtcaacatgg tggagcacga cacacttgtc tactccaaaa atatcaaaga | 2940 |
| tacagtctca gaagaccaaa gggcaattga acttttcaa caaagggtaa tatccggaaa | 3000 |
| cctcctcgga ttccattgcc cagctatctg tcactttatt gtgaagatag tggaaaagga | 3060 |
| aggtggctcc tacaaatgcc atcattgcga taaaggaaag gccatcgttg aagatgcctc | 3120 |
| tgccgacagt ggtcccaaag atggaccccc acccacgagg agcatcgtgg aaaaagaaga | 3180 |
| cgttccaacc acgtcttcaa agcaagtgga ttgatgtgat atctccactg acgtaaggga | 3240 |
| tgacgcacaa tcccactatc cttcgcaaga cccttcctct atataaggaa gttcatttca | 3300 |
| tttggagaga acacggggga ctctagagga tccgtccgga attcccgggt cgacccacgc | 3360 |
| gtccgggaga ttcagcgaga taagcaattg gattatctga tgaaaggctt aaggcagctt | 3420 |
| ggtccgcagt tttcttcctt agatgctaat cgaccttggc tttgttactg gattcttcat | 3480 |
| tcaatagctt tgcttgggga gactgtggat gatgaattag aaagcaatgc cattgacttc | 3540 |
| cttggacgct gccagggctc tgaaggtgga tacggtggtg gtcctggcca acttccacat | 3600 |
| cttgcaacta cttatgctgc agtgaatgca cttgttactt taggaggtga caaagccctt | 3660 |
| tcttcaatta atagagaaaa aatgtcttgt ttttttaagac ggatgaagga tacaagtgga | 3720 |
| ggtttcagga tgcatgatat gggagaaatg gatgttcgtg catgctacac tgcaatttcg | 3780 |
| gttgcaagca tcctaaatat tatggatgat gaactcaccc agggcctagg agattacatc | 3840 |
| ttgagttgcc aaacttatga aggtggcatt ggaggggaac ctggctccga agctcacggt | 3900 |
| gggtatacct actgtggttt ggctgctatg attttaatca atgaggtcga ccgtttgaat | 3960 |
| ttggattcat taatgaattg ggctgtacat cgacaaggag tagaaatggg atttcaaggt | 4020 |
| aggacgaaca aattggtcga tggttgctac acattttggc aggcagcccc ttgtgttcta | 4080 |
| ctacaaagat tatattcaac caatgatcat gacgttcatg gatcatcaca tatatcagaa | 4140 |
| gggacaaatg aagaacatca tgctcatgat gaagatgacc ttgaagacag tgatgatgat | 4200 |
| gatgattctg atgaggacaa cgatgaagat tcagtgaatg gtcacagaat ccatcataca | 4260 |
| tccacctaca ttaacaggag aatgcaactg gttttttgata gcctcggctt gcagagatat | 4320 |
| gtactcttgt gctctaagat ccctgacggt ggattcagag acaagccgag gaaacccgt | 4380 |
| gacttctacc acacatgtta ctgcctgagc ggcttgtctg tggctcagca cgcttggtta | 4440 |
| aaagacgagg acactcctcc tttgactcgc gacattatgg gtggctactc gaatctcctt | 4500 |
| gaacctgttc aacttcttca caacattgtc atggatcagt ataatgaagc tatcgagttc | 4560 |

-continued

```
ttctttaaag cagcatgact cgaatttccc cgatcgttca aacatttggc aataaagttt      4620
cttaagattg aatcctgttg ccggtcttgc gatgattatc atataatttc tgttgaatta      4680
cgttaagcat gtaataatta acatgtaatg catgacgtta tttatgagat gggtttttat      4740
gattagagtc ccgcaattat acatttaata cgcgatagaa acaaaatat agcgcgcaaa       4800 ctaggataaa ttatcgcgcg cggtgtcatc tatgttacta gatcgggaat tcactggccg      4860
tcgttttaca acgtcgtgac tgggaaaacc ctggcgttac ccaacttaat cgccttgcag      4920
cacatccccc tttcgccagc tggcgtaata gcgaagaggc ccgcaccgat cgcccttccc      4980
aacagttgcg cagcctgaat ggcgcccgct cctttcgctt tcttcccttc ctttctcgcc      5040
acgttcgccg gctttccccg tcaagctcta atcggggggc tccctttagg gttccgattt     5100
agtgctttac ggcacctcga cccaaaaaa cttgatttgg gtgatggttc acgtagtggg       5160
ccatcgccct gatagacggt ttttcgccct tgacgttgg agtccacgtt ctttaatagt       5220
ggactcttgt tccaaactgg aacaacactc aaccctatct cggctattc ttttgattta      5280 taagggattt tgccgatttc ggaaccacca tcaaacagga ttttcgcctg ctggggcaaa      5340
ccagcgtgga ccgcttgctg caactctctc agggccaggc ggtgaaggc aatcagctgt      5400 tgcccgtctc actggtgaaa agaaaaacca ccccagtaca ttaaaaacgt ccgcaatgtg      5460
ttattaagtt gtctaagcgt caatttgttt acaccacaat atatcctgcc a              5511
```

<210> SEQ ID NO 49
<211> LENGTH: 5635
<212> TYPE: DNA
<213> ORGANISM: Artificial Sequence
<220> FEATURE:
<223> OTHER INFORMATION: Description of Artificial Sequence: Plasmid pBI121-RD29AP-Anti-AtFTB

<400> SEQUENCE: 49

```
gtttaccgc caatatatcc tgtcaaacac tgatagttta aactgaaggc gggaaacgac        60
aatctgatca tgagcggaga attaagggag tcacgttatg accccgccg atgacgcggg       120 acaagccgtt ttacgtttgg aactgacaga accgcaacgt tgaaggagcc actcagccgc      180
gggtttctgg agtttaatga gctaagcaca tacgtcagaa accattattg cgcgttcaaa      240
agtcgcctaa ggtcactatc agctagcaaa tatttcttgt caaaaatgct ccactgacgt      300
tccataaatt cccctcggta tccaattaga gtctcatatt cactctcaat ccaaataatc      360
tgcaccggat ctggatcgtt tcgcatgatt gaacaagatg gattgcacgc aggttctccg      420
gccgcttggg tggagaggct attcggctat gactgggcac aacagacaat cggctgctct      480
gatgccgccg tgttccggct gtcagcgcag gggcgcccgg ttcttttgt caagaccgac       540 ctgtccggtg ccctgaatga actgcaggac gaggcagcgc ggctatcgtg gctggccacg      600
acgggcgttc cttgcgcagc tgtgctcgac gttgtcactg aagcgggaag gactggctg      660 ctattgggcg aagtgccggg gcaggatctc ctgtcatctc accttgctcc tgccgagaaa      720
gtatccatca tggctgatgc aatgcggcgg ctgcatacgc ttgatccggc tacctgccca      780
ttcgaccacc aagcgaaaca tcgcatcgag cgagcacgta ctcggatgga agccggtctt      840
gtcgatcagg atgatctgga cgaagagcat caggggctcg cgccagccga actgttcgcc      900
aggctcaagg cgcgcatgcc cgacggcgat gatctcgtcg tgacccatgg cgatgcctgc      960
ttgccgaata tcatggtgga aaatggccgc ttttctggat tcatcgactg tggccggctg     1020
ggtgtggcgg accgctatca ggacatagcg ttggctaccc gtgatattgc tgaagagctt     1080
```

```
ggcggcgaat gggctgaccg cttcctcgtg ctttacggta tcgccgctcc cgattcgcag    1140
cgcatcgcct tctatcgcct tcttgacgag ttcttctgag cgggactctg ggttcgaaa    1200 tgaccgacca agcgacgccc aacctgccat cacgagattt cgattccacc gccgccttct    1260
atgaaaggtt gggcttcgga atcgttttcc gggacgccgg ctggatgatc ctccagcgcg    1320
gggatctcat gctggagttc ttcgcccacg ggatctctgc ggaacaggcg gtcgaaggtg    1380
ccgatatcat tacgacagca acggccgaca agcacaacgc cacgatcctg agcgacaata    1440
tgatcgggcc cggcgtccac atcaacggcg tcggcggcga ctgcccaggc aagaccgaga    1500
tgcaccgcga tatcttgctg cgttcggata ttttcgtgga gttcccgcca cagacccgga    1560
tgatccccga tcgttcaaac atttggcaat aaagtttctt aagattgaat cctgttgccg    1620
gtcttgcgat gattatcata taatttctgt tgaattacgt taagcatgta ataattaaca    1680
tgtaatgcat gacgttattt atgagatggg ttttatgat tagagtcccg caattataca    1740
tttaatacgc gatagaaaac aaaatatagc gcgcaaacta ggataaatta tcgcgcgcgg    1800
tgtcatctat gttactagat cgggcctcct gtcaatgctg gcggcggctc tggtggtggt    1860
tctggtggcg gctctgaggg tggtggctct gagggtggcg gttctgaggg tggcggctct    1920
gagggaggcg gttccggtgg tggctctggt tccggtgatt ttgattatga aaagatggca    1980
aacgctaata aggggctat gaccgaaaat gccgatgaaa acgcgctaca gtctgacgct    2040
aaaggcaaac ttgattctgt cgctactgat tacggtgctg ctatcgatgg tttcattggt    2100
gacgtttccg gccttgctaa tggtaatggt gctactggtg attttgctgg ctctaattcc    2160
caaatggctc aagtcggtga cggtgataat tcacctttaa tgaataattt ccgtcaatat    2220
ttaccttccc tccctcaatc ggttgaatgt cgcccttttg tctttggccc aatacgcaaa    2280
ccgcctctcc ccgcgcgttg gccgattcat taatgcagct ggcacgacag gtttcccgac    2340
tggaaagcgg gcagtgagcg caacgcaatt aatgtgagtt agctcactca ttaggcaccc    2400
caggctttac actttatgct tccggctcgt atgttgtgtg gaattgtgag cggataacaa    2460
tttcacacag gaaacagcta tgaccatgat tacgccaagc ttgcatgcct gcagggagcc    2520
atagatgcaa ttcaatcaaa ctgaaatttc tgcaagaatc tcaaacacgg agatctcaaa    2580
gtttgaagaa aaatttattt cttcgactca aaacaaactt acgaaattta ggtagaactt    2640
atatacatta tattgtaatt ttttgtaaca aaatgttttt attattatta tagaattta    2700 ctggttaaat taaaaatgaa tagaaaaggt gaattaagag gagagaggag gtaaacattt    2760
tcttctattt tttcatattt tcaggataaa ttattgtaaa agtttacaag atttccattt    2820
gactagtgta aatgaggaat attctctagt aagatcatta tttcatctac ttcttttatc    2880
ttctaccagt agaggaataa acaatattta gctcctttgt aaatacaaat taattttcct    2940
tcttgacatc attcaattt aatttacgt ataaaataaa agatcatacc tattagaacg    3000
attaaggaga aatacaattc gaatgagaag gatgtgccgt tgttataat aaacagccac    3060 acgacgtaaa cgtaaaatga ccacatgatg ggccaataga catggaccga ctactaataa    3120
tagtaagtta cattttagga tggaataaat atcataccga catcagtttt gaaagaaaag    3180
ggaaaaaaag aaaaaataaa taaagatat actaccgaca tgagttccaa aaagcaaaaa    3240 aaagatcaa gccgacacag acacgcgtag agagcaaaat gactttgacg tcacaccacg    3300
aaaacagacg cttcatacgt gtccctttat ctctctcagt ctctctataa acttagtgag    3360
accctcctct gttttactca caaatatgca aactagaaaa caatcatcag gaataaaggg    3420
tttgattact tctattggaa aggactctag aggatccgtc cggaattccc gggtcgaccc    3480
```

-continued

```
acgcgtccgg gagattcagc gagataagca attggattat ctgatgaaag gcttaaggca    3540
gcttggtccg cagttttctt ccttagatgc taatcgacct tggctttgtt actggattct    3600
tcattcaata gctttgcttg gggagactgt ggatgatgaa ttagaaagca atgccattga    3660
cttccttgga cgctgccagg gctctgaagg tggatacggt ggtggtcctg gccaacttcc    3720
acatcttgca actacttatg ctgcagtgaa tgcacttgtt actttaggag gtgacaaagc    3780
cctttcttca attaatagag aaaaaatgtc ttgttttttta agacggatga aggatacaag    3840
tggaggtttc aggatgcatg atatgggaga atggatgtt cgtgcatgct acactgcaat    3900
ttcggttgca agcatcctaa atattatgga tgatgaactc acccagggcc taggagatta    3960
catcttgagt tgccaaactt atgaaggtgg cattggaggg gaacctggct ccgaagctca    4020
cggtgggtat acctactgtg gtttggctgc tatgatttta atcaatgagg tcgaccgttt    4080
gaatttggat tcattaatga attgggctgt acatcgacaa ggagtagaaa tgggatttca    4140
aggtaggacg aacaaattgg tcgatggttg ctacacattt tggcaggcag ccccttgtgt    4200
tctactacaa agattatatt caaccaatga tcatgacgtt catggatcat cacatatatc    4260
agaagggaca aatgaagaac atcatgctca tgatgaagat gaccttgaag acagtgatga    4320
tgatgatgat tctgatgagg acaacgatga agattcagtg aatggtcaca gaatccatca    4380
tacatccacc tacattaaca ggagaatgca actggttttt gatagcctcg gcttgcagag    4440
atatgtactc ttgtgctcta agatccctga cggtggattc agagacaagc cgaggaaacc    4500
ccgtgacttc taccacacat gttactgcct gagcggcttg tctgtggctc agcacgcttg    4560
gttaaaagac gaggacactc ctcctttgac tcgcgacatt atgggtggct actcgaatct    4620
ccttgaacct gttcaacttc ttcacaaacat tgtcatggat cagtataatg aagctatcga    4680
gttcttcttt aaagcagcat gactcgaatt tccccgatcg ttcaaacatt tggcaataaa    4740
gtttcttaag attgaatcct gttgccggtc ttgcgatgat tatcatataa tttctgttga    4800
attacgttaa gcatgtaata attaacatgt aatgcatgac gttatttatg agatgggttt    4860
ttatgattag agtcccgcaa ttatacattt aatacgcgat agaaaacaaa atatagcgcg    4920
caaactagga taaattatcg cgcgcggtgt catctatgtt actagatcgg gaattcactg    4980
gccgtcgttt tacaacgtcg tgactgggaa accctggcg ttacccaact taatcgcctt    5040
gcagcacatc ccccttttcgc cagctggcgt aatagcgaag aggcccgcac cgatcgccct    5100
tcccaacagt tgcgcagcct gaatggcgcc cgctcctttc gctttcttcc cttcctttct    5160
cgccacgttc gccggctttc cccgtcaagc tctaaatcgg gggctccctt tagggttccg    5220
atttagtgct ttacggcacc tcgacccccaa aaaacttgat ttgggtgatg gttcacgtag    5280
tgggccatcg ccctgataga cggttttttcg ccctttgacg ttggagtcca cgttctttaa    5340
tagtggactc ttgttccaaa ctggaacaac actcaaccct atctcgggct attcttttga    5400
tttataaggg attttgccga tttcggaacc accatcaaac aggattttcg cctgctgggg    5460
caaaccagcg tggaccgctt gctgcaactc tctcagggcc aggcggtgaa gggcaatcag    5520
ctgttgcccg tctcactggt gaaaagaaaa accacccccag tacattaaaa acgtccgcaa    5580
tgtgttatta agttgtctaa gcgtcaattt gtttacacca caatatatcc tgcca         5635
```

<210> SEQ ID NO 50
<211> LENGTH: 6299
<212> TYPE: DNA
<213> ORGANISM: Artificial Sequence
<220> FEATURE:

-continued

<223> OTHER INFORMATION: Description of Artificial Sequence: Plasmid
pBI121-35S-HP-AtFTB

<400> SEQUENCE: 50

| | | | | | |
|---|---|---|---|---|---|
| gtttacccgc | caatatatcc | tgtcaaacac | tgatagttta | aactgaaggc | gggaaacgac | 60 |
| aatctgatca | tgagcggaga | attaagggag | tcacgttatg | accccgccg | atgacgcggg | 120 |
| acaagccgtt | ttacgtttgg | aactgacaga | accgcaacgt | tgaaggagcc | actcagccgc | 180 |
| gggtttctgg | agtttaatga | gctaagcaca | tacgtcagaa | accattattg | cgcgttcaaa | 240 |
| agtcgcctaa | ggtcactatc | agctagcaaa | tatttcttgt | caaaaatgct | ccactgacgt | 300 |
| tccataaatt | ccctcggta | tccaattaga | gtctcatatt | cactctcaat | ccaaataatc | 360 |
| tgcaccggat | ctggatcgtt | tcgcatgatt | gaacaagatg | gattgcacgc | aggttctccg | 420 |
| gccgcttggg | tggagaggct | attcggctat | gactgggcac | aacagacaat | cggctgctct | 480 |
| gatgccgccg | tgttccggct | gtcagcgcag | gggcgcccgg | ttcttttgt | caagaccgac | 540 |
| ctgtccggtg | ccctgaatga | actgcaggac | gaggcagcgc | ggctatcgtg | gctggccacg | 600 |
| acgggcgttc | cttgcgcagc | tgtgctcgac | gttgtcactg | aagcgggaag | ggactggctg | 660 |
| ctattgggcg | aagtgccggg | gcaggatctc | ctgtcatctc | accttgctcc | tgccgagaaa | 720 |
| gtatccatca | tggctgatgc | aatgcggcgg | ctgcatacgc | ttgatccggc | tacctgccca | 780 |
| ttcgaccacc | aagcgaaaca | tcgcatcgag | cgagcacgta | ctcggatgga | agccggtctt | 840 |
| gtcgatcagg | atgatctgga | cgaagagcat | caggggctcg | cgccagccga | actgttcgcc | 900 |
| aggctcaagg | cgcgcatgcc | cgacggcgat | gatctcgtcg | tgacccatgg | cgatgcctgc | 960 |
| ttgccgaata | tcatggtgga | aaatggccgc | ttttctggat | tcatcgactg | tggccggctg | 1020 |
| ggtgtggcgg | accgctatca | ggacatagcg | ttggctaccc | gtgatattgc | tgaagagctt | 1080 |
| ggcggcgaat | gggctgaccg | cttcctcgtg | ctttacggta | tcgccgctcc | cgattcgcag | 1140 |
| cgcatcgcct | tctatcgcct | tcttgacgag | ttcttctgag | cgggactctg | gggttcgaaa | 1200 |
| tgaccgacca | agcgacgccc | aacctgccat | cacgagattt | cgattccacc | gccgccttct | 1260 |
| atgaaaggtt | gggcttcgga | atcgttttcc | gggacgccgg | ctggatgatc | ctccagcgcg | 1320 |
| gggatctcat | gctggagttc | ttcgcccacg | ggatctctgc | ggaacaggcg | gtcgaaggtg | 1380 |
| ccgatatcat | tacgacagca | acggccgaca | agcacaacgc | cacgatcctg | agcgacaata | 1440 |
| tgatcgggcc | cggcgtccac | atcaacggcg | tcggcggcga | ctgcccaggc | aagaccgaga | 1500 |
| tgcaccgcga | tatcttgctg | cgttcggata | ttttcgtgga | gttcccgcca | cagacccgga | 1560 |
| tgatccccga | tcgttcaaac | atttggcaat | aaagtttctt | aagattgaat | cctgttgccg | 1620 |
| gtcttgcgat | gattatcata | taatttctgt | tgaattacgt | taagcatgta | ataattaaca | 1680 |
| tgtaatgcat | gacgttattt | atgagatggg | tttttatgat | tagagtcccg | caattataca | 1740 |
| tttaatacgc | gatagaaaac | aaaatatagc | gcgcaaacta | ggataaatta | tcgcgcgcgg | 1800 |
| tgtcatctat | gttactagat | cgggcctcct | gtcaatgctg | gcggcggctc | tggtggtggt | 1860 |
| tctggtggcg | gctctgaggg | tggtggctct | gagggtggcg | gttctgaggg | tggcggctct | 1920 |
| gagggaggcg | gttccggtgg | tggctctggt | tccggtgatt | ttgattatga | aaagatggca | 1980 |
| aacgctaata | aggggctat | gaccgaaaat | gccgatgaaa | acgcgctaca | gtctgacgct | 2040 |
| aaaggcaaac | ttgattctgt | cgctactgat | tacggtgctg | ctatcgatgg | tttcattggt | 2100 |
| gacgtttccg | gccttgctaa | tggtaatggt | gctactggtg | attttgctgg | ctctaattcc | 2160 |
| caaatggctc | aagtcggtga | cggtgataat | tcacctttaa | tgaataattt | ccgtcaatat | 2220 |

```
ttaccttccc tccctcaatc ggttgaatgt cgcccttttg tctttggccc aatacgcaaa   2280
ccgcctctcc ccgcgcgttg gccgattcat taatgcagct ggcacgacag gtttcccgac   2340
tggaaagcgg gcagtgagcg caacgcaatt aatgtgagtt agctcactca ttaggcaccc   2400
caggctttac actttatgct tccggctcgt atgttgtgtg gaattgtgag cggataacaa   2460
tttcacacag gaaacagcta tgaccatgat tacgccaagc ttgcatgcct gcagcccaca   2520
gatggttaga gaggcttacg cagcaggtct catcaagacg atctacccga gcaataatct   2580
ccaggaaatc aaatacCttc ccaagaaggt taaagatgca gtcaaagat tcaggactaa    2640
ctgcatcaag aacacagaga aagatatatt tctcaagatc agaagtacta ttccagtatg   2700
gacgattcaa ggcttgcttc acaaccaag gcaagtaata gagattggag tctctaaaaa    2760
ggtagttccc actgaatcaa aggccatgga gtcaaagatt caaatagagg acctaacaga   2820
actcgccgta aagactggcg aacagttcat acagagtctc ttacgactca atgacaagaa   2880
gaaaatcttc gtcaacatgg tggagcacga cacacttgtc tactccaaaa atatcaaaga   2940
tacagtctca gaagaccaaa gggcaattga acttttcaa caaagggtaa tatccggaaa    3000
cctcctcgga ttccattgcc cagctatctg tcactttatt gtgaagatag tggaaaagga   3060
aggtggctcc tacaaatgcc atcattgcga taaaggaaag gccatcgttg aagatgcctc   3120
tgccgacagt ggtcccaaag atggaccccc acccacgagg agcatcgtgg aaaaagaaga   3180
cgttccaacc acgtcttcaa agcaagtgga ttgatgtgat atctccactg acgtaaggga   3240
tgacgcacaa tcccactatc cttcgcaaga cccttcctct atataaggaa gttcatttca   3300
tttggagaga cacgggggga ctctagagga tcctcctcct aggccctggg tgagttcatc   3360
atccataata tttaggatgc ttgcaaccga aattgcagtg tagcatgcac gaacatccat   3420
ttctcccata tcatgcatcc tgaaacctcc acttgtatcc ttcatccgtc ttaaaaaaca   3480
agacattttt tctctattaa ttgaagaaag ggctttgtca cctcctaaag taacaagtgc   3540
attcactgca gcataagtag ttgcaagatg tggaagttgg ccaggaccac caccgtatcc   3600
accttcagag ccctggcagc gtccaaggaa gtcaatggca ttgctttcta attcatcatc   3660
cacagtctcc ccaagcaaag ctattgaatg aagaatccag taacaaagcc aaggtcgatt   3720
agcatctaag gaagaaaact gcggaccaag ctgccttaag cctttcatca gataatccaa   3780
ttgcttatct cgctgaatct cccggacgcg tgggtcgacc cgggaattcc ggacgaggat   3840
ccccatctac ccgcttcgcg tcggcatccg gtcagtggca gtgaagggcg aacagttcct   3900
gattaaccac aaaccgttct actttactgg ctttggtcgt catgaagatg cggacttgcg   3960
tggcaaagga ttcgataacg tgctgatggt gcacgaccac gcattaatgg actggattgg   4020
ggccaactcc taccgtacct cgcattaccc ttacgctgaa gagatgctcg actgggcaga   4080
tgaacatggc atcgtggtga ttgatgaaac tgctgctgtc ggcttttcgc tctctttagg   4140
cattggtttc gaagcgggca acaagccgaa agaactgtac agcgaagagg cagtcaacgg   4200
ggaaactcag caagcgcact acaggcgat taagagctg atagcgcgtg acaaaaacca    4260
cccaagcgtg gtgatgtgga gtattgccaa cgaaccggat acccgtccgc aaggtgcacg   4320
ggaatatttc gcgccactgg cggaagcaac gcgtaaactc gacccgacgc gtccgatcac   4380
ctgcgtcaat gtaatgttct cgacgctca caccgatacc atcagcgatc tctttgatgt    4440
gctgtgcctg aaccgttatt acggatggta tgtccaaagc ggcgatttgg aaacggcaga   4500
gaaggtactg gaaaagaac ttctggcctg cggagagaaa ctgtacaccg acatgtggag    4560
tgaagagtat cagtgtgcat ggctggatat gtatcaccgc gtctttgatc gcgtcagcgc   4620
```

```
cgtcgtcggt gaacaggtat ggaatttcgc cgattttgcg acctcgcaag gcatattgcg    4680
cgttggcggt aacaagaaag ggatcttcac tcgcgaccgc aaaccgaagt cggcggcttt    4740
tctgctgcaa aaacgctgga ctggcatgaa cttcggtgaa aaaccgcagc agggaggcaa    4800
acaatgaatc aacaactctc ctggcgcacc atcgtcggct acagcctcgg gaattgctac    4860
cgagctcgtc cggaattccc gggtcgacca acgcgtccgg gagattcagc gagataagca    4920
attggattat ctgatgaaag gcttaaggca gcttggtccg cagttttctt ccttagatgc    4980
taatcgacct tggctttgtt actggattct tcattcaata gctttgcttg gggagactgt    5040
ggatgatgaa ttagaaagca atgccattga cttccttgga cgctgccagg gctctgaagg    5100
tggatacggt ggtggtcctg gccaacttcc acatcttgca actacttatg ctgcagtgaa    5160
tgcacttgtt actttaggag gtgacaaagc cctttcttca attaatagag aaaaaatgtc    5220 ttgttttta agacggatga aggatacaag tggaggtttc aggatgcatg atatgggaga    5280
aatggatgtt cgtgcatgct acactgcaat ttcggttgca agcatcctaa atattatgga    5340
tgatgaactc acccagggcc taggagctcg aatttccccg atcgttcaaa catttggcaa    5400
taaagtttct taagattgaa tcctgttgcc ggtcttgcga tgattatcat ataatttctg    5460
ttgaattacg ttaagcatgt aataattaac atgtaatgca tgacgttatt tatgagatgg    5520 gttttttatga ttagagtccc gcaattatac atttaatacg cgatagaaaa caaaatatag    5580
cgcgcaaact aggataaatt atcgcgcgcg gtgtcatcta tgttactaga tcgggaattc    5640
actggccgtc gttttacaac gtcgtgactg ggaaaaccct ggcgttaccc aacttaatcg    5700
ccttgcagca catccccctt tcgccagctg gcgtaatagc gaagaggccc gcaccgatcg    5760
cccttcccaa cagttgcgca gcctgaatgg cgcccgctcc tttcgctttc ttcccttcct    5820
ttctcgccac gttcgccggc tttccccgtc aagctctaaa tcggggggctc cctttagggt    5880 tccgatttag tgctttacgg cacctcgacc ccaaaaaact tgatttgggt gatggttcac    5940
gtagtgggcc atcgccctga tagacggttt ttcgcccttt gacgttggag tccacgttct    6000
ttaatagtgg actcttgttc caaactggaa caacactcaa ccctatctcg gctattctt    6060 ttgatttata agggattttg ccgatttcgg aaccaccatc aaacaggatt ttcgcctgct    6120
ggggcaaacc agcgtggacc gcttgctgca actctctcag gccaggcgg tgaagggcaa    6180 tcagctgttg cccgtctcac tggtgaaaag aaaaaccacc ccagtacatt aaaaacgtcc    6240
gcaatgtgtt attaagttgt ctaagcgtca atttgtttac accacaatat atcctgcca    6299
```

<210> SEQ ID NO 51
<211> LENGTH: 6423
<212> TYPE: DNA
<213> ORGANISM: Artificial Sequence
<220> FEATURE:
<223> OTHER INFORMATION: Description of Artificial Sequence: Plasmid pBI121-RD29AP-HP-AtFTB

<400> SEQUENCE: 51

```
gtttacccgc caatatatcc tgtcaaacac tgatagttta aactgaaggc gggaaacgac      60
aatctgatca tgagcggaga attaagggag tcacgttatg accccgccg atgacgcggg     120 acaagccgtt ttacgtttgg aactgacaga accgcaacgt tgaaggagcc actcagccgc     180
gggtttctgg agtttaatga gctaagcaca tacgtcagaa accattattg cgcgttcaaa     240
agtcgcctaa ggtcactatc agctagcaaa tatttcttgt caaaaatgct ccactgacgt     300
tccataaatt cccctcggta tccaattaga gtctcatatt cactctcaat ccaaataatc     360
```

-continued

```
tgcaccggat ctggatcgtt tcgcatgatt gaacaagatg gattgcacgc aggttctccg      420
gccgcttggg tggagaggct attcggctat gactgggcac aacagacaat cggctgctct      480
gatgccgccg tgttccggct gtcagcgcag gggcgcccgg ttcttttttgt caagaccgac     540 ctgtccggtg ccctgaatga actgcaggac gaggcagcgc ggctatcgtg gctggccacg      600
acgggcgttc cttgcgcagc tgtgctcgac gttgtcactg aagcgggaag ggactggctg      660
ctattgggcg aagtgccggg gcaggatctc ctgtcatctc accttgctcc tgccgagaaa      720
gtatccatca tggctgatgc aatgcggcgg ctgcatacgc ttgatccggc tacctgccca      780
ttcgaccacc aagcgaaaca tcgcatcgag cgagcacgta ctcggatgga agccggtctt      840
gtcgatcagg atgatctgga cgaagagcat caggggctcg cgccagccga actgttcgcc      900
aggctcaagg cgcgcatgcc cgacggcgat gatctcgtcg tgacccatgg cgatgcctgc      960
ttgccgaata tcatggtgga aaatggccgc ttttctggat tcatcgactg tggccggctg      1020
ggtgtggcgg accgctatca ggacatagcg ttggctaccc gtgatattgc tgaagagctt      1080
ggcggcgaat gggctgaccg cttcctcgtg ctttacggta tcgccgctcc cgattcgcag      1140
cgcatcgcct tctatcgcct tcttgacgag ttcttctgag cgggactctg gggttcgaaa      1200
tgaccgacca agcgacgccc aacctgccat cacgagattt cgattccacc gccgccttct      1260
atgaaaggtt gggcttcgga atcgttttcc gggacgccgg ctggatgatc ctccagcgcg      1320
gggatctcat gctggagttc ttcgcccacg ggatctctgc ggaacaggcg gtcgaaggtg      1380
ccgatatcat tacgacagca acggccgaca agcacaacgc cacgatcctg agcgacaata      1440
tgatcgggcc cggcgtccac atcaacggcg tcggcggcga ctgcccaggc aagaccgaga      1500
tgcaccgcga tatcttgctg cgttcggata ttttcgtgga gttcccgcca cagcccggaa      1560
tgatccccga tcgttcaaac atttggcaat aaagtttctt aagattgaat cctgttgccg      1620
gtcttgcgat gattatcata taatttctgt tgaattacgt taagcatgta ataattaaca      1680
tgtaatgcat gacgttattt atgagatggg tttttatgat tagagtcccg caattataca      1740
tttaatacgc gatagaaaac aaaatatagc gcgcaaacta ggataaatta tcgcgcgcgg      1800
tgtcatctat gttactagat cgggcctcct gtcaatgctg gcggcggctc tggtggtggt      1860
tctggtggcg gctctgaggg tggtggctct gagggtggcg gttctgaggg tggcggctct      1920
gagggaggcg gttccggtgg tggctctggt tccggtgatt ttgattatga aagatggca       1980 aacgctaata aggggctat gaccgaaaat gccgatgaaa acgcgctaca gtctgacgct      2040
aaaggcaaac ttgattctgt cgctactgat tacggtgctg ctatcgatgg tttcattggt      2100
gacgtttccg gccttgctaa tggtaatggt gctactggtg attttgctgg ctctaattcc      2160
caaatggctc aagtcggtga cggtgataat tcacctttaa tgaataattt ccgtcaatat      2220
ttaccttccc tccctcaatc ggttgaatgt cgccctttttg tctttggccc aatacgcaaa      2280
ccgcctctcc ccgcgcgttg gccgattcat taatgcagct ggcacgacag gtttcccgac      2340
tggaaagcgg gcagtgagcg caacgcaatt aatgtgagtt agctcactca ttaggcaccc      2400
caggctttac actttatgct tccggctcgt atgttgtgtg gaattgtgag cggataacaa      2460
tttcacacag gaaacagcta tgaccatgat tacgccaagc ttgcatgcct gcagggagcc      2520
atagatgcaa ttcaatcaaa ctgaaatttc tgcaagaatc tcaaacacgg agatctcaaa      2580
gtttgaaaga aaatttattt cttcgactca aacaaacttt acgaaattta ggtagaactt      2640
atatacatta tattgtaatt ttttgtaaca aaatgttttt attattatta tagaattta       2700
```

```
ctggttaaat taaaaatgaa tagaaaaggt gaattaagag gagagaggag gtaaacattt    2760
tcttctattt tttcatattt tcaggataaa ttattgtaaa agtttacaag atttccattt    2820
gactagtgta aatgaggaat attctctagt aagatcatta tttcatctac ttcttttatc    2880
ttctaccagt agaggaataa acaatattta gctcctttgt aaatacaaat taattttcct    2940
tcttgacatc attcaatttt aattttacgt ataaaataaa agatcatacc tattagaacg    3000
attaaggaga aatacaattc gaatgagaag gatgtgccgt ttgttataat aaacagccac    3060
acgacgtaaa cgtaaaatga ccacatgatg ggccaataga catggaccga ctactaataa    3120
tagtaagtta catttttagga tggaataaat atcataccga catcagtttt gaaagaaaag    3180
ggaaaaaaag aaaaaataaa taaaagatat actaccgaca tgagttccaa aaagcaaaaa    3240
aaaagatcaa gccgacacag acacgcgtag agagcaaaat gactttgacg tcacaccacg    3300
aaaacagacg cttcatacgt gtcccttttat ctctctcagt ctctctataa acttagtgag    3360
accctcctct gttttactca caaatatgca aactagaaaa caatcatcag gaataaaggg    3420
tttgattact tctattggaa aggactctag aggatcctcc tcctaggccc tgggtgagtt    3480
catcatccat aatatttagg atgcttgcaa ccgaaattgc agtgtagcat gcacgaacat    3540
ccatttctcc catatcatgc atcctgaaac ctccacttgt atccttcatc cgtcttaaaa    3600
aacaagacat tttttctcta ttaattgaag aaagggcttt gtcacctcct aaagtaacaa    3660
gtgcattcac tgcagcataa gtagttgcaa gatgtggaag ttggccagga ccaccaccgt    3720
atccaccttc agagccctgg cagcgtccaa ggaagtcaat ggcattgctt tctaattcat    3780
catccacagt ctccccaagc aaagctattg aatgaagaat ccagtaacaa agccaaggtc    3840
gattagcatc taaggaagaa aactgcggac caagctgcct taagcctttc atcagataat    3900
ccaattgctt atctcgctga atctcccgga cgcgtgggtc gacccgggaa ttccggacga    3960
ggatccccat ctacccgctt cgcgtcggca tccggtcagt ggcagtgaag ggcgaacagt    4020
tcctgattaa ccacaaaccg ttctacttta ctggctttgg tcgtcatgaa gatgcggact    4080
tgcgtggcaa aggattcgat aacgtgctga tggtgcacga ccacgcatta atggactgga    4140
ttggggccaa ctcctaccgt acctcgcatt acccttacgc tgaagagatg ctcgactggg    4200
cagatgaaca tggcatcgtg gtgattgatg aaactgctgc tgtcggcttt tcgctctctt    4260
taggcattgg tttcgaagcg ggcaacaagc cgaaagaact gtacagcgaa gaggcagtca    4320
acggggaaac tcagcaagcg cacttacagg cgattaaaga gctgatagcg cgtgacaaaa    4380
accacccaag cgtggtgatg tggagtattg ccaacgaacc ggataccgt ccgcaaggtg     4440 cacgggaata tttcgcgcca ctggcggaag caacgcgtaa actcgacccg acgcgtccga    4500
tcacctgcgt caatgtaatg ttctgcgacg ctcacaccga taccatcagc gatctctttg    4560
atgtgctgtg cctgaaccgt tattacggat ggtatgtcca agcggcgat ttggaaacgg     4620 cagagaaggt actggaaaaa gaacttctgg cctggcagga gaaactgtac accgacatgt    4680
ggagtgaaga gtatcagtgt gcatggctgg atatgtatca ccgcgtcttt gatcgcgtca    4740
gcgccgtcgt cggtgaacag gtatggaatt tcgccgattt tgcgacctcg caaggcatat    4800
tgcgcgttgg cggtaacaag aaagggatct tcactcgcga ccgcaaaccg aagtcggcgg    4860
cttttctgct gcaaaaacgc tggactgcat gaacttcgg tgaaaaccg cagcagggag     4920 gcaaacaatg aatcaacaac tctcctggcg caccatcgtc ggctacagcc tcgggaattg    4980
ctaccgagct cgtccggaat tcccgggtcg acccacgcgt ccgggagatt cagcgagata    5040
agcaattgga ttatctgatg aaaggcttaa ggcagcttgg tccgcagttt tcttccttag    5100
```

```
atgctaatcg accttggctt tgttactgga ttcttcattc aatagctttg cttggggaga    5160
ctgtggatga tgaattagaa agcaatgcca ttgacttcct tggacgctgc cagggctctg    5220
aaggtggata cggtggtggt cctggccaac ttccacatct tgcaactact tatgctgcag    5280
tgaatgcact tgttacttta ggaggtgaca agcccttttc ttcaattaat agagaaaaaa    5340
tgtcttgttt tttaagacgg atgaaggata caagtggagg tttcaggatg catgatatgg    5400
gagaaatgga tgttcgtgca tgctacactg caatttcggt tgcaagcatc ctaaatatta    5460
tggatgatga actcacccag ggcctaggag ctcgaatttc cccgatcgtt caaacatttg    5520
gcaataaagt ttcttaagat tgaatcctgt tgccggtctt gcgatgatta tcatataatt    5580
tctgttgaat tacgttaagc atgtaataat taacatgtaa tgcatgacgt tatttatgag    5640
atgggttttt atgattagag tcccgcaatt atacatttaa tacgcgatag aaaacaaaat    5700
atagcgcgca aactaggata aattatcgcg cgcggtgtca tctatgttac tagatcggga    5760
attcactggc cgtcgtttta caacgtcgtg actgggaaaa ccctggcgtt acccaactta    5820
atcgccttgc agcacatccc cctttcgcca gctggcgtaa tagcgaagag gcccgcaccg    5880 atcgccttc ccaacagttg cgcagcctga atggcgcccg ctcctttcgc tttcttccct    5940
tcctttctcg ccacgttcgc cggctttccc cgtcaagctc taaatcgggg gctcccttta    6000
gggttccgat ttagtgcttt acggcacctc gaccccaaaa aacttgattt gggtgatggt    6060
tcacgtagtg ggccatcgcc ctgatagacg gttttcgcc ctttgacgtt ggagtccacg    6120
ttctttaata gtggactctt gttccaaact ggaacaacac tcaaccctat ctcgggctat    6180
tcttttgatt tataagggat tttgccgatt tcggaaccac catcaaacag gattttcgcc    6240
tgctggggca aaccagcgtg gaccgcttgc tgcaactctc tcagggccag gcggtgaagg    6300
gcaatcagct gttgcccgtc tcactggtga aaagaaaaac caccccagta cattaaaaac    6360
gtccgcaatg tgttattaag ttgtctaagc gtcaatttgt ttacaccaca atatatcctg    6420
cca                                                                 6423
```

<210> SEQ ID NO 52
<211> LENGTH: 5715
<212> TYPE: DNA
<213> ORGANISM: Artificial Sequence
<220> FEATURE:
<223> OTHER INFORMATION: Description of Artificial Sequence: Plasmid
      pBI121-35S-AtFTB

<400> SEQUENCE: 52

```
gtttacccgc caatatatcc tgtcaaacac tgatagttta aactgaaggc gggaaacgac     60
aatctgatca tgagcggaga attaagggag tcacgttatg accccgccg atgacgcggg    120 acaagccgtt ttacgtttgg aactgacaga accgcaacgt tgaaggagcc actcagccgc    180
gggtttctgg agtttaatga gctaagcaca tacgtcagaa accattattg cgcgttcaaa    240
agtcgcctaa ggtcactatc agctagcaaa tatttcttgt caaaaatgct ccactgacgt    300
tccataaatt cccctcggta tccaattaga gtctcatatt cactctcaat ccaataatc    360 tgcaccggat ctggatcgtt tcgcatgatt gaacaagatg gattgcacgc aggttctccg    420
gccgcttggg tggagaggct attcggctat gactgggcac aacagacaat cggctgctct    480
gatgccgccg tgttccggct gtcagcgcag gggcgcccgg ttcttttgt caagaccgac    540 ctgtccggtg ccctgaatga actgcaggac gaggcagcgc ggctatcgtg gctggccacg    600
acgggcgttc cttgcgcagc tgtgctcgac gttgtcactg aagcgggaag ggactggctg    660
```

-continued

| | |
|---|---|
| ctattgggcg aagtgccggg gcaggatctc ctgtcatctc accttgctcc tgccgagaaa | 720 |
| gtatccatca tggctgatgc aatgcggcgg ctgcatacgc ttgatccggc tacctgccca | 780 |
| ttcgaccacc aagcgaaaca tcgcatcgag cgagcacgta ctcggatgga agccggtctt | 840 |
| gtcgatcagg atgatctgga cgaagagcat caggggctcg cgccagccga actgttcgcc | 900 |
| aggctcaagg cgcgcatgcc cgacggcgat gatctcgtcg tgacccatgg cgatgcctgc | 960 |
| ttgccgaata tcatggtgga aaatggccgc ttttctggat tcatcgactg tggccggctg | 1020 |
| ggtgtggcgg accgctatca ggacatagcg ttggctaccc gtgatattgc tgaagagctt | 1080 |
| ggcggcgaat gggctgaccg cttcctcgtg ctttacggta tcgccgctcc cgattcgcag | 1140 |
| cgcatcgcct tctatcgcct tcttgacgag ttcttctgag cgggactctg gggttcgaaa | 1200 |
| tgaccgacca agcgacgccc aacctgccat cacgagattt cgattccacc gccgccttct | 1260 |
| atgaaaggtt gggcttcgga atcgttttcc gggacgccgg ctggatgatc ctccagcgcg | 1320 |
| gggatctcat gctggagttc ttcgcccacg ggatctctgc ggaacaggcg gtcgaaggtg | 1380 |
| ccgatatcat tacgcagca acggccgaca agcacaacgc cacgatcctg agcgacaata | 1440 |
| tgatcgggcc cggcgtccac atcaacggcg tcggcggcga ctgcccaggc aagaccgaga | 1500 |
| tgcaccgcga tatcttgctg cgttcggata ttttcgtgga gttcccgcca cagacccgga | 1560 |
| tgatccccga tcgttcaaac atttggcaat aaagtttctt aagattgaat cctgttgccg | 1620 |
| gtcttgcgat gattatcata taatttctgt tgaattacgt taagcatgta ataattaaca | 1680 |
| tgtaatgcat gacgttattt atgagatggg tttttatgat tagagtcccg caattataca | 1740 |
| tttaatacgc gatagaaaac aaaatatagc gcgcaaacta ggataaatta tcgcgcgcgg | 1800 |
| tgtcatctat gttactagat cgggcctcct gtcaatgctg gcggcggctc tggtggtggt | 1860 |
| tctggtggcg gctctgaggg tggtggctct gagggtggcg gttctgaggg tggcggctct | 1920 |
| gagggaggcg gttccggtgg tggctctggt tccggtgatt ttgattatga aaagatggca | 1980 |
| aacgctaata aggggggctat gaccgaaaat gccgatgaaa acgcgctaca gtctgacgct | 2040 |
| aaaggcaaac ttgattctgt cgctactgat tacggtgctg ctatcgatgg tttcattggt | 2100 |
| gacgtttccg gccttgctaa tggtaatggt gctactggtg attttgctgg ctctaattcc | 2160 |
| caaatggctc aagtcggtga cggtgataat tcacctttaa tgaataattt ccgtcaatat | 2220 |
| ttaccttccc tccctcaatc ggttgaatgt cgcccttttg tctttggccc aatacgcaaa | 2280 |
| ccgcctctcc ccgcgcgttg gccgattcat taatgcagct ggcacgacag gtttcccgac | 2340 |
| tggaaagcgg gcagtgagcg caacgcaatt aatgtgagtt agctcactca ttaggcaccc | 2400 |
| caggctttac actttatgct tccggctcgt atgttgtgtg gaattgtgag cggataacaa | 2460 |
| tttcacacag gaaacagcta tgaccatgat tacgccaagc ttgcatgcct gcagcccaca | 2520 |
| gatggttaga gaggcttacg cagcaggtct catcaagacg atctacccga gcaataatct | 2580 |
| ccaggaaatc aaataccttc caagaaggt taaagatgca gtcaaaagat tcaggactaa | 2640 |
| ctgcatcaag aacacagaga aagatatatt tctcaagatc agaagtacta ttccagtatg | 2700 |
| gacgattcaa ggcttgcttc acaaaccaag gcaagtaata gagattggag tctctaaaaa | 2760 |
| ggtagttccc actgaatcaa aggccatgga gtcaaagatt caaatagagg acctaacaga | 2820 |
| actcgccgta aagactggcg aacagttcat acagagtctc ttacgactca atgacaagaa | 2880 |
| gaaaatcttc gtcaacatgg tggagcacga cacacttgtc tactccaaaa atatcaaaga | 2940 |
| tacagtctca gaagaccaaa gggcaattga gacttttcaa caaagggtaa tatccggaaa | 3000 |

-continued

```
cctcctcgga ttccattgcc cagctatctg tcactttatt gtgaagatag tggaaaagga    3060
aggtggctcc tacaaatgcc atcattgcga taaaggaaag gccatcgttg aagatgcctc    3120
tgccgacagt ggtcccaaag atggaccccc acccacgagg agcatcgtgg aaaaagaaga    3180
cgttccaacc acgtcttcaa agcaagtgga ttgatgtgat atctccactg acgtaaggga    3240
tgacgcacaa tcccactatc cttcgcaaga cccttcctct atataaggaa gttcatttca    3300
tttggagaga acacggggga ctctagagga tccatgccag tagtaacccg cttgattcgt    3360
ttgaagtgtg tagggctcag acttgaccgg agtggactca atcggcgaat ctgtcacgga    3420 ggacacggg aatcaacgcg gcggagagtg atggaagagc tttcaagcct aaccgtgagt    3480
cagcgcgagc aatttctggt ggagaacgat gtgttcggga tctataatta cttcgacgcc    3540
agcgacgttt ctactcaaaa atacatgatg gagattcagc gagataagca attggattat    3600
ctgatgaaag gcttaaggca gcttggtccg cagttttctt ccttagatgc taatcgacct    3660
tggctttgtt actggattct tcattcaata gctttgcttg gggagactgt ggatgatgaa    3720
ttagaaagca atgccattga cttccttgga cgctgccagg gctctgaagg tggatacggt    3780
ggtggtcctg gccaacttcc acatcttgca actacttatg ctgcagtgaa tgcacttgtt    3840
actttaggag gtgacaaagc cctttcttca attaatagag aaaaaatgtc ttgttttta    3900 agacggatga aggatacaag tggaggtttc aggatgcatg atatgggaga atggatgtt    3960 cgtgcatgct acactgcaat tcggttgca agcatcctaa atattatgga tgatgaactc    4020
acccagggcc taggagatta catcttgagt tgccaaactt atgaaggtgg cattggaggg    4080
gaacctggct ccgaagctca cggtgggtat acctactgtg gtttggctgc tatgatttta    4140
atcaatgagg tcgaccgttt gaatttggat tcattaatga attgggctgt acatcgacaa    4200
ggagtagaaa tgggatttca aggtaggacg aacaaattgg tcgatggttg ctacacattt    4260
tggcaggcag ccccttgtgt tctactacaa agattatatt caaccaatga tcatgacgtt    4320
catggatcat cacatatatc agaagggaca aatgaagaac atcatgctca tgatgaagat    4380
gaccttgaag acagtgatga tgatgatgat tctgatgagg acaacgatga agattcagtg    4440
aatggtcaca gaatccatca tacatccacc tacattaaca ggagaatgca actggttttt    4500
gatagcctcg gcttgcagag atatgtactc ttgtgctcta agatccctga cggtggattc    4560
agagacaagc cgaggaaacc ccgtgacttc taccacacat gttactgcct gagcggcttg    4620
tctgtggctc agcacgcttg gttaaaagac gaggacactc ctcctttgac tcgcgacatt    4680
atgggtggct actcgaatct ccttgaacct gttcaacttc ttcacaacat tgtcatggat    4740
cagtataatg aagctatcga gttcttcttt aaagcagcat gactcgaatt tccccgatcg    4800
ttcaaacatt tggcaataaa gtttcttaag attgaatcct gttgccggtc ttgcgatgat    4860
tatcatataa tttctgttga attacgttaa gcatgtaata attaacatgt aatgcatgac    4920
gttatttatg agatgggttt ttatgattag agtcccgcaa ttatacattt aatacgcgat    4980
agaaaacaaa atatagcgcg caaactagga taaattatcg cgcgcggtgt catctatgtt    5040
actagatcgg gaattcactg gccgtcgttt tacaacgtcg tgactgggaa accctggcg    5100 ttacccaact taatcgcctt gcagcacatc cccctttcgc cagctggcgt aatagcgaag    5160
aggcccgcac cgatcgccct tcccaacagt tgcgcagcct gaatggcgcc cgctcctttc    5220
gctttcttcc cttcctttct cgccacgttc gccggctttc cccgtcaagc tctaaatcgg    5280
gggctccctt tagggttccg atttagtgct ttacggcacc tcgaccccaa aaaacttgat    5340
ttgggtgatg gttcacgtag tgggccatcg ccctgataga cggttttcg ccctttgacg    5400
```

-continued

| | |
|---|---|
| ttggagtcca cgttctttaa tagtggactc ttgttccaaa ctggaacaac actcaaccct | 5460 |
| atctcgggct attcttttga tttataaggg attttgccga tttcggaacc accatcaaac | 5520 |
| aggattttcg cctgctgggg caaaccagcg tggaccgctt gctgcaactc tctcagggcc | 5580 |
| aggcggtgaa gggcaatcag ctgttgcccg tctcactggt gaaagaaaa accacccag | 5640 |
| tacattaaaa acgtccgcaa tgtgttatta agttgtctaa gcgtcaattt gtttacacca | 5700 |
| caatatatcc tgcca | 5715 |

<210> SEQ ID NO 53
<211> LENGTH: 1772
<212> TYPE: DNA
<213> ORGANISM: Artificial Sequence
<220> FEATURE:
<223> OTHER INFORMATION: Description of Artificial Sequence: Plasmid
    MuA-anti-GmFTB-Nos-Term

<400> SEQUENCE: 53

| | |
|---|---|
| gaattcaaat ttttcgccag ttctaaatat ccggaaacct cttgggatgc cattgcccat | 60 |
| ctatctgtaa tttattgacg aaatagacga aaggaaggt ggctcctata aagcacatca | 120 |
| ttgcgataac agaaaggcca ttgttgaaga tacctctgct gacattggtc cccaagtgga | 180 |
| agcaccaccc catgaggagc accgtggagt aagaagacgt tcgagccacg tcgaaaaagc | 240 |
| aagtgtgttg atgtagtatc tccattgacg taagggatga cgcacaatcc aactatccat | 300 |
| cgcaagacca ttgctctata taagaaagtt aaatatcattt cgagtggcca cgctgagctc | 360 |
| gtggtggaga atctgggtgc tttgaccaac tatactggca caatgagagt ccacttaaac | 420 |
| agtaacatgt gtgataatga tctctacgtt tacccggttt gtctctcagt ccaccctctt | 480 |
| gctcctgtgc acataagaga atatattgct gtaaagcaat actgtgaaaa agtggttctt | 540 |
| gtgctctcca ctcattaata aatttatagg caatattttt aaaatcagat gaactggatt | 600 |
| cactggtgcc ttcatgctca ccacggcatg ttgcatgact agaggttcca tccaaacttt | 660 |
| cttttgcttc agatacataa gataccgcaa aaatctgtga tgtctcttcc atctgtttgt | 720 |
| tgataataga agataatctt tgcaatagag caacagcacc tccctgccaa aaggaatagc | 780 |
| atccatccac cagtttattt gttctcccct ggaatccaca ttccttacct tgtcggaata | 840 |
| ccacccagtc aactaatcga ggcagatcca agtgattaac ctcaccaatc agaatcattg | 900 |
| tagctaatcc acaaaaggtg tacccaccat gagcctcaga accaggctca ccagcaatgc | 960 |
| caccctcata tgtttgacag cttataatgt agtctccaac attctggatc agctcatcat | 1020 |
| ccaaaatgtt caaacactt gcaacagaaa tggcagtgta gcaagctcga acatcaattt | 1080 |
| caccttcatc atgcatcctg aatccaccat ttggttgctt catccgccgc agaaacccat | 1140 |
| acagtttatc tctattaatt gatgccaggg atttctcacc acccaaagta ataagtgaat | 1200 |
| taacagcagc ataagttgtg gcaatatgag gcatctggcc tggtccccg gcatatccac | 1260 |
| cattcggatc ctggcaacgg ttaagaaaat cgatagcgtt atcttcgagt tcatcatcga | 1320 |
| cggattctcc caacaaagca atggagtgga agatccagta gcagagccag ggtcgattag | 1380 |
| cgtccaaaac ggaaaatgcg gaactgagat ggcgaaggcc tttggagaca tactgcatgt | 1440 |
| gattatcgcg ttgaagctcc aacatgaggg tttgggcgtt gcgaggaatg gtggcgagct | 1500 |
| cgaatttccc cgatcgttca acatttggc aataaagttt cttaagattg aatcctgttg | 1560 |
| ccggtcttgc gatgattatc atataatttc tgttgaatta cgttaagcat gtaataatta | 1620 |
| acatgtaatg catgacgtta tttatgagat gggtttttat gattagagtc cgcaattat | 1680 |

-continued

| acatttaata cgcgatagaa acaaaatat agcgcgcaaa ctaggataaa ttatcgcgcg | 1740 |
| cggtgtcatc tatgttacta gatcgggaat tc | 1772 |

<210> SEQ ID NO 54
<211> LENGTH: 2340
<212> TYPE: DNA
<213> ORGANISM: Artificial Sequence
<220> FEATURE:
<223> OTHER INFORMATION: Description of Artificial Sequence: Plasmid RD29AP-anti-GmFTB-Nos-Term

<400> SEQUENCE: 54

| ggagccatag atgcaattca atcaaactga aatttctgca agaatctcaa acacggagat | 60 |
| ctcaaagttt gaaagaaaat ttatttcttc gactcaaaac aaacttacga aatttaggta | 120 |
| gaacttatat acattatatt gtaattttt gtaacaaaat gttttattta ttattataga | 180 |
| attttactgg ttaaattaaa aatgaataga aaggtgaat taagaggaga gaggaggtaa | 240 |
| acatttcctt ctatttttc atatttcag gataaattat tgtaaagtt tacaagattt | 300 |
| ccatttgact agtgtaaatg aggaatattc tctagtaaga tcattatttc atctacttct | 360 |
| tttatcttct accagtagag gaataaacaa tatttagctc ctttgtaaat acaaattaat | 420 |
| tttccttctt gacatcattc aattttaatt ttacgtataa aataaaagat catacctatt | 480 |
| agaacgatta aggagaaata caattcgaat gagaaggatg tgccgtttgt tataataaac | 540 |
| agccacacga cgtaaacgta aaatgaccac atgatgggcc aatagacatg gaccgactac | 600 |
| taataatagt aagttacatt ttaggatgga ataaatatca taccgacatc agttttgaaa | 660 |
| gaaaagggaa aaaagaaaa aataaataaa agatatacta ccgacatgag ttccaaaaag | 720 |
| caaaaaaaa gatcaagccg acacagacac gcgtagagag caaaatgact ttgacgtcac | 780 |
| accacgaaaa cagacgcttc atacgtgtcc ctttatctct ctcagtctct ctataaactt | 840 |
| agtgagaccc tcctctgttt tactcacaaa tatgcaaact agaaaacaat catcaggaat | 900 |
| aaagggtttg attacttcta ttggaaaggt ggtggagaat ctgggtgctt tgaccaacta | 960 |
| tactggcaca atgagagtcc acttaaacag taacatgtgt gataatgatc tctacgttta | 1020 |
| cccggtttgt ctctcagtcc accctcttgc tcctgtgcac ataagagaat atattgctgt | 1080 |
| aaagcaatac tgtgaaaaag tggttcttgt gctctccact cattaataaa tttataggca | 1140 |
| atattttaa aatcagatga actggattca ctggtgcctt catgctcacc acggcatgtt | 1200 |
| gcatgactag aggttccatc caaactttct tttgcttcag atacataaga taccgcaaaa | 1260 |
| atctgtgatg tctcttccat ctgtttgttg ataatagaag ataatctttg caatagagca | 1320 |
| acagcacctc cctgccaaaa ggaatagcat ccatccacca gtttatttgt tctcccctgg | 1380 |
| aatccacatt ccttaccttg tcggaatacc acccagtcaa ctaatcgagg cagatccaag | 1440 |
| tgattaacct caccaatcag aatcattgta gctaatccac aaaaggtgta cccaccatga | 1500 |
| gcctcagaac caggctcacc agcaatgcca ccctcatatg tttgacagct tataatgtag | 1560 |
| tctccaacat tctggatcag ctcatcatcc aaaatgttca aaacacttgc aacagaaatg | 1620 |
| gcagtgtagc aagctcgaac atcaatttca ccttcatcat gcatcctgaa tccaccattt | 1680 |
| ggttgcttca tccgccgcag aaacccatac agtttatctc tattaattga tgccagggat | 1740 |
| ttctcaccac ccaaagtaat aagtgaatta acagcagcat aagttgtggc aatatgaggc | 1800 |
| atctggcctg gtcccccggc atatccacca ttcggatcct ggcaacggtt aagaaaatcg | 1860 |
| atagcgttat cttcgagttc atcatcgacg gattctccca acaaagcaat ggagtggaag | 1920 |

-continued

```
atccagtagc agagccaggg tcgattagcg tccaaaacgg aaaatgcgga actgagatgg   1980
cgaaggcctt tggagacata ctgcatgtga ttatcgcgtt gaagctccaa catgagggtt   2040
tgggcgttgc gaggaatggt ggcgagctcg aatttccccg atcgttcaaa catttggcaa   2100
taaagtttct taagattgaa tcctgttgcc ggtcttgcga tgattatcat ataatttctg   2160
ttgaattacg ttaagcatgt aataattaac atgtaatgca tgacgttatt tatgagatgg   2220
gtttttatga ttagagtccc gcaattatac atttaatacg cgatagaaaa caaaatatag   2280
cgcgcaaact aggataaatt atcgcgcgcg gtgtcatcta tgttactaga tcgggaattc   2340
```

<210> SEQ ID NO 55
<211> LENGTH: 2298
<212> TYPE: DNA
<213> ORGANISM: Artificial Sequence
<220> FEATURE:
<223> OTHER INFORMATION: Description of Artificial Sequence: Plasmid
    MuA-HP-GmFTB-Nos-Term

<400> SEQUENCE: 55

```
gaattcaaat ttttcgccag ttctaaatat ccggaaacct cttgggatgc cattgcccat     60
ctatctgtaa tttattgacg aaatagacga aaggaaggt ggctcctata agcacatca    120 ttgcgataac agaaaggcca ttgttgaaga tacctctgct gacattggtc ccaagtgga    180 agcaccaccc catgaggagc accgtggagt aagaagacgt tcgagccacg tcgaaaaagc    240
aagtgtgttg atgtagtatc tccattgacg taagggatga cgcacaatcc aactatccat    300
cgcaagacca ttgctctata taagaaagtt aatatcattt cgagtggcca cgctgagctc    360
gtggtggaga atctgggtgc tttgaccaac tatactggca caatgagagt ccacttaaac    420
agtaacatgt gtgataatga tctctacgtt tacccggttt gtctctcagt ccaccctctt    480
gctcctgtgc acataagaga atatattgct gtaaagcaat actgtgaaaa agtggttctt    540
gtgctctcca ctcattaata aatttatagg caatattttt aaaatcagat gaactggatt    600
cactggtgcc ttcatgctca ccacggcatg ttgcatgact agaggttcca tccaaacttt    660
cttttgcttc agatacataa gataccgcaa aaatctgtga tgtctcttcc atctgtttgt    720
tgataataga agataatctt tgcaatagag caacagcacc tccctgccaa aaggaatagc    780
atccatccac cagtttattt gttctcccct ggaatccaca ttccttacct tgtcggaata    840
ccacccagtc aactaatcga ggcagatcca agtgattaac ctcaccaatc agaatcattg    900
tagctaatcc acaaaaggtg tacccaccat gagcctcaga accaggctca ccagcaatgc    960 cacccctcata tgtttgacag cttataatgt agtctccaac attctggatc agctcatcat   1020
ccaaaatgtt caaaacactt gcaacagaaa tggcagtgta gcaagctcga acatcaattt   1080
caccttcatc atgcatcctg aatccaccat ttggttgctt catccgccgc agaaacccat   1140
acagtttatc tctattaatt gatgccaggg atttctcacc acccaaagta ataagtgaat   1200
taacagcagc ataagttgtg gcaatatgag gcatctggcc tggtccccg gcatatccac    1260 cattcggatc ctggcaacgg ttaagaaaat cgatagcgtt atcttcgagt tcatcatcga   1320
cggattctcc caacaaagca atggagtgga agatccagta gcagagccag ggtcgattag   1380
cgtccaaaac ggaaaatgcg gaactgagat ggcgaaggcc tttggagaca tactgcatgt   1440
gattatcgcg ttgaagctcc aacatgaggg tttgggcgtt gcgaggaatg gtggcggtga   1500
ggttaatcac ttggatctgc ctcgattagt tgactgggtg gtattccgac aaggtaagga   1560
atgtggattc caggggagaa caaataaact ggtggatgga tgctattcct tttggcaggg   1620
```

```
aggtgctgtt gctctattgc aaagattatc ttctattatc aacaaacaga tggaagagac    1680
atcacagatt tttgcggtat cttatgtatc tgaagcaaaa gaaagtttgg atggaacctc    1740
tagtcatgca acatgccgtg gtgagcatga aggcaccagt gaatccagtt catctgattt    1800
taaaaatatt gcctataaat ttattaatga gtggagagca caagaaccac ttttttcacag   1860 tattgcttta cagcaatata ttctcttatg tgcacaggag caagagggtg gactgagaga    1920
caaaccgggt aaacgtagag atcattatca cacatgttac tgtttaagtg gactctcatt    1980
gtgccagtat agttggtcaa agcacccaga ttctccacca cgagctcgaa tttccccgat    2040
cgttcaaaca tttggcaata agtttcttta agattgaatc ctgttgccgg tcttgcgatg    2100
attatcatat aatttctgtt gaattacgtt aagcatgtaa taattaacat gtaatgcatg    2160
acgttattta tgagatgggt ttttatgatt agagtcccgc aattatacat ttaatacgcg    2220
atagaaaaca aaatatagcg cgcaaactag gataaattat cgcgcgcggt gtcatctatg    2280
ttactagatc gggaattc                                                  2298
```

<210> SEQ ID NO 56
<211> LENGTH: 2866
<212> TYPE: DNA
<213> ORGANISM: Artificial Sequence
<220> FEATURE:
<223> OTHER INFORMATION: Description of Artificial Sequence: Plasmid
    RD29AP-HP-GmFTB-Nos-Term

<400> SEQUENCE: 56

```
ggagccatag atgcaattca atcaaactga aatttctgca agaatctcaa acacggagat     60
ctcaaagttt gaaagaaaat ttatttcttc gactcaaaac aaacttacga aatttaggta    120
gaacttatat acattatatt gtaatttttt gtaacaaaat gtttttatta ttattataga    180
attttactgg ttaaattaaa aatgaataga aaggtgaat taagaggaga gaggaggtaa     240
acatttcctt ctatttttc atattttcag gataaattat tgtaaaagtt tacaagattt     300
ccatttgact agtgtaaatg aggaatattc tctagtaaga tcattatttc atctacttct    360
tttatcttct accagtagag gaataaacaa tatttagctc ctttgtaaat acaaattaat    420
tttccttctt gacatcattc aatttttaatt ttacgtataa aataaaagat catacctatt    480
agaacgatta aggagaaata caattcgaat gagaaggatg tgccgtttgt tataataaac    540
agccacacga cgtaaacgta aaatgaccac atgatgggcc aatagacatg gaccgactac    600
taataatagt aagttacatt ttaggatgga ataaatatca taccgacatc agttttgaaa    660
gaaaagggaa aaaagaaaa aataaataaa agatatacta ccgacatgag ttccaaaaag    720
caaaaaaaaa gatcaagccg acacagacac gcgtagagag caaaatgact ttgacgtcac    780
accacgaaaa cagacgcttc atacgtgtcc ctttatctct ctcagtctct ctataaactt    840
agtgagaccc tcctctgttt tactcacaaa tatgcaaact agaaacaat catcaggaat    900 aaagggtttg attacttcta ttggaaaggt ggtggagaat ctgggtgctt tgaccaacta    960
tactggcaca atgagagtcc acttaaacag taacatgtgt gataatgatc tctacgttta   1020
cccggtttgt ctctcagtcc accctcttgc tcctgtgcac ataagagaat atattgctgt   1080
aaagcaatac tgtgaaaaag tggttcttgt gctctccact cattaataaa tttataggca   1140
atatttttaa aatcagatga actggattca ctggtgcctt catgctcacc acggcatgtt   1200
gcatgactag aggttccatc caaactttct tttgcttcag atacataaga taccgcaaaa   1260
atctgtgatg tctcttccat ctgtttgttg ataatagaag ataatctttg caatagagca   1320
```

```
acagcacctc cctgccaaaa ggaatagcat ccatccacca gtttatttgt tctcccctgg    1380
aatccacatt ccttaccttg tcggaatacc acccagtcaa ctaatcgagg cagatccaag    1440
tgattaacct caccaatcag aatcattgta gctaatccac aaaaggtgta cccaccatga    1500
gcctcagaac caggctcacc agcaatgcca ccctcatatg tttgacagct tataatgtag    1560
tctccaacat tctggatcag ctcatcatcc aaaatgttca aaacacttgc aacagaaatg    1620
gcagtgtagc aagctcgaac atcaatttca ccttcatcat gcatcctgaa tccaccattt    1680
ggttgcttca tccgccgcag aaacccatac agtttatctc tattaattga tgccagggat    1740
ttctcaccac ccaaagtaat aagtgaatta acagcagcat aagttgtggc aatatgaggc    1800
atctggcctg gtccccggc atatccacca ttcggatcct ggcaacggtt aagaaaatcg    1860
atagcgttat cttcgagttc atcatcgacg gattctccca acaaagcaat ggagtggaag    1920
atccagtagc agagccaggg tcgattagcg tccaaaacgg aaaatgcgga actgagatgg    1980
cgaaggcctt tggagacata ctgcatgtga ttatcgcgtt gaagctccaa catgagggtt    2040
tgggcgttgc gaggaatggt ggcggtgagg ttaatcactt ggatctgcct cgattagttg    2100
actgggtggt attccgacaa ggtaaggaat gtggattcca ggggagaaca aataaactgg    2160
tggatggatg ctattccttt tggcaggag gtgctgttgc tctattgcaa agattatctt    2220
ctattatcaa caaacagatg gaagagacat cacagatttt tgcggtatct tatgtatctg    2280
aagcaaaaga agtttggat ggaacctcta gtcatgcaac atgccgtggt gagcatgaag    2340
gcaccagtga atccagttca tctgatttta aaaatattgc ctataaattt attaatgagt    2400
ggagagcaca agaaccactt tttcacagta ttgctttaca gcaatatatt ctcttatgtg    2460
cacaggagca agagggtgga ctgagagaca aaccgggtaa acgtagagat cattatcaca    2520
catgttactg tttaagtgga ctctcattgt gccagtatag ttggtcaaag cacccagatt    2580
ctccaccacg agctcgaatt tccccgatcg ttcaaacatt tggcaataaa gtttcttaag    2640
attgaatcct gttgccggtc ttgcgatgat tatcatataa tttctgttga attacgttaa    2700
gcatgtaata attaacatgt aatgcatgac gttatttatg agatgggttt ttatgattag    2760
agtcccgcaa ttatacattt aatacgcgat agaaaacaaa atatagcgcg caaactagga    2820
taaattatcg cgcgcggtgt catctatgtt actagatcgg gaattc          2866
```

<210> SEQ ID NO 57
<211> LENGTH: 1882
<212> TYPE: DNA
<213> ORGANISM: Artificial Sequence
<220> FEATURE:
<223> OTHER INFORMATION: Description of Artificial Sequence: Plasmid
      MuA-anti-Zea maizeFTB-Nos-Term

<400> SEQUENCE: 57

```
gaattcaaat ttttcgccag ttctaaatat ccggaaacct cttgggatgc cattgcccat     60
ctatctgtaa tttattgacg aaatagacga aaaggaaggt ggctcctata agcacatca    120 ttgcgataac agaaaggcca ttgttgaaga tacctctgct gacattggtc cccaagtgga    180
agcaccaccc catgaggagc accgtggagt aagaagacgt tcgagccacg tcgaaaaagc    240
aagtgtgttg atgtagtatc tccattgacg taagggatga cgcacaatcc aactatccat    300
cgcaagacca ttgctctata taagaaagtt aatatcattt cgagtggcca cgctgagctc    360
ggatggattg gctccagcaa attagagtac ggtccaagca catgctgagg taatgggcac    420
gaaccagtat cagtcatggc actgtactgg ctaactgcga ggccactgag gcagtagcat    480
```

```
gaatgatagt gatctctgtt ctttccaggc ttatccctca agcctccctc tagtacctga      540
gaacaaagta ggatgtattg ttgcagggca atgttatgga agagtgggcc aatttggttg      600
ctctgttgta taaaatcaaa tccaaacttc gcatagtcca cagcagagga agacttattc      660
gcggtgcacc catatgaact ggtgctgcag gcatcctctc ctgatggcct tttgcaggaa      720
tacgaggacc tcaattgctt atcaacaatc gtaattaact tttgtgtgaa agcaatggca      780
gctccctgcc aaaaggagta gcaaccatca accaatttat tagttcgtcc ttgaaatccg      840
cattccactc cttgacgaaa agccacccag ccaatcaaac taggcaagtc aactttctct      900
gcctcattaa gcaggatcaa agcagccaat ccacagaatg tatacccacc atgtgcttca      960
gcataaggct ccccagcaat accaccttca taagtttgac atcttgctat gtagtcgcct     1020
acaccttttg ccagtttaaa atcaagaata ttcacaaggc tggcaaccga tatagcggtg     1080
taggaagcac ggacatcaat ttcgccacca tcatgcattc tgaaagcacc tgatacatct     1140
ttcatctgca gcataaaatt gtacaggttg cccctattga ttgatgacaa tgctctttcg     1200
ctccctattg tcacaagtgt atttacagca gcataagtcg tagctaggtg aggcaactgt     1260
ccaggtccac cactatatcc accatcttta tcctgacatc gagctaagaa gtctatgata     1320
tcattctcaa gatcatcatc aagtgcttca tccagcaaag caagtggatg aaccatccag     1380
tagcatagcc aagggcgatt ggcatctaga acatgaaagg ctggtcccat atgcctcagc     1440
ccaggcgtca gatactcgat atgctgatca cgccacagct ctagcatgat ggatttcgtg     1500
ttgggcgcgg ccccgaagag ggagcggtag atgtcgccaa ccctgcctc cacccttcatc     1560 tgctccacct gcgtcaccgt gagcctcggt aggtcgggat ccgccgagct cgaatttccc     1620
cgatcgttca acatttggc aataaagttt cttaagattg aatcctgttg ccggtcttgc     1680
gatgattatc atataatttc tgttgaatta cgttaagcat gtaataatta acatgtaatg     1740
catgacgtta tttatgagat gggttttttat gattagagtc ccgcaattat acatttaata     1800
cgcgatagaa aacaaaatat agcgcgcaaa ctaggataaa ttatcgcgcg cggtgtcatc     1860
tatgttacta gatcgggaat tc                                              1882
```

<210> SEQ ID NO 58
<211> LENGTH: 2505
<212> TYPE: DNA
<213> ORGANISM: Artificial Sequence
<220> FEATURE:
<223> OTHER INFORMATION: Description of Artificial Sequence: Plasmid
      MuA-HP-Zea maizeFTB-Nos-Term

<400> SEQUENCE: 58

```
gaattcaaat ttttcgccag ttctaaatat ccggaaacct cttgggatgc cattgcccat       60
ctatctgtaa tttattgacg aaatagacga aaaggaaggt ggctcctata agcacatca      120 ttgcgataac agaaaggcca ttgttgaaga tacctctgct gacattggtc cccaagtgga     180
agcaccaccc catgaggagc accgtggagt aagaagacgt tcgagccacg tcgaaaaagc     240
aagtgtgttg atgtagtatc tccattgacg taagggatga cgcacaatcc aactatccat     300
cgcaagacca ttgctctata taagaaagtt aatatcattt cgagtggcca cgctgagctc     360
ggatggattg gctccagcaa attagagtac ggtccaagca catgctgagg taatgggcac     420
gaaccagtat cagtcatggc actgtactgg ctaactgcga ggccactgag gcagtagcat     480
gaatgatagt gatctctgtt ctttccaggc ttatccctca agcctccctc tagtacctga     540
gaacaaagta ggatgtattg ttgcagggca atgttatgga agagtgggcc aatttggttg     600
```

-continued

```
ctctgttgta taaaatcaaa tccaaacttc gcatagtcca cagcagagga agacttattc    660
gcggtgcacc catatgaact ggtgctgcag gcatcctctc ctgatggcct tttgcaggaa    720
tacgaggacc tcaattgctt atcaacaatc gtaattaact tttgtgtgaa agcaatggca    780
gctccctgcc aaaaggagta gcaaccatca accaatttat tagttcgtcc ttgaaatccg    840
cattccactc cttgacgaaa agccacccag ccaatcaaac taggcaagtc aactttctct    900
gcctcattaa gcaggatcaa agcagccaat ccacagaatg tatacccacc atgtgcttca    960
gcataaggct ccccagcaat accaccttca taagtttgac atcttgctat gtagtcgcct   1020
acacctttg ccagtttaaa atcaagaata ttcacaaggc tggcaaccga tatagcggtg   1080
taggaagcac ggacatcaat ttcgccacca tcatgcattc tgaaagcacc tgatacatct   1140
ttcatctgca gcataaaatt gtacaggttg ccctattga ttgatgacaa tgctctttcg   1200
ctccctattg tcacaagtgt atttacagca gcataagtcg tagctaggtg aggcaactgt   1260
ccaggtccac cactatatcc accatcttta tcctgacatc gagctaagaa gtctatgata   1320
tcattctcaa gatcatcatc aagtgcttca tccagcaaag caagtggatg aaccatccag   1380
tagcatagcc aagggcgatt ggcatctaga acatgaaagg ctggtcccat atgcctcagc   1440
ccaggcgtca gatactcgat atgctgatca cgccacagct ctagcatgat ggatttcgtg   1500
ttgggcgcgg ccccgaagag ggagcggtag atgtcgccaa ccctggcctc caccttcatc   1560
tgctccacct gcgtcaccgt gagcctcggt aggtcgggat ccgccggatc cgctggggag   1620
ccttatgctg aagcacatgg tgggtataca ttctgtggat tggctgcttt gatcctgctt   1680
aatgaggcag agaaagttga cttgcctagt ttgattggct gggtggcttt tcgtcaagga   1740
gtggaatgcg gatttcaagg acgaactaat aaattggttg atggttgcta ctccttttgg   1800
cagggagctg ccattgcttt cacacaaaag ttaattacga ttgttgataa gcaattgagg   1860
tcctcgtatt cctgcaaaag gccatcagga gaggatgcct gcagcaccag ttcatatggg   1920
tgcaccgcga ataagtcttc ctctgctgtg gactatgcga agtttggatt tgattttata   1980
caacagagca accaaattgg cccactcttc cataacattg ccctgcaaca atacatccta   2040
ctttgttctc aggtactaga gggaggcttg agggataagc ctggaaagaa cagagatcac   2100
tatcattcat gctactgcct cagtggcctc gcagttagcc agtacagtgc catgactgat   2160
actggttcgt gcccattacc tcagcatgtg cttggaccgt actctaattt gctggagcca   2220
atccatccaa gcttgaattt ccccgatcgt tcaaacattt ggcaataaag tttcttaaga   2280
ttgaatcctg ttgccggtct tgcgatgatt atcatataat ttctgttgaa ttacgttaag   2340
catgtaataa ttaacatgta atgcatgacg ttatttatga gatgggtttt tatgattaga   2400
gtcccgcaat tatacattta atacgcgata gaaaacaaaa tatagcgcgc aaactaggat   2460
aaattatcgc gcgcggtgtc atctatgtta ctagatcgga agctt                   2505
```

<210> SEQ ID NO 59
<211> LENGTH: 1323
<212> TYPE: DNA
<213> ORGANISM: Pisum sativum

<400> SEQUENCE: 59

```
caacacctac ctagtgcttc tagttctggt tctaggactg agagtaaaca gaagtgaaga    60
agaatccaga acatggccgg gaatatcgaa gttgaagaag acgatcgtgt gccgctaaga   120
ttacgacctg agtggtcaga tgttactccg atcccacaag acgatggccc tagtcccgtc   180
```

-continued

```
gtgccgatca actactccga agagttttca gaagttatgg attactttcg tgctgtttac        240
ttcgccaaag aactttcctc tcgcgctctt gctctcaccg ccgaagctat cggtttaaac        300
gccggaaact acactgtgtg gcatttccgg cggttattac ttgagtcact gaaagttgac        360
ctacatgttg aacgggaatt cgtggagcgt gttgccagtg gcaattcaaa aaattatcag        420
atttggcatc atagacgatg ggttgctgag aaattaggac ctgaagctag aaacagtgaa        480
cttgagttca ccaaaaagat tctgtctgtt gacgccaaac actatcatgc atggtctcat        540
aggcagtggg ttcttcaaaa tctaggagga tgggaagatg aactcagtta ttgtagtgaa        600
ctgcttgcag aagacatatt taacaattct gcttggaatc agagatactt cgtcataaca        660
aggtctcccg tcttgggagg gctaaaagcc atgagagagt ctgaagtgct tttcaccgtt        720
gaagccatta tttcttaccc agaaaatgaa agctcatgga gatatcttcg aggacttttc        780
aaagatgaat ccacgttata tgtaaatgat gcccaagtat cttcattatg tttaaagatt        840
ttgaaaacta agagcaacta tttgtttgct ctaagtactc tgctggatct atctgcctcg        900
gttattcaac caaatgaaga tttcagagat gccattgagg ctttaagact tcagattttg        960
ataaaacaag attcagatat agcaataact atttgttcta ttttagaaca agttgatcca       1020
attagagtca actattgggt ctggcggaag agtagacttc ctcaggcagc gtaaaggaca       1080
aacttatgtc atatgtgtaa ttttttagtct attggaattt gacgtcatgg ataacagggt       1140
ggttgttttt gttatgatat gttttccaga tgtatttcta tatttaacag caaagttgat       1200
ttaacattgg tgttaacaaa ccaatgatct ccaaaaaatc aatgttttat ttctcttcat       1260
ttgtctgatt ttgtggcata acattcttga tgattttgtg gtaaaaaaaa aaaaaaaaaa       1320
aaa                                                                      1323
```

<210> SEQ ID NO 60
<211> LENGTH: 1505
<212> TYPE: DNA
<213> ORGANISM: Lycopersicon esculentum

<400> SEQUENCE: 60

```
taccccgaag gcaattccag tattgaacta ccgccggcag ttttccgatc ggatcccgga         60
gccgagtatc aaatggacag ttgtgaggtg acgaaaacgc gaattccttt caaggaaagg        120
cccgactggg ccgatgtgaa gcccgttccg caagacgacg ggccctgccc ggttgttccc        180
atagcctaca cagaagactt ctctgaaacc atggactact ccgggcaatt tacgtagcc         240 gatgagcgat ctacacgcgc cctccagctt actggtgaag ctattcagct aaaccctgga        300
aattacactg tatggcaatt taggcgtgtt gtgctggagg cattgggtgt tgatttacgt        360
gaagaattga agtttgttga tcgcattgct ggggagaata ccaaaaatta tcaaatatgg        420
catcatagac ggtggcttgc tgagaagctg ggagctgatg ctgtgacaaa tgagctagaa        480
ttcaccaaga aaatattttc tcaggatgca aaaaattatc atgcttggtc ccatcggcag        540
tgggtccttc aagcacttgg aggatgggaa gatgagcttg cttattgtca caactccttt        600
gaagatgata tttacaacaa ttctgcttgg aatcagagat actttgtcgt aacacgatca        660
cctctactag ggggcctagt ggcaatgagg gaattggaag tgaattacac agttcaagcc        720
atcagagcta gtccagagaa tgaaagtcct tggaggtatc ttcgtggtct ttacaagaat        780
gatacacaat ctctagttca ggattctcaa gtagcatcag tactttggga cgtcttaacc        840
tcccaaaata gtcatgtgca cgctctgagg ttccttgttgg atcttctttg tcatgatttg        900
gaaccgagcc aagaattgaa aagtgctgta gatgttctta ctccccagtc atgctcacca        960
```

```
gatttagcac tgacaaagaa aatttgttcc atcttggaac atgctgatcc aatgagagta   1020
aaatattgga attggcgcaa gagcatggtt cgggttcaat tacttcagag tcagaatgca   1080
gagaggttgg ctaatttgag tgttcaagaa tgacttgtga gaatattgta ctgtgtttac   1140
gaaatacata cttgcatcta aggtgatcct tcgggcacat gtgctgggaa gtgactgaat   1200
atcacgaaga actaaaaaaa ctgtgattgg caacattgta ctactccaaa taggtcactt   1260
tcgatgactt tttgtactgc cttgagtttt ggctctgcta tgttttgtaa gttttggata   1320
tggatgcata gcttattgat acttttggtg acttaaaata ctctggaagg caggtagcat   1380
gtgtataatt cactgttact tcccatgtcg agttagatgc ttgaaaattt tagtaggtgt   1440
tcttttatga agcacacatt aatgtggaaa aaaaaaaaa aaaaaaaaa aaaaaaaaa     1500 aaaaa                                                              1505

<210> SEQ ID NO 61
<211> LENGTH: 1218
<212> TYPE: DNA
<213> ORGANISM: Oryza sp.

<400> SEQUENCE: 61
gcacgaggtt ctaacgccgc cgccgccgcc gccgtctccg cagaatctga tcgatggcgc     60
cgtcgtcgac gtcgtcggag ggtgcctccg acgagtggtt gccacccagc cggcggccgg    120
agctggcgga cgtggtcccc gtgacgcagg acgacgggcc ccaccccgtg gtggccatcg    180
cctaccggga cgagttccgc gaggtcatgg actacttccg cgccctctac ttcgccggcg    240
agcgcagcgt ccgcgccctc cacctcaccg ccgaggtcat cgaccttaat cccggcaact    300
acacggtgtg gcatttttagg cgtcttgttc tagaggcact ggatgctgat ctgcgtgagg   360
aaatggattt tgtggaccga attgtcgaat gtaacccaaa aaattatcaa atctggcatc    420
acaagagatg gcttgcggag aaattaggac cagatattgc aaataaagag cacgaattta    480
caaggaagat actttctatg gatgctaaaa attaccatgc ttggtctcat aggcagtggg    540
ttcttcaagc actgggtgga tgggagactg aactacagta ttgcaaccag ctgcttgagg    600
aagacgtctt caataattca gcttggaatc agagatacct tgtaataaca agttcaccac    660
ttcttggagg ccttgcagca atgcgtgact cggaagtgga ttacacagtt ggggctattc    720
tggctaaccc tcagaatgaa agccctggaa gataccctcaa aggcctgtac aagggtgaaa   780
ataacttgct gatggctgat gagcgcatct ctgatgtttg tctcaaggtc ctgaaacatg    840
attcgacctg cgtatttgct ttgagcttgc tgctcgatct tcttcaaatt ggtttacaac    900
cttcagatga actcaaagga actatcgaag caataaagaa ctctgatcct gaagcagatg    960
aagcagtaga tgctgatctt gcgactgcaa tctgctcaat attgcagaga tgtgatcccc   1020
tgcggataaa ttactggtcc tggtacagga ccactatttc ttctcaaacc tgaagcatgc   1080
agtggcctcc atgaggtcat aatggagata tcttctatct tcgtgtgatt ctgggcgttg   1140
aggtgcctag ctacatttgt tatgaacttt ccttgggcat aactgatcac tgatattact   1200
ccaatattgt gttctaaa                                                 1218

<210> SEQ ID NO 62
<211> LENGTH: 1426
<212> TYPE: DNA
<213> ORGANISM: Zea mays

<400> SEQUENCE: 62
```

```
gcacgagaca cgcgcaattac ttaagctatt tgtattcgga tctgatccaa ccctggtggt    60
cagctggact catcgcccat ggagcacact aagtcaggcc ccagcagttg ccagaactg    120 gccgacgtgg tgccggtgcc gcaggacgat gggcctagcc ctgtggtgtc catcgcctat   180
cgagatgact ttcgtgaggt catggattac ttccgcgccc tctacctcac cggtgagcga   240
agccctcgcg ctctccgcct caccgccgag gccatcgagc tcaaccccgg caactacact   300
gtctggcatt tccggcgcct tattctggag tcactagatt ttgatttact agaggagatg   360
aaatttgtcg aaaaaattgc tgaatgcaat ccaaaaaatt accaaatctg caccataag    420 agatggcttg ctgagaaatt aggacctggt attgcaaaca aagagcatga attcacaatg   480
aagatacttg ctattgatgc aaaaaattat catgcttggt ctcataggca gtgggttctt   540
caagcgttgg ggggatggga gactgaatta gaatactgtg accacttact taaggaagac   600
gtcttcaata attcagcttg gaatcagaga tactttgtta taacaagatc accatttctt   660
ggtggccttg cggcaatgcg tgattcagaa gtagactaca caattgaagc tattctagca   720
aacgctcaga atgaaagccc ctggaggtac ctcaagggtc tatacaaggg tgagaataac   780
ctgctagtag aggacgagcg catctctgct gtttgtttca aggtcctgaa gaatgattgg   840
acttgtgtat tgctttgag tttgctgctc gatcttctct gcactggttt gcagccttca    900
gatgaactta ggtccactct tgaaacaata aggagctccc atcctgaaac gcggatgat    960 gatcctgcag ccgctgtttg ctgtatcctg cagaaatgtg atccctgcg ggtaaattat    1020 tggtcttggt tcaaggacac tctttctcag atctcatgac ttcacatggg ttcaccccctt 1080 gtccgcgctg gtccgggctc tgtgagatag acatgtttta gatagtttca ttggacaccc   1140
aaacagagcg gacagagtgt atggctgcta ccttctccgt gactgaaagc agtgcttgta   1200
acgattttgt ttagtaaaat ttgtgagtgt tactgctcca acaacaccct tatgcaacca   1260
tatttgaata tttcacatgt aagcttgaat ccaggtgtgt ttgttaatgt attcacttg    1320 ccatgggagc ctaaatgaga cccataatca cttccactag agtcggaaga ccgtgtcgag   1380
cagttcactc atatggtcac ttaaagcaaa aaaaaaaaaa aaaaaa                  1426
```

<210> SEQ ID NO 63
<211> LENGTH: 1261
<212> TYPE: DNA
<213> ORGANISM: Glycine max

<400> SEQUENCE: 63

```
gcacgaggat taacgaagga tggaatctgg gtctagcgaa ggagaagagg tgcagcaacg    60
cgtgccgttg agggagagag tggagtggtc agatgttact ccggttcctc aaaacgacgg   120 ccctaacccct gtcgttccga tccagtacac tgaagagttt tccgaagtta tggattactt   180
tcgcgccgtt tacctcaccg atgaacgctc ccctcgcgcc ctcgctctca cagccgaagc    240
cgttcaattc aactccggca actacactgt gtggcatttc cgacggttgt tacttgagtc    300
gctaaaagtc gacttgaacg atgaactgga ttttgtggag cgtatggccg ctggaaattc    360
taaaaattat cagatgtggc atcatagacg atgggttgcc gagaagttag gtcctgaagc    420
tagaaacaat gagctcgagt tcaccaaaaa gatactgtcc gttgatgcca acattatca    480 tgcatggtct catagacagt gggctcttca acactagga ggatgggaag atgaacttaa    540
ttattgcaca gaactactta agaagacat ttttaacaat tctgcttgga atcagagata    600
ttttgtcata acaaggtctc ctttcttggg gggcctaaaa gctatgagag agtctgaagt   660
gctttacacc attgaagcca ttatagccta ccctgaaaat gaaagctcgt ggagatatct   720
```

-continued

```
acgaggactt tataaaggtg aaactacttc atgggtaaat gatcctcaag tttcttcagt      780
atgcttaaag attttgagaa ctaagagcaa ctacgtgttt gctcttagca ctattttaga      840
tcttatatgc tttggttatc aaccaaatga agacattaga gatgccattg acgccttaaa      900
gaccgcagat atggataaac aagatttaga tgatgatgag aaagggggaac aacaaaattt     960
aaatatagca cgaaatattt gttctatcct aaaacaagtt gatccaatta gaaccaacta    1020
ttggatttgg cgcaagagca gacttcctct atcagcttag taaccaaagt aattaaaggg    1080
caactctgtg ttatgtgtaa cctagtttat tgaaactgga ttttttattta ttattattt    1140
ttatgttgtc atgtatctgt tgtgcaaat ttatctttt gtcatgccat tactggcatt      1200
tgagtgtaag gattgaaagc catgcagaat aagaaattta agtttttttt tccgttgaaa    1260
a                                                                    1261
```

<210> SEQ ID NO 64
<211> LENGTH: 1333
<212> TYPE: DNA
<213> ORGANISM: Glycine max

<400> SEQUENCE: 64

```
gcacgagctt gcgtgtggag tgaagaagat taacgaagga tggaatctgg gtctagcgaa      60
ggagaagagg tgcagcaacg cgtgccgttg agggagagag tggagtggtc agatgttact     120
ccggttcctc aaaacgacgg ccctaaccct gtcgttccga tccagtacac tgaagagttt     180
tccgaagtta tggattactt tcgcgccgtt tacctcaccg atgaacgctc ccctcgcgcc     240
ctcgctctca cagccgaagc cgttcaattc aactccggca actacactgt gtggcatttc     300
cgacggttgt tacttgagtc gctaaaagtc gacttgaacg atgaactgga gtttgtggag     360
cgtatggccg ctggaaaattc taaaaattat cagatgtggt gtgatgctct gctctgctct     420
ttcttccata ctttgcatca tagacgatgg gttgccgaga agttaggtcc tgaagctaga     480
aacaatgagc tcgagttcac caaaaagata ctgtccgttg atgccaaaca ttatcatgca     540
tggtctcata gacagtgggc tcttcaaaca ctaggaggat gggaagatga acttaattat     600
tgcacagaac tacttaaaga agacattttt aacaattctg cttggaatca gagatatttt     660
gtcataacaa ggtctccttt cttgggggggc ctaaaagcta tgagagagtc tgaagtgctt     720
tacaccattg aagccattat agcctaccct gaaaatgaaa gctcgtggag atatctacga     780
ggactttata aaggtgaaac tacttcatgg gtaaatgatc ctcaagtttc ttcagtatgc     840
ttaaagattt tgagaactaa gagcaactac gtgtttgctc ttagcactat tttagatctt     900
atatgctttg gttatcaacc aaatgaagac attagagatg ccattgacgc cttaaagacc     960
gcagatatgg ataaacaaga tttagatgat gatgagaaag gggaacaaca aaatttaaat    1020
atagcacgaa atatttgttc tatcctaaaa caagttgatc caattagaac caactattgg    1080
atttggcgca agagcagact tcctctatca gcttagtaac caaagtaatt aaagggcaac    1140
tctgtgttat gtgtaaccta gtttattgaa actggatgtt tatttattat tattttttat    1200
gttgtcatgt atctgtttgt gcaaatttat cttttgtca tgccattact ggcatttgag    1260
tgtaaggatt gaaagccatg cagaataaga aatttaagtt tttttttccg ttgaaaaaaa    1320
aaaaaaaaaa aaa                                                       1333
```

<210> SEQ ID NO 65
<211> LENGTH: 1339
<212> TYPE: DNA

<213> ORGANISM: Triticum sp.

<400> SEQUENCE: 65

```
cggacgtggc gccgctgccg caggccgacg ggccctgccc cgtcgtctcc atcgcttacc      60
gcggcgactt ccgcgaggtc atggactact tccgcgccct ctacgccgcc ggcgagcgca     120
gcccccgcgc cctccgcctc accgccgacg ccatccacct caaccccggc aactacactg     180
tatggcattt caggcgcgtt gttctagagg cactggatgc tgatttattg ctagaaatgc     240
attttgtgga ccaaattgct gaatctaatc caaaaaatta ccaagtctgg catcacaaga     300
gatggcttgc tgagaaaata ggaccagatg ctgcaaatag tgaacatgac ttcacaagga     360
agatacttgc tatggatgct aaaaactacc atgcttggtc ccataggcag tgggttcttc     420
aagcattggg tggatgggag agtgaactgc agtactgcaa ccagcttctt gaggaagatg     480
tcttcaataa ctcagcttgg aatcagagat accttgtggt aacacgatca ccaattcttg     540
ggggccttgc ggcaatgcgc gactcagaag tagattacac agttgaggcc attatggtga     600
accctcagaa tgaaagcccc tggagatacc tcagaggttt atataaggat gataacaatt     660
tgctggtggc tgataatcgc atttctgatg cttgcctcaa ggtcctgaat aaggattgga     720
catgcgtatt tgctttgagc ttcctgcttg atcttcttcg catgggtttg cagccttcga     780
atgaacttaa aggaaccatc gaagcaatgg agaactctga tcctgaaacg ggacatgctg     840
atattgcagt agctgtctgc tcaatcctgc agaaatgtga tccctgcgg ataaactact     900
ggtcatggta ccagaccact cttttcttct agacatctga aaattcagct gaagacagtt     960
ttagcagcat gatgtaaact caatcgaagg ggttgacgca gtgtatgaaa aacctttcct    1020
gtgatcttgg tgcggagcaa tttgtactga ttttactggg aaaaatcaat caatgacagc    1080
atgcccaaca atgtcttgtg tgaatatgtt actgcctgat attcacatgt tagcagaatg    1140
agaataacca atcaaactcc aacgagcaga ttgttacagt aacggccact ggtggtgtga    1200
aaatcctgaa atctgcttca gtcactttgc cttgtttaca gttgagtctg ttgttgtgat    1260
ctgtacctaa tgcatgtaca caatcatcaa attattagtt tttgtaccaa tgagtattcg    1320
atgaaaaaaa aaaaaaaaa                                                 1339
```

<210> SEQ ID NO 66
<211> LENGTH: 333
<212> TYPE: PRT
<213> ORGANISM: Pisum sativum

<400> SEQUENCE: 66

```
Met Ala Gly Asn Ile Glu Val Glu Glu Asp Asp Arg Val Pro Leu Arg
 1               5                  10                  15

Leu Arg Pro Glu Trp Ser Asp Val Thr Pro Ile Pro Gln Asp Asp Gly
            20                  25                  30

Pro Ser Pro Val Val Pro Ile Asn Tyr Ser Glu Glu Phe Ser Glu Val
        35                  40                  45

Met Asp Tyr Phe Arg Ala Val Tyr Phe Ala Lys Glu Leu Ser Ser Arg
    50                  55                  60

Ala Leu Ala Leu Thr Ala Glu Ala Ile Gly Leu Asn Ala Gly Asn Tyr
65                  70                  75                  80

Thr Val Trp His Phe Arg Arg Leu Leu Leu Glu Ser Leu Lys Val Asp
                85                  90                  95

Leu His Val Glu Arg Glu Phe Val Glu Arg Val Ala Ser Gly Asn Ser
            100                 105                 110
```

```
Lys Asn Tyr Gln Ile Trp His His Arg Arg Trp Val Ala Glu Lys Leu
        115                 120                 125

Gly Pro Glu Ala Arg Asn Ser Glu Leu Glu Phe Thr Lys Lys Ile Leu
    130                 135                 140

Ser Val Asp Ala Lys His Tyr His Ala Trp Ser His Arg Gln Trp Val
145                 150                 155                 160

Leu Gln Asn Leu Gly Gly Trp Glu Asp Glu Leu Ser Tyr Cys Ser Glu
                165                 170                 175

Leu Leu Ala Glu Asp Ile Phe Asn Asn Ser Ala Trp Asn Gln Arg Tyr
            180                 185                 190

Phe Val Ile Thr Arg Ser Pro Val Leu Gly Leu Lys Ala Met Arg
        195                 200                 205

Glu Ser Glu Val Leu Phe Thr Val Glu Ala Ile Ile Ser Tyr Pro Glu
    210                 215                 220

Asn Glu Ser Ser Trp Arg Tyr Leu Arg Gly Leu Phe Lys Asp Glu Ser
225                 230                 235                 240

Thr Leu Tyr Val Asn Asp Ala Gln Val Ser Ser Leu Cys Leu Lys Ile
                245                 250                 255

Leu Lys Thr Lys Ser Asn Tyr Leu Phe Ala Leu Ser Thr Leu Leu Asp
            260                 265                 270

Leu Ser Ala Ser Val Ile Gln Pro Asn Glu Asp Phe Arg Asp Ala Ile
        275                 280                 285

Glu Ala Leu Arg Leu Gln Ile Leu Ile Lys Gln Asp Ser Asp Ile Ala
    290                 295                 300

Ile Thr Ile Cys Ser Ile Leu Glu Gln Val Asp Pro Ile Arg Val Asn
305                 310                 315                 320

Tyr Trp Val Trp Arg Lys Ser Arg Leu Pro Gln Ala Ala
                325                 330

<210> SEQ ID NO 67
<211> LENGTH: 346
<212> TYPE: PRT
<213> ORGANISM: Lycopersicon esculentum

<400> SEQUENCE: 67

Met Asp Ser Cys Glu Val Thr Lys Thr Arg Ile Pro Phe Lys Glu Arg
1               5                   10                  15

Pro Asp Trp Ala Asp Val Lys Pro Val Pro Gln Asp Asp Gly Pro Cys
            20                  25                  30

Pro Val Val Pro Ile Ala Tyr Thr Glu Asp Phe Ser Glu Thr Met Asp
        35                  40                  45

Tyr Phe Arg Ala Ile Tyr Val Ala Asp Glu Arg Ser Thr Arg Ala Leu
    50                  55                  60

Gln Leu Thr Gly Glu Ala Ile Gln Leu Asn Pro Gly Asn Tyr Thr Val
65              70                  75                  80

Trp Gln Phe Arg Arg Val Val Leu Glu Ala Leu Gly Val Asp Leu Arg
                85                  90                  95

Glu Glu Leu Lys Phe Val Asp Arg Ile Ala Gly Glu Asn Thr Lys Asn
            100                 105                 110

Tyr Gln Ile Trp His His Arg Arg Trp Leu Ala Glu Lys Leu Gly Ala
        115                 120                 125

Asp Ala Val Thr Asn Glu Leu Glu Phe Thr Lys Lys Ile Phe Ser Gln
    130                 135                 140

Asp Ala Lys Asn Tyr His Ala Trp Ser His Arg Gln Trp Val Leu Gln
145                 150                 155                 160
```

```
Ala Leu Gly Gly Trp Glu Asp Glu Leu Ala Tyr Cys Gln Gln Leu Leu
                165                 170                 175

Glu Asp Asp Ile Tyr Asn Asn Ser Ala Trp Asn Gln Arg Tyr Phe Val
            180                 185                 190

Val Thr Arg Ser Pro Leu Leu Gly Gly Leu Val Ala Met Arg Glu Leu
        195                 200                 205

Glu Val Asn Tyr Thr Val Gln Ala Ile Arg Ala Ser Pro Glu Asn Glu
    210                 215                 220

Ser Pro Trp Arg Tyr Leu Arg Gly Leu Tyr Lys Asn Asp Thr Gln Ser
225                 230                 235                 240

Leu Val Gln Asp Ser Gln Val Ala Ser Val Leu Trp Asp Val Leu Thr
                245                 250                 255

Ser Gln Asn Ser His Val His Ala Leu Arg Phe Leu Leu Asp Leu Leu
            260                 265                 270

Cys His Asp Leu Glu Pro Ser Gln Glu Leu Lys Ser Ala Val Asp Val
        275                 280                 285

Leu Thr Pro Gln Ser Cys Ser Pro Asp Leu Ala Leu Thr Lys Lys Ile
    290                 295                 300

Cys Ser Ile Leu Glu His Ala Asp Pro Met Arg Val Lys Tyr Trp Asn
305                 310                 315                 320

Trp Arg Lys Ser Met Val Arg Val Gln Leu Leu Gln Ser Gln Asn Ala
                325                 330                 335

Glu Arg Leu Ala Asn Leu Ser Val Gln Glu
                340                 345

<210> SEQ ID NO 68
<211> LENGTH: 339
<212> TYPE: PRT
<213> ORGANISM: Oryza sp.

<400> SEQUENCE: 68

Met Ala Pro Ser Ser Thr Ser Ser Glu Gly Ala Ser Asp Glu Trp Leu
  1               5                  10                  15

Pro Pro Ser Arg Arg Pro Glu Leu Ala Asp Val Val Pro Val Thr Gln
             20                  25                  30

Asp Asp Gly Pro His Pro Val Val Ala Ile Ala Tyr Arg Asp Glu Phe
         35                  40                  45

Arg Glu Val Met Asp Tyr Phe Arg Ala Leu Tyr Phe Ala Gly Glu Arg
     50                  55                  60

Ser Val Arg Ala Leu His Leu Thr Ala Glu Val Ile Asp Leu Asn Pro
 65                  70                  75                  80

Gly Asn Tyr Thr Val Trp His Phe Arg Arg Leu Val Leu Glu Ala Leu
                 85                  90                  95

Asp Ala Asp Leu Arg Glu Glu Met Asp Phe Val Asp Arg Ile Val Glu
            100                 105                 110

Cys Asn Pro Lys Asn Tyr Gln Ile Trp His His Lys Arg Trp Leu Ala
        115                 120                 125

Glu Lys Leu Gly Pro Asp Ile Ala Asn Lys Glu His Glu Phe Thr Arg
    130                 135                 140

Lys Ile Leu Ser Met Asp Ala Lys Asn Tyr His Ala Trp Ser His Arg
145                 150                 155                 160

Gln Trp Val Leu Gln Ala Leu Gly Gly Trp Glu Thr Glu Leu Gln Tyr
                165                 170                 175

Cys Asn Gln Leu Leu Glu Glu Asp Val Phe Asn Asn Ser Ala Trp Asn
```

-continued

```
                180                 185                 190
Gln Arg Tyr Leu Val Ile Thr Ser Ser Pro Leu Leu Gly Gly Leu Ala
            195                 200                 205

Ala Met Arg Asp Ser Glu Val Asp Tyr Thr Val Gly Ala Ile Leu Ala
210                 215                 220

Asn Pro Gln Asn Glu Ser Pro Trp Arg Tyr Leu Lys Gly Leu Tyr Lys
225                 230                 235                 240

Gly Glu Asn Asn Leu Leu Met Ala Asp Glu Arg Ile Ser Asp Val Cys
                245                 250                 255

Leu Lys Val Leu Lys His Asp Ser Thr Cys Val Phe Ala Leu Ser Leu
            260                 265                 270

Leu Leu Asp Leu Leu Gln Ile Gly Leu Gln Pro Ser Asp Glu Leu Lys
        275                 280                 285

Gly Thr Ile Glu Ala Ile Lys Asn Ser Asp Pro Glu Ala Asp Glu Ala
    290                 295                 300

Val Asp Ala Asp Leu Ala Thr Ala Ile Cys Ser Ile Leu Gln Arg Cys
305                 310                 315                 320

Asp Pro Leu Arg Ile Asn Tyr Trp Ser Trp Tyr Arg Thr Thr Ile Ser
                325                 330                 335

Ser Gln Thr

<210> SEQ ID NO 69
<211> LENGTH: 326
<212> TYPE: PRT
<213> ORGANISM: Zea mays

<400> SEQUENCE: 69

Met Glu His Thr Leu Ser Gly Pro Ser Ser Trp Pro Glu Leu Ala Asp
  1               5                  10                  15

Val Val Pro Val Pro Gln Asp Gly Pro Ser Pro Val Val Ser Ile
                20                  25                  30

Ala Tyr Arg Asp Asp Phe Arg Gly Val Met Asp Tyr Phe Arg Ala Leu
             35                  40                  45

Tyr Leu Thr Gly Glu Arg Ser Pro Arg Ala Leu Arg Leu Thr Ala Glu
     50                  55                  60

Ala Ile Glu Leu Asn Pro Gly Asn Tyr Thr Val Trp His Phe Arg Arg
 65                  70                  75                  80

Leu Ile Leu Glu Ser Leu Asp Phe Asp Leu Leu Glu Glu Met Lys Phe
                 85                  90                  95

Val Glu Leu Ile Ala Glu Cys Asn Pro Lys Asn Tyr Gln Ile Trp His
                100                 105                 110

His Leu Arg Trp Leu Ala Glu Lys Leu Gly Pro Gly Ile Ala Asn Lys
            115                 120                 125

Glu His Glu Phe Thr Met Lys Ile Leu Ala Ile Asp Ala Leu Asn Tyr
        130                 135                 140

His Ala Trp Ser His Arg Gln Trp Val Leu Gln Ala Leu Gly Gly Trp
145                 150                 155                 160

Glu Thr Glu Leu Glu Tyr Cys Asp His Leu Leu Lys Glu Asp Val Phe
                165                 170                 175

Asn Asn Ser Ala Trp Asn Gln Arg Tyr Phe Val Ile Thr Arg Ser Pro
            180                 185                 190

Phe Leu Gly Gly Leu Ala Ala Met Arg Asp Ser Gly Val Asp Tyr Thr
        195                 200                 205

Ile Glu Ala Ile Leu Ala Asn Ala Gln Asn Gly Ser Pro Trp Arg Tyr
```

-continued

```
            210                 215                 220
Leu Lys Gly Leu Tyr Lys Gly Glu Asn Asn Leu Leu Val Glu Asp Gly
225                 230                 235                 240

Arg Ile Ser Ala Val Cys Phe Lys Val Leu Lys Asn Asp Trp Thr Cys
                245                 250                 255

Val Phe Ala Leu Ser Leu Leu Asp Leu Leu Cys Thr Gly Leu Gln
                260                 265                 270

Pro Ser Asp Gly Leu Arg Ser Thr Leu Gly Thr Ile Arg Ser Ser His
                275                 280                 285

Pro Glu Thr Ala Asp Asp Pro Ala Ala Val Cys Cys Ile Leu
                290                 295                 300

Gln Lys Cys Asp Pro Leu Ala Val Asn Tyr Trp Ser Trp Phe Lys Asp
305                 310                 315                 320

Thr Leu Ser Gln Ile Ser
                325

<210> SEQ ID NO 70
<211> LENGTH: 346
<212> TYPE: PRT
<213> ORGANISM: Glycine max

<400> SEQUENCE: 70

Met Glu Ser Gly Ser Glu Gly Glu Val Gln Gln Arg Val Pro
1               5                   10                  15

Leu Arg Glu Arg Val Glu Trp Ser Asp Val Thr Pro Val Pro Gln Asn
                20                  25                  30

Asp Gly Pro Asn Pro Val Val Pro Ile Gln Tyr Thr Glu Glu Phe Ser
                35                  40                  45

Glu Val Met Asp Tyr Phe Arg Ala Val Tyr Leu Thr Asp Glu Arg Ser
            50                  55                  60

Pro Arg Ala Leu Ala Leu Thr Ala Glu Ala Val Gln Phe Asn Ser Gly
65                  70                  75                  80

Asn Tyr Thr Val Trp His Phe Arg Arg Leu Leu Leu Glu Ser Leu Lys
                85                  90                  95

Val Asp Leu Asn Asp Glu Leu Asp Phe Val Glu Arg Met Ala Ala Gly
                100                 105                 110

Asn Ser Lys Asn Tyr Gln Met Trp His His Arg Arg Trp Val Ala Glu
                115                 120                 125

Lys Leu Gly Pro Glu Ala Arg Asn Asn Glu Leu Glu Phe Thr Lys Lys
            130                 135                 140

Ile Leu Ser Val Asp Ala Lys His Tyr His Ala Trp Ser His Arg Gln
145                 150                 155                 160

Trp Ala Leu Gln Thr Leu Gly Gly Trp Glu Asp Glu Leu Asn Tyr Cys
                165                 170                 175

Thr Glu Leu Leu Lys Glu Asp Ile Phe Asn Asn Ser Ala Trp Asn Gln
                180                 185                 190

Arg Tyr Phe Val Ile Thr Arg Ser Pro Phe Leu Gly Gly Leu Lys Ala
                195                 200                 205

Met Arg Glu Ser Glu Val Leu Tyr Thr Ile Glu Ala Ile Ile Ala Tyr
            210                 215                 220

Pro Glu Asn Glu Ser Ser Trp Arg Tyr Leu Arg Gly Leu Tyr Lys Gly
225                 230                 235                 240

Glu Thr Thr Ser Trp Val Asn Asp Pro Gln Val Ser Ser Val Cys Leu
                245                 250                 255
```

-continued

```
Lys Ile Leu Arg Thr Lys Ser Asn Tyr Val Phe Ala Leu Ser Thr Ile
            260                 265                 270

Leu Asp Leu Ile Cys Phe Gly Tyr Gln Pro Asn Glu Asp Ile Arg Asp
        275                 280                 285

Ala Ile Asp Ala Leu Lys Thr Ala Asp Met Asp Lys Gln Asp Leu Asp
    290                 295                 300

Asp Asp Glu Lys Gly Glu Gln Gln Asn Leu Asn Ile Ala Arg Asn Ile
305                 310                 315                 320

Cys Ser Ile Leu Lys Gln Val Asp Pro Ile Arg Thr Asn Tyr Trp Ile
                325                 330                 335

Trp Arg Lys Ser Arg Leu Pro Leu Ser Ala
                340                 345

<210> SEQ ID NO 71
<211> LENGTH: 358
<212> TYPE: PRT
<213> ORGANISM: Glycine max

<400> SEQUENCE: 71

Met Glu Ser Gly Ser Ser Glu Gly Glu Val Gln Gln Arg Val Pro
 1               5                  10                  15

Leu Arg Glu Arg Val Glu Trp Ser Asp Val Thr Pro Val Pro Gln Asn
            20                  25                  30

Asp Gly Pro Asn Pro Val Val Pro Ile Gln Tyr Thr Glu Glu Phe Ser
        35                  40                  45

Glu Val Met Asp Tyr Phe Arg Ala Val Tyr Leu Thr Asp Glu Arg Ser
    50                  55                  60

Pro Arg Ala Leu Ala Leu Thr Ala Glu Ala Val Gln Phe Asn Ser Gly
65                  70                  75                  80

Asn Tyr Thr Val Trp His Phe Arg Arg Leu Leu Leu Glu Ser Leu Lys
                85                  90                  95

Val Asp Leu Asn Asp Glu Leu Glu Phe Val Glu Arg Met Ala Ala Gly
            100                 105                 110

Asn Ser Lys Asn Tyr Gln Met Trp Cys Asp Ala Leu Leu Cys Ser Phe
        115                 120                 125

Phe His Thr Leu His His Arg Arg Trp Val Ala Glu Lys Leu Gly Pro
    130                 135                 140

Glu Ala Arg Asn Asn Glu Leu Glu Phe Thr Lys Lys Ile Leu Ser Val
145                 150                 155                 160

Asp Ala Lys His Tyr His Ala Trp Ser His Arg Gln Trp Ala Leu Gln
                165                 170                 175

Thr Leu Gly Gly Trp Glu Asp Glu Leu Asn Tyr Cys Thr Glu Leu Leu
            180                 185                 190

Lys Glu Asp Ile Phe Asn Asn Ser Ala Trp Asn Gln Arg Tyr Phe Val
        195                 200                 205

Ile Thr Arg Ser Pro Phe Leu Gly Gly Leu Lys Ala Met Arg Glu Ser
    210                 215                 220

Glu Val Leu Tyr Thr Ile Glu Ala Ile Ile Ala Tyr Pro Glu Asn Glu
225                 230                 235                 240

Ser Ser Trp Arg Tyr Leu Arg Gly Leu Tyr Lys Gly Glu Thr Thr Ser
                245                 250                 255

Trp Val Asn Asp Pro Gln Val Ser Ser Val Cys Leu Lys Ile Leu Arg
            260                 265                 270

Thr Lys Ser Asn Tyr Val Phe Ala Leu Ser Thr Ile Leu Asp Leu Ile
        275                 280                 285
```

```
Cys Phe Gly Tyr Gln Pro Asn Glu Asp Ile Arg Asp Ala Ile Asp Ala
        290                 295                 300

Leu Lys Thr Ala Asp Met Asp Lys Gln Asp Leu Asp Asp Asp Glu Lys
305                 310                 315                 320

Gly Glu Gln Gln Asn Leu Asn Ile Ala Arg Asn Ile Cys Ser Ile Leu
                325                 330                 335

Lys Gln Val Asp Pro Ile Arg Thr Asn Tyr Trp Ile Trp Arg Lys Ser
            340                 345                 350

Arg Leu Pro Leu Ser Ala
        355

<210> SEQ ID NO 72
<211> LENGTH: 309
<212> TYPE: PRT
<213> ORGANISM: Triticum sp.

<400> SEQUENCE: 72

Asp Val Ala Pro Leu Pro Gln Ala Asp Gly Pro Cys Pro Val Val Ser
1               5                   10                  15

Ile Ala Tyr Arg Gly Asp Phe Arg Glu Val Met Asp Tyr Phe Arg Ala
            20                  25                  30

Leu Tyr Ala Ala Gly Glu Arg Ser Pro Arg Ala Leu Arg Leu Thr Ala
        35                  40                  45

Asp Ala Ile His Leu Asn Pro Gly Asn Tyr Thr Val Trp His Phe Arg
    50                  55                  60

Arg Val Val Leu Gly Ala Leu Asp Ala Asp Leu Leu Glu Met His
65                  70                  75                  80

Phe Val Asp Gln Ile Ala Glu Ser Asn Pro Leu Asn Tyr Gln Val Trp
                85                  90                  95

His His Lys Arg Trp Leu Ala Glu Lys Ile Gly Pro Asp Ala Ala Asn
            100                 105                 110

Ser Glu His Asp Phe Thr Arg Lys Ile Leu Ala Met Asp Ala Lys Asn
        115                 120                 125

Tyr His Ala Trp Ser His Arg Gln Trp Val Leu Gln Ala Leu Gly Gly
    130                 135                 140

Trp Glu Ser Glu Leu Gln Tyr Cys Asn Gln Leu Leu Glu Glu Asp Val
145                 150                 155                 160

Phe Asn Asn Ser Ala Trp Asn Gln Arg Tyr Leu Val Val Thr Arg Ser
                165                 170                 175

Pro Ile Leu Gly Gly Leu Ala Ala Met Arg Asp Ser Glu Val Asp Tyr
            180                 185                 190

Thr Val Glu Ala Ile Met Val Asn Pro Gln Asn Glu Ser Pro Trp Arg
        195                 200                 205

Tyr Leu Arg Gly Leu Tyr Lys Asp Asp Asn Leu Leu Val Ala Asp
    210                 215                 220

Asn Arg Ile Ser Asp Ala Cys Leu Lys Val Leu Asn Lys Asp Trp Thr
225                 230                 235                 240

Cys Val Phe Ala Leu Ser Phe Leu Leu Asp Leu Leu Arg Met Gly Leu
                245                 250                 255

Gln Pro Ser Asn Glu Leu Lys Gly Thr Ile Glu Ala Met Glu Asn Ser
            260                 265                 270

Asp Pro Glu Thr Gly His Ala Asp Ile Ala Val Ala Val Cys Ser Ile
        275                 280                 285

Leu Gln Lys Cys Asp Pro Leu Arg Ile Asn Tyr Trp Ser Trp Tyr Gln
```

```
              290             295             300
Thr Thr Leu Ser Ser
305

<210> SEQ ID NO 73
<211> LENGTH: 1290
<212> TYPE: DNA
<213> ORGANISM: Unknown Organism
<220> FEATURE:
<223> OTHER INFORMATION: Description of Unknown Organism: Protein
      similar to FT Beta subunit

<400> SEQUENCE: 73
atggagattc agcgagataa gcaattggat tatctgatga aaggcttaag gcagcttggt      60
ccgcagtttt cttccttaga tgctaatcga ccttggcttt gttactggat tcttcattca     120
atagctttgc ttggggagac tgtggatgat gaattagaaa gcaatgccat tgacttcctt     180
ggacgctgcc agggctctga aggtggatac ggtggtggtc ctggccaact tccacatctt     240
gcaactactt atgctgcagt gaatgcactt gttactttag gaggtgacaa gcccttttct     300
tcaattaata gagaaaaaat gtcttgtttt ttaagacgga tgaaggatac aagtggaggt     360
ttcaggatgc atgatatggg agaaattgat gttcgtgcat gctacactgc aatttcggtt     420
gcaagcatcc taaatattat ggatgatgaa ctcacccagg gcctaggaga ttacatcttg     480
agttgccaaa cttatgaagg tggcattgga ggggaacctg gctccgaagc tcacggtggg     540
tatacctact gtggtttggc tgctatgatt ttaatcaatg aggtcgaccg tttgaatttg     600
gattcattaa tgaattgggc tgtacatcga caaggagtag aaatgggatt tcaaggtagg     660
acgaacaaat tggtcgatgg ttgctacaca ttttggcagg cagccccttg tgttctacta     720
caaagattat attcaaccaa tgatcatgac gttcatggat catcacatat atcagaaggg     780
acaaatgaag aacatcatgc tcatgatgaa gatgaccttg aagacagtga tgatgatgat     840
gattctgatg aggacaacga tgaagattca gtgaatggtc acagaatcca tcatacatcc     900
acctacatta acaggagaat gcaactggtt tttgatagcc tcggcttgca gagatatgta     960
ctcttgtgct ctaagatccc tgacggtgga ttcagagaca agccgaggaa accccgtgac    1020
ttctaccaca catgttactg cctgagcggc ttgtctgtgg ctcagcacgc ttggttaaaa    1080
gacgaggaca ctcctccttt gactcgcgac attatgggtg gctactcgaa tctccttgaa    1140
cctgttcaac ttcttcacaa cattgtcatg gatcagtata atgaagctat cgagttcttc    1200
tttaaagcag catgacccgt tgttgctaat gtatgggaaa ccccaaacat aagagtttcc    1260
gtagtgttgt aacttgtaag atttcaaaag                                    1290

<210> SEQ ID NO 74
<211> LENGTH: 1627
<212> TYPE: DNA
<213> ORGANISM: Arabidopsis thaliana

<400> SEQUENCE: 74
atgccagtag taacccgctt gattcgtttg aagtgtgtag ggctcagact tgaccggagt      60
ggactcaatc ggcgaatctg tcacggagga cacggggaat caacgcggcg gagagtgatg     120
gaagagcttt caagcctaac cgtgagtcag cgcgagcaat ttctggtgga gaacgatgtg     180
ttcgggatct ataattactt cgacgccagc gacgtttcta ctcaaaaata catgatggag     240
attcagcgag ataagcaatt ggattatctg atgaaaggct taaggcagct tggtccgcag     300
ttttcttcct tagatgctaa tcgaccttgg ctttgttact ggattcttca ttcaatagct     360
```

```
ttgcttgggg agactgtgga tgatgaatta gaaagcaatg ccattgactt ccttggacgc    420
tgccagggct ctgaaggtgg atacggtggt ggtcctggcc aacttccaca tcttgcaact    480
acttatgctg cagtgaatgc acttgttact ttaggaggtg acaaagccct tcttcaatt     540 aatagagaaa aaatgtcttg ttttttaaga cggatgaagg atacaagtgg aggtttcagg    600
atgcatgata tgggagaaat ggatgttcgt gcatgctaca ctgcaatttc ggttgcaagc    660
atcctaaata ttatggatga tgaactcacc cagggcctag agattacat  cttgagttgc    720 caaacttatg aaggtggcat tggaggggaa cctggctccg aagctcacgg tgggtatacc    780
tactgtggtt tggctgctat gattttaatc aatgaggtcg accgtttgaa tttggattca    840
ttaatgaatt gggctgtaca tcgacaagga gtagaaatgg gatttcaagg taggacgaac    900
aaattggtcg atggttgcta cacattttgg caggcagccc cttgtgttct actacaaaga    960
ttatattcaa ccaatgatca tgacgttcat ggatcatcac atatatcaga agggacaaat   1020
gaagaacatc atgctcatga tgaagatgac cttgaagaca gtgatgatga tgatgattct   1080
gatgaggaca acgatgaaga ttcagtgaat ggtcacagaa tccatcatac atccacctac   1140
attaacagga gaatgcaact ggttttttgat agcctcggct tgcagagata tgtactcttg   1200
tgctctaaga tccctgacgg tggattcaga gacaagccga ggaaaccccg tgacttctac   1260
cacacatgtt actgcctgag cggcttgtct gtggctcagc acgcttggtt aaaagacgag   1320
gacactcctc ctttgactcg cgacattatg ggtggctact cgaatctcct tgaacctgtt   1380
caacttcttc acaacattgt catggatcag tataatgaag ctatcgagtt cttctttaaa   1440
gcagcatgac ccgttgttgc taatgtatgg gaaactccaa acataagagt tttcgtagtg   1500
ttgtaacttg taagatttca aaagaagttt cactaattta accttaaaac ctgttacttt   1560
tttattacgt ataccatt tatcatatct ttggtttacg acttaaagaa tttgatgatt     1620
gttgaaa                                                             1627

<210> SEQ ID NO 75
<211> LENGTH: 1135
<212> TYPE: DNA
<213> ORGANISM: Glycine max

<400> SEQUENCE: 75
gccaccattc ctcgcaacgc ccaaaccctc atgttggagc ttcaacgcga taatcacatg     60
cagtatgtct ccaaaggcct tcgccatctc agttccgcat tttccgtttt ggacgctaat    120
cgaccctggc tctgctactg gatcttccac tccattgctt tgtcgggaga atccgtcgat    180
gatgaactcg aagataacgc tatcgatttt cttaaccgtt gccaggatcc gaatggtgga    240
tatgccgggg gaccaggcca gatgcctcat attgccacaa cttatgctgc tgttaattca    300
cttattactt tgggtggtga gaaatccctg gcatcaatta atagagataa actgtatggg    360
tttctgcggc ggatgaagca accaaatggt ggattcagga tgcatgatga aggtgaaatt    420
gatgttcgag cttgctacac tgccatttct gttgcaagtg ttttgaacat tttggatgat    480
gagctgatcc agaatgttgg agactacatt ataagctgtc aaacatatga gggtggcatt    540
gctggtgagc ctggttctga ggctcatggt gggtacacct tttgtggatt agctacaatg    600
attctgattg gtgaggttaa tcacttggat ctgcctcgat tagttgactg gtggtattc    660 cgacaaggta aggaatgtgg attccagggg agaacaaata aactggtgga tgatgctat    720 tcctttggc aggaggtgc tgttgctcta ttgcaaagat tatcttctat tatcaacaaa     780
```

| | |
|---|---|
| cagatggaag agacatcaca gattttttgcg gtatcttatg tatctgaagc aaaagaaagt | 840 |
| ttggatggaa cctctagtca tgcaacatgc cgtggtgagc atgaaggcac cagtgaatcc | 900 |
| agttcatctg attttaaaaa tattgcctat aaatttatta atgagtggag agcacaagaa | 960 |
| ccactttttc acagtattgc tttacagcaa tatattctct tatgtgcaca ggagcaagag | 1020 |
| ggtggactga gagacaaacc gggtaaacgt agagatcatt atcacacatg ttactgttta | 1080 |
| agtggactct cattgtgcca gtatagttgg tcaaagcacc cagattctcc accac | 1135 |

<210> SEQ ID NO 76
<211> LENGTH: 1245
<212> TYPE: DNA
<213> ORGANISM: Zea mays

<400> SEQUENCE: 76

| | |
|---|---|
| ggcggatccc gacctaccga ggctcacggt gacgcaggtg gagcagatga aggtggaggc | 60 |
| cagggttggc gacatctacc gctccctctt cggggccgcg cccaacacga aatccatcat | 120 |
| gctagagctg tggcgtgatc agcatatcga gtatctgacg cctgggctga ggcatatggg | 180 |
| accagccttt catgttctag atgccaatcg cccttggcta tgctactgga tggttcatcc | 240 |
| acttgctttg ctggatgaag cacttgatga tgatcttgag aatgatatca tagacttctt | 300 |
| agctcgatgt caggataaag atggtggata tagtggtgga cctggacagt tgcctcacct | 360 |
| agctacgact tatgctgctg taaatacact tgtgacaata gggagccaaa gagcattgtc | 420 |
| atcaatcaat agggcaacc tgtacaattt tatgctgcag atgaaagatg tatcaggtgc | 480 |
| tttcagaatg catgatggtg gcgaaattga tgtccgtgct tcctacaccg ctatatcggt | 540 |
| tgccagcctt gtgaatattc ttgattttaa actggcaaaa ggtgtaggcg actacatagc | 600 |
| aagatgtcaa acttatgaag gtggtattgc tggggagcct tatgctgaag cacatggtgg | 660 |
| gtatacattc tgtggattgg ctgctttgat cctgcttaat gaggcagaga agttgacttt | 720 |
| gcctagtttg attggctggg tggcttttcg tcaaggagtg gaatgcggat ttcaaggacg | 780 |
| aactaataaa ttggttgatg gttgctactc cttttggcag ggagctgcca ttgctttcac | 840 |
| acaaaagtta attacgattg ttgataagca attgaagtcc tcgtattcct gcaaaaggcc | 900 |
| atcaggagag gatgcctgca gcaccagttc atatgggtgc accgcgaaaa agtcttcctc | 960 |
| tgctgtggac tatgcgaagt ttggatttga ttttatacaa cagagcaacc aaattggccc | 1020 |
| actcttccat aacattgccc tgcaacaata catcctactt tgttctcagg tactagaggg | 1080 |
| aggcttgagg ataagcctg gaaagaacag agatcactac cattcatgct actgcctcag | 1140 |
| tggcctcgca gttagccagt acagtgccat gactgatact ggttcgtgcc cattacctca | 1200 |
| gcatgtgctt ggaccgtact ctaatttgct ggagccaatc catcc | 1245 |

<210> SEQ ID NO 77
<211> LENGTH: 1648
<212> TYPE: DNA
<213> ORGANISM: Pisum sativum

<400> SEQUENCE: 77

| | |
|---|---|
| cggaccccc cgtccacaat cgtgatgatg acgtctccgc gagcatttca acaaccagtt | 60 |
| actcaaacca ccgcggagta acacatggaa gcttcaaccg cggcggagac accaactccg | 120 |
| acggtgagtc agagagatca atggatagta gaatcacagg tctttcatat ttatcaactc | 180 |
| ttcgccaata ttcctcctaa cgcccaatct atcattcgac cttggctgtg ttactggatt | 240 |
| attcattcaa ttgctttgtt gggagaatct attgatgatg atctcgaaga taacactgtc | 300 |

-continued

```
gattttctta accgttgcca ggatccaaat ggtggatatg ctgggggacc tggtcagatg       360
cctcatcttg ccacaactta tgctgcagtc aatactctta ttactctggg tggtgagaaa       420
tctttggcat ctattaatag aaataagttg tacgggttta tgcggcggat gaaacagcca       480
aacggcggat tcaggatgca tgacgaggga gaaattgacg ttcgagcttg ctacactgcc       540
atctctgtgg caagtgttct gaacattttg gatgatgagc tgatcaagaa tgttggagac       600
ttcattttaa gctgtcaaac atatgaggga ggccttgctg gtgagcctgg gtctgaggct       660
catggcgggt atacctttg tgggttagct gcaatgattc tgattggtga ggttaatcgc        720
ttggatctgc ctcgtttact tgattgggtt gtgtttcggc aaggtaaaga gtgtggattt       780
caggggagaa cgaataaatt ggtagatgga tgctactcgt tttggcaggg aggtgctgtt       840
gccctattgc aaagattaca ttctattatc gacgaacaaa tggcagaggc atcacagttt       900
gttacagtat ctgatgcacc tgaagaaaag gaatgtttgg acggaacctc aagtcatgca       960
acttcccata ttaggcatga aggcatgaat gaatcctgct catctgacgt taaaaatatt      1020
ggttataact ttattagtga gtggagacaa agtgaaccac ttttttcacag cattgcctta      1080 cagcaatata ttctttttatg ttcacaggag caagatggtg ggctcaggga caaaccgggt     1140
aaacgcaggg atcattatca ttcatgttac tgtttaagtg ggttgtcact gtgccagtat      1200
agttggtcga agcgcccaga ttctccaccg ctgcctaagg tagtaatggg cccatactcc      1260
aatctcttag aacccatcca tcctctcttt aatgttgttt tggatcgata tcgtgaagct      1320
catgaattct tttctcagtt gtgacggatg acaaggtttt agctaccaat agctcgatca      1380
ttagaatgta aaatgtaaac taaaatatga aatatgaaat accaaaaaga tattattgga      1440
tgaaattcac gtggatctaa tacaactgcg tggttttcat tcctgatttg attttgattt      1500
acatgagtta aaacgttaaa cccttcttat tcatacattt gttaagagct taaggcttaa      1560
tggttaagcc aatgatataa atatttatgc agaaagctgt tgcttatcac caacggtaat      1620
attaataagc aaacaagtat tctgtgat                                         1648
```

<210> SEQ ID NO 78
<211> LENGTH: 1832
<212> TYPE: DNA
<213> ORGANISM: Lycopersicon esculentum

<400> SEQUENCE: 78

```
gtaaacgagc gttgatttgt cgctgacgaa atttacagtc aagagtagta accggttgta        60
gtgaaaaaat ggagtcgagg aaagtgacga agacgctgga agatcaatgg gtggtggagc       120
gtcgagtccg agagatatac gattatttct acagcatttc ccccaactct ccgtccgacc       180
tcatagagat cgaacgtgac aaacacttcg gttatctaag ccaaggtctc agaaaacttg       240
gtccgtcgtt ttccgttttg gatgccagtc gaccatggct ttgctactgg acacttcatt       300
caatcgcttt gttgggagaa tctattggtg gcaaactgga aaatgatgca attgactttc       360
tgacccgttg ccaggataaa gatggtggct atggaggtgg acctggtcag atgcctcatc       420
ttgcaactac ttatgctgca gtcaattcac taataacttt gggcaaacct gaagctctgt       480
catcaattaa tagagaaaag ttgtacacat ttttgctgcg aatgaaagac gcaagtggtg       540
gattcaggat gcacgatggt ggagaagtag atgttcgtgc ctgttatact gccatttctg       600
ttgcaaatat attaaacatt gtggatgacg agctgattca tggtgttgga aattacatcc       660
taagttgtca gacttatgaa ggtggaattg ctggcgaacc aggttctgaa gctcatggtg       720
```

-continued

```
ggtatacttt ctgtgggttg gctgcaatga ttctgatcaa cgaagtagat cgattggact      780
tgccaggttt aattgattgg gtggtattta gacaagggt  cgaaggtgga tttcaaggca      840
ggacaaataa attagtcgat ggctgctatt cctttggca  gggcgcggta gtgtttctta      900
tacaaagact aaatttgata gtccatgaac aactagggct gtcaaatgac ctcagtacag      960
aaagtgctga tgattcttca gagtcagagt tatctgatga agaagagcat ttggaaggga     1020
tatcctctca tgttcaggat actttccctc ttggacaagc aggtgcttgt caagaaaatg     1080
cttctcatag cccaaaaata gcagatactg gatatgagtt tatcaaccga cccatagcta     1140
tgaggcctct ctttgacagc atgtatctgc agcaatatgt tcttctttgc tctcagattg     1200
aagttggtgg tttcagagac aaacctggga agggtagaga ctactaccat acctgttact     1260
gtttaagtgg tctttcaatt gctcagtata gctggaccga cgaagctgat tctacaccat     1320
tacccaggga tgtatttggt ccttattcca aatgtctgtt ggaacaggtt cacccactct     1380
tcaacgtagt gttggatcgg tattatgaag ctcgcgaata ctctcaggct tgtgagactg     1440
tttcaccact ttcattagca ccaactttt  cagaaactta gttgcaatcc agaagttaaa     1500
agtgtcattg ggttcaaaag agttgtgatc gtttatgtac atatccttgc atttgtatac     1560
gtgatacaag ttgagagaat aacgggtact ttctgaactt gctgaactag cacgtaaatt     1620
cgtctctggt ttagtgaggt ctgtaaacat caatgtgaaa ttgcgagata tgcatgtaat     1680
agtggctaag atttacaaat ctggataccg gttattagtg atcagaaatt tcattcaatt     1740
tcccaaacgg tcacctaagt ttaggatatt gctttaaaat attatttatt tttcatttaa     1800
gaatcaaaaa aaaaaaaaaa aaaaaaaaaa aa                                   1832
```

```
<210> SEQ ID NO 79
<211> LENGTH: 1449
<212> TYPE: DNA
<213> ORGANISM: Nicotiana tabacum
<220> FEATURE:
<221> NAME/KEY: misc_feature
<222> LOCATION: (87)...*87)
<223> OTHER INFORMATION: Wherein "n" is A, T, C or G
<220> FEATURE:
<221> NAME/KEY: misc_difference
<222> LOCATION: (1038)...(1038)
<223> OTHER INFORMATION: Wherein "n" is A, T, C or G

<400> SEQUENCE: 79
```

```
ggcacgagcg gcacgaggac actggaagat caatggatgg tggagcgtca agttcgggag       60
atatacaatt ttttctacag cattccnccc aattcccact tagagacttc aacagaaaag      120
cacttcgatt atctcactcg aggtctcaga aacttggtc  cgtcgttctc cgtcttggat      180
gctaatcgac catggctttg ctactggata cttcattcaa tcgctttgtt gggagaatct      240
attgatgccc aactggaaaa tgatgcaatt gactttctga ccgttgcca  ggatgaagat      300 ggtggctatg tggtggacc  tggtcagatg cctcatcttg caactactta tgctgcagtc      360
aattcactca taactttggg cagccctaaa gctctgtcat caatcaatag agaaaaattg      420
tatacatttt ggctgcaaat gaaagacaca agtggtggct tcaggatgca tgatggtgga      480
gaagtagatg ttcgtgcctg ttatactgcc atttctgttg caagtatatt gcaaattgtg      540
gatgatgaac tgattaatga tgtgggaat  tacatcctaa gttgtcagac ttatgaaggt      600
ggaattgctg gcgaaccagg ttctgaagct catggtgggt ataccttctg tgggttggct      660
gcaatgattc tgattaacga agcgaatcga ttggacttgc caagattaat tgattgggtg      720
gtatttagac aaggagtcga aggtggattt caaggcagga caaataaatt agtcgatggc      780
```

-continued

```
tgctattcct tttggcaggc cgcggtagct tttcttatac aaagattaaa atcgacagtc    840
catgaacaac tagggctgtc aaatgaactc agtacagaaa gtgctgatga ttcttcggag    900
tcagagttat ctgatgaaga gcatttgcaa gggacatcat ctcatgttca gaagacttgc    960
cctcttggac aagaaggaca ggaaaatgct tcagatccca caaagatagc agatactggt   1020
tatgattttg tcaatcgnac gatagctatg cgacctgtgt ttgacagctt ttatctgcag   1080
caatacgttc ttctctgctc ccagatagat ggaggtttca gagacaaacc tgggaagggt   1140
agagaccact accatacttg ctactgttta agtggtcttt caattgctca atatagctgg   1200
accaacgaag ctgatgcgcc accattaccc agggatgtat ttggtcctta ttctcaaaat   1260
cttttggaac agattcaccc actttacaac gtagtgttgg atcggtatta tgaagctcgt   1320
agcttcttct catgcttgtg ataatatttt acgcgatagc tgtagctgga atgttacctc   1380
tagttgttca gaatcagaga ctaatctatt attttgaggg attggattca aaaaaaaaaa   1440
aaaaaaaaa                                                            1449
```

<210> SEQ ID NO 80
<211> LENGTH: 404
<212> TYPE: PRT
<213> ORGANISM: Unknown Organism
<220> FEATURE:
<223> OTHER INFORMATION: Description of Unknown Organism: Protein similar to FT Beta Subunit

<400> SEQUENCE: 80

```
Met Glu Ile Gln Arg Asp Lys Gln Leu Asp Tyr Leu Met Lys Gly Leu
 1               5                  10                  15

Arg Gln Leu Gly Pro Gln Phe Ser Ser Leu Asp Ala Asn Arg Pro Trp
            20                  25                  30

Leu Cys Tyr Trp Ile Leu His Ser Ile Ala Leu Leu Gly Glu Thr Val
        35                  40                  45

Asp Asp Glu Leu Glu Ser Asn Ala Ile Asp Phe Leu Gly Arg Cys Gln
    50                  55                  60

Gly Ser Glu Gly Gly Tyr Gly Gly Gly Pro Gly Gln Leu Pro His Leu
65                  70                  75                  80

Ala Thr Thr Tyr Ala Ala Val Asn Ala Leu Val Thr Leu Gly Gly Asp
                85                  90                  95

Lys Ala Leu Ser Ser Ile Asn Arg Glu Lys Met Ser Cys Phe Leu Arg
            100                 105                 110

Arg Met Lys Asp Thr Ser Gly Gly Phe Arg Met His Asp Met Gly Glu
        115                 120                 125

Ile Asp Val Arg Ala Cys Tyr Thr Ala Ile Ser Val Ala Ser Ile Leu
    130                 135                 140

Asn Ile Met Asp Asp Glu Leu Thr Gln Gly Leu Gly Asp Tyr Ile Leu
145                 150                 155                 160

Ser Cys Gln Thr Tyr Glu Gly Gly Ile Gly Gly Glu Pro Gly Ser Glu
                165                 170                 175

Ala His Gly Gly Tyr Thr Tyr Cys Gly Leu Ala Ala Met Ile Leu Ile
            180                 185                 190

Asn Glu Val Asp Arg Leu Asn Leu Asp Ser Leu Met Asn Trp Ala Val
        195                 200                 205

His Arg Gln Gly Val Glu Met Gly Phe Gln Gly Arg Thr Asn Lys Leu
    210                 215                 220

Val Asp Gly Cys Tyr Thr Phe Trp Gln Ala Ala Pro Cys Val Leu Leu
```

-continued

```
                225                 230                 235                 240
Gln Arg Leu Tyr Ser Thr Asn Asp His Asp Val His Gly Ser Ser His
                245                 250                 255
Ile Ser Glu Gly Thr Asn Glu Glu His His Ala His Asp Glu Asp Asp
            260                 265                 270
Leu Glu Asp Ser Asp Asp Asp Asp Ser Asp Glu Asp Asn Asp Glu
        275                 280                 285
Asp Ser Val Asn Gly His Arg Ile His His Thr Ser Thr Tyr Ile Asn
    290                 295                 300
Arg Arg Met Gln Leu Val Phe Asp Ser Leu Gly Leu Gln Arg Tyr Val
305                 310                 315                 320
Leu Leu Cys Ser Lys Ile Pro Asp Gly Gly Phe Arg Asp Lys Pro Arg
                325                 330                 335
Lys Pro Arg Asp Phe Tyr His Thr Cys Tyr Cys Leu Ser Gly Leu Ser
            340                 345                 350
Val Ala Gln His Ala Trp Leu Lys Asp Glu Asp Thr Pro Pro Leu Thr
        355                 360                 365
Arg Asp Ile Met Gly Gly Tyr Ser Asn Leu Leu Glu Pro Val Gln Leu
    370                 375                 380
Leu His Asn Ile Val Met Asp Gln Tyr Asn Glu Ala Ile Glu Phe Phe
385                 390                 395                 400
Phe Lys Ala Ala

<210> SEQ ID NO 81
<211> LENGTH: 482
<212> TYPE: PRT
<213> ORGANISM: Arabidopsis thaliana

<400> SEQUENCE: 81

Met Pro Val Val Thr Arg Leu Ile Arg Leu Lys Cys Val Gly Leu Arg
  1               5                  10                  15
Leu Asp Arg Ser Gly Leu Asn Arg Arg Ile Cys His Gly Gly His Gly
                 20                  25                  30
Glu Ser Thr Arg Arg Val Met Glu Glu Leu Ser Ser Leu Thr Val
             35                  40                  45
Ser Gln Arg Glu Gln Phe Leu Val Glu Asn Asp Val Phe Gly Ile Tyr
         50                  55                  60
Asn Tyr Phe Asp Ala Ser Asp Val Ser Thr Gln Lys Tyr Met Met Glu
 65                  70                  75                  80
Ile Gln Arg Asp Lys Gln Leu Asp Tyr Leu Met Lys Gly Leu Arg Gln
                 85                  90                  95
Leu Gly Pro Gln Phe Ser Ser Leu Asp Ala Asn Arg Pro Trp Leu Cys
            100                 105                 110
Tyr Trp Ile Leu His Ser Ile Ala Leu Leu Gly Glu Thr Val Asp Asp
         115                 120                 125
Glu Leu Glu Ser Asn Ala Ile Asp Phe Leu Gly Arg Cys Gln Gly Ser
     130                 135                 140
Glu Gly Gly Tyr Gly Gly Gly Pro Gly Gln Leu Pro His Leu Ala Thr
145                 150                 155                 160
Thr Tyr Ala Ala Val Asn Ala Leu Val Thr Leu Gly Asp Lys Ala
                 165                 170                 175
Leu Ser Ser Ile Asn Arg Glu Lys Met Ser Cys Phe Leu Arg Arg Met
             180                 185                 190
Lys Asp Thr Ser Gly Gly Phe Arg Met His Asp Met Gly Glu Met Asp
```

```
                    195                 200                 205
Val Arg Ala Cys Tyr Thr Ala Ile Ser Val Ala Ser Ile Leu Asn Ile
    210                 215                 220

Met Asp Asp Glu Leu Thr Gln Gly Leu Gly Asp Tyr Ile Leu Ser Cys
225                 230                 235                 240

Gln Thr Tyr Glu Gly Ile Gly Gly Glu Pro Gly Ser Glu Ala His
                245                 250                 255

Gly Gly Tyr Thr Tyr Cys Gly Leu Ala Ala Met Ile Leu Ile Asn Glu
                260                 265                 270

Val Asp Arg Leu Asn Leu Asp Ser Leu Met Asn Trp Ala Val His Arg
            275                 280                 285

Gln Gly Val Glu Met Gly Phe Gln Gly Arg Thr Asn Lys Leu Val Asp
    290                 295                 300

Gly Cys Tyr Thr Phe Trp Gln Ala Ala Pro Cys Val Leu Leu Gln Arg
305                 310                 315                 320

Leu Tyr Ser Thr Asn Asp His Asp Val His Gly Ser Ser His Ile Ser
                325                 330                 335

Glu Gly Thr Asn Glu Glu His His Ala His Asp Glu Asp Leu Glu
            340                 345                 350

Asp Ser Asp Asp Asp Asp Ser Asp Glu Asp Asn Asp Glu Asp Ser
                355                 360                 365

Val Asn Gly His Arg Ile His His Thr Ser Thr Tyr Ile Asn Arg Arg
    370                 375                 380

Met Gln Leu Val Phe Asp Ser Leu Gly Leu Gln Arg Tyr Val Leu Leu
385                 390                 395                 400

Cys Ser Lys Ile Pro Asp Gly Gly Phe Arg Asp Lys Pro Arg Lys Pro
                405                 410                 415

Arg Asp Phe Tyr His Thr Cys Tyr Cys Leu Ser Gly Leu Ser Val Ala
                420                 425                 430

Gln His Ala Trp Leu Lys Asp Glu Asp Thr Pro Pro Leu Thr Arg Asp
            435                 440                 445

Ile Met Gly Gly Tyr Ser Asn Leu Leu Glu Pro Val Gln Leu Leu His
    450                 455                 460

Asn Ile Val Met Asp Gln Tyr Asn Glu Ala Ile Glu Phe Phe Lys
465                 470                 475                 480

Ala Ala

<210> SEQ ID NO 82
<211> LENGTH: 378
<212> TYPE: PRT
<213> ORGANISM: Glycine max

<400> SEQUENCE: 82

Ala Thr Ile Pro Arg Asn Ala Gln Thr Leu Met Leu Glu Leu Gln Arg
1               5                   10                  15

Asp Asn His Met Gln Tyr Val Ser Lys Gly Leu Arg His Leu Ser Ser
                20                  25                  30

Ala Phe Ser Val Leu Asp Ala Asn Arg Pro Trp Leu Cys Tyr Trp Ile
            35                  40                  45

Phe His Ser Ile Ala Leu Ser Gly Glu Ser Val Asp Asp Glu Leu Glu
        50                  55                  60

Asp Asn Ala Ile Asp Phe Leu Asn Arg Cys Gln Asp Pro Asn Gly Gly
65              70                  75                  80

Tyr Ala Gly Gly Pro Gly Gln Met Pro His Ile Ala Thr Thr Tyr Ala
```

```
                85                 90                 95
Ala Val Asn Ser Leu Ile Thr Leu Gly Gly Glu Lys Ser Leu Ala Ser
            100                105                110

Ile Asn Arg Asp Lys Leu Tyr Gly Phe Leu Arg Arg Met Lys Gln Pro
            115                120                125

Asn Gly Gly Phe Arg Met His Asp Glu Gly Glu Ile Asp Val Arg Ala
            130                135                140

Cys Tyr Thr Ala Ile Ser Val Ala Ser Val Leu Asn Ile Leu Asp Asp
145                150                155                160

Glu Leu Ile Gln Asn Val Gly Asp Tyr Ile Ile Ser Cys Gln Thr Tyr
            165                170                175

Glu Gly Gly Ile Ala Gly Glu Pro Gly Ser Glu Ala His Gly Gly Tyr
            180                185                190

Thr Phe Cys Gly Leu Ala Thr Met Ile Leu Ile Gly Glu Val Asn His
            195                200                205

Leu Asp Leu Pro Arg Leu Val Asp Trp Val Val Phe Arg Gln Gly Lys
210                215                220

Glu Cys Gly Phe Gln Gly Arg Thr Asn Lys Leu Val Asp Gly Cys Tyr
225                230                235                240

Ser Phe Trp Gln Gly Gly Ala Val Ala Leu Leu Gln Arg Leu Ser Ser
            245                250                255

Ile Ile Asn Lys Gln Met Glu Glu Thr Ser Gln Ile Phe Ala Val Ser
            260                265                270

Tyr Val Ser Glu Ala Lys Glu Ser Leu Asp Gly Thr Ser Ser His Ala
            275                280                285

Thr Cys Arg Gly Glu His Glu Gly Thr Ser Glu Ser Ser Ser Ser Asp
290                295                300

Phe Lys Asn Ile Ala Tyr Lys Phe Ile Asn Glu Trp Arg Ala Gln Glu
305                310                315                320

Pro Leu Phe His Ser Ile Ala Leu Gln Gln Tyr Ile Leu Leu Cys Ala
            325                330                335

Gln Glu Gln Glu Gly Gly Leu Arg Asp Lys Pro Gly Lys Arg Arg Asp
            340                345                350

His Tyr His Thr Cys Tyr Cys Leu Ser Gly Leu Ser Leu Cys Gln Tyr
            355                360                365

Ser Trp Ser Lys His Pro Asp Ser Pro Pro
            370                375

<210> SEQ ID NO 83
<211> LENGTH: 414
<212> TYPE: PRT
<213> ORGANISM: Zea mays

<400> SEQUENCE: 83

Ala Asp Pro Asp Leu Pro Arg Leu Thr Val Thr Gln Val Glu Gln Met
1               5                  10                 15

Lys Val Glu Ala Arg Val Gly Asp Ile Tyr Arg Ser Leu Phe Gly Ala
            20                 25                 30

Ala Pro Asn Thr Lys Ser Ile Met Leu Glu Leu Trp Arg Asp Gln His
            35                 40                 45

Ile Glu Tyr Leu Thr Pro Gly Leu Arg His Met Gly Pro Ala Phe His
            50                 55                 60

Val Leu Asp Ala Asn Arg Pro Trp Leu Cys Tyr Trp Met Val His Pro
65              70                 75                 80
```

```
Leu Ala Leu Leu Asp Glu Ala Leu Asp Asp Leu Glu Asn Asp Ile
                85                  90                  95

Ile Asp Phe Leu Ala Arg Cys Gln Asp Lys Asp Gly Gly Tyr Ser Gly
            100                 105                 110

Gly Pro Gly Gln Leu Pro His Leu Ala Thr Thr Tyr Ala Ala Val Asn
        115                 120                 125

Thr Leu Val Thr Ile Gly Ser Gln Arg Ala Leu Ser Ser Ile Asn Arg
130                 135                 140

Gly Asn Leu Tyr Asn Phe Met Leu Gln Met Lys Asp Val Ser Gly Ala
145                 150                 155                 160

Phe Arg Met His Asp Gly Gly Glu Ile Asp Val Arg Ala Ser Tyr Thr
                165                 170                 175

Ala Ile Ser Val Ala Ser Leu Val Asn Ile Leu Asp Phe Lys Leu Ala
            180                 185                 190

Lys Gly Val Gly Asp Tyr Ile Ala Arg Cys Gln Thr Tyr Glu Gly Gly
        195                 200                 205

Ile Ala Gly Glu Pro Tyr Ala Glu Ala His Gly Gly Tyr Thr Phe Cys
210                 215                 220

Gly Leu Ala Ala Leu Ile Leu Leu Asn Glu Ala Glu Lys Val Asp Leu
225                 230                 235                 240

Pro Ser Leu Ile Gly Trp Val Ala Phe Arg Gln Gly Val Glu Cys Gly
                245                 250                 255

Phe Gln Gly Arg Thr Asn Lys Leu Val Asp Gly Cys Tyr Ser Phe Trp
            260                 265                 270

Gln Gly Ala Ala Ile Ala Phe Thr Gln Lys Leu Ile Thr Ile Val Asp
        275                 280                 285

Lys Gln Leu Lys Ser Ser Tyr Ser Cys Lys Arg Pro Ser Gly Glu Asp
290                 295                 300

Ala Cys Ser Thr Ser Ser Tyr Gly Cys Thr Ala Lys Lys Ser Ser Ser
305                 310                 315                 320

Ala Val Asp Tyr Ala Lys Phe Gly Phe Asp Phe Ile Gln Gln Ser Asn
                325                 330                 335

Gln Ile Gly Pro Leu Phe His Asn Ile Ala Leu Gln Gln Tyr Ile Leu
            340                 345                 350

Leu Cys Ser Gln Val Leu Glu Gly Gly Leu Arg Asp Lys Pro Gly Lys
        355                 360                 365

Asn Arg Asp His Tyr His Ser Cys Tyr Cys Leu Ser Gly Leu Ala Val
370                 375                 380

Ser Gln Tyr Ser Ala Met Thr Asp Thr Gly Ser Cys Pro Leu Pro Gln
385                 390                 395                 400

His Val Leu Gly Pro Tyr Ser Asn Leu Leu Glu Pro Ile His
                405                 410

<210> SEQ ID NO 84
<211> LENGTH: 420
<212> TYPE: PRT
<213> ORGANISM: Pisum sativum

<400> SEQUENCE: 84

Met Glu Ala Ser Thr Ala Ala Glu Thr Pro Thr Pro Thr Val Ser Gln
1               5                   10                  15

Arg Asp Gln Trp Ile Val Glu Ser Gln Val Phe His Ile Tyr Gln Leu
            20                  25                  30

Phe Ala Asn Ile Pro Pro Asn Ala Gln Ser Ile Ile Arg Pro Trp Leu
        35                  40                  45
```

```
Cys Tyr Trp Ile Ile His Ser Ile Ala Leu Leu Gly Glu Ser Ile Asp
 50                  55                  60

Asp Leu Glu Asp Asn Thr Val Asp Phe Leu Asn Arg Cys Gln Asp
 65                  70                  75                  80

Pro Asn Gly Gly Tyr Ala Gly Pro Gly Gln Met Pro His Leu Ala
                 85                  90                  95

Thr Thr Tyr Ala Ala Val Asn Thr Leu Ile Thr Leu Gly Gly Glu Lys
                100                 105                 110

Ser Leu Ala Ser Ile Asn Arg Asn Lys Leu Tyr Gly Phe Met Arg Arg
                115                 120                 125

Met Lys Gln Pro Asn Gly Gly Phe Arg Met His Asp Glu Gly Glu Ile
130                 135                 140

Asp Val Arg Ala Cys Tyr Thr Ala Ile Ser Val Ala Ser Val Leu Asn
145                 150                 155                 160

Ile Leu Asp Asp Glu Leu Ile Lys Asn Val Gly Asp Phe Ile Leu Ser
                165                 170                 175

Cys Gln Thr Tyr Glu Gly Gly Leu Ala Gly Glu Pro Gly Ser Glu Ala
                180                 185                 190

His Gly Gly Tyr Thr Phe Cys Gly Leu Ala Ala Met Ile Leu Ile Gly
                195                 200                 205

Glu Val Asn Arg Leu Asp Leu Pro Arg Leu Leu Asp Trp Val Val Phe
210                 215                 220

Arg Gln Gly Lys Glu Cys Gly Phe Gln Gly Arg Thr Asn Lys Leu Val
225                 230                 235                 240

Asp Gly Cys Tyr Ser Phe Trp Gln Gly Gly Ala Val Ala Leu Leu Gln
                245                 250                 255

Arg Leu His Ser Ile Ile Asp Glu Gln Met Ala Glu Ala Ser Gln Phe
                260                 265                 270

Val Thr Val Ser Asp Ala Pro Glu Glu Lys Glu Cys Leu Asp Gly Thr
                275                 280                 285

Ser Ser His Ala Thr Ser His Ile Arg His Glu Gly Met Asn Glu Ser
290                 295                 300

Cys Ser Ser Asp Val Lys Asn Ile Gly Tyr Asn Phe Ile Ser Glu Trp
305                 310                 315                 320

Arg Gln Ser Glu Pro Leu Phe His Ser Ile Ala Leu Gln Gln Tyr Ile
                325                 330                 335

Leu Leu Cys Ser Gln Glu Gln Asp Gly Gly Leu Arg Asp Lys Pro Gly
                340                 345                 350

Lys Arg Arg Asp His Tyr His Ser Cys Tyr Cys Leu Ser Gly Leu Ser
                355                 360                 365

Leu Cys Gln Tyr Ser Trp Ser Lys Arg Pro Asp Ser Pro Pro Leu Pro
                370                 375                 380

Lys Val Val Met Gly Pro Tyr Ser Ser Asn Leu Leu Glu Pro Ile His
385                 390                 395                 400

Pro Leu Phe Asn Val Val Leu Asp Arg Tyr Arg Glu Ala His Glu Phe
                405                 410                 415

Phe Ser Gln Leu
            420

<210> SEQ ID NO 85
<211> LENGTH: 470
<212> TYPE: PRT
<213> ORGANISM: Lycopersicon esculentum
```

<400> SEQUENCE: 85

```
Met Glu Ser Arg Lys Val Thr Lys Thr Leu Glu Asp Gln Trp Val Val
 1               5                  10                  15

Glu Arg Arg Val Arg Glu Ile Tyr Asp Tyr Phe Tyr Ser Ile Ser Pro
             20                  25                  30

Asn Ser Pro Ser Asp Leu Ile Glu Ile Glu Arg Asp Lys His Phe Gly
         35                  40                  45

Tyr Leu Ser Gln Gly Leu Arg Lys Leu Gly Pro Ser Phe Ser Val Leu
     50                  55                  60

Asp Ala Ser Arg Pro Trp Leu Cys Tyr Trp Thr Leu His Ser Ile Ala
 65                  70                  75                  80

Leu Leu Gly Glu Ser Ile Gly Gly Lys Leu Glu Asn Asp Ala Ile Asp
                 85                  90                  95

Phe Leu Thr Arg Cys Gln Asp Lys Asp Gly Tyr Gly Gly Gly Pro
            100                 105                 110

Gly Gln Met Pro His Leu Ala Thr Thr Tyr Ala Ala Val Asn Ser Leu
            115                 120                 125

Ile Thr Leu Gly Lys Pro Glu Ala Leu Ser Ser Ile Asn Arg Glu Lys
        130                 135                 140

Leu Tyr Thr Phe Leu Leu Arg Met Lys Asp Ala Ser Gly Gly Phe Arg
145                 150                 155                 160

Met His Asp Gly Gly Glu Val Asp Val Arg Ala Cys Tyr Thr Ala Ile
                165                 170                 175

Ser Val Ala Asn Ile Leu Asn Ile Val Asp Asp Glu Leu Ile His Gly
            180                 185                 190

Val Gly Asn Tyr Ile Leu Ser Cys Gln Thr Tyr Glu Gly Gly Ile Ala
        195                 200                 205

Gly Glu Pro Gly Ser Glu Ala His Gly Gly Tyr Thr Phe Cys Gly Leu
    210                 215                 220

Ala Ala Met Ile Leu Ile Asn Glu Val Asp Arg Leu Asp Leu Pro Gly
225                 230                 235                 240

Leu Ile Asp Trp Val Val Phe Arg Gln Gly Val Glu Gly Gly Phe Gln
                245                 250                 255

Gly Arg Thr Asn Lys Leu Val Asp Gly Cys Tyr Ser Phe Trp Gln Gly
            260                 265                 270

Ala Val Val Phe Leu Ile Gln Arg Leu Asn Leu Ile Val His Glu Gln
        275                 280                 285

Leu Gly Leu Ser Asn Asp Leu Ser Thr Glu Ser Ala Asp Ser Ser
    290                 295                 300

Glu Ser Glu Leu Ser Asp Glu Glu His Leu Glu Gly Ile Ser Ser
305                 310                 315                 320

His Val Gln Asp Thr Phe Pro Leu Gly Gln Ala Gly Ala Cys Gln Glu
                325                 330                 335

Asn Ala Ser His Ser Pro Lys Ile Ala Asp Thr Gly Tyr Glu Phe Ile
            340                 345                 350

Asn Arg Pro Ile Ala Met Arg Pro Leu Phe Asp Ser Met Tyr Leu Gln
        355                 360                 365

Gln Tyr Val Leu Leu Cys Ser Gln Ile Glu Val Gly Gly Phe Arg Asp
    370                 375                 380

Lys Pro Gly Lys Gly Arg Asp Tyr Tyr His Thr Cys Tyr Cys Leu Ser
385                 390                 395                 400

Gly Leu Ser Ile Ala Gln Tyr Ser Trp Thr Asp Glu Ala Asp Ser Thr
                405                 410                 415
```

```
Pro Leu Pro Arg Asp Val Phe Gly Pro Tyr Ser Lys Cys Leu Leu Glu
            420                 425                 430

Gln Val His Pro Leu Phe Asn Val Val Leu Asp Arg Tyr Tyr Glu Ala
            435                 440                 445

Arg Glu Tyr Ser Gln Ala Cys Glu Thr Val Ser Pro Leu Ser Leu Ala
            450                 455                 460

Pro Thr Phe Ser Glu Thr
465                 470

<210> SEQ ID NO 86
<211> LENGTH: 446
<212> TYPE: PRT
<213> ORGANISM: Nicotiana tabacum

<400> SEQUENCE: 86

Gly Thr Ser Gly Thr Arg Thr Leu Glu Asp Gln Trp Met Val Glu Arg
  1               5                  10                  15

Gln Val Arg Glu Ile Tyr Asn Phe Phe Tyr Ser Ile Pro Pro Asn Ser
             20                  25                  30

His Leu Glu Thr Ser Thr Glu Lys His Phe Asp Tyr Leu Thr Arg Gly
         35                  40                  45

Leu Arg Lys Leu Gly Pro Ser Phe Ser Val Leu Asp Ala Asn Arg Pro
     50                  55                  60

Trp Leu Cys Tyr Trp Ile Leu His Ser Ile Ala Leu Leu Gly Glu Ser
 65                  70                  75                  80

Ile Asp Ala Gln Leu Glu Asn Asp Ala Ile Asp Phe Leu Ser Arg Cys
                 85                  90                  95

Gln Asp Glu Asp Gly Gly Tyr Gly Gly Gly Pro Gly Gln Met Pro His
            100                 105                 110

Leu Ala Thr Thr Tyr Ala Ala Val Asn Ser Leu Ile Thr Leu Gly Ser
            115                 120                 125

Pro Lys Ala Leu Ser Ser Ile Asn Arg Glu Lys Leu Tyr Thr Phe Trp
        130                 135                 140

Leu Gln Met Lys Asp Thr Ser Gly Gly Phe Arg Met His Asp Gly Gly
145                 150                 155                 160

Glu Val Asp Val Arg Ala Cys Tyr Thr Ala Ile Ser Val Ala Ser Ile
                165                 170                 175

Leu Gln Ile Val Asp Asp Glu Leu Ile Asn Asp Val Gly Asn Tyr Ile
            180                 185                 190

Leu Ser Cys Gln Thr Tyr Glu Gly Gly Ile Ala Gly Glu Pro Gly Ser
        195                 200                 205

Glu Ala His Gly Gly Tyr Thr Phe Cys Gly Leu Ala Ala Met Ile Leu
    210                 215                 220

Ile Asn Glu Ala Asn Arg Leu Asp Leu Pro Arg Leu Ile Asp Trp Val
225                 230                 235                 240

Val Phe Arg Gln Gly Val Glu Gly Phe Gln Gly Arg Thr Asn Lys
                245                 250                 255

Leu Val Asp Gly Cys Tyr Ser Phe Trp Gln Ala Ala Val Ala Phe Leu
            260                 265                 270

Ile Gln Arg Leu Lys Ser Thr Val His Glu Gln Leu Gly Leu Ser Asn
        275                 280                 285

Glu Leu Ser Thr Glu Ser Ala Asp Asp Ser Ser Glu Ser Glu Leu Ser
    290                 295                 300

Asp Glu Glu His Leu Gln Gly Thr Ser Ser His Val Gln Lys Thr Cys
```

```
                305                 310                 315                 320
Pro Leu Gly Gln Glu Gly Gln Glu Asn Ala Ser Asp Pro Thr Lys Ile
                325                 330                 335

Ala Asp Thr Gly Tyr Asp Phe Val Asn Arg Thr Ile Ala Met Arg Pro
                340                 345                 350

Val Phe Asp Ser Phe Tyr Leu Gln Gln Tyr Val Leu Leu Cys Ser Gln
                355                 360                 365

Ile Asp Gly Gly Phe Arg Asp Lys Pro Gly Lys Gly Arg Asp His Tyr
        370                 375                 380

His Thr Cys Tyr Cys Leu Ser Gly Leu Ser Ile Ala Gln Tyr Ser Trp
385                 390                 395                 400

Thr Asn Glu Ala Asp Ala Pro Pro Leu Pro Arg Asp Val Phe Gly Pro
                405                 410                 415

Tyr Ser Gln Asn Leu Leu Glu Gln Ile His Pro Leu Tyr Asn Val Val
                420                 425                 430

Leu Asp Arg Tyr Tyr Glu Ala Arg Ser Phe Phe Ser Cys Leu
                435                 440                 445

<210> SEQ ID NO 87
<211> LENGTH: 323
<212> TYPE: PRT
<213> ORGANISM: Artificial Sequence
<220> FEATURE:
<223> OTHER INFORMATION: Description of Artificial Sequence:Consensus
      sequence where Xaa can be any amino acid
<220> FEATURE:
<221> NAME/KEY: VARIANT
<222> LOCATION: (1)...(6)
<223> OTHER INFORMATION: Wherein "Xaa" is any amino acid
<220> FEATURE:
<221> NAME/KEY: VARIANT
<222> LOCATION: (10)...(11)
<223> OTHER INFORMATION: Wherein "Xaa" is any amino acid
<220> FEATURE:
<221> NAME/KEY: VARIANT
<222> LOCATION: (13)
<223> OTHER INFORMATION: Wherein "Xaa" is any amino acid
<220> FEATURE:
<221> NAME/KEY: VARIANT
<222> LOCATION: (19)
<223> OTHER INFORMATION: Wherein "Xaa" is any amino acid
<220> FEATURE:
<221> NAME/KEY: VARIANT
<222> LOCATION: (21)...(22)
<223> OTHER INFORMATION: Wherein "Xaa" is any amino acid
<220> FEATURE:
<221> NAME/KEY: VARIANT
<222> LOCATION: (24)
<223> OTHER INFORMATION: Wherein "Xaa" is any amino acid
<220> FEATURE:
<221> NAME/KEY: VARIANT
<222> LOCATION: (34)
<223> OTHER INFORMATION: Wherein "Xaa" is any amino acid
<220> FEATURE:
<221> NAME/KEY: VARIANT
<222> LOCATION: (36)
<223> OTHER INFORMATION: Wherein "Xaa" is any amino acid
<220> FEATURE:
<221> NAME/KEY: VARIANT
<222> LOCATION: (40)
<223> OTHER INFORMATION: Wherein "Xaa" is any amino acid
<220> FEATURE:
<221> NAME/KEY: VARIANT
<222> LOCATION: (42)
<223> OTHER INFORMATION: Wherein "Xaa" is any amino acid
<220> FEATURE:
<221> NAME/KEY: VARIANT
<222> LOCATION: (68)
<223> OTHER INFORMATION: Wherein "Xaa" is any amino acid
<220> FEATURE:
```

-continued

```
<221> NAME/KEY: VARIANT
<222> LOCATION: (86)
<223> OTHER INFORMATION: Wherein "Xaa" is any amino acid
<220> FEATURE:
<221> NAME/KEY: VARIANT
<222> LOCATION: (89)
<223> OTHER INFORMATION: Wherein "Xaa" is any amino acid
<220> FEATURE:
<221> NAME/KEY: VARIANT
<222> LOCATION: (92)
<223> OTHER INFORMATION: Wherein "Xaa" is any amino acid
<220> FEATURE:
<221> NAME/KEY: VARIANT
<222> LOCATION: (129)
<223> OTHER INFORMATION: Wherein "Xaa" is any amino acid
<220> FEATURE:
<221> NAME/KEY: VARIANT
<222> LOCATION: (194)
<223> OTHER INFORMATION: Wherein "Xaa" is any amino acid
<220> FEATURE:
<221> NAME/KEY: VARIANT
<222> LOCATION: (218)
<223> OTHER INFORMATION: Wherein "Xaa" is any amino acid
<220> FEATURE:
<221> NAME/KEY: VARIANT
<222> LOCATION: (284)
<223> OTHER INFORMATION: Wherein "Xaa" is any amino acid
<220> FEATURE:
<221> NAME/KEY: VARIANT
<222> LOCATION: (304)
<223> OTHER INFORMATION: Wherein "Xaa" is any amino acid
<220> FEATURE:
<221> NAME/KEY: VARIANT
<222> LOCATION: (320)...(323)
<223> OTHER INFORMATION: Wherein "Xaa" is any amino acid

<400> SEQUENCE: 87

Xaa Xaa Xaa Xaa Xaa Val Pro Leu Xaa Xaa Arg Xaa Glu Trp Ser
 1               5                  10                  15

Asp Val Xaa Pro Xaa Xaa Gln Xaa Asp Gly Pro Asn Pro Val Val Pro
             20                  25                  30

Ile Xaa Tyr Xaa Glu Glu Phe Xaa Glu Xaa Met Asp Tyr Phe Arg Ala
         35                  40                  45

Ile Tyr Phe Ser Asp Glu Arg Ser Pro Arg Ala Leu Arg Leu Thr Glu
     50                  55                  60

Glu Ala Leu Xaa Leu Asn Ser Gly Asn Tyr Thr Val Trp His Phe Arg
 65                  70                  75                  80

Arg Leu Val Leu Glu Xaa Leu Asn Xaa Asp Leu Xaa Glu Glu Leu Glu
                 85                  90                  95

Phe Ile Glu Arg Ile Ala Glu Asp Asn Ser Lys Asn Tyr Gln Leu Trp
            100                 105                 110

His His Arg Arg Trp Val Ala Glu Lys Leu Gly Pro Asp Val Ala Gly
        115                 120                 125

Xaa Glu Leu Glu Phe Thr Arg Arg Val Leu Ser Leu Asp Ala Lys His
130                 135                 140

Tyr His Ala Trp Ser His Arg Gln Trp Ala Leu Gln Ala Leu Gly Gly
145                 150                 155                 160

Trp Glu Asp Glu Leu Asn Tyr Cys His Glu Leu Leu Glu Ala Asp Val
                165                 170                 175

Phe Asn Asn Ser Ala Trp Asn Gln Arg Tyr Tyr Val Ile Thr Arg Ser
            180                 185                 190

Pro Xaa Leu Gly Gly Leu Glu Ala Met Arg Glu Ser Glu Val Ser Tyr
        195                 200                 205

Thr Ile Lys Ala Ile Leu Ala Asn Pro Xaa Asn Glu Ser Ser Trp Arg
210                 215                 220
```

```
Tyr Leu Lys Ala Leu Tyr Lys Asp Asp Thr Glu Ser Trp Ile Ser Asp
225                 230                 235                 240

Pro Ser Val Ser Ser Val Cys Leu Lys Val Leu Ser Arg Thr Asp Cys
            245                 250                 255

Phe His Gly Phe Ala Leu Ser Thr Leu Leu Asp Leu Leu Cys Asp Gly
        260                 265                 270

Leu Arg Pro Thr Asn Glu His Arg Asp Ser Val Xaa Ala Leu Ala Asn
        275                 280                 285

Glu Glu Pro Glu Thr Asn Leu Ala Asn Leu Val Cys Thr Ile Leu Xaa
    290                 295                 300

Arg Val Asp Pro Ile Arg Ala Asn Tyr Trp Ala Trp Arg Lys Ser Xaa
305                 310                 315                 320

Xaa Xaa Xaa

<210> SEQ ID NO 88
<211> LENGTH: 394
<212> TYPE: PRT
<213> ORGANISM: Artificial Sequence
<220> FEATURE:
<223> OTHER INFORMATION: Description of Artificial Sequence: Consensus
      sequence where X can be any amino acid
<220> FEATURE:
<221> NAME/KEY: VARIANT
<222> LOCATION: (1)
<223> OTHER INFORMATION: Wherein "Xaa" is any amino acid
<220> FEATURE:
<221> NAME/KEY: VARIANT
<222> LOCATION: (3)...(5)
<223> OTHER INFORMATION: Wherein "Xaa" is any amino acid
<220> FEATURE:
<221> NAME/KEY: VARIANT
<222> LOCATION: (7)...(10)
<223> OTHER INFORMATION: Wherein "Xaa" is any amino acid
<220> FEATURE:
<221> NAME/KEY: VARIANT
<222> LOCATION: (15)
<223> OTHER INFORMATION: Wherein "Xaa" is any amino acid
<220> FEATURE:
<221> NAME/KEY: VARIANT
<222> LOCATION: (18)
<223> OTHER INFORMATION: Wherein "Xaa" is any amino acid
<220> FEATURE:
<221> NAME/KEY: VARIANT
<222> LOCATION: (20)...(21)
<223> OTHER INFORMATION: Wherein "Xaa" is any amino acid
<220> FEATURE:
<221> NAME/KEY: VARIANT
<222> LOCATION: (23)...(25)
<223> OTHER INFORMATION: Wherein "Xaa" is any amino acid
<220> FEATURE:
<221> NAME/KEY: VARIANT
<222> LOCATION: (30)...(32)
<223> OTHER INFORMATION: Wherein "Xaa" is any amino acid
<220> FEATURE:
<221> NAME/KEY: VARIANT
<222> LOCATION: (35)
<223> OTHER INFORMATION: Wherein "Xaa" is any amino acid
<220> FEATURE:
<221> NAME/KEY: VARIANT
<222> LOCATION: (49)
<223> OTHER INFORMATION: Wherein "Xaa" is any amino acid
<220> FEATURE:
<221> NAME/KEY: VARIANT
<222> LOCATION: (72)
<223> OTHER INFORMATION: Wherein "Xaa" is any amino acid
<220> FEATURE:
<221> NAME/KEY: VARIANT
<222> LOCATION: (77)
<223> OTHER INFORMATION: Wherein "Xaa" is any amino acid
<220> FEATURE:
<221> NAME/KEY: VARIANT
```

-continued

```
<222> LOCATION: (82)
<223> OTHER INFORMATION: Wherein "Xaa" is any amino acid
<220> FEATURE:
<221> NAME/KEY: VARIANT
<222> LOCATION: (116)...(117)
<223> OTHER INFORMATION: Wherein "Xaa" is any amino acid
<220> FEATURE:
<221> NAME/KEY: VARIANT
<222> LOCATION: (120)
<223> OTHER INFORMATION: Wherein "Xaa" is any amino acid
<220> FEATURE:
<221> NAME/KEY: VARIANT
<222> LOCATION: (128)
<223> OTHER INFORMATION: Wherein "Xaa" is any amino acid
<220> FEATURE:
<221> NAME/KEY: VARIANT
<222> LOCATION: (137)
<223> OTHER INFORMATION: Wherein "Xaa" is any amino acid
<220> FEATURE:
<221> NAME/KEY: VARIANT
<222> LOCATION: (154)
<223> OTHER INFORMATION: Wherein "Xaa" is any amino acid
<220> FEATURE:
<221> NAME/KEY: VARIANT
<222> LOCATION: (163)...(164)
<223> OTHER INFORMATION: Wherein "Xaa" is any amino acid
<220> FEATURE:
<221> NAME/KEY: VARIANT
<222> LOCATION: (171)
<223> OTHER INFORMATION: Wherein "Xaa" is any amino acid
<220> FEATURE:
<221> NAME/KEY: VARIANT
<222> LOCATION: (207)...(208)
<223> OTHER INFORMATION: Wherein "Xaa" is any amino acid
<220> FEATURE:
<221> NAME/KEY: VARIANT
<222> LOCATION: (215)...(216)
<223> OTHER INFORMATION: Wherein "Xaa" is any amino acid
<220> FEATURE:
<221> NAME/KEY: VARIANT
<222> LOCATION: (248)
<223> OTHER INFORMATION: Wherein "Xaa" is any amino acid
<220> FEATURE:
<221> NAME/KEY: VARIANT
<222> LOCATION: (255)
<223> OTHER INFORMATION: Wherein "Xaa" is any amino acid
<220> FEATURE:
<221> NAME/KEY: VARIANT
<222> LOCATION: (258)
<223> OTHER INFORMATION: Wherein "Xaa" is any amino acid
<220> FEATURE:
<221> NAME/KEY: VARIANT
<222> LOCATION: (262)...(264)
<223> OTHER INFORMATION: Wherein "Xaa" is any amino acid
<220> FEATURE:
<221> NAME/KEY: VARIANT
<222> LOCATION: (267)...(269)
<223> OTHER INFORMATION: Wherein "Xaa" is any amino acid
<220> FEATURE:
<221> NAME/KEY: VARIANT
<222> LOCATION: (271)...(276)
<223> OTHER INFORMATION: Wherein "Xaa" is any amino acid
<220> FEATURE:
<221> NAME/KEY: VARIANT
<222> LOCATION: (278)...(280)
<223> OTHER INFORMATION: Wherein "Xaa" is any amino acid
<220> FEATURE:
<221> NAME/KEY: VARIANT
<222> LOCATION: (285)...(287)
<223> OTHER INFORMATION: Wherein "Xaa" is any amino acid
<220> FEATURE:
<221> NAME/KEY: VARIANT
<222> LOCATION: (289)...(296)
<223> OTHER INFORMATION: Wherein "Xaa" is any amino acid
<220> FEATURE:
<221> NAME/KEY: VARIANT
<222> LOCATION: (300)...(301)
<223> OTHER INFORMATION: Wherein "Xaa" is any amino acid
<220> FEATURE:
```

-continued

```
<221> NAME/KEY: VARIANT
<222> LOCATION: (303)...(304)
<223> OTHER INFORMATION: Wherein "Xaa" is any amino acid
<220> FEATURE:
<221> NAME/KEY: VARIANT
<222> LOCATION: (306)...(309)
<223> OTHER INFORMATION: Wherein "Xaa" is any amino acid
<220> FEATURE:
<221> NAME/KEY: VARIANT
<222> LOCATION: (312)...(314)
<223> OTHER INFORMATION: Wherein "Xaa" is any amino acid
<220> FEATURE:
<221> NAME/KEY: VARIANT
<222> LOCATION: (316)
<223> OTHER INFORMATION: Wherein "Xaa" is any amino acid
<220> FEATURE:
<221> NAME/KEY: VARIANT
<222> LOCATION: (318)
<223> OTHER INFORMATION: Wherein "Xaa" is any amino acid
<220> FEATURE:
<221> NAME/KEY: VARIANT
<222> LOCATION: (337)
<223> OTHER INFORMATION: Wherein "Xaa" is any amino acid
<220> FEATURE:
<221> NAME/KEY: VARIANT
<222> LOCATION: (348)
<223> OTHER INFORMATION: Wherein "Xaa" is any amino acid
<220> FEATURE:
<221> NAME/KEY: VARIANT
<222> LOCATION: (364)
<223> OTHER INFORMATION: Wherein "Xaa" is any amino acid
<220> FEATURE:
<221> NAME/KEY: VARIANT
<222> LOCATION: (372)
<223> OTHER INFORMATION: Wherein "Xaa" is any amino acid
<220> FEATURE:
<221> NAME/KEY: VARIANT
<222> LOCATION: (378)...(381)
<223> OTHER INFORMATION: Wherein "Xaa" is any amino acid
<220> FEATURE:
<221> NAME/KEY: VARIANT
<222> LOCATION: (384)
<223> OTHER INFORMATION: Wherein "Xaa" is any amino acid
<220> FEATURE:
<221> NAME/KEY: VARIANT
<222> LOCATION: (386)
<223> OTHER INFORMATION: Wherein "Xaa" is any amino acid
<220> FEATURE:
<221> NAME/KEY: VARIANT
<222> LOCATION: (388)
<223> OTHER INFORMATION: Wherein "Xaa" is any amino acid
<220> FEATURE:
<221> NAME/KEY: VARIANT
<222> LOCATION: (392)
<223> OTHER INFORMATION: Wherein "Xaa" is any amino acid
<220> FEATURE:
<221> NAME/KEY: VARIANT
<222> LOCATION: (394)
<223> OTHER INFORMATION: Wherein "Xaa" is any amino acid

<400> SEQUENCE: 88

Xaa Thr Xaa Xaa Xaa Asn Xaa Xaa Xaa Met Leu Glu Leu Xaa Arg
  1               5                  10                  15

Asp Xaa His Xaa Xaa Tyr Xaa Xaa Xaa Gly Leu Arg His Xaa Xaa Xaa
             20                  25                  30

Ala Phe Xaa Val Leu Asp Ala Asn Arg Pro Trp Leu Cys Tyr Trp Ile
         35                  40                  45

Xaa His Ser Ile Ala Leu Leu Gly Glu Ser Val Asp Asp Leu Glu
     50                  55                  60

Asn Asn Ala Ile Asp Phe Leu Xaa Arg Cys Gln Asp Xaa Asp Gly Gly
 65                  70                  75                  80

Tyr Xaa Gly Gly Pro Gly Gln Leu Pro His Leu Ala Thr Thr Tyr Ala
             85                  90                  95
```

```
Ala Val Asn Thr Leu Val Thr Leu Gly Gly Glu Lys Ala Leu Ser Ser
                100                 105                 110

Ile Asn Arg Xaa Xaa Leu Tyr Xaa Phe Leu Arg Arg Met Lys Asp Xaa
            115                 120                 125

Asn Gly Gly Phe Arg Met His Asp Xaa Gly Glu Ile Asp Val Arg Ala
        130                 135                 140

Cys Tyr Thr Ala Ile Ser Val Ala Ser Xaa Leu Asn Ile Leu Asp Asp
145                 150                 155                 160

Glu Leu Xaa Xaa Gly Val Gly Asp Tyr Ile Xaa Ser Cys Gln Thr Tyr
                165                 170                 175

Glu Gly Gly Ile Ala Gly Glu Pro Gly Ser Glu Ala His Gly Gly Tyr
            180                 185                 190

Thr Phe Cys Gly Leu Ala Thr Met Ile Leu Ile Asn Glu Val Xaa Xaa
        195                 200                 205

Leu Asp Leu Pro Ser Leu Xaa Xaa Trp Val Val Phe Arg Gln Gly Val
210                 215                 220

Glu Cys Gly Phe Gln Gly Arg Thr Asn Lys Leu Val Asp Gly Cys Tyr
225                 230                 235                 240

Ser Phe Trp Gln Gly Ala Ala Xaa Ala Leu Leu Gln Arg Leu Xaa Ser
                245                 250                 255

Ile Xaa Asp Lys Gln Xaa Xaa Xaa Ser Ser Xaa Xaa Ser Xaa Xaa
            260                 265                 270

Xaa Xaa Xaa Xaa Glu Xaa Xaa Xaa Gly Thr Ser Ser Xaa Xaa Xaa Cys
            275                 280                 285

Xaa Xaa Xaa Xaa Xaa Xaa Xaa Glu Ser Ser Xaa Xaa Asp Xaa Xaa
        290                 295                 300

Asn Xaa Xaa Xaa Xaa Phe Ile Xaa Xaa Xaa Arg Xaa Ile Xaa Pro Leu
305                 310                 315                 320

Phe His Ser Ile Ala Leu Gln Gln Tyr Ile Leu Leu Cys Ser Gln Val
                325                 330                 335

Xaa Glu Gly Gly Leu Arg Asp Lys Pro Gly Lys Xaa Arg Asp His Tyr
            340                 345                 350

His Thr Cys Tyr Cys Leu Ser Gly Leu Ser Val Xaa Gln Tyr Ser Trp
        355                 360                 365

Ser Lys Asp Xaa Asp Ser Pro Pro Leu Xaa Xaa Xaa Leu Gly Xaa
            370                 375                 380

Tyr Xaa Asn Xaa Leu Glu Pro Xaa His Xaa
385                 390

<210> SEQ ID NO 89
<211> LENGTH: 1018
<212> TYPE: DNA
<213> ORGANISM: Artificial Sequence
<220> FEATURE:
<221> NAME/KEY: misc_feature
<222> LOCATION: (1)...(4)
<223> OTHER INFORMATION: Wherein "n" is A, T, C or G
<220> FEATURE:
<221> NAME/KEY: misc_feature
<222> LOCATION: (7)...(8)
<223> OTHER INFORMATION: Wherein "n" is A, T, C or G
<220> FEATURE:
<221> NAME/KEY: misc_feature
<222> LOCATION: (10)...(10)
<223> OTHER INFORMATION: Wherein "n" is A, T, C or G
<220> FEATURE:
<221> NAME/KEY: misc_feature
<222> LOCATION: (12)...(12)
<223> OTHER INFORMATION: Wherein "n" is A, T, C or G
```

```
<220> FEATURE:
<221> NAME/KEY: misc_feature
<222> LOCATION: (14)...(14)
<223> OTHER INFORMATION: Wherein "n" is A, T, C or G
<220> FEATURE:
<221> NAME/KEY: misc_feature
<222> LOCATION: (17)...(18)
<223> OTHER INFORMATION: Wherein "n" is A, T, C or G
<220> FEATURE:
<221> NAME/KEY: misc_feature
<222> LOCATION: (20)...(20)
<223> OTHER INFORMATION: Wherein "n" is A, T, C or G
<220> FEATURE:
<221> NAME/KEY: misc_feature
<222> LOCATION: (22)...(23)
<223> OTHER INFORMATION: Wherein "n" is A, T, C or G
<220> FEATURE:
<221> NAME/KEY: misc_feature
<222> LOCATION: (25)...(25)
<223> OTHER INFORMATION: Wherein "n" is A, T, C or G
<220> FEATURE:
<221> NAME/KEY: misc_feature
<222> LOCATION: (27)...(28)
<223> OTHER INFORMATION: Wherein "n" is A, T, C or G
<220> FEATURE:
<221> NAME/KEY: misc_feature
<222> LOCATION: (35)...(36)
<223> OTHER INFORMATION: Wherein "n" is A, T, C or G
<220> FEATURE:
<221> NAME/KEY: misc_feature
<222> LOCATION: (41)...(42)
<223> OTHER INFORMATION: Wherein "n" is A, T, C or G
<220> FEATURE:
<221> NAME/KEY: misc_feature
<222> LOCATION: (44)...(45)
<223> OTHER INFORMATION: Wherein "n" is A, T, C or G
<220> FEATURE:
<221> NAME/KEY: misc_feature
<222> LOCATION: (48)...(48)
<223> OTHER INFORMATION: Wherein "n" is A, T, C or G
<220> FEATURE:
<221> NAME/KEY: misc_feature
<222> LOCATION: (62)...(62)
<223> OTHER INFORMATION: Wherein "n" is A, T, C or G
<220> FEATURE:
<221> NAME/KEY: misc_feature
<222> LOCATION: (65)...(68)
<223> OTHER INFORMATION: Wherein "n" is A, T, C or G
<220> FEATURE:
<221> NAME/KEY: misc_feature
<222> LOCATION: (71)...(72)
<223> OTHER INFORMATION: Wherein "n" is A, T, C or G
<220> FEATURE:
<221> NAME/KEY: misc_feature
<222> LOCATION: (74)...(75)
<223> OTHER INFORMATION: Wherein "n" is A, T, C or G
<220> FEATURE:
<221> NAME/KEY: misc_feature
<222> LOCATION: (80)...(81)
<223> OTHER INFORMATION: Wherein "n" is A, T, C or G
<220> FEATURE:
<221> NAME/KEY: misc_feature
<222> LOCATION: (86)...(86)
<223> OTHER INFORMATION: Wherein "n" is A, T, C or G
<220> FEATURE:
<221> NAME/KEY: misc_feature
<222> LOCATION: (89)...(89)
<223> OTHER INFORMATION: Wherein "n" is A, T, C or G
<220> FEATURE:
<221> NAME/KEY: misc_feature
<222> LOCATION: (92)...(92)
<223> OTHER INFORMATION: Wherein "n" is A, T, C or G
<220> FEATURE:
<221> NAME/KEY: misc_feature
<222> LOCATION: (95)...(95)
<223> OTHER INFORMATION: Wherein "n" is A, T, C or G
<220> FEATURE:
<221> NAME/KEY: misc_feature
<222> LOCATION: (98)...(98)
```

-continued

```
<223> OTHER INFORMATION: Wherein "n" is A, T, C or G
<220> FEATURE:
<221> NAME/KEY: misc_feature
<222> LOCATION: (101)...(101)
<223> OTHER INFORMATION: Wherein "n" is A, T, C or G
<220> FEATURE:
<221> NAME/KEY: misc_feature
<222> LOCATION: (104)...(104)
<223> OTHER INFORMATION: Wherein "n" is A, T, C or G
<220> FEATURE:
<221> NAME/KEY: misc_feature
<222> LOCATION: (107)...(107)
<223> OTHER INFORMATION: Wherein "n" is A, T, C or G
<220> FEATURE:
<221> NAME/KEY: misc_feature
<222> LOCATION: (110)...(113)
<223> OTHER INFORMATION: Wherein "n" is A, T, C or G
<220> FEATURE:
<221> NAME/KEY: misc_feature
<222> LOCATION: (22)...(23)
<223> OTHER INFORMATION: Wherein "n" is A, T, C or G
<220> FEATURE:
<221> NAME/KEY: misc_feature
<222> LOCATION: (118)...(119)
<223> OTHER INFORMATION: Wherein "n" is A, T, C or G
<220> FEATURE:
<221> NAME/KEY: misc_feature
<222> LOCATION: (128)...(130)
<223> OTHER INFORMATION: Wherein "n" is A, T, C or G
<220> FEATURE:
<221> NAME/KEY: misc_feature
<222> LOCATION: (134)...(136)
<223> OTHER INFORMATION: Wherein "n" is A, T, C or G
<220> FEATURE:
<221> NAME/KEY: misc_feature
<222> LOCATION: (176)...(188)
<223> OTHER INFORMATION: Wherein "n" is A, T, C or G
<220> FEATURE:
<221> NAME/KEY: misc_feature
<222> LOCATION: (191)...(191)
<223> OTHER INFORMATION: Wherein "n" is A, T, C or G
<220> FEATURE:
<221> NAME/KEY: misc_feature
<222> LOCATION: (214)...(214)
<223> OTHER INFORMATION: Wherein "n" is A, T, C or G
<220> FEATURE:
<221> NAME/KEY: misc_feature
<222> LOCATION: (236)...(236)
<223> OTHER INFORMATION: Wherein "n" is A, T, C or G
<220> FEATURE:
<221> NAME/KEY: misc_feature
<222> LOCATION: (249)...(249)
<223> OTHER INFORMATION: Wherein "n" is A, T, C or G
<220> FEATURE:
<221> NAME/KEY: misc_feature
<222> LOCATION: (276)...(276)
<223> OTHER INFORMATION: Wherein "n" is A, T, C or G
<220> FEATURE:
<221> NAME/KEY: misc_feature
<222> LOCATION: (342)...(342)
<223> OTHER INFORMATION: Wherein "n" is A, T, C or G
<220> FEATURE:
<221> NAME/KEY: misc_feature
<222> LOCATION: (395)...(395)
<223> OTHER INFORMATION: Wherein "n" is A, T, C or G
<220> FEATURE:
<221> NAME/KEY: misc_feature
<222> LOCATION: (398)...(398)
<223> OTHER INFORMATION: Wherein "n" is A, T, C or G
<220> FEATURE:
<221> NAME/KEY: misc_feature
<222> LOCATION: (416)...(416)
<223> OTHER INFORMATION: Wherein "n" is A, T, C or G
<220> FEATURE:
<221> NAME/KEY: misc_feature
<222> LOCATION: (425)...(425)
<223> OTHER INFORMATION: Wherein "n" is A, T, C or G
<220> FEATURE:
<221> NAME/KEY: misc_feature
```

-continued

```
<222> LOCATION: (473)...(473)
<223> OTHER INFORMATION: Wherein "n" is A, T, C or G
<220> FEATURE:
<221> NAME/KEY: misc_feature
<222> LOCATION: (554)...(554)
<223> OTHER INFORMATION: Wherein "n" is A, T, C or G
<220> FEATURE:
<221> NAME/KEY: misc_feature
<222> LOCATION: (581)...(581)
<223> OTHER INFORMATION: Wherein "n" is A, T, C or G
<220> FEATURE:
<221> NAME/KEY: misc_feature
<222> LOCATION: (664)...(664)
<223> OTHER INFORMATION: Wherein "n" is A, T, C or G
<220> FEATURE:
<221> NAME/KEY: misc_feature
<222> LOCATION: (677)...(677)
<223> OTHER INFORMATION: Wherein "n" is A, T, C or G
<220> FEATURE:
<221> NAME/KEY: misc_feature
<222> LOCATION: (695)...(695)
<223> OTHER INFORMATION: Wherein "n" is A, T, C or G
<220> FEATURE:
<221> NAME/KEY: misc_feature
<222> LOCATION: (716)...(716)
<223> OTHER INFORMATION: Wherein "n" is A, T, C or G
<220> FEATURE:
<221> NAME/KEY: misc_feature
<222> LOCATION: (719)...(719)
<223> OTHER INFORMATION: Wherein "n" is A, T, C or G
<220> FEATURE:
<221> NAME/KEY: misc_feature
<222> LOCATION: (758)...(758)
<223> OTHER INFORMATION: Wherein "n" is A, T, C or G
<220> FEATURE:
<221> NAME/KEY: misc_feature
<222> LOCATION: (764)...(764)
<223> OTHER INFORMATION: Wherein "n" is A, T, C or G
<220> FEATURE:
<221> NAME/KEY: misc_feature
<222> LOCATION: (767)...(767)
<223> OTHER INFORMATION: Wherein "n" is A, T, C or G
<220> FEATURE:
<221> NAME/KEY: misc_feature
<222> LOCATION: (773)...(773)
<223> OTHER INFORMATION: Wherein "n" is A, T, C or G
<220> FEATURE:
<221> NAME/KEY: misc_feature
<222> LOCATION: (776)...(776)
<223> OTHER INFORMATION: Wherein "n" is A, T, C or G
<220> FEATURE:
<221> NAME/KEY: misc_feature
<222> LOCATION: (827)...(827)
<223> OTHER INFORMATION: Wherein "n" is A, T, C or G
<220> FEATURE:
<221> NAME/KEY: misc_feature
<222> LOCATION: (857)...(857)
<223> OTHER INFORMATION: Wherein "n" is A, T, C or G
<220> FEATURE:
<221> NAME/KEY: misc_feature
<222> LOCATION: (914)...(914)
<223> OTHER INFORMATION: Wherein "n" is A, T, C or G
<220> FEATURE:
<221> NAME/KEY: misc_feature
<222> LOCATION: (921)...(921)
<223> OTHER INFORMATION: Wherein "n" is A, T, C or G
<220> FEATURE:
<221> NAME/KEY: misc_feature
<222> LOCATION: (960)...(962)
<223> OTHER INFORMATION: Wherein "n" is A, T, C or G
<220> FEATURE:
<221> NAME/KEY: misc_feature
<222> LOCATION: (965)...(967)
<223> OTHER INFORMATION: Wherein "n" is A, T, C or G
<220> FEATURE:
<221> NAME/KEY: misc_feature
<222> LOCATION: (970)...(970)
<223> OTHER INFORMATION: Wherein "n" is A, T, C or G
<220> FEATURE:
```

-continued

```
<221> NAME/KEY: misc_feature
<222> LOCATION: (974)...(976)
<223> OTHER INFORMATION: Wherein "n" is A, T, C or G
<220> FEATURE:
<221> NAME/KEY: misc_feature
<222> LOCATION: (978)...(978)
<223> OTHER INFORMATION: Wherein "n" is A, T, C or G
<220> FEATURE:
<221> NAME/KEY: misc_feature
<222> LOCATION: (980)...(980)
<223> OTHER INFORMATION: Wherein "n" is A, T, C or G
<220> FEATURE:
<221> NAME/KEY: misc_feature
<222> LOCATION: (982)...(982)
<223> OTHER INFORMATION: Wherein "n" is A, T, C or G
<220> FEATURE:
<221> NAME/KEY: misc_feature
<222> LOCATION: (984)...(984)
<223> OTHER INFORMATION: Wherein "n" is A, T, C or G
<220> FEATURE:
<221> NAME/KEY: misc_feature
<222> LOCATION: (988)...(988)
<223> OTHER INFORMATION: Wherein "n" is A, T, C or G
<220> FEATURE:
<221> NAME/KEY: misc_feature
<222> LOCATION: (990)...(994)
<223> OTHER INFORMATION: Wherein "n" is A, T, C or G
<220> FEATURE:
<221> NAME/KEY: misc_feature
<222> LOCATION: (997)...(997)
<223> OTHER INFORMATION: Wherein "n" is A, T, C or G
<220> FEATURE:
<221> NAME/KEY: misc_feature
<222> LOCATION: (1000)...(1000)
<223> OTHER INFORMATION: Wherein "n" is A, T, C or G
<220> FEATURE:
<221> NAME/KEY: misc_feature
<222> LOCATION: (1004)...(1006)
<223> OTHER INFORMATION: Wherein "n" is A, T, C or G
<220> FEATURE:
<221> NAME/KEY: misc_feature
<222> LOCATION: (1008)...(1009)
<223> OTHER INFORMATION: Wherein "n" is A, T, C or G
<220> FEATURE:
<221> NAME/KEY: misc_feature
<222> LOCATION: (1110)...(1115)
<223> OTHER INFORMATION: Wherein "n" is A, T, C or G
<220> FEATURE:
<221> NAME/KEY: misc_feature
<222> LOCATION: (1117)...(1117)
<223> OTHER INFORMATION: Wherein "n" is A, T, C or G

<400> SEQUENCE: 89
nnnncgnngn ananganntn cnncnanncg tgccnntgag nnanngantg gagtggtcag      60
angtnnnncc nntnnctcan nacganggnc cnaanccngt ngtnccnatn nnntacanng    120
aagagttnnn cgannntatg gattacttcc gtgcgattta cttctccgac gagcgntctc    180
ctcgcgcnct ncgactcacg gaagaagccc tccncttaaa ctccggcaac tacacngtgt    240
ggcatttcng gcgcttagta ctcgaggcgc ttaatnacga cttgtatgaa gaactcgagt    300
tcatcgaacg cattgctgag gataactcta agaactacca gntgtggcat catcgacgat    360
gggttgcaga gaaactgggt cctgatgttg caggnaanga acttgagttt acccgnaggg    420
tactntcact tgatgccaaa cattatcatg cttggtcaca taggcagtgg gcnctacaag    480
cattaggagg atgggaagat gagcttaatt actgccacga gctccttgaa gctgacgtct    540
ttaacaattc tgcntggaat cagaggtatt atgtcataac nagatctcct ttgttgggag    600
gcctagaagc catgagagaa tctgaagtaa gctacacaat caaagccatt ttagccaatc    660
ctgnaaacga gagctcntgg agatacctaa aagcncttta caaagacgac acagantcnt    720
ggattagtga tccaagtgtt tcctcagtct gtttgaangt tctntcncgc acngantgct    780
```

```
tccatggatt cgctctgagc acccttttgg atcttctatg cgatggnttg agaccaacca      840
acgagcatag agactcngtg aaagctctag ctaatgaaga accagagact aacttggcca      900
atttggtgtg tacnattctg ngtcgtgtag atccaataag agctaactat tgggcatggn      960
nnaanannnn gatnnnantn gnancaantn nnnnatntgn cgcnnnanna nnnnncnt       1018
```

<210> SEQ ID NO 90
<211> LENGTH: 1237
<212> TYPE: DNA
<213> ORGANISM: Artificial Sequence
<220> FEATURE:
<223> OTHER INFORMATION: Description of Artificial Sequence: Consensus
      sequence where N can be any A, C, T or G
<220> FEATURE:
<221> NAME/KEY: misc_feature
<222> LOCATION: (1)...(34)
<223> OTHER INFORMATION: Wherein "n" is A, T, C or G
<220> FEATURE:
<221> NAME/KEY: misc_feature
<222> LOCATION: (36)...(36)
<223> OTHER INFORMATION: Wherein "n" is A, T, C or G
<220> FEATURE:
<221> NAME/KEY: misc_feature
<222> LOCATION: (40)...(40)
<223> OTHER INFORMATION: Wherein "n" is A, T, C or G
<220> FEATURE:
<221> NAME/KEY: misc_feature
<222> LOCATION: (42)...(45)
<223> OTHER INFORMATION: Wherein "n" is A, T, C or G
<220> FEATURE:
<221> NAME/KEY: misc_feature
<222> LOCATION: (48)...(48)
<223> OTHER INFORMATION: Wherein "n" is A, T, C or G
<220> FEATURE:
<221> NAME/KEY: misc_feature
<222> LOCATION: (52)...(52)
<223> OTHER INFORMATION: Wherein "n" is A, T, C or G
<220> FEATURE:
<221> NAME/KEY: misc_feature
<222> LOCATION: (54)...(54)
<223> OTHER INFORMATION: Wherein "n" is A, T, C or G
<220> FEATURE:
<221> NAME/KEY: misc_feature
<222> LOCATION: (57)...(58)
<223> OTHER INFORMATION: Wherein "n" is A, T, C or G
<220> FEATURE:
<221> NAME/KEY: misc_feature
<222> LOCATION: (60)...(61)
<223> OTHER INFORMATION: Wherein "n" is A, T, C or G
<220> FEATURE:
<221> NAME/KEY: misc_feature
<222> LOCATION: (63)...(63)
<223> OTHER INFORMATION: Wherein "n" is A, T, C or G
<220> FEATURE:
<221> NAME/KEY: misc_feature
<222> LOCATION: (67)...(67)
<223> OTHER INFORMATION: Wherein "n" is A, T, C or G
<220> FEATURE:
<221> NAME/KEY: misc_feature
<222> LOCATION: (69)...(75)
<223> OTHER INFORMATION: Wherein "n" is A, T, C or G
<220> FEATURE:
<221> NAME/KEY: misc_feature
<222> LOCATION: (78)...(79)
<223> OTHER INFORMATION: Wherein "n" is A, T, C or G
<220> FEATURE:
<221> NAME/KEY: misc_feature
<222> LOCATION: (81)...(82)
<223> OTHER INFORMATION: Wherein "n" is A, T, C or G
<220> FEATURE:
<221> NAME/KEY: misc_feature
<222> LOCATION: (84)...(84)
<223> OTHER INFORMATION: Wherein "n" is A, T, C or G
<220> FEATURE:
<221> NAME/KEY: misc_feature -continued

```
<222> LOCATION: (87)...(88)
<223> OTHER INFORMATION: Wherein "n" is A, T, C or G
<220> FEATURE:
<221> NAME/KEY: misc_feature
<222> LOCATION: (90)...(91)
<223> OTHER INFORMATION: Wherein "n" is A, T, C or G
<220> FEATURE:
<221> NAME/KEY: misc_feature
<222> LOCATION: (93)...(94)
<223> OTHER INFORMATION: Wherein "n" is A, T, C or G
<220> FEATURE:
<221> NAME/KEY: misc_feature
<222> LOCATION: (96)...(99)
<223> OTHER INFORMATION: Wherein "n" is A, T, C or G
<220> FEATURE:
<221> NAME/KEY: misc_feature
<222> LOCATION: (103)...(109)
<223> OTHER INFORMATION: Wherein "n" is A, T, C or G
<220> FEATURE:
<221> NAME/KEY: misc_feature
<222> LOCATION: (111)...(111)
<223> OTHER INFORMATION: Wherein "n" is A, T, C or G
<220> FEATURE:
<221> NAME/KEY: misc_feature
<222> LOCATION: (114)...(114)
<223> OTHER INFORMATION: Wherein "n" is A, T, C or G
<220> FEATURE:
<221> NAME/KEY: misc_feature
<222> LOCATION: (117)...(117)
<223> OTHER INFORMATION: Wherein "n" is A, T, C or G
<220> FEATURE:
<221> NAME/KEY: misc_feature
<222> LOCATION: (123)...(123)
<223> OTHER INFORMATION: Wherein "n" is A, T, C or G
<220> FEATURE:
<221> NAME/KEY: misc_feature
<222> LOCATION: (126)...(126)
<223> OTHER INFORMATION: Wherein "n" is A, T, C or G
<220> FEATURE:
<221> NAME/KEY: misc_feature
<222> LOCATION: (132)...(132)
<223> OTHER INFORMATION: Wherein "n" is A, T, C or G
<220> FEATURE:
<221> NAME/KEY: misc_feature
<222> LOCATION: (135)...(135)
<223> OTHER INFORMATION: Wherein "n" is A, T, C or G
<220> FEATURE:
<221> NAME/KEY: misc_feature
<222> LOCATION: (144)...(145)
<223> OTHER INFORMATION: Wherein "n" is A, T, C or G
<220> FEATURE:
<221> NAME/KEY: misc_feature
<222> LOCATION: (165)...(165)
<223> OTHER INFORMATION: Wherein "n" is A, T, C or G
<220> FEATURE:
<221> NAME/KEY: misc_feature
<222> LOCATION: (168)...(168)
<223> OTHER INFORMATION: Wherein "n" is A, T, C or G
<220> FEATURE:
<221> NAME/KEY: misc_feature
<222> LOCATION: (171)...(172)
<223> OTHER INFORMATION: Wherein "n" is A, T, C or G
<220> FEATURE:
<221> NAME/KEY: misc_feature
<222> LOCATION: (174)...(174)
<223> OTHER INFORMATION: Wherein "n" is A, T, C or G
<220> FEATURE:
<221> NAME/KEY: misc_feature
<222> LOCATION: (177)...(177)
<223> OTHER INFORMATION: Wherein "n" is A, T, C or G
<220> FEATURE:
<221> NAME/KEY: misc_feature
<222> LOCATION: (186)...(187)
<223> OTHER INFORMATION: Wherein "n" is A, T, C or G
<220> FEATURE:
<221> NAME/KEY: misc_feature
<222> LOCATION: (189)...(189)
<223> OTHER INFORMATION: Wherein "n" is A, T, C or G
<220> FEATURE:
```

-continued

```
<221> NAME/KEY: misc_feature
<222> LOCATION: (195)...(195)
<223> OTHER INFORMATION: Wherein "n" is A, T, C or G
<220> FEATURE:
<221> NAME/KEY: misc_feature
<222> LOCATION: (201)...(201)
<223> OTHER INFORMATION: Wherein "n" is A, T, C or G
<220> FEATURE:
<221> NAME/KEY: misc_feature
<222> LOCATION: (204)...(204)
<223> OTHER INFORMATION: Wherein "n" is A, T, C or G
<220> FEATURE:
<221> NAME/KEY: misc_feature
<222> LOCATION: (207)...(207)
<223> OTHER INFORMATION: Wherein "n" is A, T, C or G
<220> FEATURE:
<221> NAME/KEY: misc_feature
<222> LOCATION: (210)...(210)
<223> OTHER INFORMATION: Wherein "n" is A, T, C or G
<220> FEATURE:
<221> NAME/KEY: misc_feature
<222> LOCATION: (215)...(216)
<223> OTHER INFORMATION: Wherein "n" is A, T, C or G
<220> FEATURE:
<221> NAME/KEY: misc_feature
<222> LOCATION: (219)...(219)
<223> OTHER INFORMATION: Wherein "n" is A, T, C or G
<220> FEATURE:
<221> NAME/KEY: misc_feature
<222> LOCATION: (227)...(227)
<223> OTHER INFORMATION: Wherein "n" is A, T, C or G
<220> FEATURE:
<221> NAME/KEY: misc_feature
<222> LOCATION: (229)...(229)
<223> OTHER INFORMATION: Wherein "n" is A, T, C or G
<220> FEATURE:
<221> NAME/KEY: misc_feature
<222> LOCATION: (231)...(231)
<223> OTHER INFORMATION: Wherein "n" is A, T, C or G
<220> FEATURE:
<221> NAME/KEY: misc_feature
<222> LOCATION: (252)...(252)
<223> OTHER INFORMATION: Wherein "n" is A, T, C or G
<220> FEATURE:
<221> NAME/KEY: misc_feature
<222> LOCATION: (261)...(262)
<223> OTHER INFORMATION: Wherein "n" is A, T, C or G
<220> FEATURE:
<221> NAME/KEY: misc_feature
<222> LOCATION: (264)...(264)
<223> OTHER INFORMATION: Wherein "n" is A, T, C or G
<220> FEATURE:
<221> NAME/KEY: misc_feature
<222> LOCATION: (267)...(267)
<223> OTHER INFORMATION: Wherein "n" is A, T, C or G
<220> FEATURE:
<221> NAME/KEY: misc_feature
<222> LOCATION: (276)...(276)
<223> OTHER INFORMATION: Wherein "n" is A, T, C or G
<220> FEATURE:
<221> NAME/KEY: misc_feature
<222> LOCATION: (279)...(279)
<223> OTHER INFORMATION: Wherein "n" is A, T, C or G
<220> FEATURE:
<221> NAME/KEY: misc_feature
<222> LOCATION: (291)...(291)
<223> OTHER INFORMATION: Wherein "n" is A, T, C or G
<220> FEATURE:
<221> NAME/KEY: misc_feature
<222> LOCATION: (294)...(294)
<223> OTHER INFORMATION: Wherein "n" is A, T, C or G
<220> FEATURE:
<221> NAME/KEY: misc_feature
<222> LOCATION: (298)...(298)
<223> OTHER INFORMATION: Wherein "n" is A, T, C or G
<220> FEATURE:
<221> NAME/KEY: misc_feature
<222> LOCATION: (315)...(315)
<223> OTHER INFORMATION: Wherein "n" is A, T, C or G
```

```
<220> FEATURE:
<221> NAME/KEY: misc_feature
<222> LOCATION: (321)...(321)
<223> OTHER INFORMATION: Wherein "n" is A, T, C or G
<220> FEATURE:
<221> NAME/KEY: misc_feature
<222> LOCATION: (328)...(328)
<223> OTHER INFORMATION: Wherein "n" is A, T, C or G
<220> FEATURE:
<221> NAME/KEY: misc_feature
<222> LOCATION: (330)...(330)
<223> OTHER INFORMATION: Wherein "n" is A, T, C or G
<220> FEATURE:
<221> NAME/KEY: misc_feature
<222> LOCATION: (333)...(333)
<223> OTHER INFORMATION: Wherein "n" is A, T, C or G
<220> FEATURE:
<221> NAME/KEY: misc_feature
<222> LOCATION: (348)...(348)
<223> OTHER INFORMATION: Wherein "n" is A, T, C or G
<220> FEATURE:
<221> NAME/KEY: misc_feature
<222> LOCATION: (352)...(352)
<223> OTHER INFORMATION: Wherein "n" is A, T, C or G
<220> FEATURE:
<221> NAME/KEY: misc_feature
<222> LOCATION: (356)...(356)
<223> OTHER INFORMATION: Wherein "n" is A, T, C or G
<220> FEATURE:
<221> NAME/KEY: misc_feature
<222> LOCATION: (358)...(358)
<223> OTHER INFORMATION: Wherein "n" is A, T, C or G
<220> FEATURE:
<221> NAME/KEY: misc_feature
<222> LOCATION: (364)...(364)
<223> OTHER INFORMATION: Wherein "n" is A, T, C or G
<220> FEATURE:
<221> NAME/KEY: misc_feature
<222> LOCATION: (336)...(367)
<223> OTHER INFORMATION: Wherein "n" is A, T, C or G
<220> FEATURE:
<221> NAME/KEY: misc_feature
<222> LOCATION: (369)...(369)
<223> OTHER INFORMATION: Wherein "n" is A, T, C or G
<220> FEATURE:
<221> NAME/KEY: misc_feature
<222> LOCATION: (382)...(382)
<223> OTHER INFORMATION: Wherein "n" is A, T, C or G
<220> FEATURE:
<221> NAME/KEY: misc_feature
<222> LOCATION: (386)...(386)
<223> OTHER INFORMATION: Wherein "n" is A, T, C or G
<220> FEATURE:
<221> NAME/KEY: misc_feature
<222> LOCATION: (390)...(390)
<223> OTHER INFORMATION: Wherein "n" is A, T, C or G
<220> FEATURE:
<221> NAME/KEY: misc_feature
<222> LOCATION: (409)...(411)
<223> OTHER INFORMATION: Wherein "n" is A, T, C or G
<220> FEATURE:
<221> NAME/KEY: misc_feature
<222> LOCATION: (414)...(414)
<223> OTHER INFORMATION: Wherein "n" is A, T, C or G
<220> FEATURE:
<221> NAME/KEY: misc_feature
<222> LOCATION: (426)...(426)
<223> OTHER INFORMATION: Wherein "n" is A, T, C or G
<220> FEATURE:
<221> NAME/KEY: misc_feature
<222> LOCATION: (429)...(429)
<223> OTHER INFORMATION: Wherein "n" is A, T, C or G
<220> FEATURE:
<221> NAME/KEY: misc_feature
<222> LOCATION: (432)...(432)
<223> OTHER INFORMATION: Wherein "n" is A, T, C or G
<220> FEATURE:
<221> NAME/KEY: misc_feature
<222> LOCATION: (444)...(444)
```

```
<223> OTHER INFORMATION: Wherein "n" is A, T, C or G
<220> FEATURE:
<221> NAME/KEY: misc_feature
<222> LOCATION: (460)...(460)
<223> OTHER INFORMATION: Wherein "n" is A, T, C or G
<220> FEATURE:
<221> NAME/KEY: misc_feature
<222> LOCATION: (462)...(463)
<223> OTHER INFORMATION: Wherein "n" is A, T, C or G
<220> FEATURE:
<221> NAME/KEY: misc_feature
<222> LOCATION: (468)...(468)
<223> OTHER INFORMATION: Wherein "n" is A, T, C or G
<220> FEATURE:
<221> NAME/KEY: misc_feature
<222> LOCATION: (472)...(472)
<223> OTHER INFORMATION: Wherein "n" is A, T, C or G
<220> FEATURE:
<221> NAME/KEY: misc_feature
<222> LOCATION: (486)...(486)
<223> OTHER INFORMATION: Wherein "n" is A, T, C or G
<220> FEATURE:
<221> NAME/KEY: misc_feature
<222> LOCATION: (492)...(492)
<223> OTHER INFORMATION: Wherein "n" is A, T, C or G
<220> FEATURE:
<221> NAME/KEY: misc_feature
<222> LOCATION: (495)...(496)
<223> OTHER INFORMATION: Wherein "n" is A, T, C or G
<220> FEATURE:
<221> NAME/KEY: misc_feature
<222> LOCATION: (504)...(504)
<223> OTHER INFORMATION: Wherein "n" is A, T, C or G
<220> FEATURE:
<221> NAME/KEY: misc_feature
<222> LOCATION: (510)...(511)
<223> OTHER INFORMATION: Wherein "n" is A, T, C or G
<220> FEATURE:
<221> NAME/KEY: misc_feature
<222> LOCATION: (513)...(513)
<223> OTHER INFORMATION: Wherein "n" is A, T, C or G
<220> FEATURE:
<221> NAME/KEY: misc_feature
<222> LOCATION: (516)...(516)
<223> OTHER INFORMATION: Wherein "n" is A, T, C or G
<220> FEATURE:
<221> NAME/KEY: misc_feature
<222> LOCATION: (519)...(519)
<223> OTHER INFORMATION: Wherein "n" is A, T, C or G
<220> FEATURE:
<221> NAME/KEY: misc_feature
<222> LOCATION: (542)...(543)
<223> OTHER INFORMATION: Wherein "n" is A, T, C or G
<220> FEATURE:
<221> NAME/KEY: misc_feature
<222> LOCATION: (549)...(549)
<223> OTHER INFORMATION: Wherein "n" is A, T, C or G
<220> FEATURE:
<221> NAME/KEY: misc_feature
<222> LOCATION: (555)...(555)
<223> OTHER INFORMATION: Wherein "n" is A, T, C or G
<220> FEATURE:
<221> NAME/KEY: misc_feature
<222> LOCATION: (558)...(558)
<223> OTHER INFORMATION: Wherein "n" is A, T, C or G
<220> FEATURE:
<221> NAME/KEY: misc_feature
<222> LOCATION: (576)...(576)
<223> OTHER INFORMATION: Wherein "n" is A, T, C or G
<220> FEATURE:
<221> NAME/KEY: misc_feature
<222> LOCATION: (579)...(579)
<223> OTHER INFORMATION: Wherein "n" is A, T, C or G
<220> FEATURE:
<221> NAME/KEY: misc_feature
<222> LOCATION: (581)...(581)
<223> OTHER INFORMATION: Wherein "n" is A, T, C or G
<220> FEATURE:
<221> NAME/KEY: misc_feature
```

-continued

```
<222> LOCATION: (588)...(588)
<223> OTHER INFORMATION: Wherein "n" is A, T, C or G
<220> FEATURE:
<221> NAME/KEY: misc_feature
<222> LOCATION: (595)...(595)
<223> OTHER INFORMATION: Wherein "n" is A, T, C or G
<220> FEATURE:
<221> NAME/KEY: misc_feature
<222> LOCATION: (605)...(606)
<223> OTHER INFORMATION: Wherein "n" is A, T, C or G
<220> FEATURE:
<221> NAME/KEY: misc_feature
<222> LOCATION: (609)...(609)
<223> OTHER INFORMATION: Wherein "n" is A, T, C or G
<220> FEATURE:
<221> NAME/KEY: misc_feature
<222> LOCATION: (618)...(618)
<223> OTHER INFORMATION: Wherein "n" is A, T, C or G
<220> FEATURE:
<221> NAME/KEY: misc_feature
<222> LOCATION: (621)...(621)
<223> OTHER INFORMATION: Wherein "n" is A, T, C or G
<220> FEATURE:
<221> NAME/KEY: misc_feature
<222> LOCATION: (623)...(624)
<223> OTHER INFORMATION: Wherein "n" is A, T, C or G
<220> FEATURE:
<221> NAME/KEY: misc_feature
<222> LOCATION: (628)...(628)
<223> OTHER INFORMATION: Wherein "n" is A, T, C or G
<220> FEATURE:
<221> NAME/KEY: misc_feature
<222> LOCATION: (634)...(635)
<223> OTHER INFORMATION: Wherein "n" is A, T, C or G
<220> FEATURE:
<221> NAME/KEY: misc_feature
<222> LOCATION: (637)...(639)
<223> OTHER INFORMATION: Wherein "n" is A, T, C or G
<220> FEATURE:
<221> NAME/KEY: misc_feature
<222> LOCATION: (645)...(646)
<223> OTHER INFORMATION: Wherein "n" is A, T, C or G
<220> FEATURE:
<221> NAME/KEY: misc_feature
<222> LOCATION: (648)...(648)
<223> OTHER INFORMATION: Wherein "n" is A, T, C or G
<220> FEATURE:
<221> NAME/KEY: misc_feature
<222> LOCATION: (654)...(654)
<223> OTHER INFORMATION: Wherein "n" is A, T, C or G
<220> FEATURE:
<221> NAME/KEY: misc_feature
<222> LOCATION: (658)...(659)
<223> OTHER INFORMATION: Wherein "n" is A, T, C or G
<220> FEATURE:
<221> NAME/KEY: misc_feature
<222> LOCATION: (672)...(672)
<223> OTHER INFORMATION: Wherein "n" is A, T, C or G
<220> FEATURE:
<221> NAME/KEY: misc_feature
<222> LOCATION: (676)...(678)
<223> OTHER INFORMATION: Wherein "n" is A, T, C or G
<220> FEATURE:
<221> NAME/KEY: misc_feature
<222> LOCATION: (684)...(684)
<223> OTHER INFORMATION: Wherein "n" is A, T, C or G
<220> FEATURE:
<221> NAME/KEY: misc_feature
<222> LOCATION: (690)...(690)
<223> OTHER INFORMATION: Wherein "n" is A, T, C or G
<220> FEATURE:
<221> NAME/KEY: misc_feature
<222> LOCATION: (693)...(693)
<223> OTHER INFORMATION: Wherein "n" is A, T, C or G
<220> FEATURE:
<221> NAME/KEY: misc_feature
<222> LOCATION: (696)...(696)
<223> OTHER INFORMATION: Wherein "n" is A, T, C or G
<220> FEATURE:
```

-continued

```
<221> NAME/KEY: misc_feature
<222> LOCATION: (699)...(699)
<223> OTHER INFORMATION: Wherein "n" is A, T, C or G
<220> FEATURE:
<221> NAME/KEY: misc_feature
<222> LOCATION: (708)...(708)
<223> OTHER INFORMATION: Wherein "n" is A, T, C or G
<220> FEATURE:
<221> NAME/KEY: misc_feature
<222> LOCATION: (721)...(721)
<223> OTHER INFORMATION: Wherein "n" is A, T, C or G
<220> FEATURE:
<221> NAME/KEY: misc_feature
<222> LOCATION: (723)...(723)
<223> OTHER INFORMATION: Wherein "n" is A, T, C or G
<220> FEATURE:
<221> NAME/KEY: misc_feature
<222> LOCATION: (734)...(734)
<223> OTHER INFORMATION: Wherein "n" is A, T, C or G
<220> FEATURE:
<221> NAME/KEY: misc_feature
<222> LOCATION: (738)...(739)
<223> OTHER INFORMATION: Wherein "n" is A, T, C or G
<220> FEATURE:
<221> NAME/KEY: misc_feature
<222> LOCATION: (741)...(743)
<223> OTHER INFORMATION: Wherein "n" is A, T, C or G
<220> FEATURE:
<221> NAME/KEY: misc_feature
<222> LOCATION: (746)...(746)
<223> OTHER INFORMATION: Wherein "n" is A, T, C or G
<220> FEATURE:
<221> NAME/KEY: misc_feature
<222> LOCATION: (751)...(751)
<223> OTHER INFORMATION: Wherein "n" is A, T, C or G
<220> FEATURE:
<221> NAME/KEY: misc_feature
<222> LOCATION: (764)...(764)
<223> OTHER INFORMATION: Wherein "n" is A, T, C or G
<220> FEATURE:
<221> NAME/KEY: misc_feature
<222> LOCATION: (768)...(768)
<223> OTHER INFORMATION: Wherein "n" is A, T, C or G
<220> FEATURE:
<221> NAME/KEY: misc_feature
<222> LOCATION: (770)...(774)
<223> OTHER INFORMATION: Wherein "n" is A, T, C or G
<220> FEATURE:
<221> NAME/KEY: misc_feature
<222> LOCATION: (779)...(779)
<223> OTHER INFORMATION: Wherein "n" is A, T, C or G
<220> FEATURE:
<221> NAME/KEY: misc_feature
<222> LOCATION: (781)...(787)
<223> OTHER INFORMATION: Wherein "n" is A, T, C or G
<220> FEATURE:
<221> NAME/KEY: misc_feature
<222> LOCATION: (789)...(789)
<223> OTHER INFORMATION: Wherein "n" is A, T, C or G
<220> FEATURE:
<221> NAME/KEY: misc_feature
<222> LOCATION: (791)...(793)
<223> OTHER INFORMATION: Wherein "n" is A, T, C or G
<220> FEATURE:
<221> NAME/KEY: misc_feature
<222> LOCATION: (799)...(801)
<223> OTHER INFORMATION: Wherein "n" is A, T, C or G
<220> FEATURE:
<221> NAME/KEY: misc_feature
<222> LOCATION: (813)...(813)
<223> OTHER INFORMATION: Wherein "n" is A, T, C or G
<220> FEATURE:
<221> NAME/KEY: misc_feature
<222> LOCATION: (815)...(816)
<223> OTHER INFORMATION: Wherein "n" is A, T, C or G
<220> FEATURE:
<221> NAME/KEY: misc_feature
<222> LOCATION: (818)...(819)
<223> OTHER INFORMATION: Wherein "n" is A, T, C or G
```

-continued

```
<220> FEATURE:
<221> NAME/KEY: misc_feature
<222> LOCATION: (821)...(821)
<223> OTHER INFORMATION: Wherein "n" is A, T, C or G
<220> FEATURE:
<221> NAME/KEY: misc_feature
<222> LOCATION: (823)...(823)
<223> OTHER INFORMATION: Wherein "n" is A, T, C or G
<220> FEATURE:
<221> NAME/KEY: misc_feature
<222> LOCATION: (825)...(826)
<223> OTHER INFORMATION: Wherein "n" is A, T, C or G
<220> FEATURE:
<221> NAME/KEY: misc_feature
<222> LOCATION: (828)...(828)
<223> OTHER INFORMATION: Wherein "n" is A, T, C or G
<220> FEATURE:
<221> NAME/KEY: misc_feature
<222> LOCATION: (831)...(834)
<223> OTHER INFORMATION: Wherein "n" is A, T, C or G
<220> FEATURE:
<221> NAME/KEY: misc_feature
<222> LOCATION: (836)...(836)
<223> OTHER INFORMATION: Wherein "n" is A, T, C or G
<220> FEATURE:
<221> NAME/KEY: misc_feature
<222> LOCATION: (838)...(838)
<223> OTHER INFORMATION: Wherein "n" is A, T, C or G
<220> FEATURE:
<221> NAME/KEY: misc_feature
<222> LOCATION: (840)...(841)
<223> OTHER INFORMATION: Wherein "n" is A, T, C or G
<220> FEATURE:
<221> NAME/KEY: misc_feature
<222> LOCATION: (845)...(845)
<223> OTHER INFORMATION: Wherein "n" is A, T, C or G
<220> FEATURE:
<221> NAME/KEY: misc_feature
<222> LOCATION: (847)...(847)
<223> OTHER INFORMATION: Wherein "n" is A, T, C or G
<220> FEATURE:
<221> NAME/KEY: misc_feature
<222> LOCATION: (850)...(850)
<223> OTHER INFORMATION: Wherein "n" is A, T, C or G
<220> FEATURE:
<221> NAME/KEY: misc_feature
<222> LOCATION: (852)...(856)
<223> OTHER INFORMATION: Wherein "n" is A, T, C or G
<220> FEATURE:
<221> NAME/KEY: misc_feature
<222> LOCATION: (861)...(863)
<223> OTHER INFORMATION: Wherein "n" is A, T, C or G
<220> FEATURE:
<221> NAME/KEY: misc_feature
<222> LOCATION: (865)...(871)
<223> OTHER INFORMATION: Wherein "n" is A, T, C or G
<220> FEATURE:
<221> NAME/KEY: misc_feature
<222> LOCATION: (873)...(875)
<223> OTHER INFORMATION: Wherein "n" is A, T, C or G
<220> FEATURE:
<221> NAME/KEY: misc_feature
<222> LOCATION: (879)...(879)
<223> OTHER INFORMATION: Wherein "n" is A, T, C or G
<220> FEATURE:
<221> NAME/KEY: misc_feature
<222> LOCATION: (882)...(883)
<223> OTHER INFORMATION: Wherein "n" is A, T, C or G
<220> FEATURE:
<221> NAME/KEY: misc_feature
<222> LOCATION: (885)...(885)
<223> OTHER INFORMATION: Wherein "n" is A, T, C or G
<220> FEATURE:
<221> NAME/KEY: misc_feature
<222> LOCATION: (889)...(889)
<223> OTHER INFORMATION: Wherein "n" is A, T, C or G
<220> FEATURE:
<221> NAME/KEY: misc_feature
<222> LOCATION: (891)...(891)
```

-continued

```
<223> OTHER INFORMATION: Wherein "n" is A, T, C or G
<220> FEATURE:
<221> NAME/KEY: misc_feature
<222> LOCATION: (893)...(893)
<223> OTHER INFORMATION: Wherein "n" is A, T, C or G
<220> FEATURE:
<221> NAME/KEY: misc_feature
<222> LOCATION: (895)...(895)
<223> OTHER INFORMATION: Wherein "n" is A, T, C or G
<220> FEATURE:
<221> NAME/KEY: misc_feature
<222> LOCATION: (897)...(898)
<223> OTHER INFORMATION: Wherein "n" is A, T, C or G

<400> SEQUENCE: 90
nnnnnnnnnn nnnnnnnnnn nnnnnnnnnn nnnntngagn tnnnncgnga tnancanntn      60
nantatntnn nnnnnggnnt nngncanntn ngnncnnnnt ttnnnnnnnt ngangcnaat     120
cgnccntggc tntgntactg gatnnttcat tcaattgctt tgctnggnga nncngtngat     180
gatgannntg aaaanaatgc natngantnn cttgnncgnt gccaggntnc ngatggtgga     240
tatggtggtg gncctggcca nntccncat cttgcnacna cttatgctgc ngtnaatnca      300
cttgttactt taggnggtga naaagccntn tcntcaatta atagaganaa antgtntngt     360
tttntnngnc ggatgaagga tncaantggn ggtttcagga tgcatgatnn nggngaaatt     420
gatgtncgng cntgctacac tgcnatttcg gttgcaagcn tnntgaanat tntggatgat     480
gaactnaccc anggnntagg agantacatn ntnagntgnc aaacttatga aggtggcatt     540 gnnggggganc ctggntcnga agctcatggt gggtanacnt nctgtggntt ggctnctatg    600
attntnatna atgaggtnga ncnnttgnat ttgnntnnnt taatnnantg ggtngtannt     660
cgacaaggag tngaannggg attncaaggn agnacnaana aattggtnga tggttgctac     720
ncnttttggc aggnagcnnc nnntgntcta ntacaaagat tatnttcnan nnnngatang    780
nnnnnnnang nnncatcann nnnnnnnnnn ngngnnannt nangnncntg nnnnanangn    840
ncatnangan gnnnnnnnctg nnnannnnnn ngnnnatgnt gnntntgang ngnanannga    900
tnnnnnttca gngnatnntn anaannttnn nnatanntnt annnannnnn ncagnnnaat    960
nnaaccnntt tttnatagcn tngncttgca nnnatatntn ctcttntgnt ctcaggtncn    1020
nganggtgga ttnagagaca agccgngnaa acncngngan nnctancaca catgttactg    1080
cctnagnggn ctntcngtgn nncagnacnn ttggtnaaan gacnnngann ctccnccntt    1140
nnctcnnnan ntnntnggnn nntacncnaa nnnnctngan ccnntncanc nnnnnnnnnn    1200
nnnnnnnnnn nnnnnnnnnn nnnnnnnnnn nnnnnnn                              1237
```